(12) United States Patent
Bhuniya et al.

(10) Patent No.: US 8,501,955 B2
(45) Date of Patent: *Aug. 6, 2013

(54) ACETAMIDE DERIVATIVES AS GLUCOKINASE ACTIVATORS, THEIR PROCESS AND MEDICINAL APPLICATION

(75) Inventors: Debnath Bhuniya, Maharashtra (IN); Sandeep Bhausaheb Bhosale, Maharashtra (IN); Gobind Sing Kapkoti, Maharashtra (IN); Venkata Poornapragnacharyulu Palle, Maharashtra (IN); Siddhartha De, Maharashtra (IN); Kasim A. Mookhtiar, Maharashtra (IN); Bhavesh Dave, Maharashtra (IN); Anil Deshpande, Maharashtra (IN); Santosh Kurhade, Maharashtra (IN); Balasaheb Kobal, Maharashtra (IN); Keshav Naik, Maharashtra (IN); Sachin Kandalkar, Maharashtra (IN)

(73) Assignee: Advinus Therapeutics Private Limited, Bangalore (IN)

( * ) Notice: Subject to any disclaimer, the term of this patent is extended or adjusted under 35 U.S.C. 154(b) by 243 days.

This patent is subject to a terminal disclaimer.

(21) Appl. No.: 12/681,845

(22) PCT Filed: Oct. 7, 2008

(86) PCT No.: PCT/IN2008/000650
§ 371 (c)(1),
(2), (4) Date: Aug. 23, 2010

(87) PCT Pub. No.: WO2009/047798
PCT Pub. Date: Apr. 16, 2009

(65) Prior Publication Data
US 2010/0310493 A1     Dec. 9, 2010

(30) Foreign Application Priority Data
Oct. 8, 2007  (IN) .......................... 2266/CHE/2007

(51) Int. Cl.
| | |
|---|---|
| C07D 277/34 | (2006.01) |
| C07D 277/38 | (2006.01) |
| C07D 513/04 | (2006.01) |
| A61K 31/397 | (2006.01) |
| A61K 31/44 | (2006.01) |
| A61K 31/437 | (2006.01) |
| A61K 31/427 | (2006.01) |

(52) U.S. Cl.
USPC ........ 548/185; 548/195; 546/114; 514/210.2; 514/301; 514/369; 514/371

(58) Field of Classification Search
None
See application file for complete search history.

(56) References Cited

U.S. PATENT DOCUMENTS
2010/0144772 A1 * 6/2010 Mookhtiar et al. ........... 514/275

FOREIGN PATENT DOCUMENTS
| WO | 02/08209 | 1/2002 |
|---|---|---|
| WO | 03/015774 | 2/2003 |
| WO | 03/055482 | 7/2003 |
| WO | WO 2008104994 A2 * | 9/2008 |

OTHER PUBLICATIONS

Office Action for corresponding Application No. 08 838 336 dated Jan. 23, 2012.
Written Opinion for International Application No. PCT/IN2008/000650 dated Apr. 13, 2010.
International Search Report for Application No. PCT/IN2008/00650 dated Apr. 15, 2009.

* cited by examiner

*Primary Examiner* — Nyeemah A Grazier
(74) *Attorney, Agent, or Firm* — K&L Gates LLP

(57) ABSTRACT

Acetamide derivatives, their stereoisomers, tautomers, prodrugs, pharmaceutically acceptable salts, polymorphs, solvates and formulations thereof for the prophylaxis, management, treatment, control of progression, or adjunct treatment of diseases and/or medical conditions where the activation of glucokinase would be beneficial, are disclosed.

(I)

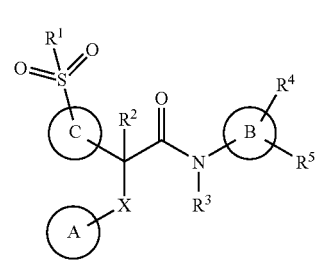

The disclosure also provides process of preparation of these acetamide derivatives.

21 Claims, No Drawings

ACETAMIDE DERIVATIVES AS GLUCOKINASE ACTIVATORS, THEIR PROCESS AND MEDICINAL APPLICATION

PRIORITY CLAIM

This application is a national stage entry of International Application No. PCT/IN2008/000650, filed Oct. 7, 2008, which claims priority to India Patent Application No. 2266/CHE/2007, filed Oct. 8, 2007, each of which are incorporated herein by reference in their entireties.

FIELD OF THE INVENTION

This disclosure relates to a series of acetamide derivatives, their stereoisomers, tautomers, prodrugs, pharmaceutically acceptable salts, polymorphs, solvates and formulations thereof. The disclosure also relates to the process of preparation of acetamide derivatives along with their glucokinase activating effects, which are beneficial for the prophylaxis, management, treatment, control of progression, or adjunct treatment of diseases and/or medical conditions where the activation of glucokinase would be beneficial, such as diabetes, metabolic syndrome, and/or diabetes-related complications including retinopathy, nephropathy, neuropathy, ischemic heart disease, arteriosclerosis, 0-cell dysfunction, and as therapeutic and/or prophylactic agents for obesity.

It also relates to compounds with liver selective Glucokinase activation, useful for the treatment of hyperglycemia, diabetes, obesity, dyslipidemia, metabolic syndrome and like, in mammals and have minimum hypoglycemic potential.

BACKGROUND

Diabetes mellitus is a metabolic disorder characterized by recurrent or persistent hyperglycemia (high blood glucose) and other signs, as distinct from a single disease or condition. Glucose level abnormalities can result in serious long-term complications, which include cardiovascular disease, chronic renal failure, retinal damage, nerve damage (of several kinds), microvascular damage and obesity.

Type 1 diabetes, also known as Insulin Dependent Diabetes Mellitus (IDDM), is characterized by loss of the insulin-producing β-cells of the islets of Langerhans of the pancreas leading to a deficiency of insulin. Type-2 diabetes previously known as adult-onset diabetes, maturity-onset diabetes, or Non-Insulin Dependent Diabetes Mellitus (NIDDM)—is due to a combination of increased hepatic glucose output, defective insulin secretion, and insulin resistance or reduced insulin sensitivity (defective responsiveness of tissues to insulin).

Chronic elevation of blood glucose level leads to damage of blood vessels. In diabetes, the resultant problems are grouped under "microvascular disease" (due to damage of small blood vessels) and "macrovascular disease" (due to damage of the arteries). Examples of microvascular disease include diabetic retinopathy, neuropathy and nephropathy, while examples of macrovascular disease include coronary artery disease, stroke, peripheral vascular disease, and diabetic myonecrosis.

Diabetic retinopathy, characterized by the growth of weakened blood vessels in the retina as well as macular edema (swelling of the macula), can lead to severe vision loss or blindness. Retinal damage (from microangiopathy) makes it the most common cause of blindness among non-elderly adults in the US. Diabetic neuropathy is characterized by compromised nerve function in the lower extremities. When combined with damaged blood vessels, diabetic neuropathy can lead to diabetic foot. Other forms of diabetic neuropathy may present as mononeuritis or autonomic neuropathy. Diabetic nephropathy is characterized by damage to the kidney, which can lead to chronic renal failure, eventually requiring dialysis. Diabetes mellitus is the most common cause of adult kidney failure worldwide. A high glycemic diet (i.e., a diet that consists of meals that give high postprandial blood sugar) is known to be one of the causative factors contributing to the development of obesity.

Glucokinase (GK), also known as hexokinase IV or D, is one of four glucose-phosphorylating enzymes called hexokinases that catalyze the first step of glycolysis, the conversion of glucose to glucose 6-phosphate (G6P), in vertebrate tissues. GK functions in a dual role, with distinct functions in the pancreas and liver; (a) as a molecular glucose sensor in the insulin-producing pancreatic β-cells, and (b) as the high-capacity enzymatic step initiating the storage of glucose in the form of glycogen in the liver and uptake of glucose during hyperglycemia. Therefore, GK plays a central role in glucose homeostasis, through the phosphorylation of glucose in the liver, and the modulation of insulin secretion in the pancreas (Postic, C. et al (1999) *J. Biol. Chem.* 274: 305-315). GK also functions as a sensor in other neuroendocrine cells of the gastrointestinal tract and in various brain cells including specific cells in the hypothalamus (Jetton, T. A. et al (1994) *J. Biol. Chem.* 269: 3641-3654).

The physiological concentration of glucose in human plasma is approximately 5.5 mM under fasting conditions, and increases to about 12 mM in the fed state. This concentration is dependent on and maintained by the activity of GK, which senses glucose and controls metabolic flux in key cell types. The glucose concentration, at which GK activity is at half of its maximal velocity or $V_{max}$, is defined as its $S_{0.5}$. The $S_{0.5}$ of GK for glucose lies in the middle of the physiological glucose concentration range at approximately 8 mM, allowing this enzyme to act as a molecular glucose sensor crucial for glucose homeostasis. The limited tissue distribution and unique kinetic properties of GK allow it to play a critical role in pancreatic β-cell insulin secretion and hepatic glucose utilization. GK differs from the other members of the mammalian hexokinase family in its unique sigmoidal kinetics with respect to glucose, a high $S_{0.5}$ that lies in the physiological glucose concentration range (the other three mammalian hexokinases have $S_{0.5}$ values less than 0.5 mM), the lack of product inhibition by G6P, and its tissue distribution in cell types that are thought to be responsive to changing plasma glucose levels.

Tissue-specific differences have been observed between the regulation of GK in the liver and the pancreas. In the liver, GK is allosterically inhibited by the glucokinase regulatory protein (GKRP), which results in its sequestration in the nucleus and subsequent protection from proteolytic degradation. This inhibition is reversed by high concentrations of glucose and by fructose 1-phosphate, and is potentiated by fructose 6-phosphate. In the pancreatic β-cells, GK expression is believed to be constitutive. GK is also known to be expressed in the hypothalamus, where it may exert effects on feeding behavior, and in the intestine K and L cells, where it may contribute to the secretion of enteroincretins such as glucagon-like peptide-1 (GLP-1), glucose dependent insulinotropic peptide (GIP) (Matschinsky F. M. et al (2006) *Diabetes* 55: 1-12; Theodorakis M. J. et al (2006) *Am. J. Physiol. Endocrinol. Metab.* 290: E550-E559). Given the role of GK as a molecular glucose sensor, it is not surprising that GK mutations have a profound influence on glucose homeostasis. About 2000 GK mutations that have been identified in humans result in impaired glucose-mediated insulin secretion and maturity-onset diabetes of the young type 2 (MODY-2). Some of these mutations result in decreased accumulation of hepatic glycogen, while others decrease GK activity by reducing the stability of the enzyme or by decreasing its $V_{max}$. Mutations that result in activation of GK are implicated in the onset of persistent hyperinsulinemic hypoglycemia of infancy (PHHI). Single point mutations (e.g. V62M, D158A, Y214A, V455M, and F456V) in regions distinct from the substrate binding site of the enzyme lead to modulation of GK activity (Glaser, B. et al (1998) *N. Engl. J. Med.* 338: 226-230; Gloyn, A. L. (2003) *Hum. Mutat.* 22: 353-362; Gloyn, A. L. et al (2003) *Diabetes* 52: 2433-2440). These observations highlight that GK activity can be regulated through allosteric modulation.

Homozygous knock out of GK in mice results in severe diabetes and death, while heterozygous disruption results in a milder diabetic phenotype, decreased hepatic glucose uptake and impaired insulin secretion in response to glucose. Conversely, over-expression of GK in fat-induced diabetic as well as non-diabetic mice results in improved glucose tolerance. Transgenic mice over-expressing GK in the liver show a modest (20%) increase in fasting GK activity, which correlates with lower fasting plasma glucose and insulin, and improved glucose tolerance (Hariharan, N. et al (1997) *Diabetes* 46: 11-16).

The enzymatic properties of GK can be described in terms of its velocity (i.e. its rate of converting glucose to G6P) and its $S_{0.5}$ for glucose (i.e. the apparent glucose concentration at which GK converts glucose to G6P at half of its maximal velocity). The $S_{0.5}$ of human GK for glucose is approximately 8 mM in enzyme based assay. GKAs induce increased conversion by GK of glucose to G6P by either decreasing the $S_{0.5}$ of GK for glucose, increasing its $V_{max}$, or by a combination of both, and can potentially lower blood glucose concentrations to hypoglycemic levels.

Several patent applications and publications describe the discovery of small-molecule glucokinase activators (GKAs) that allosterically modulate or activate the activity of GK (Kamata, K. et al (2004) *Structure* 12: 429-438; WO 2003/055482 A1; WO 2005/123132 A2; WO 2004/002481 A2; U.S. Pat. No. 6,486,184 B2; WO 2006/040528 A1; Fyfe, M. C. T. (2007) *Diabetologia*, 50: 1277-1287; McKerrecher, D. et al *Bioorg. Med. Chem. Lett.* 15 (2005) 2103-2106; Efanov, A. M. et al (2005) *Endocrinology* 146: 3696-3701; Printz, R. L. and Granner, D. K. (2005) *Endocrinology* 146: 3693-3695; Brocklehurst, K. J. et al (2004) *Diabetes*, 53: 535-541; Grimsby, J. et al (2003) *Science* 301: 370-373). These GKAs increase GK activity by decreasing its $S_{0.5}$ for glucose, and, in some cases, also increasing its $V_{max}$. However, for many of these compounds, hypoglycemia has been reported in animal studies which may be a consequence of excessive GK activation. For example, GK activators like Ro-28-1675 cause hypoglycemia in animal efficacy models (Kamata, K. et al (2004) *Structure* 12: 429-438). Similar hypoglycemic potential is seen in another GK activator, PSN-GK1, at higher dose (Fyfe, M. C. T. (2007) *Diabetologia*, 50: 1277-1287).

Rat liver glucokinase is inhibited by long chain acyl-CoA. Deinhibition of such inhibition may also result into glucokinase activation (Tippett P. S. et. al (1982) *J. Biol. Chem.* 25712839-12845, Tippett P. S. et. al (1982) *J. Biol. Chem.* 257, 12846-12852.

A concept of minimizing hypoglycemic potential by liver selective glucokinase activation has been mentioned in patent application no. WO 2005/123123 wherein, compounds described in WO 2004/002481 are identified as liver selective glucokinase activators which increase glucose utilization in the liver without inducing an increase in insulin secretion in response to glucose.

The present disclosure provides a novel class of compounds characterized as glucokinase activators or modulators, and their potential use as medicament for the prophylactic or therapeutic treatment of hyperglycemia, diabetes, obesity, dyslipidemia, metabolic syndrome and like.

SUMMARY OF THE INVENTION

The present disclosure relates to a series of acetamide derivatives described by formula (I), their stereoisomers, tautomers, prodrugs, pharmaceutically acceptable salts, polymorphs, solvates and formulations thereof as glucokinase activators (GKAs);

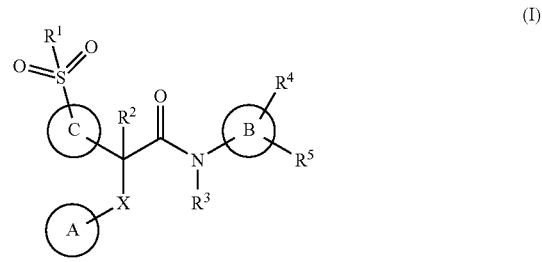

(I)

wherein
ring A and ring C are mono or bicyclic ring independently selected from aryl, heteroaryl or heterocyclyl;
wherein aryl and heteroaryl are optionally substituted with 1 to 4 substituents independently selected from halogen, monohaloalkyl, dihaloalkyl or perhaloalkyl, monohaloalkoxy, dihaloalkoxy or perhaloalkoxy, cyano, nitro, alkyl, alkenyl, alkynyl, methylenedioxy, amidino —NR$^6$R$^7$, —OR$^6$, —S(O)$_p$R$^6$, —S(O)$_p$NR$^6$R$^7$, —NR$^6$S(O)$_p$R$^7$, —NR$^6$C(O)R$^7$, —OS(O)$_p$R$^7$, —NR$^6$C(O)OR$^7$, —NR$^6$C(O)NR$^6$R$^7$, —(CR$^8$R$^9$)$_n$C(O)OR$^6$, —(CR$^8$R$^9$)$_n$C(O)NR$^6$R$^7$, —(CR$^8$R$^9$)$_n$C(O)R$^6$, cycloalkyl, cycloalkylalkyl, heterocyclyl, heterocycloalkyl, aryl, arylalkyl, heteroaryl, heteroarylalkyl, cycloalkenyl, aryloxy or heteroaryloxy groups; heterocyclyl is optionally substituted with 1 to 4 substituents independently selected from halogen, monohaloalkyl, dihaloalkyl or perhaloalkyl, monohaloalkoxy, dihaloalkoxy or perhaloalkoxy, oxo, cyano, nitro, alkyl, alkenyl, alkynyl, methylenedioxy, amidino —NR$^6$R$^7$, —OR$^6$, —S(O)$_p$R$^6$, —S(O)$_p$NR$^6$R$^7$, —NR$^6$S(O)$_p$R$^7$, —NR$^6$C(O)R$^7$, —OS(O)$_p$R$^7$, —NR$^6$C(O)OR$^7$, —NR$^6$C(O)NR$^6$R$^7$, —(CR$^8$R$^9$)$_n$C(O)OR$^6$, —(CR$^8$R$^9$)$_n$C(O)NR$^6$R$^7$, —(CR$^8$R$^9$)$_n$C(O)R$^6$, cycloalkyl, cycloalkylalkyl, heterocyclyl, heterocycloalkyl, aryl, arylalkyl, heteroaryl, heteroarylalkyl, aryloxy or heteroaryloxy groups;
p=0-2; n=0-4;
R$^6$ and R$^7$ are independently selected from the group consisting of hydrogen, alkyl, alkenyl, alkynyl, aryl, arylalkyl, heteroaryl, heteroarylalkyl, cycloalkyl, cycloalkylalkyl, heterocyclyl and heterocyclylalkyl, or
R$^6$ and R$^7$ taken together to form a monocyclic or a bicyclic ring system which is saturated or partially unsaturated and optionally have additional heteroatoms selected from O, N or S, said ring system is further optionally substituted with 1 to 4 substituents independently selected from halo, alkyl, alkenyl, alkynyl, nito, cyano, —OR$^6$, —SR$^6$, —NR$^6$R$^7$, oxo, alkylsulfonyl, —COOR$^6$, —C(O)NR$^6$R$^7$, cycloalkyl, cycloalkylalkyl, aryl, arylalkyl, heterocyclyl, heterocyclylalkyl, heteroaryl, or heteroarylalkyl;

wherein R$^6$ and R$^7$ are as described above;

R$^8$ and R$^9$ are independently selected from the group consisting of hydrogen, fluorine, OR$^6$, alkyl, and perfluoroalkyl; or R$^8$ and R$^9$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, alkenyl, alkynyl, nito, cyano, oxo, —OR$^6$, —SR$^6$, —NR$^6$R$^7$, alkylsulfonyl, —COOR$^6$, —C(O)NR$^6$R$^7$, cycloalkyl, cycloalkylalkyl, aryl, arylalkyl, heterocyclyl, heterocyclylalkyl, heteroaryl, or heteroarylalkyl;

wherein R$^6$ and R$^7$ are as described above;

X represents O, NR$^6$, or S(O)$_p$;

wherein R$^6$ is as described above;

p=0-2;

R$^1$ is selected from cycloalkyl or heterocyclyl, each optionally substituted with halogen, monohaloalkyl, dihaloalkyl, perhaloalkyl, monohaloalkoxy, dihaloalkoxy, perhaloalkoxy, oxo, cyano, nitro, alkyl, alkenyl, alkynyl, methylenedioxy, amidino —NR$^6$R$^7$, —OR$^6$, —S(O)$_p$R$^6$, —S(O)$_p$NR$^6$R$^7$, —NR$^6$S(O)$_p$R$^7$, —NR$^6$C(O)R$^7$, —OS(O)pR$^7$, —NR$^6$C(O)OR$^7$, —NR$^6$C(O)NR$^6$R$^7$, —(CR$^8$R$^9$)$_n$C(O)OR$^6$, —(CR$^8$R$^9$)$_n$C(O)NR$^6$R$^7$, —(CR$^8$R$^9$)$_n$C(O)R$^6$, cycloalkyl, cycloalkylalkyl, heterocyclyl, heterocycloalkyl, aryl, arylalkyl, heteroaryl, heteroarylalkyl, aryloxy or heteroaryloxy;

R$^2$ is hydrogen;

R$^3$ is selected from the group consisting of hydrogen, alkyl and perfluoroalkyl; ring-B is an optionally substituted 4-12 membered mono or bicyclic ring containing 1-4 hetero atoms selected from N, O, or S with at least one nitrogen in the ring;

R$^4$ and R$^5$ are independently selected from the group consisting of hydrogen, halogen, alkyl, alkenyl, alkynyl, cycloalkyl, cycloalkylalkyl, heterocyclyl, heterocycloalkyl, aryl, arylalkyl, heteroaryl, heteroarylalkyl, mono, di or tri substituted haloalkyl, nitrile, nitro, oxo, —NR$^6$R$^7$, —OR$^6$, —S(O)$_p$R$^6$, —S(O)$_p$NR$^6$R$^7$, —NR$^6$S(O)$_p$R$^7$, —NR$^6$C(O) R$^7$, —OS(O)$_p$R$^7$, —NR$^6$C(O)OR$^7$, (CR$^8$R$^9$)$_n$C(O)OR$^6$, —(CR$^8$R$^9$)$_n$(CO)NR$^6$R$^7$, —(CR$^8$R$^9$)$_n$S(O)$_p$NR$^6$R$^7$, —(CR$^8$R$^9$)$_n$N(R$^6$)C(O)R$^6$, —(CR$^8$R$^9$)$_n$OR$^6$, —C(R$^8$R$^9$)$_n$NR$^6$R$^7$, —C(R$^8$R$^9$)$_n$CO(R$^6$) and —S(O)$_p$C(R$^8$R$^9$)$_n$C(O)OR$^6$; wherein R$^4$ and R$^5$ is each optionally substituted with one or more substituents selected from halo, straight chain or branched chain alkyl, alkenyl, alkynyl, cycloalkyl, aryl, heteroaryl, heterocycle, alkylsulfonyl, oxo, nitro, cyano, —COOR$^6$, —C(O)NR$^6$R$^7$, —OR$^6$, —SR$^6$ or —NR$^6$R$^7$;

wherein n=0-4;

R$^6$, R$^7$, R$^8$ and R$^9$ are as described in the text;

in addition to R$^4$ and R$^5$, ring-B is further optionally substituted with one or more substituents selected from halo, straight chain or branched chain alkyl, alkenyl, alkynyl, cycloalkyl, aryl, heteroaryl, heterocyclyl, alkylsulfonyl, oxo, nitro, cyano, —COOR$^6$, —C(O)NR$^6$R$^7$, —OR$^6$, —SR$^6$ or —NR$^6$R$^7$.

The disclosure also relates to the process of preparation of acetamide derivatives of formula-I.

These GKAs are beneficial for the prophylaxis, management, treatment, control of progression, or adjunct treatment of diseases and/or medical conditions such as Type-I and Type-II diabetes, obesity, dyslipidemia, metabolic syndrome and/or diabetes-related complications including retinopathy, nephropathy, neuropathy, ischemic heart disease, arteriosclerosis, β-cell dysfunction, and as therapeutic and/or prophylactic agents for obesity where the activation of glucokinase would be beneficial.

The present disclosure also relates to the compounds of formula (I) that are liver selective GK activators. Such liver selective GK activators may be useful for the treatment of hyperglycemia, diabetes, obesity; dyslipidemia, metabolic syndrome and the like, in mammals and have minimum hypoglycemic potential.

Surprisingly, compounds of the present invention were found to have superior glucokinase activating properties over the compounds disclosed in co-pending application 409/CHE/2007.

These and other features, aspects, and advantages of the present subject matter will become better understood with reference to the following description and appended claims. This Summary is provided to introduce a selection of concepts in a simplified form. This Summary is not intended to identify key features or essential features of the claimed subject matter, nor is it intended to be used to limit the scope of the claimed subject matter.

DETAILED DESCRIPTION OF THE INVENTION

Definitions

In the structural formulae given herein and throughout the present disclosure, the following terms have the indicated meaning:

The term "optionally substituted" as used herein means that the group in question is either unsubstituted or substituted with one or more of the substituents specified. When the group in question is substituted with more than one substituent, the substituent may be same or different.

The term "mono or bicyclic ring" refers to a carbocycle, an aryl, a heterocycle or a heteroaryl which can be aromatic or non-aromatic, saturated or unsaturated, 3 to 18 ring atoms system including 0 to 5 heteroatoms independently selected from S, N, O; the said rings can be optionally substituted with common substituents.

The term "aryl", alone or in combination with any other term, refers to a monocyclic or a polycyclic aromatic ring system containing carbon-ring atoms, such as phenyl, biphenyl, naphthyl or anthryl which optionally carries one or more substituents, preferably one to three, each independently selected from halogen, trifluoromethyl, trifluoromethoxy, amino, alkyl, alkenyl, alkynyl, alkoxy, alkylcarbonyl, alkoxycarbamoyl, aminocarbonyl, cycloalkyl, cycloalkenyl, acyl, cyano, carbamoyl, methylendioxy, carboxy, alkoxycarbonyl, aryloxy, alkylaminocarbonyl, dialkylaminocarbonyl, hydroxy, heteroaryl, heterocyclyl, nitro, SO$_2$alkyl, SO$_2$cycloalkyl and the like.

"Heteroaryl", alone or in combination with any other term, refers to a monocyclic aromatic ring structure containing 5 or 6 ring atoms, or a bicyclic aromatic group having 8 to 12 atoms, containing one or more heteroatoms independently selected from O, S, and N, and optionally substituted with 1 to 3 groups or substituents such as halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. "Heteroaryl" is also intended to include oxidized S or N, such as sulfinyl, sulfonyl and N-oxide of tertiary ring nitrogen. A carbon or hetero-atom is the point of attachment of the heteroaryl ring structure such that a stable aromatic ring is retained. Examples of heteroaryl groups are azepinyl, benzimidazolyl, benisoxazolyl, benzofurazanyl, benzopyranyl, benzothiazolyl, benzothienyl, benzoxazolyl, cinnolinyl, pyridinyl, pyridazinyl, pyrazinyl, quinazolinyl, purinyl, indolyl, quinolinyl, pyrimidinyl, pyrrolyl, oxazolyl, oxadiazolyl, thiazolyl, thienyl, isooxazolyl, oxathiadiazolyl, isothiazolyl, tetrazolyl, imidazolyl, triazinyl, furanyl, benzofuryl, naphthyridinyl, thiadiazolyl, triazolyl, oxazolopyridinyl, imidazopyridinyl, thiazolopyridinyl, thiazolotraizinyl, thiazolopyrazinyl, quinoxalinyl and the like. A substituted heteroaryl contains a substituent attached to an available carbon or heteroatom to produce a stable compound. "Heteroaryl" is also intended to encompass compounds where a heteroaryl is attached to another non-aromatic cyclyl or heterocyclyl rings. Non-limiting examples include chromanyl, dihydrobenzofuranyl, indalinyl, dihydrobenzothienyl, benzodioxolyl dihydrobenzothienyl, dihydrobenzothiopyranyl, isochromanyl, dihydrobenzothiopyranyl sulfone, 1,3-dioxolanyl, benzofuryl, and the like.

As used herein, "heterocycle" or "heterocyclyl" refers to a stable 4 to 7-membered monocyclic or stable 8 to 12 membered bicyclic heterocyclic non-aromatic ring which is either saturated or unsaturated, and which consists of carbon atoms and from one to five heteroatoms selected from the group consisting of N, O, and S. "Heterocyclyl" is also intended to include oxidized S or N, such as sulfinyl, sulfonyl and N-oxide of tertiary ring nitrogen. The heterocyclic ring may be attached at any heteroatom or carbon atom which results in the creation of a stable structure. Non-limiting examples include imidazolidinyl, imidazolinyl, indolinyl, isoindolinyl, isoquinolinyl, isothiazolidinyl, isothiazolidinyl, morpholinyl, 2-oxopiperazinyl, 2-oxopiperdinyl, 2-oxopyrrolidinyl, piperidyl, piperazinyl, pyrazolidinyl, pyrrolidinyl, quinoxalinyl, dihydroimidazole-one, tetrahydrofuryl, tetrahydroisoquinolinyl, tetrahydroquinolinyl, tetrahydroquinoxalinyl, thiamorpholinyl sulfoxide, thiazolinyl, thiazolidine, benzooxazinone, benzothiazinone, isoxazoline, oxazolidin, dihydropyrazinyl, dihydrobezoxazinyl, dihydrobenzothiazinyl, benzodioxolyl, dihydrobenzodioxolyl, dihydropyridyl and dihydrobenzodiazepinone.

"Alkyl" refers to straight or branched chain having 1 to 10 carbon atoms which is/are further substituted with one or more common substituents. Examples of alkyl groups include, but are not limited to methyl, ethyl, propyl, isopropyl, butyl, t-butyl and the like.

"Cycloalkyl" refers to a cyclic or polycyclic alkyl group containing 3 to 15 carbon atoms which are further substituted with one or more common substituents. Examples of cycloalkyl groups include, but are not limited to cyclopropyl, cyclobutyl, cyclopentyl, bicyclo[4.4.0]decane, adamantanyl, and the like. "Cycloalkyl" is also intended to encompass cyclic alkyl group attached to an aryl group such as 1,2,3,4-tetrahydronaphthalenyl, indanyl and the like.

"Alkenyl", alone or in combination refers to a straight, branched, mono cyclic or polycyclic unsaturated hydrocarbon preferably containing 2 to 10 carbon atoms, and having 1 to 5 double bonds and preferably 1 double bond. Examples of alkenyl groups include, but are not limited to are ethenyl, propenyl, isopropenyl, butenyl, bicycle[2.2.1]heptene and the like.

"Alkynyl", alone or in combination with any other term means a straight or branched hydrocarbon containing 2 to 10 carbon atoms containing 1 to 3 carbon to carbon triple bonds and at least one carbon to carbon triple bond. Examples of alkynyl groups include but are not limited to ethynyl, propynyl, butynyl and the like.

"Halo" or "Halogen", alone or in combination with any other term means halogens such as chloro (Cl), fluoro (F), bromo (Br) and iodo (I).

Common substitution or common substituents are defined as halo, straight chain or branched chain alkyl, alkenyl, alkynyl, cycloalkyl, aryl, heteroaryl, heterocycle, alkylsulfonyl, nitro, cyano, —COOR$^6$, —C(O)NR$^6$R$^7$, —OR$^6$, —SR$^6$, —NR$^6$R$^7$, oxo.

The compounds of the present disclosure may have the ability to crystallize in more than one form, a characteristic known as polymorphism, and all such polymorphic forms ("polymorphs") are encompassed within the scope of the disclosure. Polymorphism generally can occur as a response to changes in temperature or pressure or both, and can also result from variations in the crystallization process. Polymorphs can be distinguished by various physical characteristics, and typically the x-ray diffraction patterns, solubility behavior, and melting point of the compound are used to distinguish polymorphs.

The compounds described herein may contain one or more chiral centers and/or double bonds and therefore, may exist as stereoisomers, such as geometric isomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form and mixtures thereof. Accordingly, the chemical structures depicted herein encompass all possible tautomeric forms of the illustrated or identified compounds.

Compounds may exist in unsolvated forms as well as solvated forms, including hydrated forms. In general, compounds may be hydrated, solvated or N-oxides. Certain compounds may exist in multiple crystalline or amorphous forms. Also contemplated within the scope of the disclosure are congeners, analogs, hydrolysis products, metabolites and precursor or prodrugs of the compound. In general, unless otherwise indicated, all physical forms are equivalent for the uses contemplated herein and are intended to be within the scope of the present disclosure.

"Prodrug" refers to a derivative of a drug molecule as, for example, esters, carbonates, carbamates, ureas, amides or phosphates that requires a transformation within the body to release the active drug. Prodrugs are frequently, although not necessarily, pharmacologically inactive until converted to the parent drug. Prodrugs may be obtained by bonding a promoiety (defined herein) typically via a functional group, to a drug.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach or the agent may be supplied exogenously.

The present disclosure relates to a series of acetamide derivatives described in formula (I), their stereoisomers, tautomers, prodrugs, pharmaceutically acceptable salts, polymorphs, solvates and formulations thereof as glucokinase activators

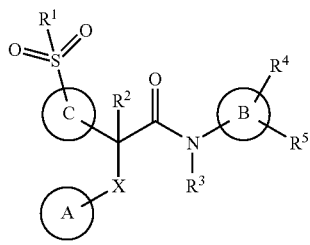

(I)

wherein;
ring A and ring C are mono or bicyclic ring independently selected from aryl, heteroaryl or heterocyclyl;
wherein aryl and heteroaryl are optionally substituted with 1 to 4 substituents independently selected from halogen, monohaloalkyl, dihaloalkyl or perhaloalkyl, monohaloalkoxy, dihaloalkoxy or perhaloalkoxy, cyano, nitro, alkyl, alkenyl, alkynyl, methylenedioxy, amidino —$NR^6R^7$, —$OR^6$, —$S(O)_pR^6$, —$S(O)_pNR^6R^7$, —$NR^6S(O)_pR^7$, —$NR^6C(O)R^7$, —$OS(O)_pR^7$, —$NR^6C(O)OR^7$, —$NR^6C(O)NR^6R^7$, —$(CR^8R^9)_nC(O)OR^6$, —$(CR^8R^9)_nC(O)NR^6R^7$, —$(CR^8R^9)_nC(O)R^6$, cycloalkyl, cycloalkylalkyl, heterocyclyl, heterocycloalkyl, aryl, arylalkyl, heteroaryl, heteroarylalkyl, cycloalkenyl, aryloxy or heteroaryloxy groups;
heterocyclyl is optionally substituted with 1 to 4 substituents independently selected from halogen, monohaloalkyl, dihaloalkyl or perhaloalkyl, monohaloalkoxy, dihaloalkoxy or perhaloalkoxy, oxo, cyano, nitro, alkyl, alkenyl, alkynyl, methylenedioxy, amidino —$NR^6R^7$, —$OR^6$, —$S(O)_pR^6$, —$S(O)_pNR^6R^7$, —$NR^6S(O)_pR^7$, —$NR^6C(O)R^7$, —$OS(O)_pR^7$, —$NR^6C(O)OR^7$, —$NR^6C(O)NR^6R^7$, —$(CR^8R^9)_nC(O)OR^6$, —$(CR^8R^9)_nC(O)NR^6R^7$, —$(CR^8R^9)_nC(O)R^6$, cycloalkyl, cycloalkylalkyl, heterocyclyl, heterocycloalkyl, aryl, arylalkyl, heteroaryl, heteroarylalkyl, aryloxy or heteroaryloxy groups;
p=0-2; n=0-4;
$R^6$ and $R^7$ are independently selected from the group consisting of hydrogen, alkyl, alkenyl, alkynyl, aryl, arylalkyl, heteroaryl, heteroarylalkyl, cycloalkyl, cycloalkylalkyl, heterocyclyl and heterocyclylalkyl, or
$R^6$ and $R^7$ taken together to form a monocyclic or a bicyclic ring system which is saturated or partially unsaturated and optionally have additional heteroatoms selected from O, N or S, said ring system is further optionally substituted with 1 to 4 substituents independently selected from halo, alkyl, alkenyl, alkynyl, nito, cyano, —$OR^6$, —$SR^6$, —$NR^6R^7$, oxo, alkylsulfonyl, —$COOR^6$, —$C(O)NR^6R^7$, cycloalkyl, cycloalkylalkyl, aryl, arylalkyl, heterocyclyl, heterocyclylalkyl, heteroaryl, or heteroarylalkyl;
wherein $R^6$ and $R^7$ are as described above;
$R^8$ and $R^9$ are independently selected from the group consisting of hydrogen, fluorine, $OR^6$, alkyl, and perfluoroalkyl; or
$R^8$ and $R^9$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, alkenyl, alkynyl, nito, cyano, oxo, —$OR^6$, —$SR^6$, —$NR^6R^7$, alkylsulfonyl, —$COOR^6$, —$C(O)NR^6R^7$, cycloalkyl, cycloalkylalkyl, aryl, arylalkyl, heterocyclyl, heterocyclylalkyl, heteroaryl, or heteroarylalkyl;
wherein $R^6$ and $R^7$ are as described above;
X represents O, $NR^6$, or $S(O)_p$;
wherein $R^6$ is as described above;
p=0-2;
$R^1$ is selected from cycloalkyl or heterocyclyl, each optionally substituted with halogen, monohaloalkyl, dihalo alkyl, perhalo alkyl, monohaloalkoxy, dihaloalkoxy, perhaloalkoxy, oxo, cyano, nitro, alkyl, alkenyl, alkynyl, methylenedioxy, amidino —$NR^6R^7$, —$OR^6$, —$S(O)_pR^6$, —$S(O)_pNR^6R^7$, —$NR^6S(O)_pR^7$, —$NR^6C(O)R^7$, —$OS(O)pR^7$, —$NR^6C(O)OR^7$, —$NR^6C(O)NR^6R^7$, —$(CR^8R^9)_nC(O)OR^6$, —$(CR^8R^9)_nC(O)NR^6R^7$, —$(CR^8R^9)_nC(O)R^6$, cycloalkyl, cycloalkylalkyl, heterocyclyl, heterocycloalkyl, aryl, arylalkyl, heteroaryl, heteroarylalkyl, aryloxy or heteroaryloxy;
$R^2$ is hydrogen;
$R^3$ is selected from the group consisting of hydrogen, alkyl and perfluoroalkyl;
ring-B is an optionally substituted 4-12 membered mono or bicyclic ring containing 1-4 hetero atoms selected from N, O, or S with at least one nitrogen in the ring;
$R^4$ and $R^5$ are independently selected from the group consisting of hydrogen, halogen, alkyl, alkenyl, alkynyl, cycloalkyl, cycloalkylalkyl, heterocyclyl, heterocycloalkyl, aryl, arylalkyl, heteroaryl, heteroarylalkyl, mono, di or tri substituted haloalkyl, nitrile, nitro, oxo, —$NR^6R^7$, —$OR^6$, —$S(O)_pR^6$, —$S(O)_pNR^6R^7$, —$NR^6S(O)_pR^7$, —$NR^6C(O)R^7$, —$OS(O)_pR^7$, —$NR^6C(O)OR^7$, —$(CR^8R^9)_nC(O)OR^6$, —$(CR^8R^9)_n(CO)NR^6R^7$, —$(CR^8R^9)_nS(O)_pNR^6R^7$, $(CR^8R^9)_nN(R^6)C(O)R^6$, —$(CR^8R^9)_nOR^6$, —$C(R^8R^9)_nNR^6R^7$, —$C(R^8R^9)_nCO(R^6)$ and —$S(O)_pC(R^8R^9)_nC(O)OR^6$;
wherein $R^4$ and $R^5$ is each optionally substituted with one or more substituents selected from halo, straight chain or branched chain alkyl, alkenyl, alkynyl, cycloalkyl, aryl, heteroaryl, heterocycle, alkylsulfonyl, oxo, nitro, cyano, —$COOR^6$, —$C(O)NR^6R^7$, —$OR^6$, —$SR^6$ or —$NR^6R^7$;
wherein n=0-4;
$R^6$, $R^7$, $R^8$ and $R^9$ are as described in the text;
in addition to $R^4$ and $R^5$, ring-B is further optionally substituted with one or more substituents selected from halo, straight chain or branched chain alkyl, alkenyl, alkynyl, cycloalkyl, aryl, heteroaryl, heterocyclyl, alkylsulfonyl, oxo, nitro, cyano, —$COOR^6$, —$C(O)NR^6R^7$, —$OR^6$, —$SR^6$ or —$NR^6R^7$.

According to an embodiment, the present disclosure relates to compounds of formula (I) wherein ring A is selected from

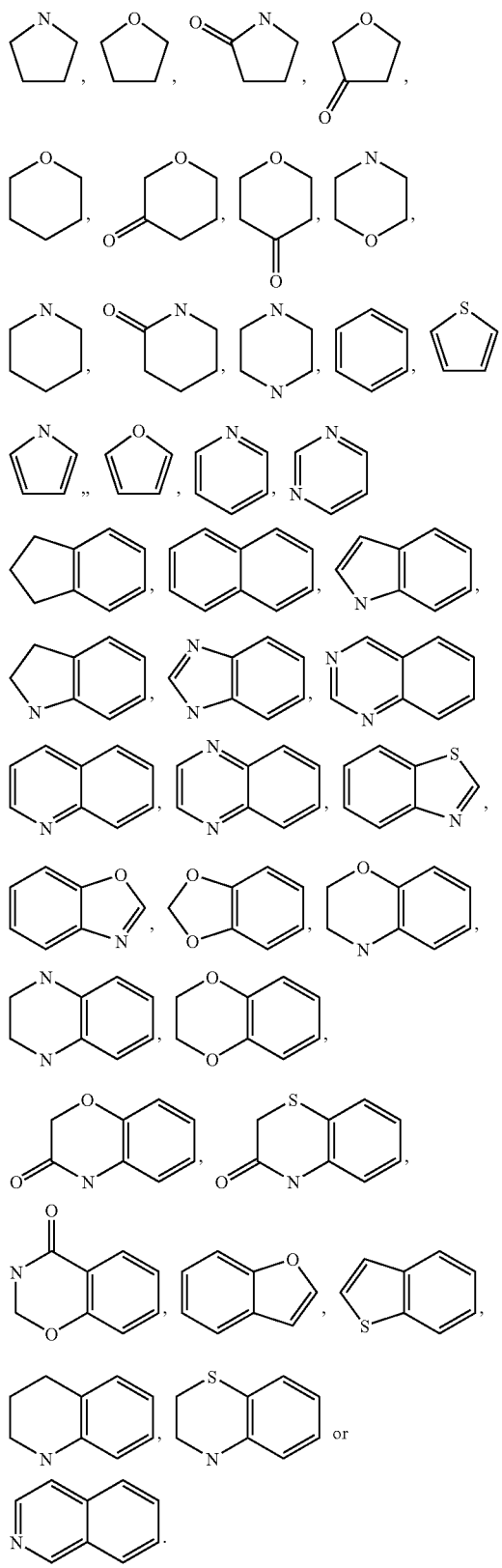
According to another embodiment, the present disclosure relates to compounds of formula (I) wherein ring B is selected from
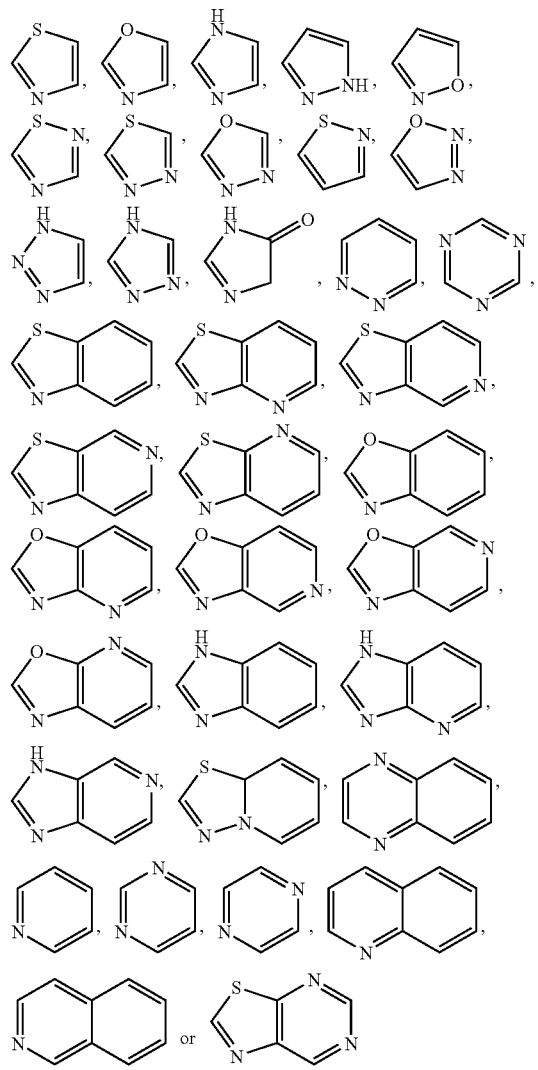
According to another embodiment, the present disclosure relates to compounds of formula (I) wherein ring C is selected from
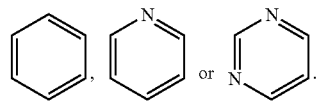
In another embodiment, the present disclosure relates to compounds of formula (I) wherein $R^1$ is selected from
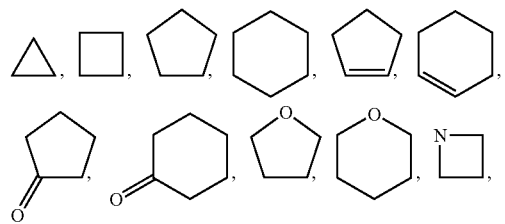

-continued

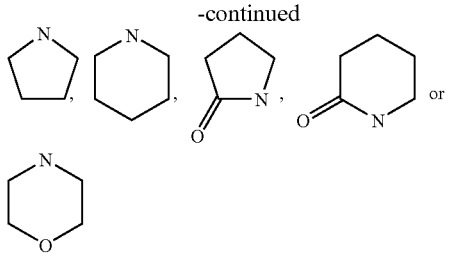

According to another embodiment, the present disclosure relates to compounds of formula (I), or its stereoisomers, tautomers, prodrugs, pharmaceutically acceptable salts, polymorphs, solvates and formulations thereof wherein ring-A is selected from

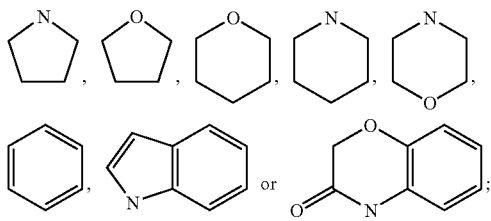

ring-B is selected from

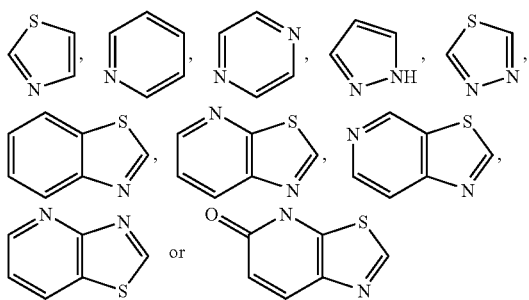

ring-C is

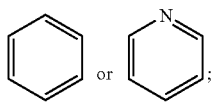

ring A is optionally substituted with 1 to 4 substituents independently selected from alkyl, alkenyl, alkynyl, halogen, monohaloalkyl, dihaloalkyl or perhaloalkyl, monohaloalkoxy, dihaloalkoxy or perhaloalkoxy, nitrile, nitro, —$NR^6R^7$, —$OR^6$, —$S(O)_pR^6$, —$S(O)_pNR^6R^7$, —$NR^6S(O)_pR^7$, —$NR^6C(O)R^7$, $OS(O)_pR^7$, —$NR^6C(O)OR^7$, —$(CR^8R^9)_nC(O)OR^6$, —$(CR^8R^9)_nC(O)NR^6R^7$, $(CR^8R^9)_nC(O)R^6$, cycloalkyl, or cycloalkylalkyl;

ring C is optionally substituted with 1 to 4 substituents independently selected from alkyl, alkenyl, alkynyl, halogen, mono, di or perhaloalkyl, nitrile, nitro, —$NR^6R^7$, —$OR^6$, —$NR^6S(O)_pR^7$, —$NR^6C(O)R^7$, —$NR^6C(O)OR^7$, —$(CR^8R^9)_nC(O)OR^6$, —$(CR^8R^9)_nC(O)NR^6R^7$, —$(CR^8R^9)_nC(O)R^6$, cycloalkyl, or cycloalkylalkyl;

wherein p=0-2; n=0-4;

X is O;

$R^1$ is selected from $C_3$-$C_6$ cycloalkyl or heterocyclyl;

$R^2$ and $R^3$ are hydrogen, $R^4$ and $R^5$ are independently selected from the group consisting of hydrogen, halogen, alkyl, alkenyl, alkynyl, cycloalkyl, cycloalkylalkyl, aryl, arylalkyl, heterocyclyl, heterocyclylalkyl, heteroaryl, heteroarylalkyl, —$OR^6$, —$S(O)_pR^6$, —$NR^6C(O)R^7$, —$(CR^8R^9)_nC(O)OR^6$, —$(CR^8R^9)_nOR^6$, and —$C(R^8R^9)_nCO(R^6)$, wherein n=0-4; wherein each of $R^4$ and $R^5$ is optionally substituted with one or more substituents selected from halo, straight chain or branched chain alkyl, alkenyl, alkynyl, cycloalkyl, aryl, heteroaryl, heterocycle, alkylsulfonyl, oxo, nitro, cyano, —$COOR^6$, —$C(O)NR^6R^7$, —$OR^6$, —$SR^6$ or —$NR^6R^7$;

$R^6$ and $R^7$ are independently selected from the group consisting of hydrogen, alkyl, alkenyl, alkynyl, cycloalkyl, aryl, heterocyclyl and heteroaryl; or $R^6$ and $R^7$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, cyano, —$OR^6$, —$SR^6$, —$NR^6R^7$, —$COOR^6$, —$C(O)NR^6R^7$, cycloalkyl, cycloalkylalkyl, aryl, arylalkyl, heterocyclyl, heterocyclylalkyl, or heteroaryl, heteroarylalkyl;

$R^8$ and $R^9$ are independently selected from the group consisting of hydrogen, fluorine, $OR^6$, alkyl and perfluoroalkyl.

According to an embodiment, the present disclosure relates to a process for the preparation of a compound of formula (I), their stereoisomers, tautomers, prodrugs, pharmaceutically acceptable salts, polymorphs, solvates, said process comprising:

reacting an acid of formula (II)

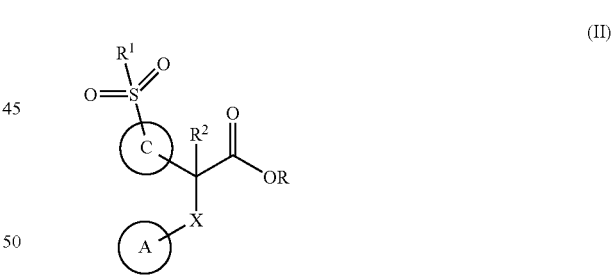

wherein R is hydrogen, alkyl or arylalkyl, with a compound of formula (III)

in presence of a suitable amide coupling reagent, optionally hydrolyzing and optionally further coupling with an amine of formula $NHR^6R^7$ to obtain compound of formula (I).

Compounds of formula I may be prepared as shown in the following reaction schemes and the description thereof, as well as relevant literature procedures that may be used by one skilled in the art. Exemplary reagents and procedures for these reactions appear hereinafter and in the working examples. Protection and deprotection in the schemes below may be carried out by procedures generally known in the art (see, for example, Greene, T. W. and Wuts, P. G. M., Protecting Groups in Organic Synthesis, 3$^{rd}$ Edition, 1999 [Wiley]).

The compounds of formula (I) may be prepared following independent general synthetic routes as outlined in the Schemes 1-6:

Scheme 1: General route for the synthesis of compounds of formula (I). Compounds of formula (II) wherein R is hydrogen, alkyl or arylalkyl, may be reacted with compounds of formula (III) following amide coupling reaction conditions to obtain compounds of formula (I), as shown herein below.

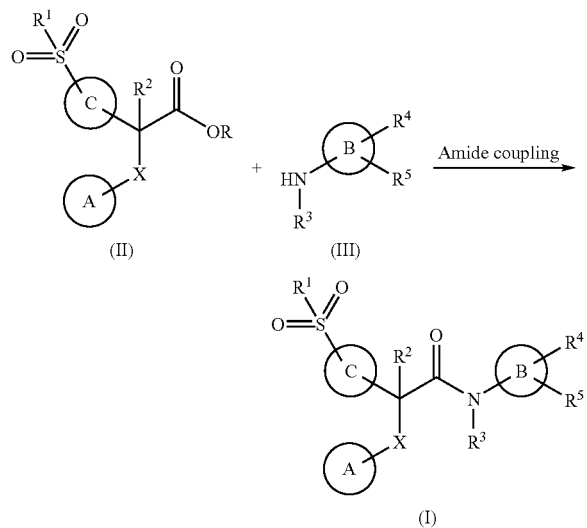

Scheme 2: Alternate route for the synthesis of compounds of formula (I). Compounds of formula (IV) wherein R is hydrogen, alkyl or arylalkyl, obtained according to WO2004072031, may be reduced to compounds of formula (V) which may be reacted with compounds of formula (III) under amide coupling conditions to provide compounds of formula (VI). Compounds of formula (VI) may be reacted with compounds of formula (VIIa) under Mitsunobu conditions to provide compounds of formula (I).

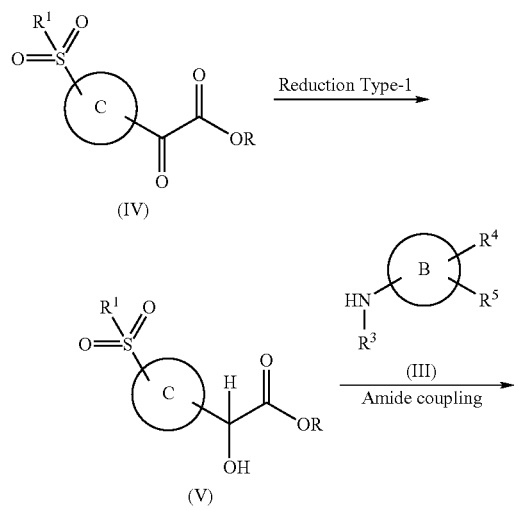

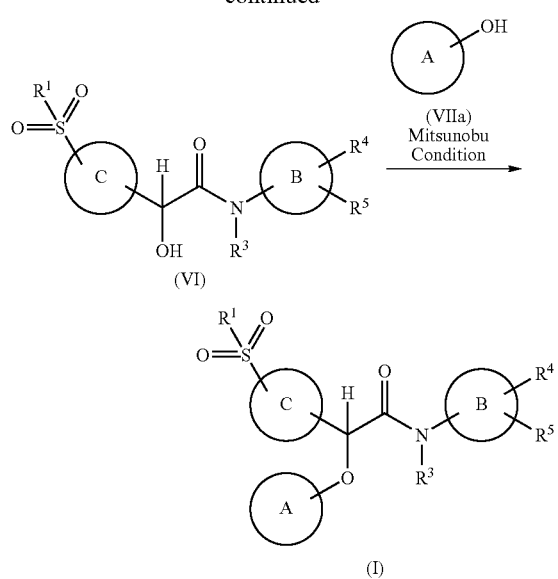

Scheme 3: General route for the synthesis of compounds of formula (Ia) wherein either of $R^4$ or $R^5$ of formula (I) is ——$(CR^8R^9)_n(CO)OH$, from compounds of formula (Ib) wherein either of R4 or R5 is ——$(CR^8R^9)_n(CO)OR$ wherein R is a suitable alkyl group, following conditions for ester hydrolysis.

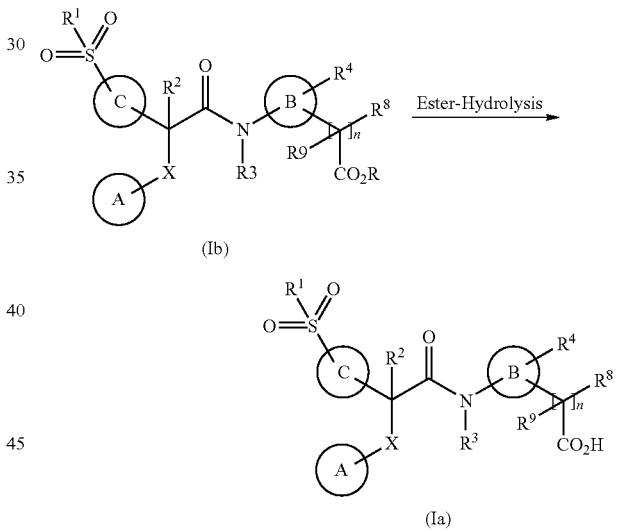

Scheme 4: General route for the synthesis of compounds of formula (Ic) wherein either of $R^4$ or $R^5$ of formula (I) is ——$(CR^8R^9)_nC(O)NR^6R^7$, from compounds of formula (Ia) wherein either of $R^4$ or $R^5$ is ——$(CR^8R^9)_n(CO)OH$ wherein conditions for amide coupling.

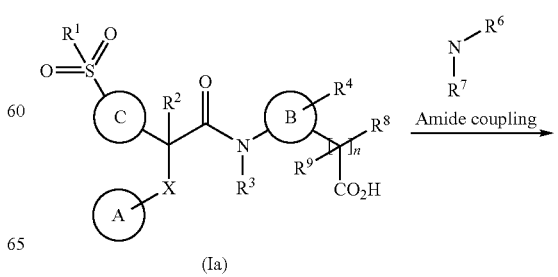

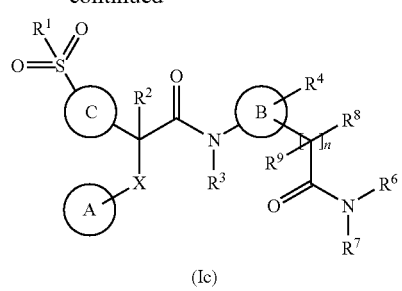

(Ic)

Scheme 5: General route for synthesis of compounds of formula (Id) wherein either of $R^4$ or $R^5$ is $OR^6$ and $R^6$ is aryl, heteroaryl described as ring D in following scheme. Compounds of formula (II) wherein R is hydrogen, alkyl or arylalkyl, may be reacted with compounds of formula (IIIa) wherein R' is alkyl following amide coupling reaction conditions to obtain compounds of formula (Id). Compounds of formula (Id) may further be hydrolysed to obtain the corresponding carboxylic acid which may further be derivatised.

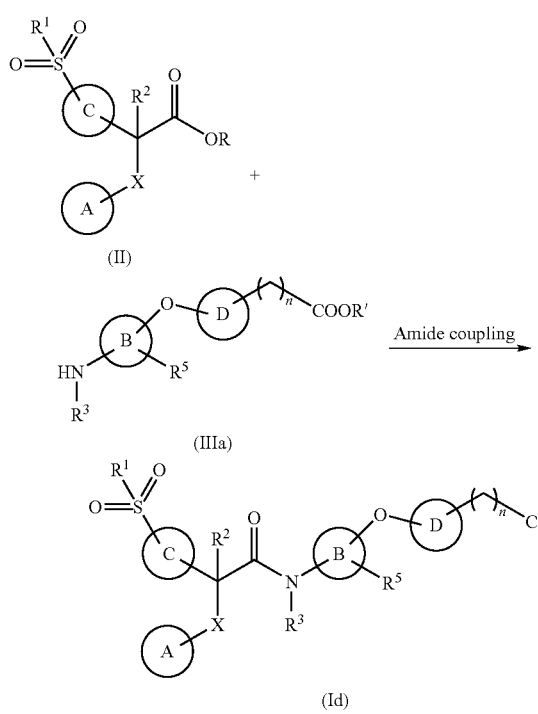

Scheme 6: General route synthesis of compounds of formula (Ie) wherein either of $R^4$ or $R^5$ is heterocycle as described in the following scheme. Compounds of formula (II) wherein R is hydrogen, alkyl or arylalkyl, may be reacted with compounds of formula (IIIb) wherein R' is alkyl following amide coupling reaction conditions to obtain compounds of formula (Ie). Compounds of formula (Ie) may further be hydrolysed to obtain the corresponding carboxylic acid which may further be derivatised.

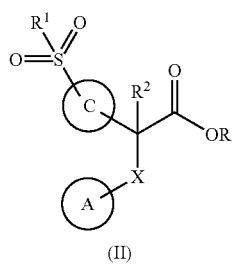

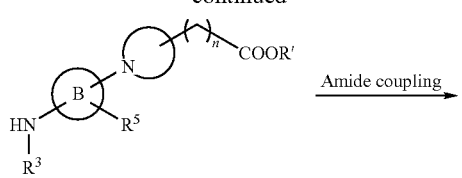

(IIIb)

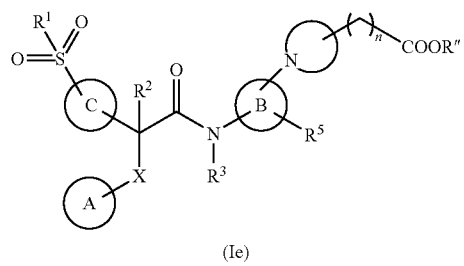

(Ie)

The compounds of formula (II), may be prepared following independent synthetic routes as outlined in Schemes 7-11.

Scheme 7: General route for the synthesis of compounds of formula (IIa). Compounds of formula (IVa) may be reduced to compounds of formula (VIIIa) followed by esterification to obtain compounds of formula (VIII), which may be halogenated to obtain compounds of (IX). Compounds of formula (IX) may be reacted with compounds of formula (VII) under nucleophilic substitution conditions to obtain compounds of formula (IIb) wherein R is alkyl or arylalky, which may be hydrolysed to obtain intermediates of formula (IIa).

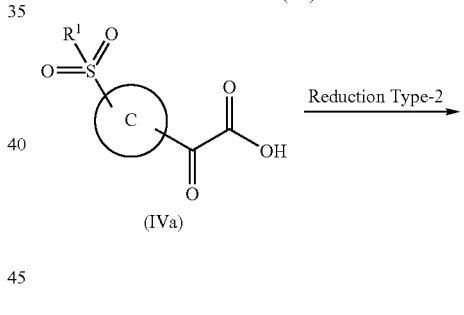

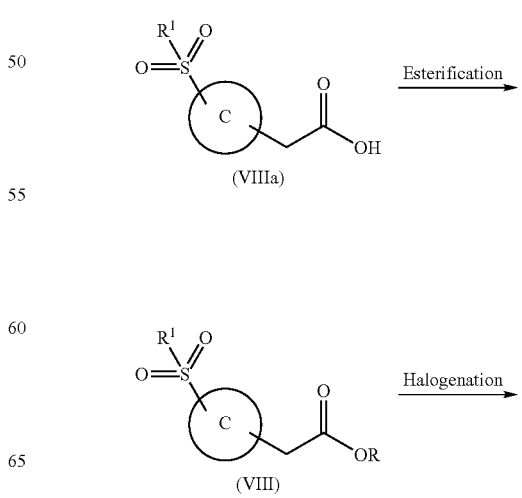

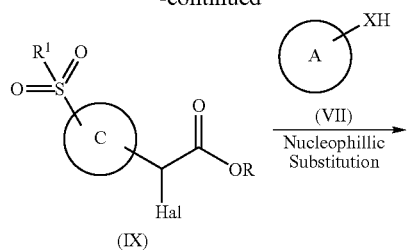

(IX)

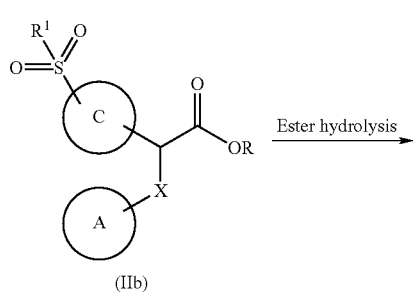

(IIb)

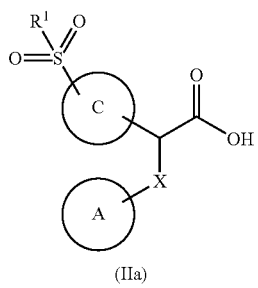

(IIa)

Scheme 8: General route for synthesis of compounds of formula (IIc). Compounds of formula (V) wherein R is hydrogen, alkyl or arylalkyl, may be reacted with compounds of formula (VIIa) under Mitsunobu conditions to obtain compounds of formula (IIc) (which is formula (II) wherein X is O).

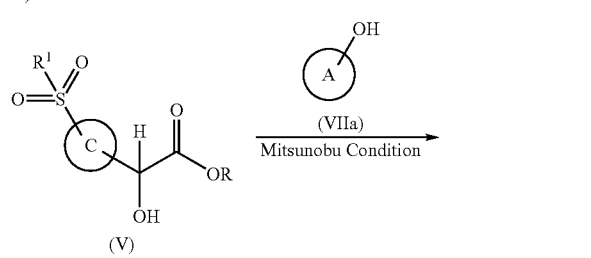

(V)

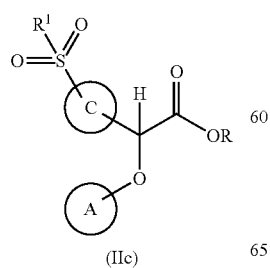

(IIc)

The compounds of formula (II), may be prepared following independent synthetic routes as outlined in Schemes 8-11.

Scheme 9: General route for synthesis of compounds of formula (IId) wherein $R^1$ is heterocycle forming sulfonamide linkage: Compounds of formula (X) on oxidative chlorination provide compounds of formula (XI) (following procedure described in J. Org. Chem. 2007, 72(15), 5847-5850). Compounds of formula (XI) may be halogenated to obtain compounds of formula (XII), which may then be subjected to soupling reaction with an heterocyclyl amine to form sulfonamide linkage, in presence of organic or inorganic bases to obtain compounds of formula (XIII). Compounds of formula (XIII) may be reacted with compounds of formula (VII) under nucleophilic substitution conditions to obtain the compounds of formula (IIe) wherein R is alkyl or arylalkyl, which may be hydrolysed to obtain intermediates of formula (IId).

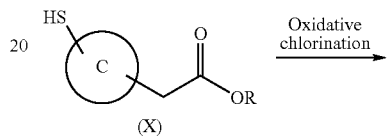

(X)

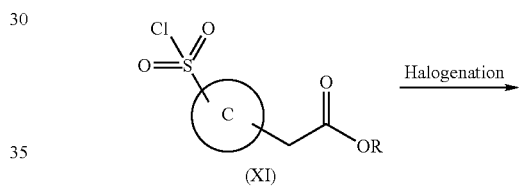

(XI)

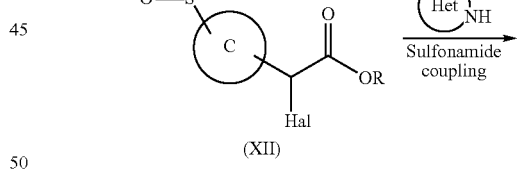

(XII)

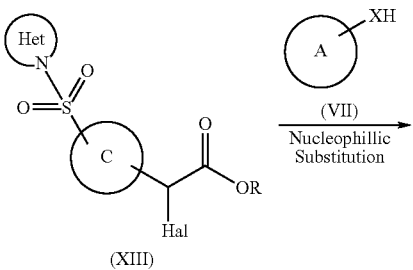

(XIII)

-continued

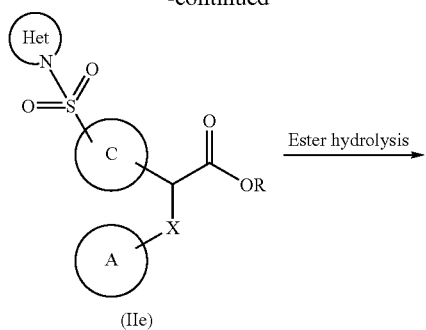

(IIe)

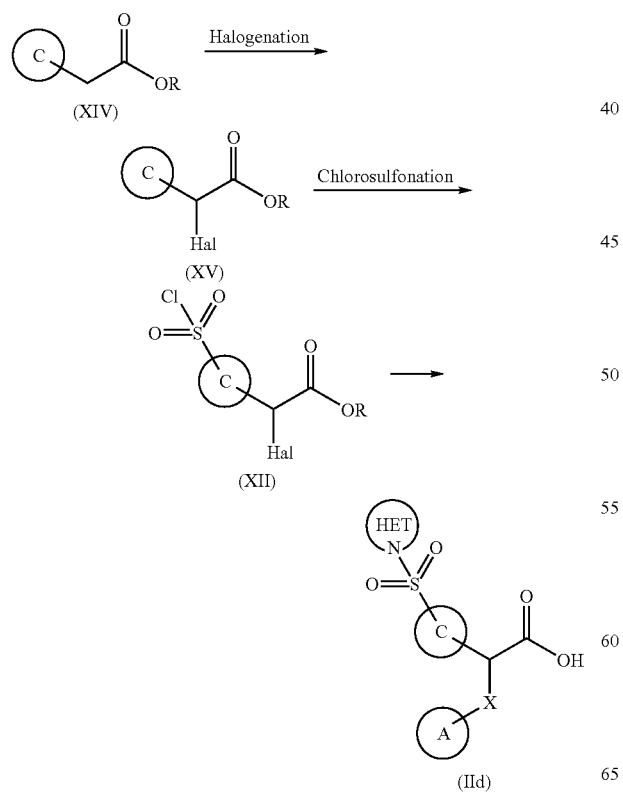

Scheme 10: General route for synthesis of compounds of formula (IId) wherein $R^1$ is heterocycle forming sulfonamide linkage: Compounds of formula (XIV) on halogenation provide compounds of formula (XV), which on chlorosulfonation may provide compounds of formula (XII) as a mixture of meta & para regioisomers. The compound of formula (XII) may be converted to compounds of formula (IId) following the route as described in scheme 9 as a mixture of regioisomers.

Scheme 11: General route for the synthesis of (IIf) wherein ring A is heterocycle. Compounds of formula (IV) wherein R is alkyl may be condensed with tosyl hydrazine to obtain compounds of formula (XVI) which may be oxidized in the presence of a base like TEA, DBU to provide compounds of formula (XVII). Alternatively, compounds of formula (XVII) may also be obtained by reacting compounds of formula (VIII) with tosylazide in presence of base. The compounds of formula (XVII) may be reacted with compounds of formula (VII) in the presence of a Rhodium catalyst to provide compounds of formula (IIe) (following procedure as described in (WO2002008209), which may be hydrolyzed to obtain intermediates of formula (IIf).

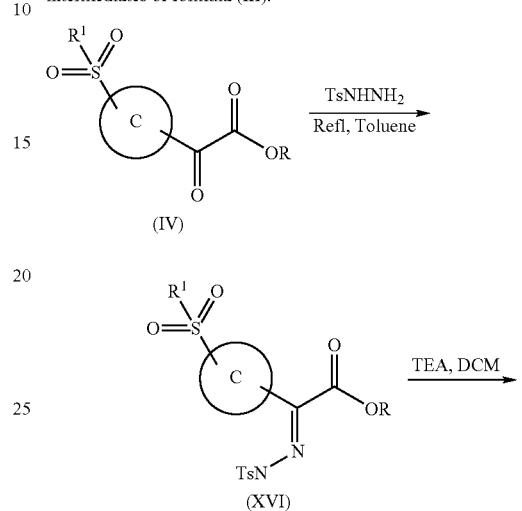

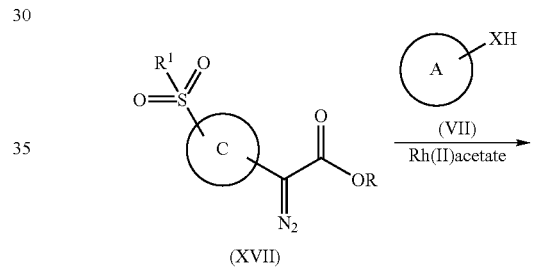

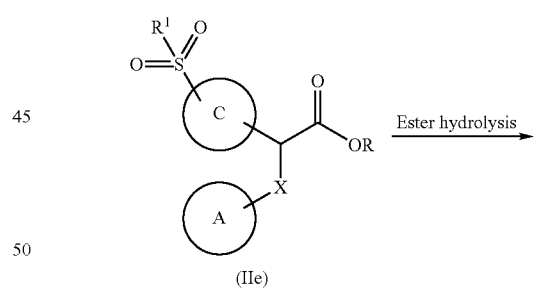

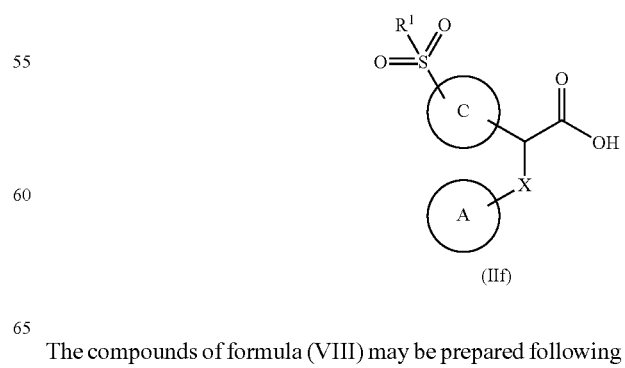

The compounds of formula (VIII) may be prepared following independent synthetic routes as outlined in Schemes 12-13.

Scheme 12: General route for the synthesis of compounds of formula (VIII): Compounds of formula (X), which are available commercially, may be reacted with $R^1$—LG, is a suitable leaving group, using reaction conditions for nucleophilic substitution to obtain S-alkylated compounds of formula (XI). The compounds of formula (XI) may be oxidized (sulfur to sulfone) to obtain compounds of formula (VIII).

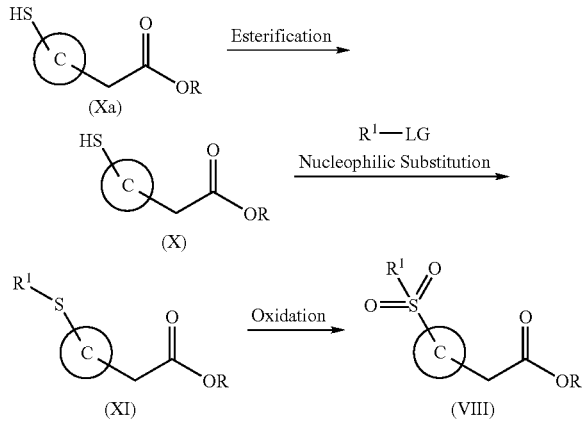

Scheme 13: General route for the synthesis of compounds of formula (VIII) wherein $R^1$ is cycloalkanon-3-yl: Compounds of formula (X) may be treated with cycloalk-2-enone such as cyclohex-2-enone or cyclopent-2-enone, under Michael addition conditions to provide compounds of formula (XI) which are then oxidized to obtain compounds of formula (VIII).

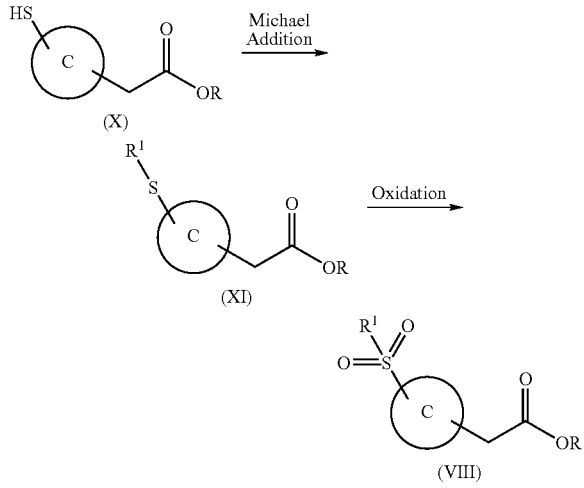

Amide Coupling Conditions: Condition-I: When R=H, the amide coupling may be carried out using any suitable amide coupling regents such as oxallyl chloride, thionyl chloride, BOP-Cl, DCC, HOBt, HOAt, HATU, EDCI, alkylchloroformate and the like in the presence of organic non-nucleophillic bases such as triethyl amine, di-isopropylethyl amine, pyridine, N-methyl pyrrolidine, N,N-dimethylaminopyridine, DBU, DABCO, other hindered amines and pyridines. The amide coupling reaction may be carried out in the presence of solvents such as dichloromethane, dichloroethane, DMF, dimethylacetamide, THF, acetonitrile or mixture of them may be used at a temperature ranging from −5 to 150° C. The reaction may be carried out optionally in presence of catalytic amount of DMF. Condition-II: When R is not H, the amide coupling may be carried out by heating ester and amine either in the absence of solvent or in presence of high boiling solvent like toluene, xylene, DMSO. Amide coupling may be carried out in presence of trialkyl aluminium (Chem. Commun., 2008, 1100-1102).

Halogenation Conditions: Halogenation reaction may be carried out using reagents such as N-halosuccinimide, dihalogens and the like, in presence of radical generating reagents like peroxides such as benzoylperoxide. Solvents used for this reaction include, but are not limited to, carbontetrachloride and ethers or mixtures thereof. The reaction may be carried out at a temperature ranging from −5 to 80° C.

Conditions for Nucleophilic Substitution: Nucleophilic substitution reaction, may be carried out using any suitable organic or inorganic bases. Organic bases may be selected from a group consisting of mono, di or trialkyl amines particularly methylamine, ethylamine, dimethylamine, diethylamine or triethylamine. Inorganic bases may be selected from a group consisting of alkali and alkaline earth metal hydrides, hyroxides, carbonates and bicarbonates or mixtures thereof. Solvents used for this reaction may be selected from a group consisting of lower alcohols, acetone, acetonitrile, DMSO, DMF, dimethylacetamide, THF and toluene, or mixtures thereof. The reaction may be carried out at a temperature in the range of 0 to 150° C.

Conditions for Ester Hydrolysis: Ester hydrolysis of carboxylic acids may be carried out using general saponification conditions employing inorganic bases such as alkali and alkaline earth metal hyroxides, carbonates and bicarbonates, for example lithium hydroxide, sodium hydride, sodium carbonate, potassium carbonate, cesium carbonate and the like; in the presence of solvents such as water, methanol, ethanol, THF and diethyl ether or mixtures thereof. These reactions may be done at 0° C. to refluxing temperature.

Conditions for Esterification: Ester formation, from the above mentioned carboxylic acids, may be carried out using general esterification conditions employing appropriate alcohol like methanol, ethanol and a suitable inorganic acid selected from HCl, $H_2SO_4$, or thionyl chloride, or base catalysed ester formation using alkyl halide and suitable base like sodium hydride, sodium hydroxide, sodium carbonate, potassium carbonate, sodium bicarbonate, potassium bicarbonate, cesium carbonate and the like in presence of solvents such as acetone, acetonitrile, DMF, DMSO, THF and diethyl ether or mixtures thereof.

Conditions for Oxidation: Oxidation of sulfanyls to sulfonyls, may be carried out using appropriate oxidizing reagent such as $H_2O_2$, perbenzoic acid, mCPBA, Oxone, dioxirane and the like in the presence of a solvent such as DCM, DCE, DMF, DMSO, THF and diethyl ether or mixtures thereof. Reagents like $OsO_4$, $KMnO_4$, PCC can also be used for such oxidation process.

Conditions for Reduction Type-1: Reduction Type-1, may be carried out using appropriate reduction conditions for transforming carbonyls to sec-alcohols employing reducing agents like hydrogenation in presence of catalysts such as Pd/C, Pt/C, $PtO_2$ and the like. Such reduction by hydrogenation can also be done using organo-metallic complexes as catalyst from metals like Iron, Rhodium, Ruthenium, and phosphorus-based organic ligands like triphenylphosphine, bidentate phosphine ligands such as bis(diphenylphosphino) ethane. Such hydrogenation based reductions can also be done under asymmetric reduction conditions to yield chiral products (in individual enantiomers and in enantiometically enriched form) if employed appropriate chiral phosphine ligands such as chiral 2,2'-bis(diphenylphosphino)-1,1'-binaphthyl (BINAP) to form the organometallic complex. Such reductions can also be done using metal hydrides such as sodium borohydride, lithium aluminiumhydride, borane reagents and like. Such metal hydride or borane reagent based reductions can also be done in asymmetric way to yield chiral products (in individual enantiomers and in enantiometically enriched form) by using appropriate chiral ligands like tartarate (EP 0320096), chiral 1,1'-bi-2-napthol (BINOL), oxazaborolidines.

Conditions for Reduction Type-2: Reduction Type-2,may be carried out using specific conditions known for transformation of arylic carbonyl group to corresponding arylalkyl functionality. Such reductions may be done using known Wolf Krishner (KOH, $NH_2$—$NH_2$) or Clemmensen (Zn/HCl) reduction conditions.

Conditions for Mitsunobu reaction: The Mitsunobu reaction between alcohol and phenol, to obtain the corresponding ether, may be carried out in THF using triphenylphosphine (TPP) and diethyl azodicarboxylate (DEAD) or diisopropyl azodicarboxylate (DIAD) as reagents.

Sulfonamide Coupling Condition: Sulfonamide may be prepared by reacting any appropriate amine with sulfonylhalide in the presence of base such as pyridine, triethylamine & diisopropylethylamine. The reaction may be carried out in suitable solvent like pyridine, dichloromethane or tetrahydrofuran.

Oxidative Chlorination: Thiols can be converted to sulfonyl chlorides under mild condition of oxidative chlorination. Here thiols are treated with combination of oxidant and chlorinating agent such as $KNO_3$-TMSCl, $H_2O_2$—$SOCl_2$, Oxone-$SOCl_2$ in appropriate solvent such as DCM, acetonitrile, DMF or combination of acetonitrile-AcOH. The reaction may be carried out at a temperature in the range of 5 to 100° C.

Chlorosulfonation: Aryl or hetroaryl sulfonyl chloride synthesis may be carried out by elecrophilic substitution reaction using reagent like chlorosulfonic acid, $SO_2Cl_2$ in appropriate solvent which are not limited to halogenated like DCM, DCE, $CHCl_3$, $CCl_4$, but also nonpolar solvents like Benzene, Toluene, Dioxane or mixture thereof. The reaction may be carried out at a temperature in the range of 0° C. to 60° C.

Above mentioned conditions, for the respective functional group transformations, are only to illustrated the type of synthesis. More specific conditions for above transformations are well documented and referred in the literature (R. C. Larock in Comprehensive Organic Transformations, Wiley-VCH Publication; B. M. Trost and I. Fleming Ed. Comprehensive Organic Synthesis, Elsevier Publication)

Wherever desired or necessary, in any of the above mentioned processes, any of the compounds of formula (I) may be converted into a pharmaceutically acceptable salt or vice versa or converting one salt form into another pharmaceutically acceptable salt form.

According to an embodiment, the present disclosure relates to compounds of formula (I) their stereoisomers, tautomers, prodrugs, pharmaceutically acceptable salts, polymorphs, solvates and formulations thereof, which are glucokinase activators, and are beneficial for the prophylaxis, management, treatment, control of progression, or adjunct treatment of diseases and/or medical conditions where the activation of glucokinase would be beneficial, such as diabetes, dyslipidemia, metabolic syndrome, and/or diabetes-related complications including retinopathy, nephropathy, neuropathy, ischemic heart disease, arteriosclerosis, β-cell dysfunction, and as therapeutic and/or prophylactic agents for obesity.

According to yet another embodiment, the present disclosure relates to compounds of formula (I) their stereoisomers, tautomers, prodrugs, pharmaceutically acceptable salts, polymorphs, solvates and formulations thereof, which are liver selective Glucokinase activators, useful for the treatment of hyperglycemia, diabetes, obesity, dyslipidemia, metabolic syndrome and like, in mammals and have minimum hypoglycemic potential.

A further embodiment of the disclosure includes a method of treatment of glucokinase activator mediated disease by administering a therapeutically effective amount of a compound of formula (I) to a mammal in need of such treatment.

By "pharmaceutically acceptable salts" as used herein, it covers salts of compounds of formula (I) prepared from pharmaceutically acceptable non-toxic bases or acids including inorganic or organic bases and inorganic or organic acids. Inorganic bases salts include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Salts in the solid form may exist in more than one crystal structure, and may also be in the form of hydrates. When the compound of the present disclosure is basic, salts may be prepared from pharmaceutically acceptable non-toxic acids, including inorganic and organic acids, such as acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are hydrochloric, maleic, phosphoric, citric, hydrobromic, sulfuric, fumaric, and tartaric acids.

By "therapeutically effective amount" in this disclosure, it means an amount of compound of formula (I), its polymorphs, stereoisomers, pharmaceutically acceptable salt, solvate or pro-drug thereof, that is sufficient for effective treatment of obesity and/or type II diabetes. The therapeutically effective amount or dosage of a compound according to this disclosure can vary within wide limits. The dosage will depend on individual requirements in each particular case including the specific compound(s) being administered, the manner of administration, the severity of condition being treated, as well as the patient being treated, which is readily determinable by a person skilled in the art.

In using a compound of formula (I), its polymorphs, stereoisomers, pharmaceutically acceptable salt, solvate or pro-drug thereof, for therapeutic or prophylactic purposes it will generally be administered so that a daily dose in the range, for example, about 0.01 mg to 100 mg per kg body weight is received, given if required in divided doses. In general lower doses will be administered when a parenteral route is employed. Thus, for example, for intravenous administration, a dose in the range, for example, about 0.01 mg to 30 mg per kg body weight will generally be used. Similarly, for administration by inhalation, a dose in the range, for example, about 0.01 mg to 30 mg per kg body weight will be used.

The disclosure also relates to compound of formula (I), or its polymorph, stereoisomer, prodrug, solvate or a pharmaceutically acceptable salt thereof, for treating a disease through Glucokinase activation.

The disclosure also relates to compounds of formula (I), or its polymorph, stereoisomer, prodrug, solvate or a pharmaceutically acceptable salt thereof, for treating a disease through Glucokinase modulation or regulation.

The disclosure also relates to compounds of formula (I), or its polymorph, stereoisomer, prodrug, solvate or a pharmaceutically acceptable salt thereof, for treating a disease through Glucokinase deinhibition.

The disclosure also relates to compounds of formula (I), or its polymorph, stereoisomer, prodrug, solvate or a pharmaceutically acceptable salt thereof, for prophylactic or therapeutic treatment of hyperglycemia or diabetes, particularly type II diabetes.

The disclosure also relates to compounds of formula (I), or its polymorph, stereoisomer, prodrug, solvate or a pharmaceutically acceptable salt thereof, for preventing diabetes, particularly type II diabetes, in a human demonstrating pre-diabetic hyperglycemia or impaired glucose tolerance.

The disclosure also relates to compounds of formula (I), or its polymorph, stereoisomer, prodrug, solvate or a pharmaceutically acceptable salt thereof, for combined treatment or preventing diabetes and obesity.

The disclosure also relates to compounds of formula (I), or its polymorph, stereoisomer, prodrug, solvate or a pharmaceutically acceptable salt thereof, for treating or preventing obesity.

The disclosure also relates to compounds of formula (I), or its polymorph, stereoisomer, prodrug, solvate or a pharmaceutically acceptable salt thereof, for enhancing the secretion of enteroincretins, like GLP-1 and GIP, thereby managing diseases or disorders associated with modulation of secretions of enteroincretins, such as hyperglycemia, insulin resistance, impaired glucose tolerance, obesity, gastric emptying, gastroparesis, satiety, leptin resistance, dyslipidemia, wound healing, diabetic complications, such as nephropathy, retinopathy, neuropathy and cataracts.

The disclosure also relates to the use of compounds of formula (I), or its polymorphs, stereoisomers, pharmaceutically acceptable salt, solvate or pro-drug thereof, in the prophylactic or therapeutic treatment of dyslipidemia.

The disclosure also relates to compound of formula (I), or its stereoisomers, tautomers, prodrugs, pharmaceutically acceptable salts, polymorphs, solvates and formulations thereof, for treating hyperglycemia, IGT, Syndrome X, type 2 diabetes, type 1 diabetes, dyslipidemia or hyperlipidemia, hypertension, for the treatment or prophylaxis of obesity, for lowering of food intake, for appetite regulation, for regulating feeding behaviour.

The disclosure also relates to identifying the compounds of formula (I), its polymorphs, stereoisomers, pharmaceutically acceptable salt, solvate or pro-drug thereof, which are beneficial for the prophylaxis, management, treatment, control of progression, or adjunct treatment of diseases and/or medical conditions where the activation of glucokinase would be beneficial, such as diabetes (both Type-I and Type-II), obesity, dyslipidemia, metabolic syndrome X, and/or diabetes-related complications and as therapeutic and/or prophylactic agents for obesity, metabolic syndrome X inclues Type-II diabetes, obesity, dyslipidemia, hypertension, and atherosclerosis and like.

The disclosure further relates to compounds of formula (I), its polymorphs, stereoisomers, pharmaceutically acceptable salt, solvate or pro-drug thereof, for use in the manufacture of medicament for the treatment of diabetes, obesity, metabolic syndrome X, insulin resistance, impaired glucose tolerance and dyslipidemia.

The disclosure also relates to the use of a compounds of formula (I), its polymorphs, stereoisomers, pharmaceutically acceptable salt, solvate or pro-drug thereof, in the manufacture of a medicament for the activation of Glucokinase.

The disclosure also relates to the use of a compounds of formula (I), its polymorphs, stereoisomers, pharmaceutically acceptable salt, solvate or pro-drug thereof, in the manufacture of a medicament for the prevention of diabetes, particularly type II diabetes, in a human demonstrating pre-diabetic hyperglycemia or impaired glucose tolerance.

The disclosure also relates to a method of prophylactic or therapeutic treatment of hyperglycemia or diabetes, particularly type II diabetes, comprising a step of administering an effective amount of a compound of formula (I), its polymorphs, stereoisomers, pharmaceutically acceptable salt, solvate or pro-drug thereof.

The disclosure also relates to a method for the prevention of diabetes, particularly type II diabetes, in a human demonstrating pre-diabetic hyperglycemia or impaired glucose tolerance comprising a step of administering an effective prophylactic amount of a compound of formula (I), its polymorphs, stereoisomers, pharmaceutically acceptable salt, solvate or pro-drug thereof.

The disclosure also relates to a method of combined treatment of diabetes and obesity by administering an effective amount of a compound of formula (I), its polymorph, stereoisomer, prodrug, solvate or a pharmaceutically acceptable salt thereof, to a mammal in need of such treatment.

The disclosure also relates to the use of a compound of formula (I), its polymorphs, stereoisomers, pharmaceutically acceptable salt, solvate or pro-drug thereof, for the prevention of diabetes, particularly type II diabetes, in a human demonstrating pre-diabetic hyperglycemia or impaired glucose tolerance.

The disclosure also relates to the use of a compound of formula (I), its polymorphs, stereoisomers, pharmaceutically acceptable salt, solvate or pro-drug thereof, for use as medicament, for the prophylactic or therapeutic treatment of hyperglycemia or diabetes, particularly type II diabetes.

The disclosure also relates to the use of a compound of formula (I), its polymorphs, stereoisomers, pharmaceutically acceptable salt, solvate or pro-drug thereof, in the manufacture of a medicament for the prophylactic, or therapeutic treatment of hyperglycemia or diabetes, particularly type II diabetes.

The disclosure also relates to the use of a compound of formula (I), their stereoisomers, tautomers, prodrugs, pharmaceutically acceptable salts, polymorphs, and solvates, in the manufacture of a medicament for use in combined treatment or prevention of diabetes and obesity.

The disclosure also relates to the use of a compound of formula (I), their stereoisomers, tautomers, prodrugs, pharmaceutically acceptable salts, polymorphs, solvates and formulations thereof for prophylactic or therapeutic treatment of a disease selected from a group consisting of a disease needing Glucokinase activation, a disease needing Glucokinase deinhibition, hyperglycemia, IGT, Syndrome X, type 2 diabetes, type 1 diabetes, dyslipidemia, hyperlipidemia, hypertension, insulin resistance, impaired glucose tolerance, obesity, gastric emptying, gastroparesis, satiety, leptin resistance, dyslipidemia, wound healing, nephropathy, retinopathy, neuropathy and cataracts.

The disclosure also relates to the use of a compound of formula (I), their stereoisomers, tautomers, prodrugs, pharmaceutically acceptable salts, polymorphs, solvates and formulations thereof for lowering of food intake, for appetite regulation, for regulating feeding behaviour, for enhancing the secretion of enteroincretins like GLP-1 and GIP.

The disclosure also relates to the use of a compound of formula (I), their stereoisomers, tautomers, prodrugs, pharmaceutically acceptable salts, polymorphs, solvates and formulations thereof for preventing diabetes, particularly type II diabetes, in a human demonstrating pre-diabetic hyperglycemia or impaired glucose tolerance, preventing obesity and preventing dyslipidemia.

The disclosure also relates to the use of a compound of formula (I), their stereoisomers, tautomers, prodrugs, pharmaceutically acceptable salts, polymorphs, solvates and formulations thereof for combined treatment or prevention of diabetes and obesity.

The disclosure also relates to pharmaceutical composition comprising, as an active ingredient, at least one compound of formula (I), or its stereoisomers, tautomers, prodrugs, pharmaceutically acceptable salts, polymorphs, and solvates thereof, together with one or more pharmaceutically acceptable carriers or excipients.

The compounds and compositions of the present disclosure may be optionally employed in combination with one or more, from current or future therapy, other anti-diabetic agents or anti-hyperglycemic agents, which include, for example, (a) insulin secretagogues such as sulfonylureas (e.g. Amaryl, glyburide, glimepiride, glipyride, glipizide, etc.); (b) Insulinotropic sulfonyl urea receptor ligands such as meglitinides (e.g. nateglinide, rapaglinide); (c) biguanides (e.g. metformin, phenformin, buformin, etc.); (d) glucagon antagonists (e.g. a peptide or non-peptide glucagon antagonist); (e) glucosidase inhibitors (e.g. acarbose, miglitol, etc.); (f) glucose sensitive insulinotropic agents (e.g. GLP-1, GLP-1 mimetics e.g. Exendin-4); (g) insulin sensitizers (e.g. troglitazone, rosiglitazone, pioglitazone, etc.); (h) Dipeptidyl peptidase-IV inhibitors (e.g. sitagliptin, vildagliptin); and the like. The said additional therapeutic agent is added in a dose range of about 0.01 mg to 100 mg per kg body weight.

The compounds and compositions of the present disclosure may also be optionally employed in combination with one or more, from current or future therapy, anti-obesity agents (e.g. sibutramine, orlistat, rimonabant etc.) and the like.

The compounds and compositions of the present disclosure may also be optionally employed in combination with one or more, from current or future therapy, dyslipidemic agents which include, for example: (a) fibrates (e.g. gemfibrozil, fenofibrate); (b) Niacin; (c) Statins (e.g. rosuvatatin, atorvastatin, simvastatin); (d) cholesterol absorption inhibitors (e.g. Ezetimibe); (e) bile acid sequestrants (e.g. cholestyramine) and the likes.

The compounds and compositions of the present disclosure may also be optionally employed in combination with one or more, from current or future therapy, antihypertensive agents such as: (a) diuretics (e.g. hydrochlorothiazides, mannitol, indapamide, furosemide); (b) angiotensin converting enzyme (ACE) inhibitors (e.g. captopril, enalapril); (c) Angiotensin-II receptor type-I blockers (ARB) (e.g. losartan, irbesartan); (d) rennin inhibitors (e.g. aliskerin); (e) β-adrenergic receptor blockers (e.g. atenolol, metoprolol); (f) calcium channel blockers (e.g. amlodipine, nifedipine); (g) aldosterone receptor antagonist (e.g. spironolactone); (h) aldosterone synthase inhibitors (e.g. FAD286). The said additional therapeutic agent is added in a dose range of about 0.01 mg to 100 mg per kg body weight.

The compounds and compositions of the present disclosure and the other therapeutic agents such as described above may be administered simultaneously, sequentially or separately.

The pharmaceutical compositions of the present disclosure comprise a compound of formula (I), polymorphs, stereoisomers, pharmaceutically acceptable salt, solvate or pro-drug thereof, as an active ingredient, a pharmaceutically acceptable carrier and optionally other therapeutic active agent in any suitable ratios.

The disclosure also relates to pharmaceutical composition comprising, as an active ingredient, at least one compound of formula (I), or its stereoisomers, tautomers, prodrugs, pharmaceutically acceptable salts, polymorphs, and solvates thereof, wherein the pharmaceutically acceptable therapeutically active agent is selected from anti-diabetic agents, anti-hyperglycemic agents, anti-obesity agents, anti-hypertensive agents or anti-dyslipidemic agents.

The pharmaceutical compositions of the present disclosure comprising compounds of formula (I), polymorphs, stereoisomers, pharmaceutically acceptable salt, solvate or prodrugs thereof, may be manufactured in a manner that is known in the art, e.g. by means of conventional mixing, encapsulating, dissolving, granulating, emulsifying, entrapping, dragee making, or lyophilizing processes. These pharmaceutical preparations can be formulated with therapeutically inert, inorganic or organic carriers such as lactose, corn starch or derivatives thereof, talc, steric acid or its salts as carriers for tablets, coated tablets, dragées and hard gelatin capsules. For soft gelatin capsules suitable carriers include vegetable oils, waxes and fats. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semiliquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula (I), its polymorphs, stereoisomers, pharmaceutically acceptable salt, solvate or prodrugs thereof.

The pharmaceutical compositions containing the active ingredient of compound of formula (I), its polymorphs, stereoisomers, pharmaceutically acceptable salt, solvate or pro-drugs thereof, maybe in a form suitable for oral use, for example, as tablets, troches, lozenges, aqueous or oily suspensions, dispersible powders or granules, emulsions, hard or soft capsules, or syrups or elixirs; sterile injectable aqueous or oleaginous suspension; suppositories; topical use, for example creams, ointments, jellies, solutions or suspension etc. including mouth washes and gargles. These compositions can be manufactured by any method known in the art with the active ingredient combined with non-toxic pharmaceutically acceptable excipients.

While the disclosure has been described and illustrated with reference to certain preferred embodiments thereof, those skilled in the art will appreciate that various changes, modifications and substitutions can be made therein without departing from the spirit and scope of the present disclosure. For example, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present disclosure.

Abbreviations

The following abbreviations are employed in the examples and elsewhere herein:

| | |
|---|---|
| DMF: | Dimethyl formamide |
| DMSO: | Dimethyl sulfoxide |
| DCM: | Dichloromethane |
| DCE: | Dichloroethane |
| THF: | Tetrahydrofuran |
| mCPBA: | meta chloro perbenzoic acid |
| BOP-Cl: | Bis(2-oxo-3-oxazolidinyl)phosphinic chloride |
| DABCO: | 1,4-Diazabicyclo[2.2.2]octane |
| DBU: | 1,8-Diazabicyclo[5.4.0]undec-7-ene |
| DCC: | N,N-Dicyclohexyl carbodiimide |
| EDCI: | 1-Ethyl-3-(3-dimetylaminopropyl)carbodiimide |
| HOBT: | 1-Hydroxybenzotriazole |
| HOAT: | 1-Hydroxy-7-azabenzotriazole |
| HBTU: | O-(benzotriazol-1-yl)-tetramethyluronium hexafluorophosphate |
| HATU: | O-(7-azabenzotriazol-1-yl)-tetramethyluronium hexafluorophosphate |
| TPP: | triphenylphosphine | atoms, consequently, compounds of formula (I) can exist in enantiomeric, or diastereomeric forms, or in mixtures thereof. The processes for preparation can utilize racemates, enantiomers, or diastereomers as starting materials. When diastereomeric or enantiomeric products are obtained as mixtures, they can be separated by conventional methods for example, chromatographic separation or fractional crystallization or through diasteriomeric salt formation. When intended, a desired enantiomer or diasteriomer can also be obtained by following appropriate enantioselective or diastereoselective reactions.

Structures of the intermediates as well as the final compounds were confirmed by nuclear magnetic resonance spectra for proton (1H NMR) and LCMS.

Preparation 1: (2,4-Difluoro-phenoxy)-[4-(tetrahydro-pyran-4-sulfonyl)-phenyl]-acetic acid

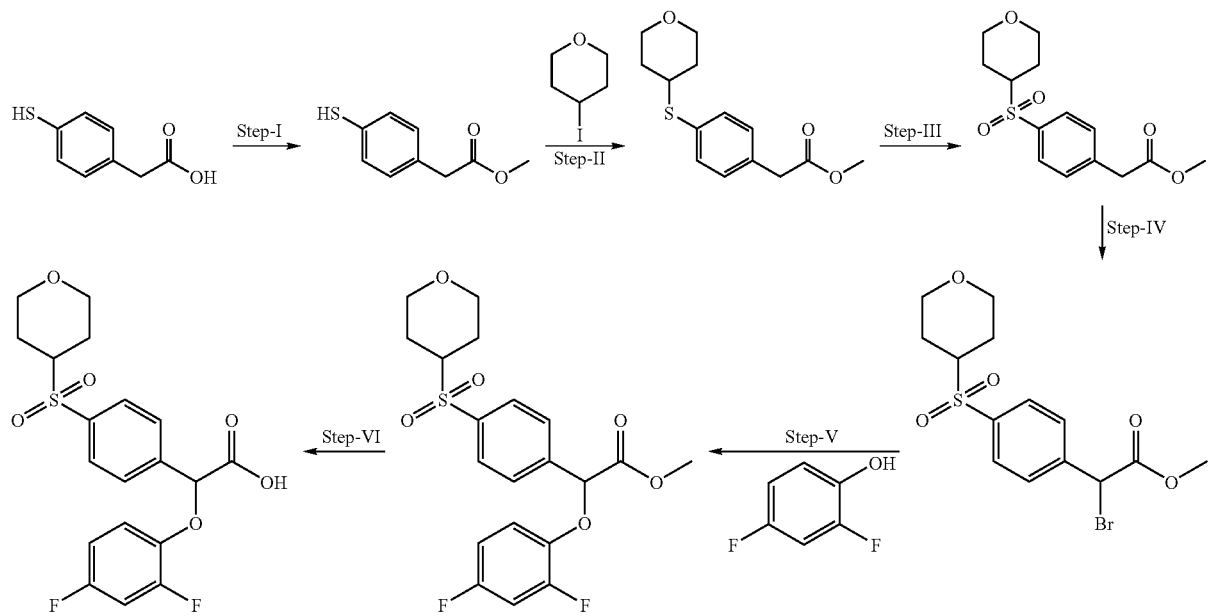

-continued

| | |
|---|---|
| DEAD: | diethyl azodicarboxylate |
| DIAD: | diisopropyl azodicarboxylate |

EXAMPLES

The disclosure is further illustrated by the following examples which in no way should be construed as being further limiting. One skilled in the art will readily appreciate that the specific methods and results described are merely illustrative. All stereoisomers of the compounds of the instant disclosure are contemplated, either in admixture or in pure or substantially pure form. The compounds of the present disclosure can have asymmetric centers at any of the carbon Step-I:-(4-Mercapto-phenyl)-acetic acid methyl ester 4-Mercato-phenyl acetic acid (10 gm, 59.5 mmol) was dissolved in methanol (300 ml). To this solution, sulfuric acid (5.8 gm, 59.5 mmol) was added and mixture was refluxed for 2 hrs. Solvent was removed under reduced pressure. The resulting residue was dissolved in ethyl acetate (200 ml), and was washed with water, sodium bicarbonate solution and brine (100 ml each), dried over anhydrous sodium sulfate, and filtered and solvent was removed under reduced pressure to provide (4-mercapto-phenyl)-acetic acid methyl ester (10 gm).

$^1$HNMR (CDCl$_3$, 400 MHz):–δ 3.44 (s, 1H), 3.58 (s, 2H), 3.70 (s, 3H), 7.16 (d, J=8.0 Hz, 2H), 7.25 (d, J=8.4 Hz, 2H).

Step-II: [4-(Tetrahydro-pyran-4-ylsulfanyl)-phenyl]acetic acid methyl ester (4-Mercapto-phenyl)-acetic acid methyl ester (1.8 g, 9.89 mmol) was dissolved in DMF (20 ml) at 0° C. Triethylamine (1.5 g, 14.83 mmol) was added and stirred for 15 minutes followed by addition of 4-iodo-tetrahydropyan (3.14 g, 14.83 mmol). The reaction mixture was stirred overnight at room temperature. Solvent was removed under reduced pressure, the resulting residue was taken into water and extracted with ethyl acetate (50 ml×2) washed with water and brine (50 ml each) dried over anhydrous sodium sulfate, filtered and concentrated to obtain a crude product which was purified by column chromatography over silica gel using 15% ethyl acetate in hexanes as eluent to provide [4-(Tetrahydro-pyran-4-ylsulfanyl)-phenyl]acetic acid methyl ester (2.1 gm).

$^1$HNMR (CDCl$_3$, 400 MHz):−δ 1.65-1.72 (m, 2H), 1.89-1.92 (m, 2H), 3.25-3.26(m, 1H), 3.62 (s, 2H), 3.71 (s, 3H), 3.86-4.00 (m, 2H), 7.39 (d, J=8.0 Hz, 2H), 7.45 (d, J=8.4 Hz, 2H). MS (EI) m/z: 267.20 (M+1).

Step-III: −[4-(Tetrahydro-pyran-4-sulfonyl)-phenyl]-acetic acid methyl ester

[4-(Tetrahydro-pyran-4-ylsulfanyl)-phenyl]-acetic acid methyl ester (2.1 g, 7.89 mmol) was taken in dichloromethane (100 ml) at 0° C. mCPBA (8.00 gm, 47.36 mmol) was added portion wise and stirred for 5 hrs at room temperature. Reaction mixture was diluted with dichloromethane (100 ml), solid was filtered, filtrate was washed with saturated solution of sodium thiosulphate (150 ml), organic layer was washed with saturated solution of sodium bicarbonate, water and brine (100 ml each), dried over anhydrous sodium sulfate, filtered and concentrated. Crude compound was purified by column chromatography over silica gel using 35% ethyl acetate hexane as eluent to provide pure [4-(tetrahydro-pyran-4-sulfonyl)-phenyl]-acetic acid methyl ester (1.69 gm).

$^1$HNMR (CDCl$_3$, 400 MHz):−δ 1.80-1.87 (m, 2H), 1.92-1.95 (m, 2H), 3.12-3.18 (m, 1H), 3.31-3.38 (m, 2H), 3.76 (s, 5H), 4.06-4.10 (m, 2H),), 7.53 (d, J=8.0 Hz, 2H), 7.86 (d, J=8.0 Hz, 2H).

Step-IV: Bromo-[4-(tetrahydro-pyran-4-sulfonyl)-phenyl]-acetic acid methyl ester

[4-(Tetrahydro-pyran-4-sulfonyl)-phenyl]-acetic acid methyl ester (1.60 gm, 5.36 mmol), NBS (1.04 g, 5.90 mmol) and benzoyl peroxide (0.130 g, 0.53 mmol) in carbon tetrachloride (50 ml) was refluxed for 7 hrs. Reaction mixture was diluted with DCM (50 ml), washed with water and brine (100 ml each), dried over anhydrous sodium sulfate, flitered and concentrated. Crude compound was purified by column chromatography over silica gel using 30% ethyl acetate hexane as eluent to give the pure bromo-[4-(tetrahydro-pyran-4-sulfonyl)-phenyl]-acetic acid methyl ester (0.75 gm).

$^1$HNMR (CDCl$_3$, 400 MHz):−δ 1.75-1.87 (m, 2H), 1.93-1.96 (m, 2H), 3.15-3.22 (m, 1H) 3.33-3.38 (m, 2H), 3.85 (s, 3H), 4.07-4.11 (m, 2H), 5.41 (s,1H), 7.79 (d, J=8.4 Hz, 2H), 7.90 (d, J=8.4 Hz, 2H).

Step-V: (2,4-Difluoro-phenoxy)-[4-(tetrahydro-pyran-4-sulfonyl)-phenyl]-acetic acid methyl ester A mixture of 2, 4 difluorophenol (0.28 g, 2.18 mmol) and cesium carbonate (0.39 g, 1.19 mmol) in acetonitrilie (20 ml) stirred for 30 mins. A solution of bromo-[4-(tetrahydro-pyran-4-sulfonyl)-phenyl]-acetic acid methyl ester (0.75 g, 1.98 mmol) in acetonitrile (5 ml) was added drop wise at room temperature and stirred further for 2 hrs. Reaction mixture was diluted with ethyl acetate (50 ml), washed with water, 1N NaOH (cold, 50 ml), and brine (50 ml) dried over anhydrous sodium sulfate, filtered and concentrated to provide (2,4-difluoro-phenoxy)-[4-(tetrahydro-pyran-4-sulfonyl)-phenyl]-acetic acid methyl ester (0.35 gm).

$^1$HNMR (CDCl$_3$, 400 MHz):−δ 1.80-1.87 (m, 2H), 1.93-1.96 (m, 2H), 3.15-3.22 (m, 1H), 3.33-3.38 (m, 2H), 3.80 (s, 3H), 4.07-4.11 (m, 2H), 5.70 (s, 1H), 6.78-6.83 (m, 1H), 6.89-6.95 (m, 1H), 6.98-7.04 (m, 1H), 7.83 (d, J=8.0 Hz, 2H), 7.95 (d, J=8.4 Hz, 2H). MS (EI) m/z: 444.00 (M+18)

Step VI: (2,4-Difluoro-phenoxy)-[4-(tetrahydro-pyran-4-sulfonyl)-phenyl]-acetic acid To a solution of (2,4-difluoro-phenoxy)-[4-(tetrahydro-pyran-4-sulfonyl)-phenyl]-acetic acid methyl ester (0.35 g, 0.82 mmol) in THF (3 ml), was added lithium hydroxide monohydrate (0.035 g, 2.05 mmol) in 1 ml water and stirred overnight at room temperature. Solvent was removed under reduced pressure, residue obtained was taken into water (5 ml), extracted with diethyl ether (10 ml×2). Aqueous layer was acidified with 1 N HCl solution, and extracted with ethyl acetate (10 ml×3), washed with water and brine (20 ml, each) dried over anhydrous sodium sulfate, filtered and solvent was concentrated to provide (2,4-difluoro-phenoxy)-[4-(tetrahydro-pyran-4-sulfonyl)-phenyl]-acetic acid (0.28 gm).

$^1$HNMR (CDCl$_3$, 400 MHz):−δ 1.79-1.87 (m, 2H), 1.92-1.95 (m, 2H), 3.15-3.21 (m, 1H), 3.32-3.38 (m, 2H), 4.07-4.11 (m, 2H), 5.71 (s, 1H), 6.78-6.83 (m, 1H), 6.89-6.95 (m, 1H), 6.98-7.04 (m, 1H), 7.85 (d, J=8.4 Hz, 2H), 7.95 (d, J=8.0 Hz, 2H).

Preparation 2: (2,4-Difluoro-phenoxy)-[4-(piperidine-1-sulfonyl)-phenyl]-acetic acid

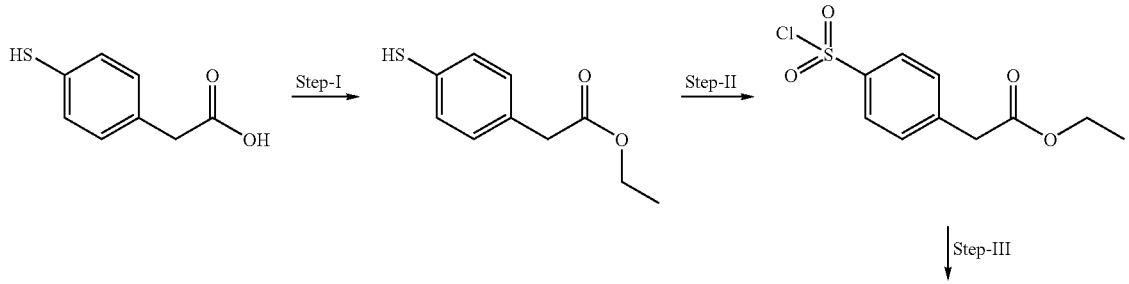

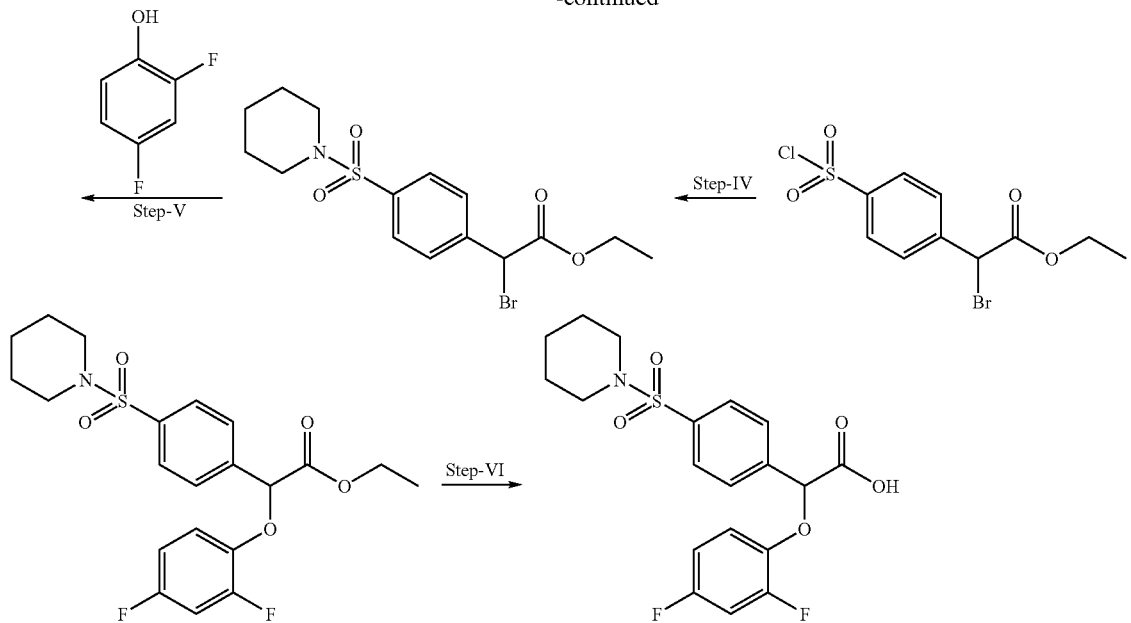

Step I: (4-Mercapto-phenyl)-acetic acid ethyl ester

To a solution of 4-mercapto-phenyl acetic acid (5 gm, 29.72 mmol) in ethanol (60 ml) was added sulfuric acid (1.58 ml, 29.72 mmol) dropwise. Reaction mixture was then heated at 60° C. for 3 hr, concentrated to remove ethanol. The residue was neutralized with satd. aq. $NaHCO_3$ solution and extracted with ethyl acetate (3×30 ml) washed with brine, dried over anhydrous sodium sulfate, filtered and concentrated under reduced pressure to provide (4-mercapto-phenyl)-acetic acid ethyl ester (5.5 gm).
$^1$H NMR (400 MHz, $CDCl_3$): δ 1.22 (t, J=6.8 Hz, 3H), 3.55 (s, 2H), 4.11 (q, J=7.2 Hz, 2H), 7.14 (d, J=8.0 Hz, 2H), 7.22 (d, J=8.0 Hz, 2H).

Step II: (4-Chlorosulfonyl-phenyl)-acetic acid ethyl ester (4-Mercapto-phenyl)-acetic acid ethyl ester (2 gm, 10.2 mmole) was taken in a seal tube. To it DCM (30 ml) was added followed by $KNO_3$ (2.42 gm, 22.4 mmole) and TMSCl (2.79 ml, 22.4 mmole). Mixture was heated at 50° C. for 24 hr, cooled to room temperature and filtered to remove solids, residue was washed with DCM (10×2 ml), combined filtrate was washed with water followed by brine solution, dried over anhydrous sodium sulfate, filtered and concentrated under reduced pressure to provide (4-chlorosulfonyl-phenyl)-acetic acid ethyl ester (1.6 gm).
$^1$H NMR (400 MHz, DMSO-$d_6$): δ 1.17 (t, J=6.8 Hz, 3H), 3.66 (s, 2H), 4.05-4.11 (m, 2H), 7.21 (d, J=8.0 Hz, 2H), 7.54 (d, J=8.0 Hz, 2H).

Step III: Bromo-(4-chlorosulfonyl-phenyl)-acetic acid ethyl ester (4-Chlorosulfonyl-phenyl)-acetic acid ethyl ester (1.6 gm, 6.45 mmol) was taken in carbon tetrachloride (13 ml). N-Bromosuccinimide (1.26 gm, 7.09 mmol) was added in one lot followed by benzoyl peroxide (171 mg, 0.7 mmol). The reaction mixture was refluxed for 2 days. The reaction mixture was cooled to room temperature and filtered; filtrate was washed with water followed by brine solution, dried over anhydrous sodium sulfate and concentrated under reduced pressure to provide bromo-(4-chlorosulfonyl-phenyl)-acetic acid ethyl ester (2.08 gm) as a gummy mass. The crude material was used as such for further reaction.

Step IV: Bromo-[4-(piperidine-1-sulfonyl)-phenyl]-acetic acid ethyl ester

Bromo-(4-chlorosulfonyl-phenyl)-acetic acid ethyl ester (2.08 gm, 6.38 mmol) was taken in DCM (63 ml) under argon atmosphere and cooled to 0-5° C., piperidine (0.56 ml, 5.74 mmol) was added dropwise to the mixture at 0-5° C. Reaction mixture was then stirred at room temperature for 30 min. Reaction mixture was washed with water followed by brine solution, dried over anhydrous sodium sulfate and concentrated under reduced pressure to give the crude product, which was purified by flash column chromatography over silica gel using 30-50% ethyl acetate in hexane as eluent to give bromo-[4-(piperidine-1-sulfonyl)-phenyl]-acetic acid ethyl ester (1.2 gm).
$^1$H NMR (400 MHz, $CDCl_3$): δ 1.31 (t, J=7.2 Hz, 3H), 1.46-1.49 (m, 2H), 1.65-1.71 (m, 4H), 2.99-3.04 (m, 4H), 4.21-4.31 (m, 2H), 5.38 (s, 1H), 7.72 (d, J=8.4 Hz, 2H), 7.76 (d, J=8.4 Hz, 2H).

Step V: (2,4-Difluoro-phenoxy)-[4-(piperidine-1-sulfonyl)-phenyl]-acetic acid ethyl ester 2,4-Difluorophenol (0.38 ml, 3.89 mmol) and cesium carbonate (0.76 gm, 2.33 mmol) were taken in acetonitrile (30 ml) under argon atmosphere and was stirred for 30 minutes. Bromo-[4-(piperidine-1-sulfonyl)-phenyl]-acetic acid ethyl ester (1.4 gm, 3.86 mmol) in acetonitrile (15 ml) was added to the mixture and stirred at 25° C. for 3 hour. Reaction mixture was diluted with water (30 ml), extracted with ethyl acetate (3×20 ml), organic layer was washed with brine solution, dried over anhydrous sodium sulfate and concentrated under reduced pressure to give a gummy mass which was purified by flash column chromatography using over silica gel using 40-60% ethyl acetate in hexane as eluent to give (2,4-difluoro-phenoxy)-[4-(piperidine-1-sulfonyl)-phenyl]-acetic acid ethyl ester (1.31 gm).

¹H NMR (400 MHz, CDCl₃): δ 1.22 (t, J=7.2 Hz, 3H), 1.44-1.46 (m, 2H), 1.66-1.67 (m, 4H), 3.0-3.04 (m, 4H), 4.21-4.27 (m, 2H), 5.66 (s, 1H), 6.80-6.82 (m, 1H), 6.89-6.95 (m, 1H), 6.95-7.29 (m, 1H), 7.76 (d, J=8.4 Hz, 2H), 7.81 (d, J=8.4 Hz, 2H).

Step VI: (2,4-Difluoro-phenoxy)-[4-(piperidine-1-sulfonyl)-phenyl]-acetic acid (2,4-Difluoro-phenoxy)-[4-(piperidine-1-sulfonyl)-phenyl]-acetic acid ethyl ester (1.3 gm, 2.98 mmol) was dissolved in THF (5 ml) and methanol (0.5 ml). To this was added a solution of lithium hydroxide (0.62 gm, 14.90 mmol) in water (5 ml) and stirred for 18 hours at 25° C. Organic solvents were evaporated from the reaction mixture and aqueous layer was acidified with 1N HCl, precipitated product was filtered off and residue was washed with water. Solid product was dried under vacuum to provide (2,4-difluoro-phenoxy)-[4-(piperidine-1-sulfonyl)-phenyl]-acetic acid (1 gm).

¹H NMR (400 MHz, DMSO-d₆): δ 1.35-1.42 (m, 2H), 1.51-1.61 (m, 4H), 2.86-2.91 (m, 4H), 6.12 (s, 1H), 7.02-7.06 (m, 1H), 7.18-7.24 (m, 1H), 7.33-7.39 (m, 1H), 7.79-7.84 (brs, 4H). MS (EI) m/z: 412.0 (M+1).

Preparations 3 to 7 were Prepared in Analogous Manner of Preparation 2.

| Preparation No. | IUPAC Name |
|---|---|
| 3 | (2,4-Difluoro-phenoxy)-[4-(morpholine-4-sulfonyl)-phenyl]-acetic acid |
| 4 | (4-Chloro-phenoxy)-[4-(morpholine-4-sulfonyl)-phenyl]-acetic acid |
| 5 | (4-Chloro-phenoxy)-[4-(piperidine-1-sulfonyl)-phenyl]-acetic acid |
| 6 | (4-Chloro-2-fluoro-phenoxy)-[4-(piperidine-1-sulfonyl)-phenyl]-aceticacid |
| 7 | (4-Chloro-2-fluoro-phenoxy)-[4-(morpholine-4-sulfonyl)-phenyl]-aceticacid |

Preparation 8: (2,4-Difluoro-phenoxy)-[4-(pyrrolidine-1-sulfonyl)-phenyl]-acetic acid Preparation 9: (2,4-Difluoro-phenoxy)-[3-(pyrrolidine-1-sulfonyl)-phenyl]-acetic acid

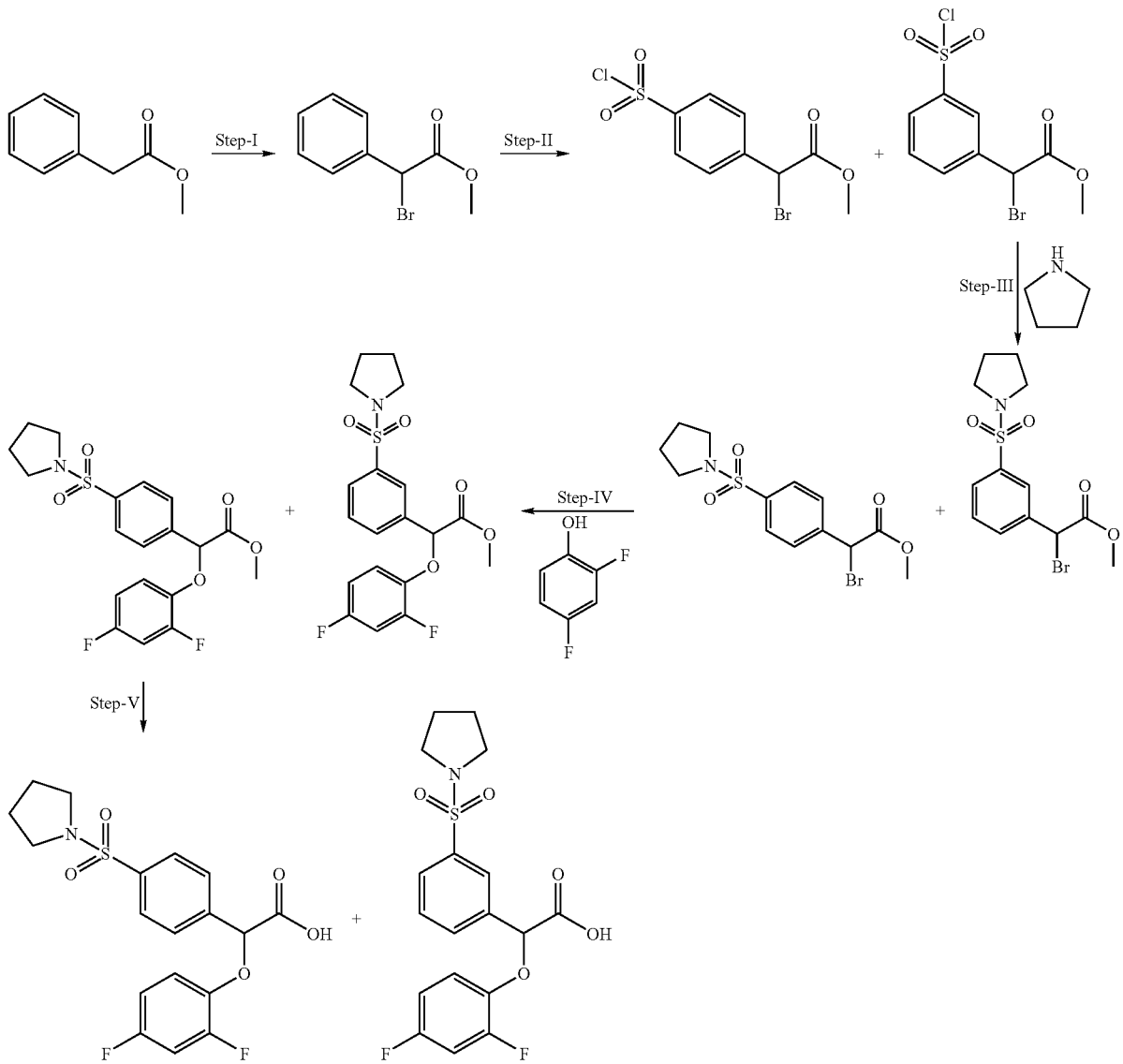

Step I: Bromo-phenyl-acetic acid methyl ester

Phenyl-acetic acid methyl ester (10 gm, 66.6 mmol) was taken in carbon tetrachloride (100 ml). N-Bromosuccinimide (13.05 gm, 73.33 mmol) was added in one lot followed by benzoyl peroxide (1.77 gm, 7.3 mmol) and refluxed for 3 hours. The reaction mixture was cooled to room temperature and filtered; filtrate was washed with water followed by brine solution, dried over anhydrous sodium sulfate and concentrated under reduced pressure to provide bromo-phenyl-acetic acid methyl ester (16.4 gm) as a gummy mass.

$^1$H NMR (400 MHz, CDCl$_3$): δ 3.82 (s, 3H), 5.39 (s, 1H), 7.39-7.41 (m, 3H), 7.56-7.58 (m, 2H).

Step II: Bromo-(4-chlorosulfonyl-phenyl)-acetic acid methyl ester and Bromo-(3-chlorosulfonyl-phenyl)-acetic acid methyl ester Chlorosulphonic acid (1.5 ml, 21.86 mmol) was dissolved in DCM (20 ml) and cooled to 0-5° C. under argon atmosphere. Bromo-phenyl-acetic acid methyl ester (1.0 gm, 4.36 mmol) was added to cooled mixture in drop wise manner and continued to stir at 0-5° C. for 1 hour then at room temperature for 1 hour. Reaction mixture was diluted with water (10 ml), organic layer was washed with brine solution, dried over anhydrous sodium sulfate, filtered and concentrated under reduced pressure to give the product as mixture of para and meta regioisomers as gummy mass. The crude material was used as such for further reaction.

Step III: Bromo-[4-(pyrrolidine-1-sulfonyl)-phenyl]-acetic acid methyl ester and Bromo-[3-(pyrrolidine-1-sulfonyl)-phenyl]acetic acid methyl ester A solution of pyrrolidine (0.14 gm, 2 mmol) in DCM (10 ml) was cooled to 0-5° C. under argon atmosphere. To this was added a solution of bromo-(4-chlorosulfonyl-phenyl)-acetic acid methyl ester and bromo-(3-chlorosulfonyl-phenyl)-acetic acid methyl ester (0.207 gm, 2.04 mmol) in DCM (10 ml) drop wise at 0-5° C. The reaction mixture was then stirred at room temperature for 18 hours, diluted with water (10 ml), organic layer was washed with brine solution, dried over anhydrous sodium sulfate, filtered and concentrated under reduced pressure to give the product as a mixture of para and meta regioisomers.

MS (EI) m/z: 363.9 (M+1)

Step IV: (2,4-Difluoro-phenoxy)-[4-(pyrrolidine-1-sulfonyl)-phenyl]-acetic acid methyl ester and (2,4-Difluoro-phenoxy)-[3-(pyrrolidine-1-sulfonyl)-phenyl]-acetic acid methyl ester 2,4-Difluorophenol (0.5 gm, 3.86 mmol) and cesium carbonate (0.75 gm, 2.32 mmol) were taken in acetonitrile (10 ml). Mixture was stirred for 30 minutes under argon atmosphere, followed by addition of regioisomers obtained in step III (1.4 gm, 3.86 mmol) in acetonitrile (15 ml). Mixture was then stirred at 25° C. for 18 hours, diluted with water (30 ml) and extracted with ethyl acetate (3×20 ml). The organic layer was washed with brine solution, dried over anhydrous sodium sulfate, filtered and concentrated under reduced pressure to give the product as a gummy mass which was purified by column chromatography(30-40% ethyl acetate in hexane) to give 0.720 gm of mixture of products as meta and para regioisomers.

MS (EI) m/z: 412.2 (M+1).

Step V: (2,4-Difluoro-phenoxy)-[4-(pyrrolidine-1-sulfonyl)-phenyl]-acetic acid and (2,4-Difluoro-phenoxy)-[3-(pyrrolidine-1-sulfonyl)-phenyl]-acetic acid Mixture of regioisomers obtained in step IV (0.6 gm, 1.45 mmol) was dissolved in THF (5 ml) and methanol (5 ml). A solution of lithium hydroxide (0.15 gm, 3.64 mmol) in water (5 ml) was added stirred for 18 hours at 25° C. Organic solvents were evaporated from the reaction mixture and aqueous layer was acidified with 1N HCl and extracted with ethylacetate (3×10 ml), organic layer was washed with brine solution, dried over anhydrous sodium sulfate, and concentrated under reduced pressure to give 0.56 gm of products as mixture of para and meta regioisomers.

MS (EI) m/z: 398.2.

Preparations 10 to 12 were Prepared in Analogous Manner of Preparations 8 and 9.

| Preparation No. | IUPAC Name |
|---|---|
| 10 | [4-(Azetidine-1-sulfonyl)-phenyl]-(2,4-difluoro-phenoxy)-acetic acid |
| 11 | [3-(Azetidine-1-sulfonyl)-phenyl]-(2,4-difluoro-phenoxy)-acetic acid |
| 12 | (2,4-Difluoro-phenoxy)-[3-(piperidine-1-sulfonyl)-phenyl]-acetic acid |

Preparation 13: (4-Cyclopropanesulfonyl-phenyl)-[(tetrahydro-furan-3-yloxy)]-acetic acid

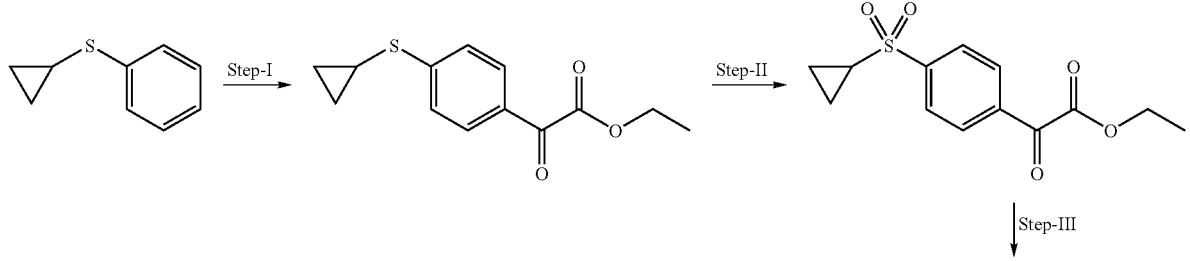

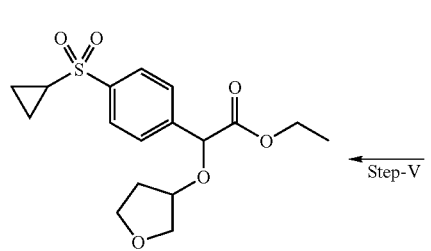
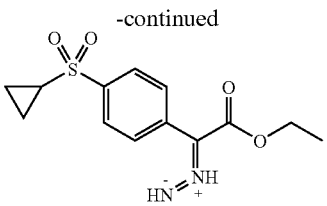
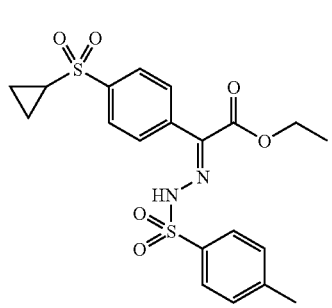

Step-V ← Step-IV ←

↓ Step-VI

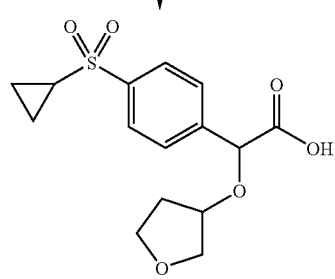

Step I: (4-Cyclopropylsulfanyl-phenyl)-oxo-acetic acid ethyl ester

AlCl$_3$ (7.98 gm, 48.42 mmole) was suspended in DCM (50 ml) and cooled to 0° C. under argon atmosphere. To this suspension was added chlorooxo ethylacetate (4.5 ml, 39.98 mmol) at 0° C. and stirred for 45 min. followed by addition of a solution of cyclopropylsulfanyl-benzene (5 gm, 33.28 mmol) in DCM (10 ml) and stirred at 25° C. for 2 hr. Reaction mixture was slowly poured over crushed ice, organic layer was separated and aqueous layer was extracted with DCM (3×50 ml), combined organic layer was washed with brine solution, dried over anhydrous sodium sulfate, filtered and concentrated under reduced pressure to obtain (4-cyclopropylsulfanyl-phenyl)-oxo-acetic acid ethyl ester (3.1 gm) as an oily product.

$^1$H NMR (400 MHz, CDCl$_3$): δ 0.72-0.73 (m, 2H), 1.15-1.17 (m, 2H), 1.40 (t, J=6.6 Hz, 3H), 2.18-2.21 (m, 1H), 4.41 (q, J=6.8 Hz, 2H), 7.43 (d, J=8.0 Hz, 2H), 7.90 (d, J=8.0 Hz, 2H). MS (EI) m/z: 250.9 (M+1).

Step II: (4-Cyclopropanesulfonyl-phenyl)oxo acetic acid ethyl ester (4-Cyclopropylsulfanyl-phenyl)-oxo-acetic acid ethyl ester (3.1 gm, 12.53 mmole) in DCM (50 ml) was cooled to 0-5° C. followed by addition of mCPBA (9.8 gm, 31.33 mmol) portion wise at 0° C. After stirring at 25° C. for 4 hr, the reaction mixture was filtered; filtrate was washed with saturated aq. Na$_2$S$_2$O$_3$ and satd. aq. sodium bicarbonate solution followed by brine solution, dried over anhydrous sodium sulfate, filtered and concentrated under reduced pressure to give (4-cyclopropanesulfonyl-phenyl)oxo acetic acid ethyl ester (3 gm).

$^1$H NMR (400 MHz, CDCl$_3$): δ 1.05-1.10 (m, 2H), 1.36-1.39 (m, 2H), 1.40 (t, J=6.8 Hz, 3H), 2.45-2.50 (m, 1H), 4.42 (q, J=7.2 Hz, 2H), 8.01 (d, J=8.4 Hz, 2H), 8.20 (d, J=8.4 Hz, 2H). MS (El) m/z: 297.1 (M+NH$_4$).

Step III: p-Toluene sulfonyl hydrazone (4-cyclopropyl sulfonyl)phenyl acetic acid ethyl ester A mixture of (4-cyclopropanesulfonyl-phenyl)oxo acetic acid ethyl ester (0.5 gm, 1.77 mmole) and p-toluene sulfonyl hydrazide (0.48 gm, 2.3 mmol) in toluene (15 ml) was refluxed for 16 hr using a Dean-Stark apparatus. Reaction mixture was concentrated to give the crude product which was purified by column chromatography over silica gel using 20-25% ethyl acetate in hexane as eluent to provide p-toluene sulfonyl hydrazone (4-cyclopropyl sulfonyl) phenyl acetic acid ethyl ester (0.5 gm).

MS (EI) m/z: 451.0 (M+1).

Step IV: (4-Cyclopropanesulfonyl-phenyl)diazo acetic acid ethyl ester

To a solution of p-toluene sulfonyl hydrazone (4-cyclopropyl sulfonyl)phenyl acetic acid ethyl ester (0.5 gm, 1.23 mmole) in dry DCM (6 ml), was added triethylamine (0.17 mL, 1.35 mmol) and stirred at 25° C. for 1 hr. Reaction mixture was concentrated to provide (4-cyclopropanesulfonyl-phenyl)diazo acetic acid ethyl ester (0.5 gm) which was used as it is for next reaction.

MS (EI) m/z: 295.1 (M+1).

Step V: (4-Cyclopropanesulfonyl-phenyl)-[(tetrahydro-furan-3-yloxy)]-acetic acid ethyl ester (4-Cyclopropanesulfonyl-phenyl)diazo acetic acid ethyl ester (2 gm, 6.74 mmol) was dissolved in DCM (33 mL) under argon atmosphere. To this solution, 3-hydroxy tetrahydrofuran (1.36 mL, 16.87 mmol) was added followed by rhodium(II)acetate dimer (62 mg, 0.14 mmol). Mixture was stirred at 25° C. for 3 hr. Reaction mixture was diluted with DCM (25 mL), organic layer was washed with water followed by brine solution, dried over anhydrous sodium sulfate, filtered and concentrated under reduced pressure to give a crude product which was purified by column chromatography using 35-40% ethyl acetate in hexane as eluent to provide (4-cyclopropanesulfonyl-phenyl)-[(tetrahydro-furan-3-yloxy)]-acetic acid ethyl ester (1 gm).

$^1$H NMR (400 MHz, CDCl$_3$): δ 0.99-1.05 (m, 2H), 1.18-1.24 (m, 3H), 1.31-1.34 (m, 2H), 1.96-2.10 (m, 2H), 2.38-2.48 (m, 1H), 3.73-3.97 (m, 4H), 4.14-4.19 (m, 2H), 4.20-4.22 (m, 1H), 4.97-4.99 (d, J=8.4, 1H), 7.61-7.64 (m, 2H), 7.85-7.88 (m, 2H).

MS (EI) m/z: 355 (M+1), 372.1 (M+18).

Step VI: (4-Cyclopropanesulfonyl-phenyl)-[(tetrahydro-furan-3-yloxy)]-acetic acid To (4-cyclopropanesulfonyl-phenyl)-[tetrahydro-furan-3-yloxy)]-acetic acid ethyl ester (1 gm, 2.82 mmol) was added a solution of lithium hydroxide (0.59 gm, 14.12 mmol) in water (5 ml) followed by THF (10 ml) and methanol (2 ml) and stirred for 2 hours at 25° C. Organic solvents were evaporated from the reaction mixture and aqueous layer was acidified 1N HCl, extracted with ethyl acetate (3×10 ml), organic layer was washed with brine solution, dried over anhydrous sodium sulfate, and washed concentrated under reduced pressure to provide (4-cyclopropanesulfonyl-phenyl)-[(tetrahydro-furan-3-yloxy)]-acetic acid (0.8 gm)

$^1$H NMR (400 MHz, CDCl$_3$): δ 1.05-1.07 (m, 2H), 1.37-1.42 (m, 2H), 2.06-2.10 (m, 2H), 2.47-2.51 (m, 1H), 3.74-4.28 (m, 4H), 4.12-4.28 (m, 1H), 5.04 (s, 1H), 7.66 (t, J=6.6 Hz, 2H), 7.91 (d, J=8.0 Hz, 2H). MS (El) m/z: 327 (M+1), 344.1 (M+18)

Preparation 14: (4-Cyclopropanesulfonyl-phenyl)-[(tetrahydro-pyran-4-yloxy)]-acetic acid

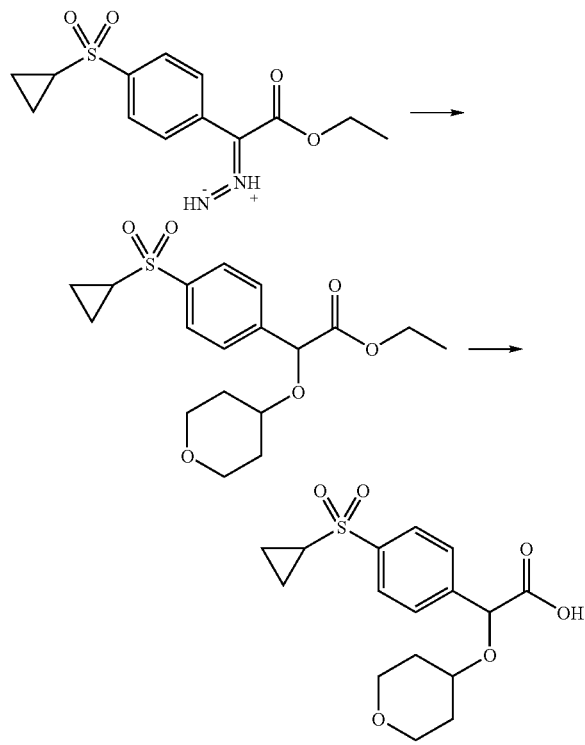

Step I: (4-Cyclopropanesulfonyl-phenyl)-[(tetrahydro-pyran-4-yloxy)]-acetic acid ethyl ester (4-Cyclopropanesulfonyl-phenyl)diazo acetic acid ethyl ester, obtained similarly as described in preparation 13, (5 gm, 16.87 mmol) was dissolved in DCM (84 mL) under argon atmosphere. To this solution, 4-hydroxy tetrahydropyran (2.0 mL, 20.24 mmol) was added followed by rhodium(II)acetate dimer (156 mg, 0.35 mmol). Mixture was stirred at 25° C. for 3 hr. Reaction mixture was diluted with DCM (50 mL), organic layer was washed with water followed by brine solution, dried over anhydrous sodium sulfate, filtered and concentrated under reduced pressure to give a crude product which was purified by column chromatography using 35-40% ethyl acetate in hexane as eluent to provide (4-cyclopropanesulfonyl-phenyl)-[(tetrahydro-pyran-4-yloxy)]-acetic acid ethyl ester (3.5 gm).

$^1$H NMR (400 MHz, CDCl$_3$): δ 1.02-1.07 (m, 2H), 1.24 (t, 3H), 1.34-1.37 (m, 2H), 1.65-1.81 (m, 2H), 1.87-1.92 (m, 1H), 1.95-2.01 (m, 1H), 2.43-2.49 (m, 1H), 3.39-3.48 (m, 2H), 3.62-3.68 (m, 1H), 3.91-4.02 (m, 2H) 4.15-4.23 (m, 2H), 5.11 (s, 1H), 7.68-(d, J=8.0 Hz, 2H), 7.90 (d, J=8.0 Hz 2H).

MS (EI) m/z: 369 (M+1), 386.1 (M+18).

Step II: (4-Cyclopropanesulfonyl-phenyl)-[(tetrahydro-pyran-4-yloxy)]-acetic acid To (4-cyclopropanesulfonyl-phenyl)-[(tetrahydro-pyran-4-yloxy)]-acetic acid ethyl ester (23.2 gm, 62.87 mmol) was added a solution of lithium hydroxide (13.0 gm, 314.36 mmol) in water (150 ml) followed by THF (200 ml) and methanol (10 ml) and stirred for 2 hours at 25° C. Organic solvents were evaporated from the reaction mixture and aqueous layer was acidified 1N HCl, extracted with ethyl acetate (3×200 ml), organic layer was washed with brine solution, dried over anhydrous sodium sulfate, and washed concentrated under reduced pressure to provide (4-cyclopropanesulfonyl-phenyl)-[(tetrahydro-pyran-4-yloxy)]-acetic acid (18.49 gm)

$^1$H NMR (400 MHz, CDCl$_3$): δ 1.02-1.06 (m, 2H), 1.07-1.15 (m, 2H) 1.23-1.56 (m, 2H), 1.83-1.94 (m, 2H), 2.83-2.89 (m, 1H), 3.28-3.35 (m, 2H), 3.69-3.65 (m, 1H), 3.74-3.85 (m, 2H) 5.26 (s, 1H), 7.69 (d, J=8.0 Hz, 211), 7.90 (d, J =8.0 Hz, 2H).

MS (EI) m/z: 341.0 (M+1), 358.0 (M+18).

Preparations 15 to 16 were Prepared in Analogous Manner of Preparation 13

| Preparation No. | IUPAC Name |
|---|---|
| 15 | (4-Cyclopropanesulfonyl-phenyl)-[(S)-(tetrahydro-furan-3-yl)oxy]-acetic acid |
| 16 | (4-Cyclopropanesulfonyl-phenyl)-[(R)-(tetrahydro-furan-3-yl)oxy]-acetic acid |

Intermediates-17-24 were either obtained from commercial source or prepared as per literature method.

| | |
|---|---|
| 17-1 | Commercial Source |
| 17-2 | Commercial Source |
| 18-1 | Commercial Source |
| 18-2 | Commercial Source |
| 19-1 | Commercial Source |
| 20-1 | J. Med. Chem. 2007, 50(8), 4464 |
| 17-3 | WO2009047798 |
| 17-4 | WO2004058752 |
| 17-5 | Chem. Pharm. Bull 36, 2969 |
| 17-6 | WO2008005914 |
| 17-7 | WO2008005914 |
| 21 | Commercial Source |
| 22 | Aq. NH4OH |
| 23-1 | J. Het. Chem. 1977, 14, 129 |
| 23-1 | WO2007007886 |
| 23-3 | WO2007041366 |
| 17-8 | WO2007099317 |
| 17-9 | Commercial Source |

-continued

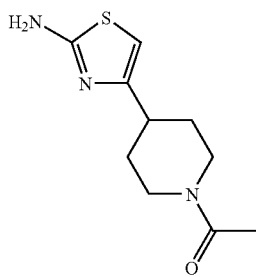

WO 2007089512A1

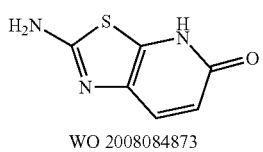

WO 2008084873

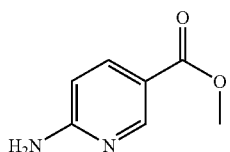

Commercial Source

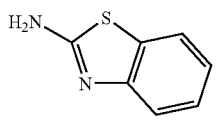

Commercial Source

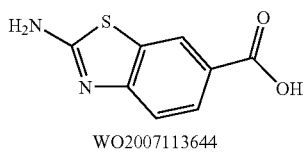

WO2007113644

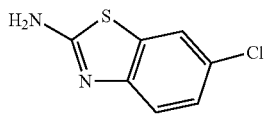

Commercial Source

Preparation 25:
4-(2-Amino-thiazol-5-yloxy)-3-fluoro-benzoic acid ethyl ester

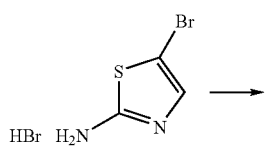

-continued

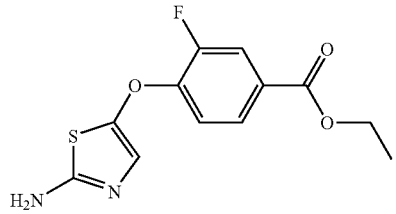

To a solution of 5-Bromothiazole-2-amine hydrobromide (1.55 g, 5.97 mmol) in acetone (100 mL) was added 3-fluoro-4-hydroxy benzoic acid ethyl ester (1.1 g, 5.97 mmol) and cesium carbonate (3.89 g, 11.94 mmol) under argon atmosphere and refluxed for 5 hrs. The reaction mixture was cooled to room temperature and filtered; the filtrate was concentrated under reduced pressure. The residue was partitioned in between ethyl acetate and water. The layers were separated, the organic layer was washed with cold 2 N NaOH (10 mL), brine and dried over anhydrous sodium sulfate, filtered and concentrated under reduced pressure to provide 4-(2-amino-thiazol-5-yloxy)-3-fluoro-benzoic acid ethyl ester (0.68 gm).
$^1$H NMR (400 MHz, CDCl$_3$): δ 1.39 (t, 3H), 4.37 (q, 2H), 6.83 (s, 1H), 7.13-7.17 (t, 1H), 7.76-7.84 (m, 2H). MS (EI) m/z: 282.9 (M+1).

Preparations 26 to 36 were Prepared in Analogous Manner of Preparation 25

| Preparation No. | IUPAC Name |
|---|---|
| 26 | 4-(2-Amino-thiazol-5-yloxy)-2-fluoro-benzoic acid methyl ester |
| 27 | 5-(2-Amino-thiazol-5-yloxy)-pyridine-2-carboxylic acid methyl ester |
| 28 | 5-(5-Trifluoromethyl-pyridin-2-yloxy)-thiazol-2-ylamine |
| 29 | 4-(2-Amino-thiazol-5-yloxy)-benzoic acid methyl ester |
| 30 | 5-(4-Fluoro-phenoxy)-thiazol-2-ylamine |
| 31 | 3-(2-Amino-thiazol-5-yloxy)-benzoic acid methyl ester |
| 32 | 6-(2-Amino-thiazol-5-yloxy)-nicotinic acid methyl ester |
| 33 | [4-(2-Amino-thiazol-5-yloxy)-phenyl]-acetic acid methyl ester |
| 34 | 4-(2-Amino-thiazol-5-yloxy)-benzonitrile |
| 35 | 4-(2-Amino-4-methyl-thiazol-5-yloxy)-benzoic acid methyl ester |

Preparation 36: 5-Morpholin-4-yl-thiazol-2-ylamine

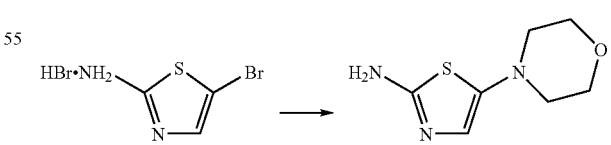

To a mixture of 2-amino-5-bromothiazole monohydrobromide (2 gm, 7.69 mmol) and powdered potassium carbonate (2.1 gm, 15.38 mmol) in DMF (20 mL) was added morpholine (1.34 ml, 15.38 mmol) under argon atmosphere and heated at 60° C. for 3 hr. Reaction mixture was cooled to rt and poured over ice cold water (100 ml), extracted with ethylacetate (3×100 ml), washed with brine solution, dried over anhydrous sodium sulfate, filtered and concentrated under reduced pressure. To the residue, diisopropyl ether (50 mL) was added, after stirring for 30 minutes product precipitated out, which was filtered and dried under vacuum to provide 5-morpholin-4-yl-thiazol-2-ylamine (0.95 gm).

$^1$H NMR (400 MHz, DMSO-d6): δ 2.80-2.82 (m, 4H), 3.66-3.68 (m, 4H), 6.30 (s, 1H)), 6.49 (bs, 2H). MS (EI) m/z: 186 (M+1).

Preparation 37 and 3R were Prepared in Analogous Manner of Preparation 36.

| Preparation No. | IUPAC Name |
|---|---|
| 37 | 1-(2-Amino-thiazol-5-yl)-piperidine-4-carboxylic acid ethyl ester |
| 38 | 5-Pyrazol-1-yl-thiazol-2-ylamine |

Preparation 39: 4-(3-Amino-pyrazol-1-ylmethyl)-benzoic acid methyl ester

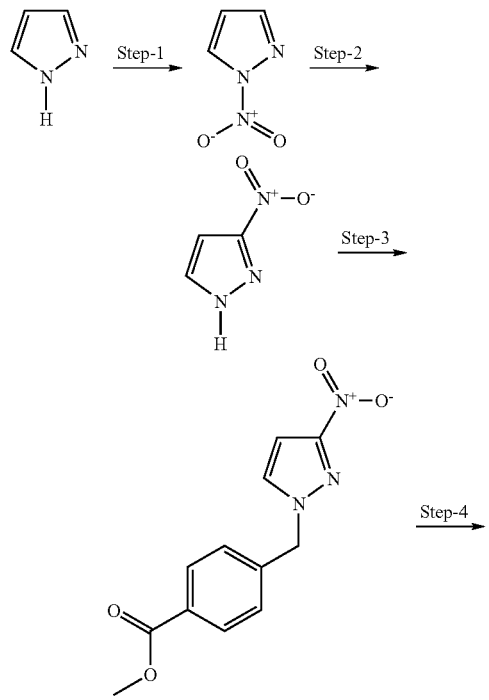

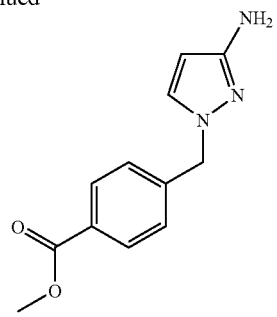

Step-1: 1-Nitro-1H-pyrazole

Obtained as described in WO2007/99317 A1

Step-2: 3-Nitro-1H-pyrazole

Obtained as described in WO2008/21032 A1

Step-3: 4-(3-Nitro-pyrazol-1-ylmethyl)-benzoic acid methyl ester

Obtained as described in US2008/146625 A1

Step-4: 4-(3-Amino-pyrazol-1-ylmethyl)-benzoic acid methyl ester 4-(3-Nitro-pyrazol-1-ylmethyl)-benzoic acid methyl ester (530 mg, 2.03 mmol) was dissolved in ethyl acetate (10 ml). Tin(II) chloride dihydrate (2.29 gm, 10.15 mmol) was added, reaction mixture was heated at 70 deg C. for 1 h. The reaction mixture was cooled to ambient temperature, the pH adjusted to pH 8-9 by addition of aq. saturated sodium carbonate and extracted with ethyl acetate (3×25 ml), dried over anhydrous Na$_2$SO$_4$ and concentrated under reduced pressure to provide 4-(3-amino-pyrazol-1-ylmethyl)-benzoic acid methyl ester (480 mg).

$^1$H NMR (400 MHz, DMSO-d6): δ 3.83(s, 3H), 4.62 (bs, 2H), 5.12 (s, 2H)), 5.43 (d, J=2.4 Hz, 1H), 7.27 (d, J=8.4 Hz, 2H), 7.47 (d, J=2.0 Hz, 1H), 7.90 (d, J=8.0 Hz, 2H).

MS (EI) m/z: 232 (M+1).

Preparation 40: (3-Amino-pyrazol-1-yl)-acetic acid methyl ester

Prepared in an analogous manner of preparation 39.

Preparation 41: (2-Amino-thiazol-5-yl)-propynoic acid ethyl ester

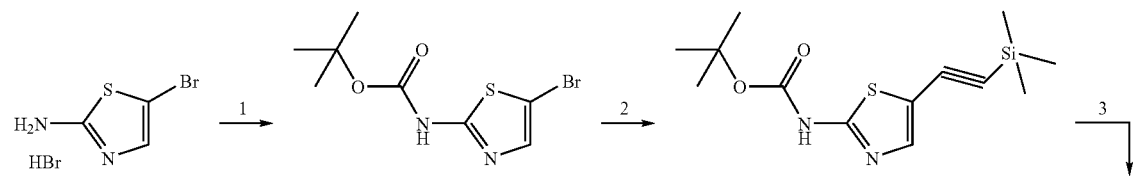

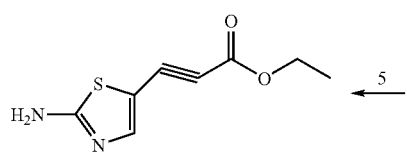 ← 5 — 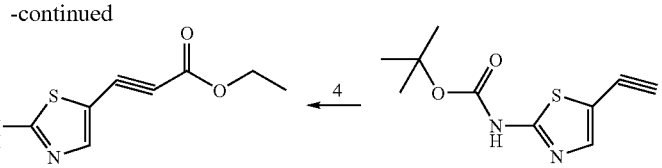 ← 4 —

Step-1: (5-Bromo-thiazol-2-yl)-carbamic acid tert-butyl ester

To a stirred suspension of 2-amino-5-bromothiazole hydrobromide (2.5 g, 9.617 mmol) in pyridine (7.5 ml) was added Di-tert-butyl dicarbonate (2.31 g, 10.584 mmol) and the reaction was stirred for 1 hr at room temperature. Pyridine was removed under reduced pressure and the residue was pardoned between water (100 ml) and ethyl acetate (100 ml). The layers were separated, the organic layer was washed with 1N HCl followed by Sat. sodium bicarbonate solution and brine, dried over anhydrous sodium sulfate, filtered and concentrated under reduced pressure to get (5-bromo-thiazol-2-yl)-carbamic acid tert-butyl ester (1.8 g).

$^1$H NMR (400 MHz, CDCl$_3$): δ 1.58 (s, 9H), 7.24 (s, 1H), 10.94(bs, 1H). MS (EI) m/z: 279.0 (M+1).

Step-2: (5-Trimethylsilanylethynyl-thiazol-2-yl)-carbamic acid tert-butyl ester (5-Bromo-thiazol-2-yl)-carbamic acid tert-butyl ester (2.0 g, 7.164 mmol) was taken in triethylamine (20 ml). To this solution was added CuI (0.041 g, 0.215 mmol), PdCl$_2$(PPh$_3$)$_2$ (0.050 g, 0.071 mmol) followed by the addition of trimethylsilylacetylene (1.055 g, 10.741 mmol). The reaction was heated at 80° C. overnight. Reaction mixture was cooled to room temperature and poured into water (50 ml), extracted with ethyl acetate (30 ml×3). The combined organic layer was washed with 1N HCl followed by brine and dried over anhydrous sodium sulfate. The solvent was removed under reduced pressure. The crude product was purified by column chromatography over silica gel using 6% ethyl acetate hexane as eluent to provide pure (5-trimethylsilanylethynyl-thiazol-2-yl)-carbamic acid tert-butyl ester (1.679 g).

$^1$H NMR (400 MHz, CDCl$_3$): δ 0.25 (s, 9H), 1.57 (s, 9H), 7.45 (s, 1H), 10.77 (bs, 1H).
MS (EI) m/z: 297.1 (M+1).

Step-3: (5-Ethynyl-thiazol-2-yl)-carbamic acid tert-butyl ester

To a solution of (5-trimethylsilanylethynyl-thiazol-2-yl)-carbamic acid tert-butyl ester (1.67 g, 5.633 mmol) was dissolved in methanol (20 ml) was added K$_2$CO$_3$ (0.389 g, 2.816 mmol) and stirred at room temperature overnight. Then the reaction was heated at 50° C. for 2 hrs. Methanol was removed under reduced pressure. The residue obtained was partioned between water (50 ml) and ethyl acetate (50 ml). The layers were separated. The organic layer was washed with brine, dried over anhydrous sodium sulfate and concentrated under reduced pressure to provide (5-ethynyl-thiazol-2-yl)-carbamic acid tert-butyl ester (1.2 g).

MS (EI) m/z: 225.1 (M+1).

Step-4: (2-tert-Butoxycarbonylamino-thiazol-5-yl)-propynoic acid ethyl ester (5-Ethynyl-thiazol-2-yl)-carbamic acid tert-butyl ester (1.2 g, 5.350 mMol) was dissolved in THF (25 ml) in inert atmosphere and stirred at −78° C., nBuLi (7.4 ml, 1.6 M solution in hexane, 11.848 mMol) was added drop wise. After complete addition the reaction was stirred for 0.5 hr. followed by addition of ethyl chloroformate (0.775 g, 7.141 mMol) at −78° C. Reaction was allowed to come to 0° C. and quenched with water (50 ml) and extracted with ethyl acetate (25 ml×3). The organic layer was washed with brine, dried over anhydrous sodium sulfate and concentrated under reduced pressure to get (2-tert-butoxycarbonylamino-thiazol-5-yl)-propynoic acid ethyl ester (1.4 g).

$^1$H NMR (400 MHz, CDCl$_3$): δ 1.35 (t, 3H), 1.57 (s, 9H), 4.27-4.32 (q, 2H), 7.71 (s, 1H), 9.95 (bs, 1H). MS (EI) m/z: 297.1 (M+1).

Step-5: (2-Amino-thiazol-5-yl)-propynoic acid ethyl ester (2-tert-Butoxycarbonylamino-thiazol-5-yl)-propynoic acid ethyl ester (1.2 g, 4.049 mmol) was dissolved in DCM (20 ml), trifluoroacetic acid (4.617 g, 40.93 mmol) was added in drop wise fashion at 0° C. After complete addition the reaction was allowed to stir for overnight at room temperature. Additional 3 ml of TFA was charged to the reaction and stirred for 2 hr. TLC showed complete reaction. Reaction was basified with sat. bicarbonate. The aqueous layer was extracted with ethyl acetate (30 ml×3). The combined organic layer was washed with water followed by brine and dried over anhydrous sodium sulfate and the solvent was removed on vacuo. The sticky solid product was obtained (0.700 g)

MS (EI) m/z: 197.0 (M+1).

Preparation 42: 4-(2-Amino-thiazol-5-yl)-benzoic acid ethyl ester

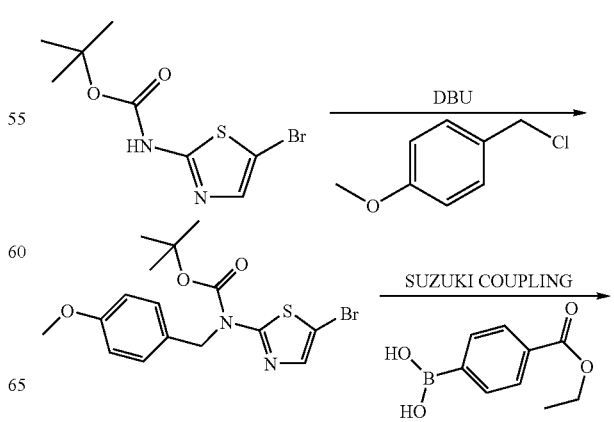

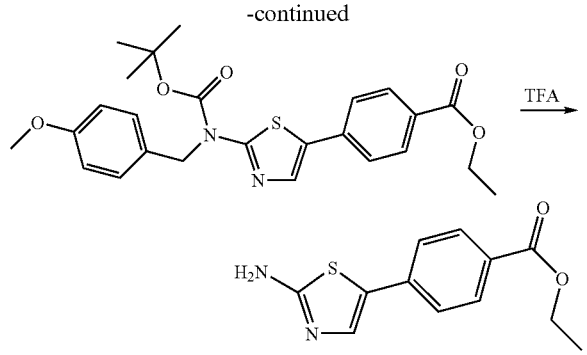

Step-1: (5-Bromo-thiazol-2-yl)-(4-methoxy-benzyl)-carbamic acid tert-butyl ester To a single necked round bottom flask (5-Bromo-thiazol-2-yl)-carbamic acid tert-butyl ester (1.4 g, 5.01 mmol) was dissolved in 25 ml dry DCM. To it 1,8-Diazabicyclo[5.4.0]undec-7-ene(DBU) (2.24 ml, 15.03 mmol) was added followed by 1-Chloromethyl-4-methoxy-benzene (1.02 ml, 7.52 mmol) addition was done and reaction mixture was stirred for overnight. Reaction was quenched by addition of water (20 ml), extracted with DCM (25 ml), Organic layer was separated and washed with brine (30 ml) and dried over anhydrous sodium sulfate, sodium sulfate was filtered and washed with DCM (20 ml) and solvent was evaporated on rotavapour to get required product. The crude material was purified by silica-gel column chromatography, eluting with 4% acetone in hexane. (1.4 g).

$^1$H NMR (400 MHz, CDCl$_3$): δ 1.44(s, 9H), 3.70(s, 3H), 5.11(s, 2H), 6.74 (d, J=8.2 Hz, 2H), 7.21 (d, J=7.9 Hz, 2H), 7.22 (s, 1H). MS (EI) m/z: 400.8 (M+1).

Step-2: 4-{2-[tert-Butoxycarbonyl-(4-methoxy-benzyl)-amino]-thiazol-5-yl}-benzoic acid ethyl ester To a stirred solution of (5-Bromo-thiazol-2-yl)-(4-methoxy-benzyl)-carbamic acid tert-butyl ester (1.0 g, 2.50 mmol) in 20 ml 1,4-dioxane, Boronic acid (0.59 g, 2.75 mmol) and CS$_2$CO$_3$ (1.78 g, 5.50 mmol) was added and degassed using argon gas for 20 min. To it tetrakis(triphenylphosphine)palladium(0) (1.44 g,1.25 mmol) was added and reaction mixture was heated at 100° C. for 7 hrs. Reaction mixture was filtered through celite pad; celite pad was washed with excess ethyl acetate. Organic solvent was concentrated to obtain crude material. The crude material was purified by silica-gel column chromatogaphy, eluting with 8% ethyl acetate in hexane. (0.5 g, 42% yield).

$^1$H NMR (400 MHz, CDCl$_3$): δ1.33(t, J=7.09 Hz , 3H) 1.47(s, 9H), 3.71(s, 3H), 4.30(q, J=7.09 Hz, 2H), 5.19 (s, 2H)), 6.66(d, J=8.5 Hz, 2H), 7.65(s, 1H), 7.25(d, J=8.5 Hz, 2H), 7.51(d, J=8.5 Hz, 2H), 7.95(d, J=8.3 Hz, 2H).
MS (EI) m/z: 469.0 (M+1).

Step-3: 4-(2-Amino-thiazol-5-yl)-benzoic acid ethyl ester

Trifluoroacetic acid (5 ml) was added to 4-{2-[tert-Butoxycarbonyl-(4-methoxy-benzyl)-amino]-thiazol-5-yl}-benzoic acid ethyl ester (300 mg, 0.64 mmol) at room temperature and reaction mixture was refluxed for 5 hrs. Trifluoroacetic acid was removed on rotavapour. The residue was taken in water (10 ml) and ethyl acetate (15 ml) and basified this with sodium bicarbonate, layers were separated, and aq. layer was re-extracted with ethyl acetate (15 ml). The combined organic layer was washed with brine (15 ml) and dried over anhydrous sodium sulfate. Solvent was evaporated on rotavapour to get the solid product. The crude material was used for the next step with out any further purification,(150 mg).

$^1$H NMR (400 MHz, CD$_3$OD): δ 1.33(t, J=7.09 Hz, 3H), 4.30(q, J=7.09 Hz, 2H), 7.41(s, 1H), 7.48(d, J=8.5 Hz, 2H), 7.95(d, J=8.5 Hz, 2H).
MS (EI) m/z: 248.9 (M+1).

Preparation 43: 1-(2-Amino-thiazol-5-ylmethyl)-piperidine-4-carboxylic acid ethyl ester

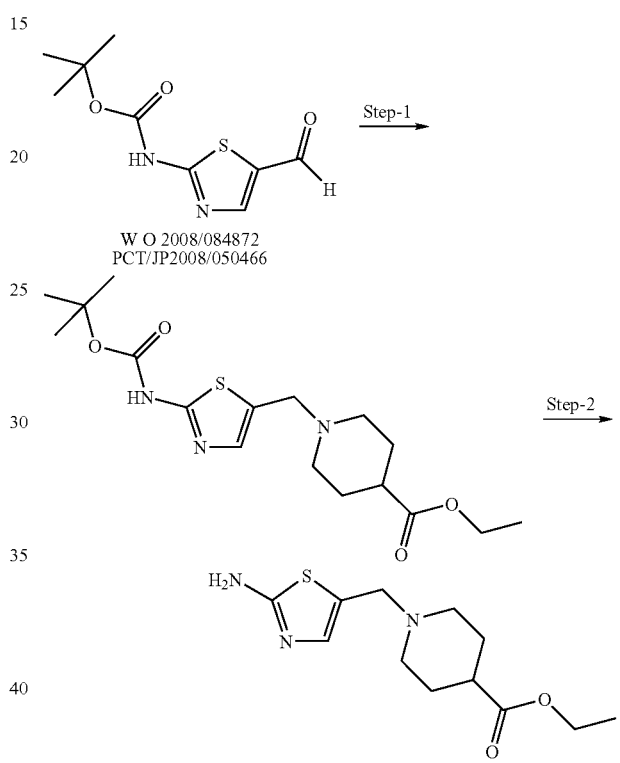

Step-1: 1-(2-tert-Butoxycarbonylamino-thiazol-5-ylmethyl)-piperidine-4-carboxylic acid ethyl ester To a single necked round bottom flask (5-Formyl-thiazol-2-yl)-carbamic acid tert-butyl ester (1 g, 4.38 mmol) was dissolved in 20 ml methanol. To it piperidine-4-carboxylic acid ethyl ester (2.02 ml, 13.15 mmol) and 4-drops of glacial acetic acid was added and reaction mixture was stirred at room temperature for 2.5 hr. To it sodium cyanoborohydride (550 mg, 8.76 mmol) was added in portions and stirred for 12 hrs. Methanol was removed under reduced pressure using rotavapour. The residue was taken in water (15 ml) and ethyl acetate (25 ml), layers were separated, and aq. layer was re-extracted with ethyl acetate (25 ml). The combined organic layer was washed with brine (25 ml) and dried over anhydrous sodium sulfate. Solvent was evaporated on rotavapour, to get the yellow solid product. The crude material was purified by silica-gel column chromatography, eluting with 30-50% ethyl acetate in hexane. (0.98 g, 60% yield).

$^1$H NMR (400 MHz, CDCl$_3$): δ 1.23-1.27 (m, 3H), 1.57 (s, 9H), 1.71-1.91 (m, 4H), 2.06-2.31 (m, 2H), 2.20-2.30 (m, 1H), 2.87-2.90 (m, 2H), 3.64 (s, 2H), 4.13 (q, 2H), 7.13 (s, 1H). MS (EI) m/z: 370.0 (M+1).

Step-2: 1-(2-Amino-thiazol-5-ylmethyl)-piperidine-4-carboxylic acid ethyl ester To a stirred solution of 1-(2-tert-Butoxycarbonylamino-thiazol-5-ylmethyl)-piperidine-4-carboxylic acid ethyl ester (0.98 g) in 2 ml of DCM, 10 ml TFA was added at room temperature and reaction mixture was stirred for 12 hrs. After completion of reaction TFA was removed under reduced pressure. The residue was taken in ethyl acetate (25 ml), and neutralized by aqueous saturated sodium bicarbonate. Organic layer was separated and aqueous layer was further extracted with ethyl acetate (25 ml). Combined organic layer was washed with water (25 ml) followed by brine (25 ml). Organic layer was dried over anhydrous sodium sulfate, sodium sulfate was filtered and washed with ethyl acetate (10 ml) and solvent was evaporated using rotavapour to get required product as solid which was dried under vacuum (2 mbar) for 2 hours. The crude yellow solid material was used for the next step with out any further purification, (0.6 g, and 84% yield).

$^1$H NMR (400 MHz, CDCl$_3$): δ 1.24 (t, 3H), 1.69-1.79 (m 2H), 1.81-1.92 (m, 2H), 2.02-2.07 (m, 2H), 2.21-2.31 (m, 1H), 2.86-2.89 (m, 2H), 3.53 (s, 2H), 4.12 (q, 2H), 4.93 (bs, 2H), 6.81 (s, 1H). MS (EI) m/z: 270.0 (M+1).

Preparation 44: 1-(2-Amino-thiazol-5-ylmethyl)-pyrrolidine-2-carboxylic acid methyl ester Prepared in analogous manner of preparation 43.

Preparation 45: 4-(2-Amino-thiazol-4-yl)-benzoic acid methyl ester

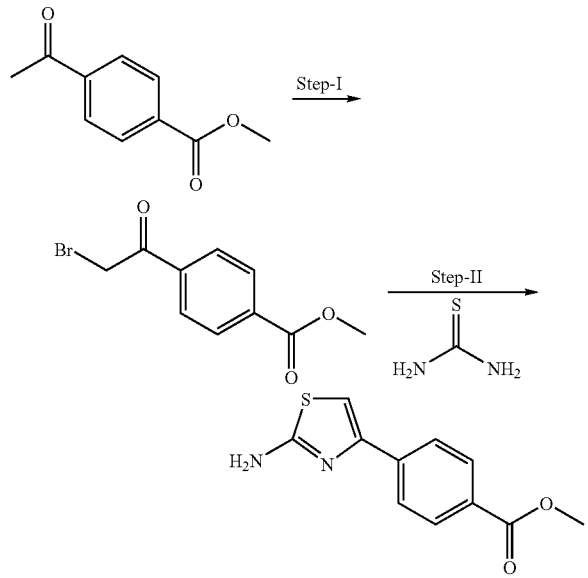

Step-I: 4-(2-Bromo-acetyl)-benzoic acid methyl ester

Obtained as described in WO2006078698

Step-II: 4-(2-Amino-thiazol-4-yl)-benzoic acid methyl ester

A mixture of 4-(2-bromo-acetyl)-benzoic acid methyl ester (1 g, 3.89 mmol) and thiourea (0.29 g, 3.89 mmol) were taken isopropyl alcohol (100 ml) and refluxed for 10 minutes followed by addition of sodium carbonate (0.206 g, 1.94 mmol) and stirred for 30 minutes. Reaction mixture was cooled to room temperature and poured in water. The precipitate obtained was filtered off, washed with water and diethyl ether and dried under vacuum to afford 4-(2-amino-thiazol-4-yl)-benzoic acid methyl ester (0.500 g, 55%).

$^1$HNMR (DMSO-d6, 400 MHz):−δ 3.88 (s, 3H), 7.17 (bs, 2H), 7.27 (s, 1H), 7.95-7.99 (m, 4H).MS (EI) m/z: 235.10 (M+1).

Preparation 46: 5-Ethoxy-thiazolo[5,4-b]pyridin-2-ylamine

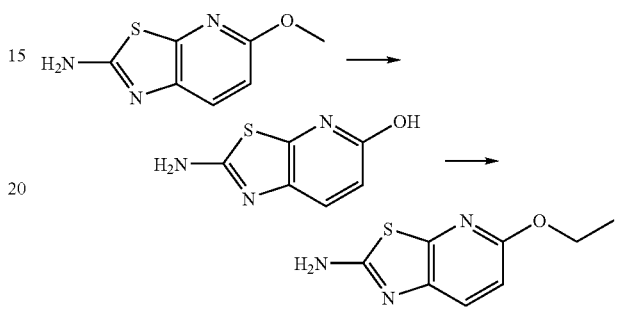

Step-I: 2-Amino-thiazolo[5,4-b]pyridin-5-ol

Synthesized as described in WO 2007/007886

Step-II: 5-Ethoxy-thiazolo[5,4-b]pyridin-2-ylamine

To a solution of 2-Amino-thiazolo[5,4-b]pyridin-5-ol (4.7 g, 28.1 mmol) in Dimethylformamide (50 ml) was added cesium fluoride (12.8 g, 84.4 mmol) under argon atmosphere. Ethyl iodide ((2.7 ml, 33.7 mmol) was added in drop wise manner at room temperature and stirred overnight. Completion of reaction was confirmed by TLC, reaction mixture was diluted with water (100 ml) and extracted with ethyl acetate (100 ml×3),combined organic extracts were washed with water and brine (100 ml each) dried over Na$_2$SO$_4$, filtered and concentrated under vaccum to afford ethoxy-thiazolo[5,4-b]pyridin-2-ylamine (2.1 g).

$^1$H NMR (400 MHz, DMSO-d$_6$):δ 1.30 (t, J=7.2 Hz, 3H), 4.23 (q, J=7.2, Hz, 2H), 6.65 (d, J=8.8 Hz, 1H), 7.42 (bs, 2H), 7.59 (d, J=8.8 Hz, 1H). MS (EI) m/z: 195.90 (M+1).

Preparation 47: 5-iso-propoxy-thiazolo[5,4-b]pyridin-2-ylamine

Prepared in analogous manner of preparation 46.

Example A1

2-(4-Cyclopropanesulfonylphenyl)-2-(2,4-difluoro-phenoxy)-N-thiazol-2-yl-acetamide

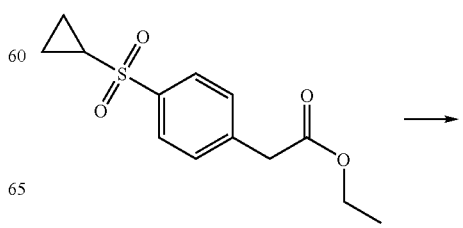

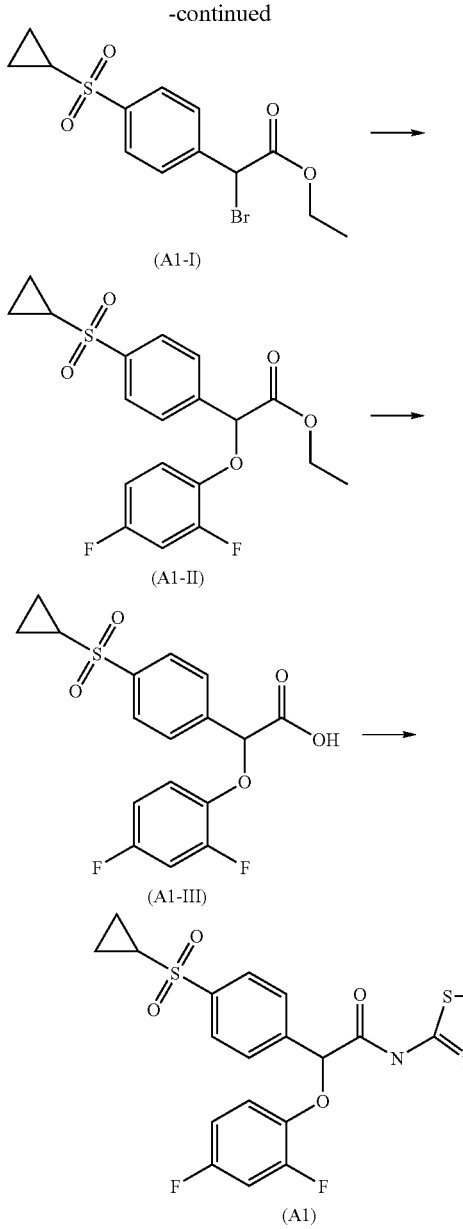

Step I: Synthesis of ethyl 2-bromo-2-(4-cyclopropanesulfonylphenyl)acetate, (A1-I)

To a solution of ethyl 2-(4-cyclopropanesulfonylphenyl) acetate, obtained according to WO2004072031, in carbon tetrachloride, was added N-Bromosuccinimide followed by catalytic amount of benzoyl peroxide. The reaction mixture was then refluxed for 4 hours. After completion, the reaction mixture was cool to room temperature, filtered; the filtrate was washed with water followed by brine solution, dried over anhydrous sodium sulfate, solvent was removed under reduced pressure to provide compound A1-I as a gummy mass which was used for the next step with out any further purification.

¹H NMR (400 MHz, CDCl₃): δ 1.04-1.10 (m, 2H), 1.31 (t, J=7.2 Hz, 3H), 1.36-1.40 (m, 2H), 2.45-2.49 (m, 1H), 4.23-4.32 (m, 2H), 5.37 (s, 1H), 7.75 (d, J=8.4 Hz, 2H), 7.91 (d, J=8.4 Hz, 2H).

MS (EI) m/z: 346.9 (M+1)

Step II: Synthesis of ethyl 2-(4-cyclopropanesulfonylphenyl)-2-(2,4-difluoro-phenoxy)acetate (A1-II):

To a solution of 2,4-difluorophenol in acetonitrile, was added potassium carbonate followed by bromo-(4-cyclopropanesulfonyl-phenyl)-acetic acid ethyl ester (obtained in step I) and stirred for 10-14 hours. After completion, the reaction mixture was filtered; the filtrate was concentrated to obtain a residue which was dissolved in ethyl acetate; this solution was washed with water followed by brine solution, dried over anhydrous sodium sulfate, solvent was removed under reduced pressure to provide a crude product which was purified by column chromatography to provide the compound A1-II.

¹H NMR (400 MHz, CDCl₃): δ 1.03-1.10 (m, 2H), 1.24 (t, J=7.2 Hz, 3H), 1.36-1.41 (m, 2H), 2.46-2.50 (m, 1H), 4.19-4.26 (m, 2H), 5.66 (s, 1H), 6.77-6.81 (m, 1H), 6.88-6.93 (m, 1H), 6.97-7.03 (m, 1H), 7.80 (d, J=8.4 Hz, 2H), 7.96 (d, J=8.4 Hz, 2H).

MS (EI) m/z: 397 (M+1).

Step III: Synthesis of 2-(4-cyclopropanesulfonylphenyl)-2-(2,4-difluorophenoxy)acetic acid (A1-III)

To a stirred solution of A1-II (obtained in step II) in tetrahydrofuran, was added aqueous solution of NaOH at room temperature and stirred for 4 h. After completion of reaction, THF was removed under reduced pressure. The residue was washed with diethyl ether. The aqueous layer was acidified using HCl and was extracted with ethyl acetate. The organic layer was washed with brine and dried over anhydrous sodium sulfate; solvent was evaporated under reduced pressure to obtain the desired compound A1-III.

¹H NMR (400 MHz, CDCl₃): δ 1.06-1.09 (m, 2H), 1.36-1.39 (m, 2H), 2.46-2.49 (m, 1H), 5.69 (s, 1H), 6.78-6.79 (m, 1H), 6.91-6.99 (m, 2H), 7.80 (d, J=8.0 Hz, 2H), 7.96 (d, J=8.4 Hz, 2H).

MS (EI) m/z: 369 (M+1)

Step IV: Synthesis of 2-(4-cyclopropanesulfonylphenyl)-2-(2,4-difluorophenoxy)-N-thiazol-2-yl-acetamide (A1)

Procedure-A: To a mixture of 2-(4-cyclopropanesulfonylphenyl)-2-(2,4-difluorophenoxy)acetic acid (obtained in step III), 2-aminothiazole, HOBt, and EDCI, in methylene chloride, was added triethyl amine. The resulting mixture was stirred at room temperature overnight followed by dilution with methylene chloride. The reaction mixture was poured into water; organic layer was washed with water, brine, dried over sodium sulfate, and the organic solvent evaporated to get a residue which was purified by preparative TLC or column chromatoghaphy to provide the title compound.

Compound (A1) can also be prepared using procedure-B or procedure-C

Procedure-B: 2-(4-cyclopropanesulfonylphenyl)-2-(2,4-difluorophenoxy)acetic acid (obtained in step III) was dissolved in DCM. To this solution was added DMF and cooled to 0° C., followed by the addition of oxalyl chloride under stirring. To this mixture, a solution of 2-aminothiazole and pyridine in DCM was added drop wise at 0° C. and was stirred further for 4 h. at room temperature. The reaction mixture was poured into 1N aqueous HCl under stirring, organic layer was again washed with 1N HCl, followed by 5% brine, dried over anhydrous sodium sulfate, solvent was removed under reduced pressure to get the crude compound which was purified by flash chromatography to get the title product.

Procedure-C: 2-(4-cyclopropanesulfonylphenyl)-2-(2,4-difluorophenoxy)acetic acid (1 equi) (obtained in step III) and HATU (1.5 equi) was dissolved in DCM. To this solution was added DIPEA (2 equi.) and stirred for 15 minutes followed by addition of 2-aminothiazole (1 equi.) and continued to stir over night at room temperature. Reaction mixture was diluted with dichloromethane, washed with water, brine, dried over anhydrous sodium sulfate, solvent was removed under reduced pressure to get the crude compound which was purified by flash chromatography to get the title product.

$^1$H NMR (400 MHz, CDCl$_3$): δ 1.03-1.05 (m, 2H), 1.33-1.36 (m, 2H), 2.40-2.46 (m, 1H), 5.76 (s, 1H), 6.75-6.77 (m, 1H), 6.84-6.95 (m, 2H), 7.04 (d, J=3.2 Hz, 1H), 7.51 (d, J=3.6 Hz, 1H), 7.77 (d, J=8.4 Hz, 2H), 7.94 (d, J=8.4 Hz, 2H). MS (EI) m/z: 450.9(M+1)

Examples A2 to A73

Were Prepared in Analogues Manner of Example (A1) from the Appropriate Intermediate that are Available Commercially or Synthesized as Above

| Example No. | MS (EI) m/z: (M + 1). | IUPAC Name |
| --- | --- | --- |
| A2 | 484.9 | N-(5-Chlorothiazol-2-yl)-2-(4-cyclopropanesulfonylphenyl)-2-(2,4-difluorophenoxy)acetamide |
| A3 | 468.9 | 2-(4-Cyclopropanesulfonylphenyl)-2-(2,4-difluorophenoxy)-N-(5-fluorothiazol-2-yl)-acetamide |
| A4 | 432.9 | 2-(4-Cyclopropanesulfonylphenyl)-2-(4-fluorophenoxy)-N-thiazol-2-yl-acetamide |
| A5 | 448.9 | 2-(4-Chlorophenoxy)-2-(4-cyclopropanesulfonylphenyl)-N-thiazol-2-yl-acetamide |
| A6 | 466.8 | 2-(3-Chloro-4-fluorophenoxy)-2-(4-cyclopropanesulfonylphenyl)-N-thiazol-2-yl-acetamide |
| A7 | 466.8 | N-(5-Chlorothiazol-2-yl)-2-(4-cyclopropanesulfonylphenyl)-2-(4-fluoro-phenoxy)acetamide |
| A8 | 484.8 | 2-(4-Chlorophenoxy)-N-(5-chlorothiazol-2-yl)-2-(4-cyclopropanesulfonylphenyl)acetamide |
| A9 | 502.8 | 2-(3-Chloro-4-fluorophenoxy)-N-(5-chlorothiazol-2-yl)-2-(4-cyclopropanesulfonylphenyl)acetamide |
| A10 | 478.9 | 2-(4-Cyclopentanesulfonylphenyl)-2-(2,4-difluorophenoxy)-N-thiazol-2-yl-acetamide |
| A11 | 496.9 | 2-(4-Cyclopentanesulfonylphenyl)-2-(2,4-difluorophenoxy)-N-(5-fluoro-thiazol-2-yl)acetamide |
| A12 | 476.8 | 2-(4-Chlorophenoxy)-2-(4-cyclopentanesulfonylphenyl)-N-thiazol-2-yl-acetamide |
| A13 | 466.8 | 2-(4-Chlorophenoxy)-2-(4-cyclopropanesulfonylphenyl)-N-(5-fluoro-thiazol-2-yl)acetamide |
| A14 | 464.9 | 2-(4-Cyclopropanesulfonylphenyl)-2-(2,4-difluorophenoxy)-N-(5-methyl-thiazol-2-yl)acetamide |
| A15 | 464.9 | 2-(4-Cyclopropanesulfonylphenyl)-2-(2,4-difluorophenoxy)-N-(4-methyl-thiazol-2-yl)acetamide |
| A16 | 452.0 | 2-(4-Cyclopropanesulfonylphenyl)-2-(2,4-difluorophenoxy)-N-[1,3,4]thiadiazol-2-yl-acetamide |
| A17 | 451.0 | 2-(4-Cyclopropanesulfonylphenyl)-2-(3,4-difluorophenoxy)-N-thiazol-2-yl-acetamide |
| A18 | 451.0 | 2-(4-Cyclopropanesulfonylphenyl)-2-(4-fluorophenoxy)-N-(5-fluorothiazol-2-yl)acetamide |
| A19 | 485.0 | 2-(3-Chloro-4-cyclopropanesulfonylphenyl)-2-(2,4-difluorophenoxy)-N-thiazol-2-yl-acetamide |
| A20 | 503.0 | 2-(3-Chloro-4-cyclopropanesulfonylphenyl)-2-(2,4-difluorophenoxy)-N-(5-fluorothiazol-2-yl)acetamide |
| A21 | 474.1 | 2-(4-Cyclopentanesulfonylphenyl)-2-(2,4-difluorophenoxy)-N-pyrazin-2-yl-acetamide |
| A22 | NA | 2-(4-Chlorophenoxy)-2-(4-cyclopentanesulfonylphenyl)-N-(5-fluoro-thiazol-2-yl)acetamide |
| A23 | 493.0 | 2-(4-Cyclohexanesulfonylphenyl)-2-(2,4-difluorophenoxy)-N-thiazol-2-yl-acetamide |
| A24 | 547.0 | 2-(3-Chloro-4-cyclopentanesulfonylphenyl)-N-(5-chlorothiazol-2-yl)-2-(2,4-difluoro-phenoxy)acetamide |
| A25 | 513.0 | N-(5-Chlorothiazol-2-yl)-2-(4-cyclopentanesulfonylphenyl)-2-(2,4-difluorophenoxy)acetamide |
| A26 | 551.1 | 2-[2-(4-Cyclopentanesulfonylphenyl)-2-(2,4-difluorophenoxy)-acetylamino]-thiazole-4-carboxylic acid ethyl ester |
| A27 | 480.0 | 2-(4-Cyclopentanesulfonylphenyl)-2-(2,4-difluorophenoxy)-N-[1,3,4]thiadiazol-2-yl-acetamide |
| A28 | 472.0 | 2-(4-Cyclopropanesulfonylphenyl)-N-(5-fluorothiazol-2-yl)-2-(1H-indol-5-yloxy)acetamide |
| A29 | 490.0 | 2-(3-Acetylaminophenoxy)-2-(4-cyclopropanesulfonylphenyl)-N-(5-fluoro-thiazol-2-yl)acetamide |
| A30 | 478.9 | N-(5-Chloropyridin-2-yl)-2-(4-cyclopropanesulfonylphenyl)-2-(2,4-difluoro-phenoxy)acetamide |
| A31 | 434.0 | 2-(4-Cyclopropanesulfonylphenyl)-2-(2,4-difluorophenoxy)-N-(1H-pyrazol-3-yl)acetamide |

-continued

| Example No. | MS (EI) m/z: (M + 1). | IUPAC Name |
|---|---|---|
| A32 | 445.0 | 2-(4-Cyclopropanesulfonylphenyl)-2-(2,4-difluorophenoxy)-N-pyridin-2-yl-acetamide |
| A33 | 503.0 | 6-[2-(4-Cyclopropanesulfonylphenyl)-2-(2,4-difluorophenoxy)-acetylamino]nicotinic acid methyl ester |
| A34 | 581.2 | {2-[2-(4-Cyclopropanesulfonylphenyl)-2-(2,4-difluorohenoxy)-acetylamino]-5-ethoxy-thiazol-4-yl}acetic acid ethyl ester |
| A35 | 486.1 | 2-(4-Cyclopropanesulfonylphenyl)-2-(3-oxo-3,4-dihydro-2H-benzo[1,4]oxazin-7-yloxy)-N-thiazol-2-yl-acetamide |
| A36 | 531.0 | 2-(3-Chloro-4-cyclopentanesulfonylphenyl)-2-(2,4-difluorophenoxy)-N-(5-fluoro-thiazol-2-yl)acetamide |
| A37 | 496.1 | 2-(3-Chloro-4-cyclopentanesulfonylphenyl)-2-(2,4-difluorophenoxy)-N-(1H-pyrazol-3-yl)acetamide |
| A38 | 476.1 | 2-(4-Cyclopentanesulfonylphenyl)-2-(2,4-difluorophenoxy)-N-(1-methyl-1H-pyrazol-3-yl)acetamide |
| A39 | 503.0 | 2-(4-Chloro-2-fluorophenoxy)-N-(5-chlorothiazol-2-yl)-2-(4-cyclopropanesulfonylphenyl)acetamide |
| A40 | 467.0 | 2-(4-Chloro-2-fluorophenoxy)-2-(4-cyclopropanesulfonylphenyl)-N-thiazol-2-yl-acetamide |
| A41 | 494.8 | 2-(4-Chloro-2-fluorophenoxy)-N-(5-chloropyridin-2-yl)-2-(4-cyclopropanesulfonylphenyl)-acetamide |
| A42 | 484.8 | 2-(4-Chloro-2-fluorophenoxy)-2-(4-cyclopropanesulfonylphenyl)-N-(5-fluorothiazol-2-yl)acetamide |
| A43 | 480.8 | 2-(4-Chloro-2-fluorophenoxy)-2-(4-cyclopropanesulfonylphenyl)-N-(5-methylthiazol-2-yl)acetamide |
| A44 | 467.8 | 2-(4-Chloro-2-fluorophenoxy)-2-(4-cyclopropanesulfonylphenyl)-N-[1,3,4]thiadiazol-2-yl-acetamide |
| A45 | 449.8 | 2-(4-Chloro-2-fluorophenoxy)-2-(4-cyclopropanesulfonylphenyl)-N-(1H-pyrazol-3-yl)acetamide |
| A46 | 463.9 | 2-(4-Chloro-2-fluorophenoxy)-2-(4-cyclopropanesulfonylphenyl)-N-(1-methyl-1H-pyrazol-3-yl)acetamide |
| A47 | 461.9 | 2-(4-Chloro-2-fluorophenoxy)-2-(4-cyclopropanesulfonylphenyl)-N-pyrazin-2-yl-acetamide |
| A48 | NA | {2-[2-(4-Cyclopropanesulfonylphenyl)-2-(4-fluoro-phenoxy)acetylamino]-thiazol-4-yl}acetic acid ethyl ester |
| A49 | 570.8 | {5-Chloro-2-[2-(4-cyclopropanesulfonylphenyl)-2-(2,4-difluorophenoxy)-acetylamino]-thiazol-4-yl}acetic acid ethyl ester |
| A50 | 534.9 | {2-[2-(4-Chlorophenoxy)-2-(4-cyclopropanesulfonylphenyl)-acetylamino]-thiazol-4-yl}acetic acid ethyl ester |
| A51 | NA | {2-[2-(3-Chloro-4-fluorophenoxy)-2-(4-cyclopropanesulfonylphenyl)-acetylamino]thiazol-4-yl}acetic acid ethyl ester |
| A52 | NA | {5-Chloro-2-[2-(4-cyclopropanesulfonylphenyl)-2-(4-fluorophenoxy)acetylamino]-thiazol-4-yl}acetic acid ethyl ester |
| A53 | NA | {5-Chloro-2-[2-(4-chlorophenoxy)-2-(4-cyclopropanesulfonylphenyl)acetylamino]thiazol-4-yl}acetic acid ethyl ester |
| A54 | NA | {5-Chloro-2-[2-(3-chloro-4-fluorophenoxy)-2-(4-cyclopropanesulfonylphenyl)-acetylamino]thiazol-4-yl}acetic acid ethyl ester |
| A55 | NA | {5-Chloro-2-[2-(3-chloro-4-cyclopropanesulfonylphenyl)-2-(2,4-difluorophenoxy)-acetylamino]thiazol-4-yl}acetic acid ethyl ester |
| A56 | NA | {5-Chloro-2-[2-(4-cyclopentanesulfonyl-phenyl)-2-(2,4-difluoro-phenoxy)-acetylamino]-thiazol-4-yl}-acetic acid ethyl ester |
| A57 | 571.0 | {2-[2-(3-Chloro-4-cyclopropanesulfonylphenyl)-2-(2,4-difluorophenoxy)acetylamino]-thiazol-4-yl}acetic acid ethyl ester |
| A58 | 537.1 | {2-[2-(4-Cyclopropanesulfonylphenyl)-2-(2,4-difluorophenoxy)-acetylamino]thiazol-4-yl}acetic acid ethyl ester |
| A59 | 536.9 | 2-[2-(4-Cyclopropanesulfonylphenyl)-2-(2,4-difluorophenoxy)-acetylamino]-4-methylthiazole-5-carboxylic acid ethyl ester |
| A60 | NA | {5-Chloro-2-[2-(4-cyclopropanesulfonylphenyl)-2-(3,4-difluorophenoxy)-acetylamino]thiazol-4-yl}acetic acid ethyl ester |
| A61 | 565.1 | {2-[2-(4-Cyclopentanesulfonylphenyl)-2-(2,4-difluorophenoxy)-acetylamino]thiazol-4-yl}acetic acid ethyl ester |
| A62 | 613.1 | {5-Chloro-2-[2-(4-cyclohexanesulfonylphenyl)-2-(2,4-difluorophenoxy)acetylamino]-thiazol-4-yl}acetic acid ethyl ester |
| A63 | NA | {2-[2-(4-Cyclohexanesulfonyl-phenyl)-2-(2,-difluorophenoxy)acetylamino]thiazol-4-yl}acetic acid ethyl ester |
| A64 | 599.0 | {2-[2-(3-Chloro-4-cyclopentanesulfonylphenyl)-2-(2,4-difluorophenoxy)-acetylamino]thiazol-4-yl}acetic acid ethyl ester |
| A65 | NA | {5-Chloro-2-[2-(3-chloro-4-cyclopentanesulfonylphenyl)-2-(2,4-difluorophenoxy)acetylamino]thiazol-4-yl}acetic acid ethyl ester |
| A66 | 574.0 | {5-Chloro-2-[2-(4-cyclopropanesulfonyl-phenyl)-2-(1H-indol-5-yloxy)-acetylamino]-thiazol-4-yl}-acetic acid ethyl ester |
| A67 | 592.0 | {2-[2-(3-Acetylaminophenoxy)-2-(4-cyclopropanesulfonylphenyl)-acetylamino]-5-chlorothiazol-4-yl}acetic acid ethyl ester |

| Example No. | MS (EI) m/z: (M + 1). | IUPAC Name |
|---|---|---|
| A68 | 585.1 | 2-[2-(3-Chloro-4-cyclopentanesulfonylphenyl)-2-(2,4-difluorophenoxy)-acetylamino]thiazole-4-carboxylic acid ethyl ester |
| A69 | 552.8 | {2-[2-(4-Chloro-2-fluorophenoxy)-2-(4-cyclopropanesulfonylphenyl)acetylamino]thiazol-4-yl}acetic acid ethyl ester |
| A70 | 588.8 | {5-Chloro-2-[2-(4-chloro-2-fluorophenoxy)-2-(4-cyclopropanesulfonylphenyl)-acetylamino] thiazol-4-yl}acetic acid ethyl ester |
| A71 | 539.8 | 2-[2-(4-Chloro-2-fluorophenoxy)-2-(4-cyclopropanesulfonylphenyl)-acetylamino]thiazole-4-carboxylic acid ethyl ester |
| A72 | NA | {2-[2-(4-Cyclopropanesulfonylphenyl)-2-(2,4-difluorophenoxy)acetylamino}-thiazol-4-ylsulfanyl}acetic acid ethyl ester |
| A73 | 551.2 | 3-{2-[2-(4-Cyclopropanesulfonyl-phenyl)-2-(2,4-difluorophenoxy)acetylamino]-thiazol-4-yl}propionic acid ethyl ester |

Example A74

4-{2-[2-(4-Cyclopropanesulfonyl-phenyl)-2-(2,4-difluoro-phenoxy)-acetylamino]-thiazol-5-yloxy}-benzoic acid methyl ester

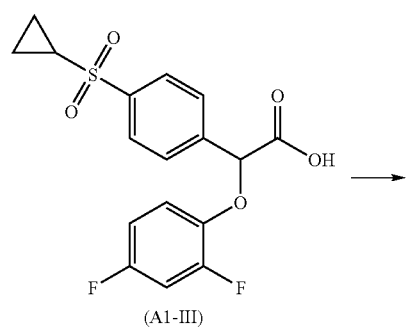

(A1-III)

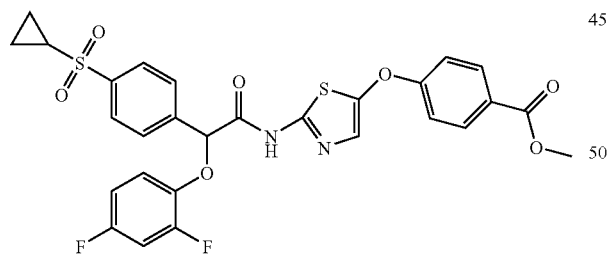

compound A1-III obtained similar to example A1:

To a mixture of 2-(4-cyclopropanesulfonylphenyl)-2-(2,4-difluorophenoxy)acetic acid (A1-III) (2 g, 5.43 mmol) & HATU (3.1 g, 8.14 mmol) in anhydrous DCM (50 mL) was added TEA (1.65 g, 16.3 mmol) & reaction mixture was kept on stirring at room temperature for 0.5 hours. To this solution was added 4-(2-Amino-thiazol-5-yloxy)-benzoic acid methyl ester (1.36 g, 5.43 mmol) and stirring was continued for another 2 hrs. The reaction mixture was quenched with 1N HCL & diluted with DCM. The organic layer was separated washed with water, brine and dried over sodium sulfate filtered and concentrated under reduced pressure to get a residue which was purified by column chromatography using 50-60% ethylacetate in hexane as eluent to provide the title compound (1.7 g).

1H NMR-(CDCl$_3$), δ 1.05-1.19 (m, 4H), 2.88 (m, 1H), 3.83 (s, 3H), 6.2 (s, 1H), 7.05-7.40 (m, 6H), 7.88-8.01 (m, 5H), 12.97 (s, 1H) MS (El) m/z: 601 (M+1)

Example A75

2-(4-Cyclopropanesulfonyl-phenyl)-2-(2,4-difluoro-phenoxy)-N-(5-methoxy-thiazol-2-yl)-acetamide

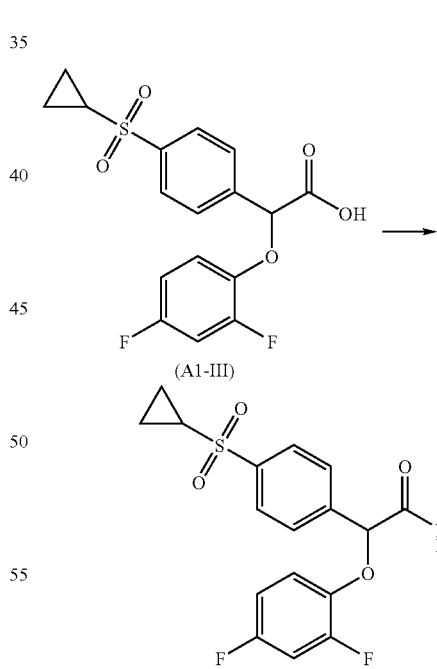

To a mixture of 2-(4-cyclopropanesulfonylphenyl)-2-(2,4-difluorophenoxy)acetic acid (0.1 g, 0.27 mmol), 5-methoxy-thiazol-2-ylamine (0.042 g, 0.33 mmol), HOBt (0.044 g, 0.33 mmol), and EDCI (0.062 g, 0.33 mmol), in DMF (10 mL), was added N-methyl morpholine (0.034 g, 0.33 mmom). The resulting mixture was stirred at room temperature overnight followed by dilution with DCM. The reaction mixture was poured into water; organic layer was washed with water, brine, dried over sodium sulfate, and the organic solvent evaporated to get a residue which was purified by column chromatoghaphy using 40-50% ethylacetate in hexane as eluent to provide the title compound (0.045 g).

¹H NMR (DMSO-d₆, 400 MHz): δ 1.02-1.08 (m, 2H), 1.09-1.15 (m, 2H), 2.82-2.92 (m, 1H), 3.82 (s, 3H), 6.15 (s, 1H), 6.89 (s, 1H), 7.04-7.12 (m, 2H), 7.36-7.40 (m, 1H), 7.87 (d, J=8.4 Hz, 2H), 7.99 (d, J=8.4 Hz, 2H). MS (EI) m/z: 480.9 (M+1).

Example A76:

4-{2-[2-(4-Cyclopropanesulfonyl-phenyl)-2-(tetrahydro-pyran-4-yloxy)-acetylamino]-thiazol-5-yloxy}-benzoic acid methyl ester

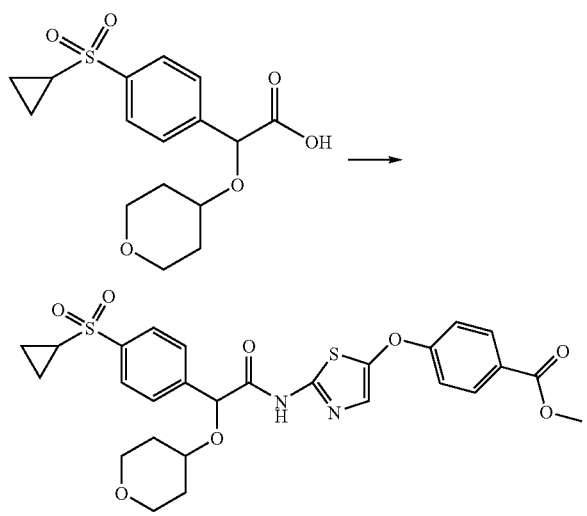

The compound of example A76 was obtained by similar method described in example A75 using (4-Cyclopropanesulfonyl-phenyl)-[(tetrahydro-pyran-4-yloxy)]-acetic acid (Preparation 14) (0.5 g, 1.47 mmol), 4-(2-Amino-thiazol-5-yloxy)-benzoicacid methyl ester (0.441 g, 1.76 mmol), HOBt (0.237 g, 1.76 mmol), and EDCI (0.337 g, 1.76 mmol), N-methyl morpholine (0.178 g, 1.76 mmom) in DMF (10 mL) to provide the title compound (280 mg).

Example A77

4-(2-{2-(4-Cyclopropanesulfonyl-phenyl)-2-[(R)-(tetrahydro-furan-3-yl)oxy]-acetylamino}-thiazol-5-yloxy)-benzoic acid methyl ester

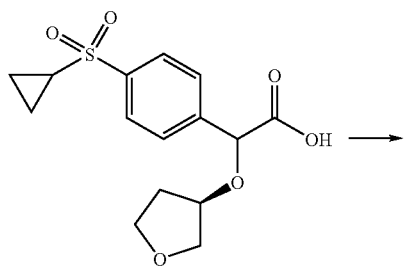

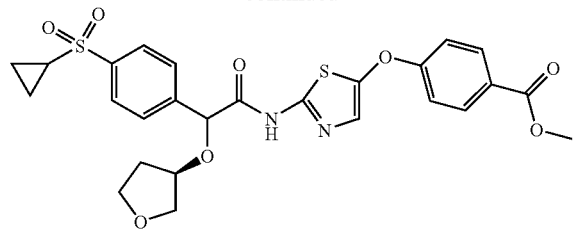

The compound of example A77 was obtained by similar method described in example A75 using (4-Cyclopropanesulfonyl-phenyl)-[(R)-(tetrahydro-furan-3-yl)oxy]-acetic acid (preparation 15) (0.150 g, 0.46 mmol), 4-(2-Aminothiazol-5-yloxy)-benzoicacid methyl ester (0.140 g, 0.55 mmol), HOBt (0.075 g,0.55 mmol), and EDCI (0.106 g, 0.55 mmol), N-methyl morpholine (0.055 g, 0.55 mmom) in DMF (10 mL) to provide the title compound (185 mg).

¹H NMR (CDCl₃, 400 MHz): δ-1.04-1.07 (m, 2H), 1.34-1.37 (m, 2H), 1.68-1.79 (m, 2H), 1.85-1.90 (m, 1H), 2.02-2.10 (m, 1H), 2.42-2.47 (m, 1H), 3.34-3.43 (m, 2H), 3.65-3.70 (m, 1H), 3.90 (s, 3H), 3.93-4.02 (m, 2H), 5.21 (s, 1H), 7.06 (d, J=7.2 Hz, 2H), 7.15 (s, 1H), 7.68 (d, J=7.6 Hz, 2H), 7.93 (d, J=8.4 Hz, 2H), 7.99 (d, J=7.2 Hz, 2H).

MS (EI) m/z: 572.8 (M+1).

Example A78

2-(2,4-Difluoro-phenoxy)-2-[4-(piperidine-1-sulfonyl)-phenyl]-N-thiazolo[5,4-b]pyridin-2-yl-acetamide

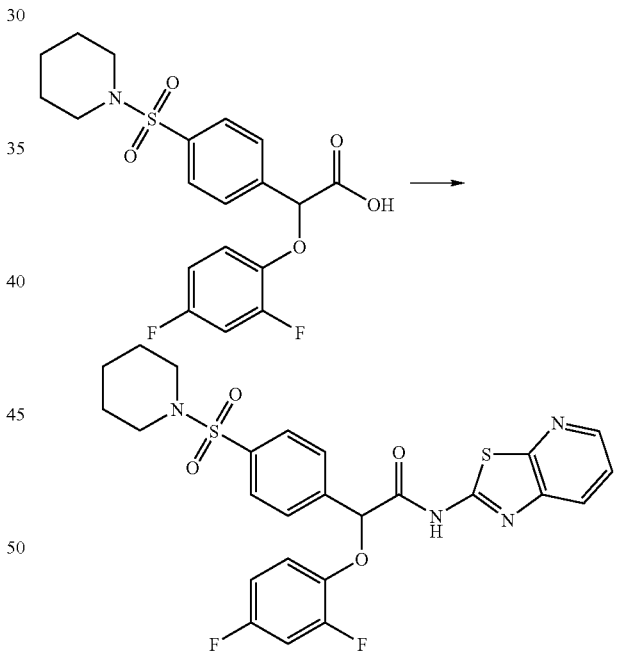

The compound of example A78 was obtained by similar method described in example A75 using (2,4-Difluoro-phenoxy)-[4-(piperidine-1-sulfonyl)-phenyl]-acetic acid (Preparation 2) (0.1 g, 0.27 mmol), thiazolo[5,4-b]pyridin-2-ylamine (0.042 g, 0.33 mmol), HOBt (0.044 g, 0.33 mmol), and EDCI (0.062 g, 0.33 mmol), N-methyl morpholine (0.034 g, 0.33 mmom) in DMF (10 mL) to provide the title compound (0.175 g).

¹H NMR (400 MHz, DMSO- d₆):-δ 1.34 (bs, 2H), 1.53 (bs, 4H), 2.90 (bs, 4H), 6.27 (s, 1H), 7.02-7.06 (m, 1H), 7.14-7.20 (m, 1H), 7.36-7.41 (m, 1H), 7.50-7.53 (m, 1H), 7.84 (d, J=8.0 Hz, 2H), 7.91 (d, J=8.0 Hz, 2H), 8.14 (d, J=8.0 Hz, 1H), 8.49 (d, J=4.4 Hz, 1H).

MS (EI) m/z: 545.0 (M+1).

Example A79

2-(4-Cyclopropanesulfonyl-phenyl)-2-(tetrahydro-pyran-4-yloxy)-N-thiazolo[5,4-b]pyridin-2-yl-acetamide

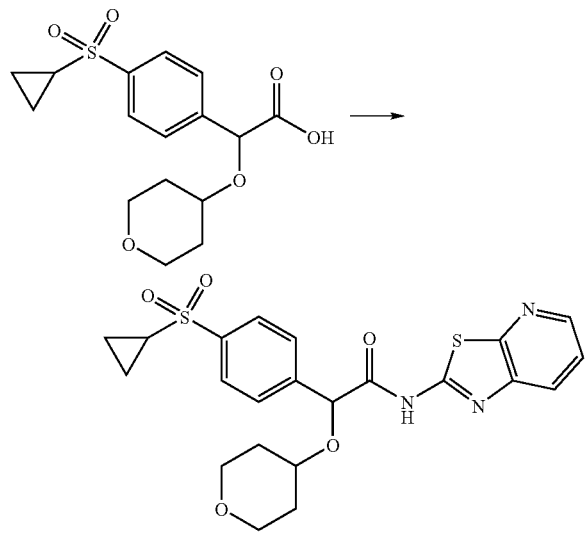

The compound of example A79 was obtained by similar method described in example A75 using (4-cyclopropane-sulfonyl-phenyl)-[(tetrahydro-pyran-4-yloxy)]-acetic acid (Preparation 14) (0.2 g, 0.58 mmol), thiazolo[5,4-b]pyridin-2-ylamine (0.133 g, 0.88 mmol), HOBt (0.119 g, 0.88 mmol), and EDCI (0.168 g, 0.88 mmol), N-methyl morpholine (0.178 g, 0.88 mmol) in DMF (10 mL) to provide the title compound (0.175 g).

$^1$H NMR (400 MHz, DMSO-$d_6$):–δ 1.00-1.04 (m, 2H), 1.05-1.15 (m, 2H), 1.46-1.61 (m, 2H), 1.62-1.96 (m, 2H), 2.83-2.86 (m, 1H), 3.28-3.34 (m, 2H), 3.65-3.76 (m, 1H), 3.78-3.85 (m, 2H), 5.55 (s, 1H), 7.48 (dd, J=4.4 Hz, J=8.0 Hz, 1H), 7.79 (d, J=8.4 Hz, 2H), 7.92 (d, J=8.4 Hz, 2H), 8.12 (d, J=8.0 Hz, 1H), 8.46(dd, J=1.6 Hz, J=4.8 Hz, 1H), 12.80 (s, 1H).

MS (EI) m/z: 474.20 (M+1).

Example A80

2-(4-Cyclopropanesulfonyl-phenyl)-N-(5-methoxy-thiazolo[5,4-b]pyridin-2-yl)-2-(tetrahydro-pyran-4-yloxy)-acetamide

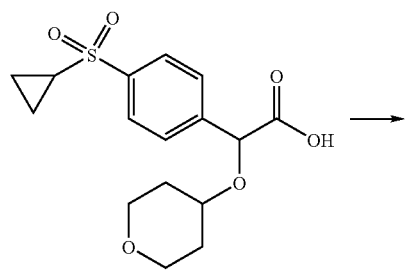

-continued

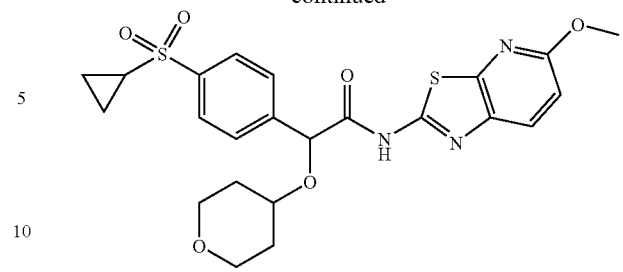

The compound of example A80 was obtained by similar method described in example A75 using (4-cyclopropane-sulfonyl-phenyl)-[(tetrahydro-pyran-4-yloxy)]-acetic acid (Preparation 14) (0.5 g,1.32 mmol), 5-methoxy-thiazolo[5,4-b]pyridin-2-ylamine (0.286 g, 1.59 mmol), HOBt (0.267 g, 1.98 mmol), and EDCI (0.378 g,1.98 mmol), N-methyl morpholine (0.4 g, 3.97 mmol) in DMF (10 mL) to provide the title compound (0.280 g).

$^1$H NMR (400 MHz, DMSO-$d_6$):–δ 1.02-1.06 (m, 2H), 1.11-1.14 (m, 2H), 1.49-1.63 (m, 2H), 1.85-1.99 (m, 2H), 2.82-2.89 (m, 1H), 3.29-3.36 (m, 2H), 3.65-3.72 (m, 1H), 3.78-3.86 (m, 2H), 3.90 (s, 3H), 5.54 (s, 1H), 6.93 (d, J=8.8 Hz, 1H), 7.80 (d, J=8.8 Hz, 2H), 7.94 (d, J=8.4 Hz, 2H), 8.06 (d, J=8.8 Hz, 1H), 12.70 (s, 1H).

MS (EI) m/z: 504.10 (M+1).

Example A81

2-(4-Cyclopropanesulfonyl-phenyl)-N-(5-ethoxy-thiazolo[5,4-b]pyridin-2-yl)-2-(tetrahydro-pyran-4-yloxy)-acetamide

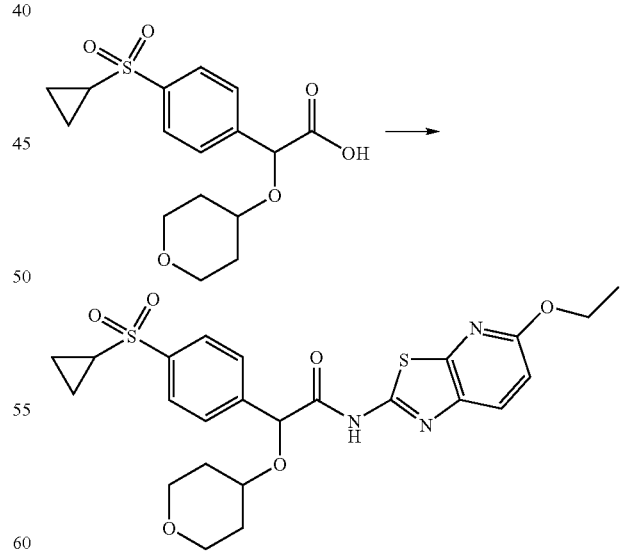

The compound of example A81 was obtained by similar method described in example A75 using (4-cyclopropane-sulfonyl-phenyl)-[(tetrahydro-pyran-4-yloxy)]-acetic acid (Preparation 14) (0.25 g, 0.73 mmol), 5-ethoxy-thiazolo[5,4-b]pyridin-2-ylamine (0.157 g, 0.80 mmol), HOBt (0.148 g, 1.10 mmol), and EDCI (0.210 g, 1.10 mmol), N-methyl morpholine (0.22, 2.20 mmol) in DMF (5 mL) to provide the title compound (0.140 g).

$^1$H NMR (400 MHz, DMSO-d$_6$):−δ 1.00-1.04 (m, 2H), 1.05-1.13 (m, 2H), 1.35 (t, J=7.2 Hz, 3H), 1.50-1.60 (m, 2H), 1.85-1.97 (m, 2H), 2.84-2.89 (m, 1H), 3.29-3.34 (m, 2H), 3.65-3.71 (m, 1H), 3.78-3.86 (m, 2H), 4.33 (q, J=7.2 Hz, 2H), 5.54 (s, 1H), 6.90 (d, J=8.8 Hz, 1H), 7.80 (d, J=8.4 Hz, 2H), 7.94 (d, J=8.0 Hz, 2H), 8.05 (d, J=8.8 Hz, 1H), 12.70 (s, 1H). MS (EI) m/z: 518.00 (M+1).

Example A82

2-(4-Cyclopropanesulfonyl-phenyl)-N-(5-isopropoxy-thiazolo[5,4-b]pyridin-2-yl)-2-(tetrahydro-pyran-4-yloxy)-acetamide

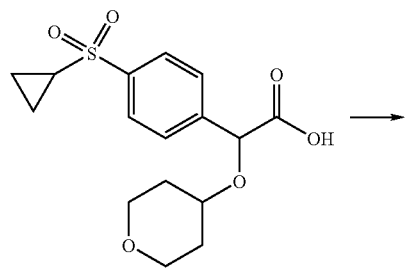

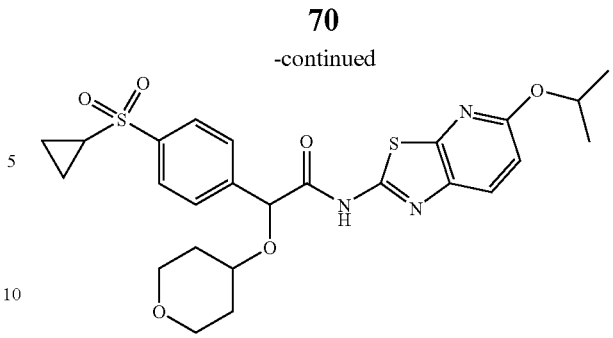

The compound of example A82 was obtained by similar method described in example A75 using (4-cyclopropanesulfonyl-phenyl)-[(tetrahydro-pyran-4-yloxy)]-acetic acid (Preparation 14) (0.100 g,0.29 mmol), 5-iso-propoxy-thiazolo[5,4-b]pyridin-2-ylamine (0.067 g, 0.32 mmol), HOBt (0.047 g, 0.35 mmol), and EDCI (0.067 g, 0.35 mmol), N-methyl morpholine (0.065 g, 0.58 mmol) in DMF (5 mL) to provide the title compound (0.060 g).

$^1$H NMR (DMSO-d$_6$, 400 MHz): δ 1.01-1.10 (m, 2H), 1.11-1.18 (m, 2H), 1.30 (d, 6H), 1.50-1.60 (m 2H), 1.85-1.96 (m, 2H), 2.70-2.84 (m, 1H), 3.35-3.40 (m, 2H), 3.61-3.72 (m, 1H), 3.79-3.85 (m, 2H), 5.24-5.27 (m, 1H), 5.54 (s, 1H), 6.84 (d, J=8.8 Hz, 1H), 7.80 (d, J=8.4 Hz, 2H), 7.94 (d, J=8.4 Hz, 2H), 8.03 (d, J=8.8 Hz, 1H).

MS (EI) m/z: 532.2 (M+1).

Examples A83 to A192

Were Prepared in Analogues Manner of Examples A74-A82 from the Appropriate Intermediate that are Available Commercially or Synthesized as Above

| Example No. | MS (EI) m/z: (M + 1). | IUPAC Name |
| --- | --- | --- |
| A83 | 512.0 | 2-(2,4-Difluoro-phenoxy)-N-(5-fluoro-thiazol-2-yl)-2-[4-(piperidine-1-sulfonyl)-phenyl]-acetamide |
| A84 | 528.0 | N-(5-Chloro-thiazol-2-yl)-2-(2,4-difluoro-phenoxy)-2-[4-(piperidine-1-sulfonyl)-phenyl]-acetamide |
| A85 | 512.0 | 2-(2,4-Difluoro-phenoxy)-N-(5-fluoro-thiazol-2-yl)-2-[3-(piperidine-1-sulfonyl)-phenyl]-acetamide |
| A86 | 527.9 | N-(5-Chloro-thiazol-2-yl)-2-(2,4-difluoro-phenoxy)-2-[3-(piperidine-1-sulfonyl)-phenyl]-acetamide |
| A87 | 498 | 2-(2,4-Difluoro-phenoxy)-N-(5-fluoro-thiazol-2-yl)-2-[3-(pyrrolidine-1-sulfonyl)-phenyl]-acetamide |
| A88 | 498 | 2-(2,4-Difluoro-phenoxy)-N-(5-fluoro-thiazol-2-yl)-2-[4-(pyrrolidine-1-sulfonyl)-phenyl]-acetamide |
| A89 | 514 | N-(5-Chloro-thiazol-2-yl)-2-(2,4-difluoro-phenoxy)-2-[3-(pyrrolidine-1-sulfonyl)-phenyl]-acetamide |
| A90 | 514 | N-(5-Chloro-thiazol-2-yl)-2-(2,4-difluoro-phenoxy)-2-[4-(pyrrolidine-1-sulfonyl)-phenyl]-acetamide |
| A91 | 499.90 | 2-[3-(Azetidine-1-sulfonyl)-phenyl]-N-(5-chloro-thiazol-2-yl)-2-(2,4-difluoro-phenoxy)-acetamide |
| A92 | 500.00 | 2-[4-(Azetidine-1-sulfonyl)-phenyl]-N-(5-chloro-thiazol-2-yl)-2-(2,4-difluoro-phenoxy)-acetamide |
| A93 | 484.00 | 2-[4-(Azetidine-1-sulfonyl)-phenyl]-2-(2,4-difluoro-phenoxy)-N-(5-fluoro-thiazol-2-yl)-acetamide |
| A94 | 514.2 | 2-(2,4-Difluoro-phenoxy)-N-(5-fluoro-thiazol-2-yl)-2-[4-(morpholine-4-sulfonyl)-phenyl]-acetamide |
| A95 | 530.1 | N-(5-Chloro-thiazol-2-yl)-2-(2,4-difluoro-phenoxy)-2-[4-(morpholine-4-sulfonyl)-phenyl]-acetamide |
| A96 | 477.0 | 2-(2,4-Difluoro-phenoxy)-2-[4-(piperidine-1-sulfonyl)-phenyl]-N-(1H-pyrazol-3-yl)-acetamide |
| A97 | 477.0 | 2-(4-Chloro-phenoxy)-2-[4-(morpholine-4-sulfonyl)-phenyl]-N-(1H-pyrazol-3-yl)-acetamide |
| A98 | 475.0 | 2-(4-Chloro-phenoxy)-2-[4-(piperidine-1-sulfonyl)-phenyl]-N-(1H-pyrazol-3-yl)-acetamide |
| A99 | 579.3 | 2-(2,4-Difluoro-phenoxy)-N-(5-morpholin-4-yl-thiazol-2-yl)-2-[4-(piperidine-1-sulfonyl)-phenyl]-acetamide |

| Example No. | MS (EI) m/z: (M + 1). | IUPAC Name |
|---|---|---|
| A100 | 491.3 | 2-(2,4-Difluoro-phenoxy)-N-(1-methyl-1H-pyrazol-3-yl)-2-[4-(piperidine-1-sulfonyl)-phenyl]-acetamide |
| A101 | 493.3 | 2-(2,4-Difluoro-phenoxy)-N-(1-methyl-1H-pyrazol-3-yl)-2-[4-(morpholine-4-sulfonyl)-phenyl]-acetamide |
| A102 | 491.3 | 2-(2,4-Difluoro-phenoxy)-2-[4-(morpholine-4-sulfonyl)-phenyl]-N-pyrazin-2-yl-acetamide |
| A103 | 565.3 | 2-(2,4-Difluoro-phenoxy)-N-(5-morpholin-4-yl-thiazol-2-yl)-2-[4-(pyrrolidine-1-sulfonyl)-phenyl]-acetamide |
| A104 | 547.2 | 2-(2,4-Difluoro-phenoxy)-2-[4-(morpholine-4-sulfonyl)-phenyl]-N-thiazolo[5,4-b]pyridin-2-yl-acetamide |
| A105 | 531.0 | 2-(2,4-Difluoro-phenoxy)-2-[4-(pyrrolidine-1-sulfonyl)-phenyl]-N-thiazolo[5,4-b]pyridin-2-yl-acetamide |
| A106 | 612.30 | 2-(4-Cyclopropanesulfonyl-phenyl)-2-(2,4-difluoro-phenoxy)-N-[5-(5-trifluoromethyl-pyridin-2-yloxy)-thiazol-2-yl]-acetamide |
| A107 | 536.30 | 2-(4-Cyclopropanesulfonyl-phenyl)-2-(2,4-difluoro-phenoxy)-N-(5-morpholin-4-yl-thiazol-2-yl)-acetamide |
| A108 | 502.30 | 2-(4-Cyclopropanesulfonyl-phenyl)-2-(2,4-difluoro-phenoxy)-N-thiazolo[5,4-b]pyridin-2-yl-acetamide |
| A109 | 445.70 | 2-(4-Cyclopropanesulfonyl-phenyl)-2-(2,4-difluoro-phenoxy)-N-pyrazin-2-yl-acetamide |
| A110 | 516.9 | 2-(4-Cyclopropanesulfonyl-phenyl)-2-(2,4-difluoro-phenoxy)-N-(5-pyrazol-1-yl-thiazol-2-yl)-acetamide |
| A111 | 531.8 | 2-(4-Cyclopropanesulfonyl-phenyl)-2-(2,4-difluoro-phenoxy)-N-(5-methoxy-thiazolo[5,4-b]pyridin-2-yl)-acetamide |
| A112 | 489.00 | 2-(4-Cyclopropanesulfonyl-phenyl)-N-(5-pyrazol-1-yl-thiazol-2-yl)-2-(tetrahydro-pyran-4-yloxy)-acetamide |
| A113 | 508.00 | 2-(4-Cyclopropanesulfonyl-phenyl)-N-(5-morpholin-4-yl-thiazol-2-yl)-2-(tetrahydro-pyran-4-yloxy)-acetamide |
| A114 | 440.90 | 2-(4-Cyclopropanesulfonyl-phenyl)-N-(5-fluoro-thiazol-2-yl)-2-(tetrahydro-pyran-4-yloxy)-acetamide |
| A115 | 420.1 | 2-(4-Cyclopropanesulfonyl-phenyl)-N-(1-methyl-1H-pyrazol-3-yl)-2-(tetrahydro-pyran-4-yloxy)-acetamide |
| A116 | 417.5 | 2-(4-Cyclopropanesulfonyl-phenyl)-N-pyrazin-2-yl-2-(tetrahydro-pyran-4-yloxy)-acetamide |
| A117 | 540.00 | N-[5-(4-Cyano-phenoxy)-thiazol-2-yl]-2-(4-cyclopropanesulfonyl-phenyl)-2-(tetrahydro-pyran-4-yloxy)-acetamide |
| A118 | 452.9 | 2-(4-Cyclopropanesulfonyl-phenyl)-N-(5-methoxy-thiazol-2-yl)-2-(tetrahydro-pyran-4-yloxy)-acetamide |
| A119 | NA | (5-Chloro-2-{2-(2,4-difluoro-phenoxy)-2-[4-(piperidine-1-sulfonyl)-phenyl]-acetylamino}-thiazol-4-yl)-acetic acid ethyl ester |
| A120 | NA | 4-{2-[2-(4-Cyclopropanesulfonyl-phenyl)-2-(2,4-difluoro-phenoxy)-acetylamino]-thiazol-4-yl}-benzoic acid methyl ester |
| A121 | NA | {3-[2-(4-Cyclopropanesulfonyl-phenyl)-2-(2,4-difluoro-phenoxy)-acetylamino]-pyrazol-1-yl}-acetic acid ethyl ester |
| A122 | NA | 4-(2-{2-(2,4-Difluoro-phenoxy)-2-[4-(morpholine-4-sulfonyl)-phenyl]-acetylamino}-thiazol-5-yloxy)-benzoic acid methyl ester |
| A123 | 616.2 | (5-Chloro-2-{2-(2,4-difluoro-phenoxy)-2-[4-(morpholine-4-sulfonyl)-phenyl]-acetylamino}-thiazol-4-yl)-acetic acid ethyl ester |
| A124 | NA | 3-(2-{2-(2,4-Difluoro-phenoxy)-2-[4-(morpholine-4-sulfonyl)-phenyl]-acetylamino}-thiazol-5-yloxy)-benzoic acid methyl ester |
| A125 | 635.4 | 1-(2-{2-(2,4-Difluoro-phenoxy)-2-[4-(pyrrolidine-1-sulfonyl)-phenyl]-acetylamino}-thiazol-5-yl)-piperidine-4-carboxylic acid ethyl ester |
| A126 | 630.3 | 4-(2-{2-(2,4-Difluoro-phenoxy)-2-[4-(pyrrolidine-1-sulfonyl)-phenyl]-acetylamino}-thiazol-5-yloxy)-benzoic acid methyl ester |
| A127 | 630.3 | 3-(2-{2-(2,4-Difluoro-phenoxy)-2-[4-(pyrrolidine-1-sulfonyl)-phenyl]-acetylamino}-thiazol-5-yloxy)-benzoic acid methyl ester |
| A128 | 600 | (5-Chloro-2-{2-(2,4-difluoro-phenoxy)-2-[3-(pyrrolidine-1-sulfonyl)-phenyl]-acetylamino}-thiazol-4-yl)-acetic acid ethyl ester |
| A129 | 586.00 | {2-[2-[3-(Azetidine-1-sulfonyl)-phenyl]-2-(2,4-difluoro-phenoxy)-acetylamino]-5-chloro-thiazol-4-yl}-aceticacid ethyl ester |
| A130 | 586.00 | {2-[2-[4-(Azetidine-1-sulfonyl)-phenyl]-2-(2,4-difluoro-phenoxy)-acetylamino]-5-chloro-thiazol-4-yl}-acetic acid |
| A131 | NA | (5-Chloro-2-{2-(4-chloro-phenoxy)-2-[4-(piperidine-1-sulfonyl)-phenyl]-acetylamino}-thiazol-4-yl)-acetic acid ethyl ester |

-continued

| Example No. | MS (EI) m/z: (M + 1). | IUPAC Name |
|---|---|---|
| A132 | NA | (5-Chloro-2-{2-(4-chloro-2-fluoro-phenoxy)-2-[4-(piperidine-1-sulfonyl)-phenyl]-acetylamino}-thiazol-4-yl)-acetic acid ethyl ester |
| A133 | NA | (5-Chloro-2-{2-(4-chloro-phenoxy)-2-[4-(morpholine-4-sulfonyl)-phenyl]-acetylamino}-thiazol-4-yl)-acetic acid ethyl ester |
| A134 | NA | 3-(2-{2-(4-Chloro-phenoxy)-2-[4-(piperidine-1-sulfonyl)-phenyl]-acetylamino}-thiazol-5-yloxy)-benzoic acid methyl ester |
| A135 | NA | 4-(2-{2-(4-Chloro-phenoxy)-2-[4-(piperidine-1-sulfonyl)-phenyl]-acetylamino}-thiazol-5-yloxy)-benzoic acid methyl ester |
| A136 | NA | 1-(2-{2-(2,4-Difluoro-phenoxy)-2-[4-(piperidine-1-sulfonyl)-phenyl]-acetylamino}-thiazol-5-yl)-iperidine-4-carboxylic acid ethyl ester |
| A137 | 634.1 | (5-Chloro-2-{2-(4-chloro-2-fluoro-phenoxy)-2-[4-(morpholine-4-sulfonyl)-phenyl]-acetylamino}-thiazol-4-yl)-acetic acid ethyl eter |
| A138 | 644.2 | 4-(2-{2-(2,4-Difluoro-phenoxy)-2-[4-(piperidine-1-sulfonyl)-phenyl]-acetylamino}-thiazol-5-yloxy)-benzoic acid methyl ester |
| A139 | 644.2 | 3-(2-{2-(2,4-Difluoro-phenoxy)-2-[4-(piperidine-1-sulfonyl)-phenyl]-acetylamino}-thiazol-5-yloxy)-benzoic acid methyl ester |
| A140 | 598.1 | (2-{2-(4-Chloro-2-fluoro-phenoxy)-2-[4-(morpholine-4-sulfonyl)-phenyl]-acetylamino}-thiazol-4-yl)-acetic acid ethyl ester |
| A141 | 645.30 | 4-(2-{2-(2,4-Difluoro-phenoxy)-2-[4-(tetrahydro-pyran-4-sulfonyl)-phenyl]-acetylamino}-thiazol-5-yloxy)-benzoicacid methyl ester |
| A142 | 606.30 | 1-{2-[2-(4-Cyclopropanesulfonyl-phenyl)-2-(2,4-difluoro-phenoxy)-acetylamino]-thiazol-5-yl}-piperidine-4-carboxylicacid ethyl ester |
| A143 | 601.3 | 3-{2-[2-(4-Cyclopropanesulfonyl-phenyl)-2-(2,4-difluoro-phenoxy)-acetylamino]-thiazol-5-yloxy}-benzoicacid methyl ester |
| A144 | 523.30 | {2-[2-(4-Cyclopropanesulfonyl-phenyl)-2-(2,4-difluoro-phenoxy)-acetylamino]-thiazol-5-yl}-aceticacid methyl ester |
| A145 | 503.20 | 6-[2-(4-Cyclopropanesulfonyl-phenyl)-2-(2,4-difluoro-phenoxy)-acetylamino]-nicotinic acid methyl ester |
| A146 | 598.5 | 4-{2-[2-(4-Chloro-phenoxy)-2-(4-cyclopropanesulfonyl-phenyl)-acetylamino]-thiazol-5-yloxy}-benzoicacid methyl ester |
| A147 | 583 | 4-{2-[2-(4-Cyclopropanesulfonyl-phenyl)-2-(4-fluoro-phenoxy)-acetylamino]-thiazol-5-yloxy}-benzoicacid methyl ester |
| A148 | 529.1 | {5-Chloro-2-[2-(4-cyclopropanesulfonyl-phenyl)-2-tetrahydro-furan-3-yloxy)-acetylamino]-thiazol-4-yl}-aceticacid ethyl ester |
| A149 | 635.1 | 4-{2-[2-(4-Cyclopropanesulfonyl-phenyl)-2-(3,4-dichloro-phenoxy)-acetylamino]-thiazol-5-yloxy}-benzoicacid methyl ester |
| A150 | 601.2 | 4-{2-[2-(4-Cyclopropanesulfonyl-phenyl)-2-(3,4-difluoro-phenoxy)-acetylamino]-thiazol-5-yloxy}-benzoic acid methyl ester |
| A151 | 583.2 | 4-{2-[2-(4-Cyclopropanesulfonyl-phenyl)-2-(3-fluoro-phenoxy)-acetylamino]-thiazol-5-yloxy}-benzoic acid methyl ester |
| A152 | 601.2 | 4-{2-[2-(3-Chloro-4-fluoro-phenoxy)-2-(4-cyclopropanesulfonyl-phenyl)-acetylamino]-thiazol-5-yloxy}-benzoic acid methyl ester |
| A153 | 595.20 | 4-{2-[2-(4-Cyclopropanesulfonyl-phenyl)-2-(4-methoxy-phenoxy)-acetylamino]-thiazol-5-yloxy}-benzoic acid methyl ester |
| A154 | 595.20 | 4-{2-[2-(4-Cyclopropanesulfonyl-phenyl)-2-(3-methoxy-phenoxy)-acetylamino]-thiazol-5-yloxy}-benzoic acid ethyl ester |
| A155 | 633.10 | 4-{2-[2-(4-Cyclopropanesulfonyl-phenyl)-2-(4-trifluoromethyl-phenoxy)-acetylamino]-thiazol-5-yloxy}-benzoic acid methyl ester |
| A156 | 633.20 | 4-{2-[2-(4-Cyclopropanesulfonyl-phenyl)-2-(3-trifluoromethyl-phenoxy)-acetylamino]-thiazol-5-yloxy}-benzoic acid methyl ester |
| A157 | 649.10 | 4-{2-[2-(4-Cyclopropanesulfonyl-phenyl)-2-(4-trifluoromethoxy-phenoxy)-acetylamino]-thiazol-5-yloxy}-benzoic acid methyl ester |

-continued

| Example No. | MS (EI) m/z: (M + 1). | IUPAC Name |
| --- | --- | --- |
| A158 | 602.20 | 6-{2-[2-(4-Cyclopropanesulfonyl-phenyl)-2-(2,4-difluoro-phenoxy)-acetylamino]-thiazol-5-yloxy}-nicotinicacid methyl ester |
| A159 | 579.2 | 4-{2-[2-(4-Cyclopropanesulfonyl-phenyl)-2-(4-methyl-phenoxy)-acetylamino]-thiazol-5-yloxy}-benzoic acid methyl ester |
| A160 | 565.2 | 4-{2-[2-(4-Cyclopropanesulfonyl-phenyl)-2-phenoxy-acetylamino]-thiazol-5-yloxy}-benzoic acid methyl ester |
| A161 | 559.2 | 4-{2-[2-(4-Cyclopropanesulfonyl-phenyl)-2-(tetrahydro-furan-3-yloxy)-acetylamino]-thiazol-5-yloxy}-benzoic acid methyl ester |
| A162 | 521.1 | {5-Chloro-2-[2-(4-cyclopropanesulfonyl-phenyl)-2-p-tolyloxy-acetylamino]-thiazol-4-yl}acetic acid ethyl ester |
| A163 | 615.1 | (4-{2-[2-(4-Cyclopropanesulfonyl-phenyl)-2-(2,4-difluoro-phenoxy)-acetylamino]-thiazol-5-yloxy}-phenyl)-acetic acid methyl ester |
| A164 | 547.1 | {2-[2-(4-Cyclopropanesulfonyl-phenyl)-2-(2,4-difluoro-phenoxy)-acetylamino]-thiazol-5-yl}propynoic acid ethyl ester |
| A165 | 614.8 | 4-{2-[2-(4-Cyclopropanesulfonyl-phenyl)-2-(2,4-difluoro-phenoxy)-acetylamino]-4-methyl-thiazol-5-yloxy}-benzoic acid methyl ester |
| A166 | 632.8 | 4-{2-[2-(4-Cyclopropanesulfonyl-phenyl)-2-(2,4-difluoro-phenoxy)-acetylamino]-thiazol-5-yloxy}-3-fluoro-benzoic acid methyl ester |
| A167 | 632.8 | 4-{2-[2-(4-Cyclopropanesulfonyl-phenyl)-2-(2,4-difluoro-phenoxy)-acetylamino]-thiazol-5-yloxy}-2-fluoro-benzoic acid methyl ester |
| A168 | 598.8 | 4-{2-[2-(4-Cyclopropanesulfonyl-phenyl)-2-(2,4-difluoro-phenoxy)-acetylamino]-thiazol-5-yl}-benzoic acid methyl ester |
| A169 | 612.80 | 4-{2-[2-(4-Cyclopropanesulfonyl-phenyl)-2-(2,4-difluoro-phenoxy)-acetylamino]-thiazol-5-ylmethyl}-benzoic acid ethyl ester |
| A170 | 582.0 | 4-{3-[2-(4-Cyclopropanesulfonyl-phenyl)-2-(2,4-difluoro-phenoxy)-acetylamino]-pyrazol-1-ylmethyl}-benzoic acid methyl ester |
| A171 | 528.9 | (5-Chloro-2-{2-(4-cyclopropanesulfonyl-phenyl)-2-[(R)-(tetrahydro-furan-3-yl)oxy]-acetylamino}-thiazol-4-yl)-acetic acid ethyl ester |
| A172 | 558.8 | 4-(2-{2-(4-Cyclopropanesulfonyl-phenyl)-2-[(S)-(tetrahydro-furan-3-yl)oxy]-acetylamino}-thiazol-5-yloxy)-benzoic acid methyl ester |
| A173 | 529.9 | (5-Chloro-2-{2-(4-cyclopropanesulfonyl-phenyl)-2-[(S)-(tetrahydro-furan-3-yl)oxy]-acetylamino}-thiazol-4-yl)-acetic acid ethyl ester |
| A174 | 619.9 | 1-{2-[2-(4-Cyclopropanesulfonyl-phenyl)-2-(2,4-difluoro-phenoxy)-acetylamino]-thiazol-5-ylmethyl}-piperidine-4-carboxylicacid ethyl ester |
| A175 | 591.9 | 1-{2-[2-(4-Cyclopropanesulfonyl-phenyl)-2-(2,4-difluoro-phenoxy)-acetylamino]-thiazol-5-ylmethyl}-pyrrolidine-2-carboxylic acid ethyl ester |
| A176 | 604.2 | {2-[2-(4-Cyclopropanesulfonyl-phenyl)-2-(2,4-difluoro-phenoxy)-acetylamino]-thiazolo[5,4-b]pyridin-5-yloxy}-acetic acid ethyl ester |
| A177 | 554.3 | 4-{3-[2-(4-Cyclopropanesulfonyl-phenyl)-2-(tetrahydro-pyran-4-yloxy)-acetylamino]-pyrazol-1-ylmethyl}-benzoic acid methyl ester |
| A178 | 542.90 | {5-Chloro-2-[2-(4-cyclopropanesulfonyl-phenyl)-2-(tetrahydro-pyran-4-yloxy)-acetylamino]-thiazol-4-yl}-acetic acid ethyl ester |
| A179 | 571 | 3-{2-[2-(4-Cyclopropanesulfonyl-phenyl)-2-(tetrahydro-pyran-4-yloxy)-acetylamino]-thiazol-5-yloxy}-benzoic acid methyl ester |
| A180 | 605.3 | 4-{2-[2-(4-Cyclopropanesulfonyl-phenyl)-2-(tetrahydro-pyran-4-yloxy)-acetylamino]-thiazol-5-yloxy}-2-fluoro-benzoic acid methyl ester |
| A181 | 605.3 | 4-{2-[2-(4-Cyclopropanesulfonyl-phenyl)-2-(tetrahydro-pyran-4-yloxy)-acetylamino]-thiazol-5-yloxy}-3-fluoro-benzoic acid methyl ester |
| A182 | 576.2 | {2-[2-(4-Cyclopropanesulfonyl-phenyl)-2-(tetrahydro-pyran-4-yloxy)-acetylamino]-thiazolo[5,4-b]pyridin-5-yloxy}-acetic acid ethyl ester |
| A183 | 502.9 | 2-(4-Cyclopropanesulfonyl-phenyl)-N-(6-methoxy-benzothiazol-2-yl)-2-(tetrahydro-pyran-4-yloxy)-acetamide |
| A184 | 489.9 | 2-(4-Cyclopropanesulfonyl-phenyl)-N-(5-methoxy-thiazolo[5,4-b]pyridin-2-yl)-2-[(R)-(tetrahydro-furan-3-yl)oxy]-acetamide |

-continued

| Example No. | MS (EI) m/z: (M + 1). | IUPAC Name |
|---|---|---|
| A185 | 540.3 | 4-[(4-Cyclopropanesulfonyl-phenyl)-(5-fluoro-thiazol-2-ylcarbamoyl)-methoxy]-piperidine-1-carboxylic acid tert-butyl ester |
| A186 | 440.2 | 2-(4-Cyclopropanesulfonyl-phenyl)-N-(5-fluoro-thiazol-2-yl)-2-(piperidin-4-yloxy)-acetamide |
| A187 | 490.1 | 2-(4-Cyclopropanesulfonyl-phenyl)-N-(5-oxo-4,5-dihydro-thiazolo[5,4-b]pyridin-2-yl)-2-(tetrahydro-pyran-4-yloxy)-acetamide |
| A188 | 518.2 | 2-(4-Cyclopropanesulfonyl-phenyl)-N-(5-isopropoxy-thiazolo[5,4-b]pyridin-2-yl)-2-[(R)-(tetrahydro-furan-3-yl)oxy]-acetamide |
| A189 | 484.1 | N-(5-Fluoro-thiazol-2-yl)-2-[4-(piperidine-1-sulfonyl)-phenyl]-2-(tetrahydro-pyran-4-yloxy)-acetamide |
| A190 | 517.2 | 2-[4-(Piperidine-1-sulfonyl)-phenyl]-2-(tetrahydro-pyran-4-yloxy)-N-thiazolo[5,4-b]pyridin-2-yl-acetamide |
| A191 | 547.2 | N-(5-Methoxy-thiazolo[5,4-b]pyridin-2-yl)-2-[4-(piperidine-1-sulfonyl)-phenyl]-2-(tetrahydro-pyran-4-yloxy)-acetamide |
| A192 | 615.0 | (5-Chloro-2-{2-(2,4-difluoro-phenoxy)-2-[4-(tetrahydro-pyran-4-sulfonyl)-phenyl]-acetylamino}-thiazol-4-yl)-acetic acid ethyl ester |

Example (B1)

{2-[2-(4-Cyclopropanesulfonylphenyl)-2-(4-fluorophenoxy)acetylamino]thiazol-4-yl}acetic acid

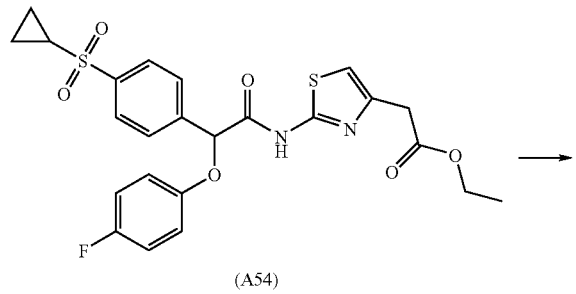

(A54)

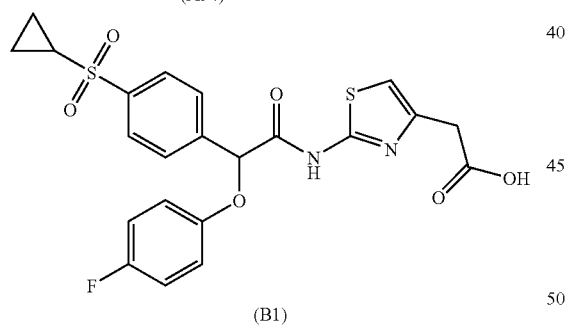

(B1)

{2-[2-(4-Cyclopropanesulfonylphenyl)-2-(4-fluorophenoxy)acetylamino]thiazol-4-yl}-acetic acid ethyl ester (obtained in example A54) was taken in THF, to it was added aqueous solution of LiOH and stirred for 1-4 h. After completion of the reaction, water and DCM was added and stirred for 5 min. The aqueous layer was acidified with 1 N HCl and extracted with ethyl acetate, washed with brine and dried over anhydrous sodium sulfate. The solvent was removed under reduced pressure to get the title compound.

1H-NMR (400 MHz, CDCl3): δ 1.00-1.03 (m, 2H), 1.32-1.35 (m, 2H), 2.42-2.46 (m, 1H), 3.77 (s, 2H), 5.80 (s, 1H), 6.86-6.92 (m, 5H), 7.76 (d, J=8.4 Hz, 2H), 7.89 (d, J=8.4 Hz, 2H).

MS (ES+) m/z:490.9(M+1); M.P: 72-73° C.

Examples B2 to B28

Were Prepared in Analogues Manner of Example (B1) from the Appropriate Intermediate that are Available Commercially or Synthesized as Above

| Example No. | MS (EI)m/z: (M + 1). | IUPAC Name |
|---|---|---|
| B2 | 542.8 | {5-Chloro-2-[2-(4-cyclopropanesulfonylphenyl)-2-(2,4-difluorophenoxy)acetylamino]thiazol-4-yl}acetic acid |
| B3 | 506.9 | {2-[2-(4-Chloro-phenoxy)-2-(4-cyclopropanesulfonylphenyl)acetylamino]thiazol-4-yl}acetic acid |
| B4 | 524.8 | {2-[2-(3-Chloro-4-fluorophenoxy)-2-(4-cyclopropanesulfonylphenyl)acetylamino]thiazol-4-yl}acetic acid |
| B5 | 524.8 | {5-Chloro-2-[2-(4-cyclopropanesulfonylphenyl)-2-(4-fluorophenoxy)-acetylamino]-thiazol-4-yl}acetic acid |

-continued

| Example No. | MS (EI)m/z: (M + 1). | IUPAC Name |
|---|---|---|
| B6 | 540.8 | {5-Chloro-2-[2-(4-chlorophenoxy)-2-(4-cyclopropanesulfonylphenyl)-acetylamino]-thiazol-4-yl}acetic acid |
| B7 | 558.8 | {5-Chloro-2-[2-(3-chloro-4-fluorophenoxy)-2-(4-cyclopropanesulfonylphenyl)acetylamino]thiazol-4-yl}acetic acid |
| B8 | 577.0 | {5-Chloro-2-[2-(3-chloro-4-cyclopropanesulfonylphenyl)-2-(2,4-difluorophenoxy)acetylamino]thiazol-4-yl}acetic acid |
| B9 | 571.0 | {5-Chloro-2-[2-(4-cyclopentanesulfonylphenyl)-2-(2,4-difluorophenoxy)acetylamino]-thiazol-4-yl}acetic acid |
| B10 | 542.9 | {2-[2-(3-Chloro-4-cyclopropanesulfonylphenyl)-2-(2,4-difluorophenoxy)acetylamino]-thiazol-4-yl}acetic acid |
| B11 | 509.0 | {2-[2-(4-Cyclopropanesulfonylphenyl)-2-(2,4-difluorophenoxy)acetylamino]-thiazol-4-yl}acetic acid |
| B12 | 509.0 | 2-[2-(4-Cyclopropanesulfonylphenyl)-2-(2,4-difluorophenoxy)acetylamino]-4-methylthiazole-5-carboxylic acid |
| B13 | 541.0 (M − 1) | {5-Chloro-2-[2-(4-cyclopropanesulfonylphenyl)-2-(3,4-difluorophenoxy)acetylamino]thiazol-4-yl}acetic acid |
| B14 |  | {2-[2-(4-Cyclopentanesulfonylphenyl)-2-(2,4-difluorophenoxy)-acetylamino]-thiazol-4-yl}acetic acid |
| B15 | 585.0 | {5-Chloro-2-[2-(4-cyclohexanesulfonylphenyl)-2-(2,4-difluorophenoxy)acetylamino]-thiazol-4-yl}acetic acid |
| B16 | 551.1 | {2-[2-(4-Cyclohexanesulfonylphenyl)-2-(2,4-difluorophenoxy)acetylamino]-thiazol-4-yl}acetic acid |
| B17 | 569.0 (M − 1) | {2-[2-(3-Chloro-4-cyclopentanesulfonylphenyl)-2-(2,4-difluorophenoxy)acetylamino]thiazol-4-yl}aceticacid |
| B18 | 605.0 | {5-Chloro-2-[2-(3-chloro-4-cyclopentanesulfonylphenyl)-2-(2,4-difluorophenoxy)acetylamino]-thiazol-4-yl}acetic acid |
| B19 | 546.0 | {5-Chloro-2-[2-(4-cyclopropanesulfonylphenyl)-2-(1H-indol-5-yloxy)acetylamino]thiazol-4-yl}acetic acid |
| B20 | 564.0 | {2-[2-(3-Acetylaminophenoxy)-2-(4-cyclopropanesulfonylphenyl)acetylamino]-5-chloro-thiazol-4-yl}acetic acid |
| B21 | 523.1 | 2-[2-(4-Cyclopentanesulfonylphenyl)-2-(2,4-difluorophenoxy)-acetylamino]thiazole-4-carboxylic acid |
| B22 | 553.1 | {2-[2-(4-Cyclopropanesulfonylphenyl)-2-(2,4-difluorophenoxy)acetylamino]-5-ethoxy-thiazol-4-yl}acetic acid |
| B23 | 557.0 | 2-[2-(3-Chloro-4-cyclopentanesulfonylphenyl)-2-(2,4-difluorophenoxy)acetylamino]thiazole-4-carboxylic acid |
| B24 | 524.8 | {2-[2-(4-Chloro-2-fluorophenoxy)-2-(4-cyclopropanesulfonylphenyl)acetylamino]thiazol-4-yl}acetic acid |
| B25 | 560.7 | {5-Chloro-2-[2-(4-chloro-2-fluorophenoxy)-2-(4-cyclopropanesulfonylphenyl)acetylamino]thiazol-4-yl}acetic acid |
| B26 | 510.8 | 2-[2-(4-Chloro-2-fluorophenoxy)-2-(4-cyclopropanesulfonylphenyl)acetylamino]thiazole-4-carboxylic acid |
| B27 | 557.1 (M + 18) | {2-[2-(4-Cyclopropanesulfonyl-phenyl)-2-(2,4-difluoro-phenoxy)-acetylamino]-thiazol-4-ylsulfanyl}-acetic acid |
| B28 | 523.2 | 3-{2-[2-(4-Cyclopropanesulfonyl-phenyl)-2-(2,4-difluoro-phenoxy)-acetylamino]-thiazol-4-yl}-propionic acid |

Example B29

4-{2-[2-(4-Cyclopropanesulfonyl-phenyl)-2-(2,4-difluoro-phenoxy)-acetylamino]-thiazol-5-yloxy}-benzoic acid

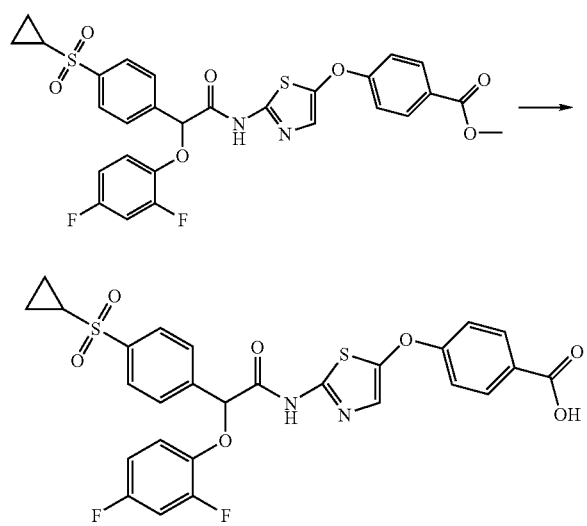

4-{2-[2-(4-Cyclopropanesulfonyl-phenyl)-2-(2,4-difluoro-phenoxy)-acetylamino]thiazol-5-yloxy}-benzoic acid methyl ester (1.4 g, 2.33 mmol, obtained in example A74) was taken in THF: MeOH (1:1, 20 mL), to it was added aqueous solution of LiOH (0.34 g, 7.94 mmol in 10 mL water) and stirred for 1-4 h. After completion of the reaction, organic solvent was removed under reduced pressure. The aqueous layer was washed with diisopropyl ether then acidified with 1 N HCl to pH 2. The solid formed was filtered, washed with water, followed by washing with diisopropyl ether & dried under vacuum to get the title compound (1.17 g, 86%).

1H NMR- (CDCl3), δ 1.04-1.13 (m, 4H), 2.88 (m, 1H), 6.2 (s, 1H), 7.05-7.39 (m, 6H), 7.88-8.01 (m, 5H), 12.94 (bs, 1H). MS (EI) m/z: 587 (M+1)

Example B30

4-{2-[2-(4-Cyclopropanesulfonyl-phenyl)-2-(tetrahydro-pyran-4-yloxy)-acetylamino]-thiazol-5-yloxy}-benzoic acid

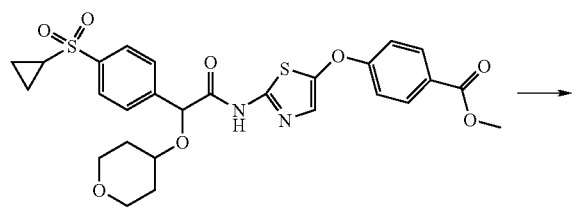

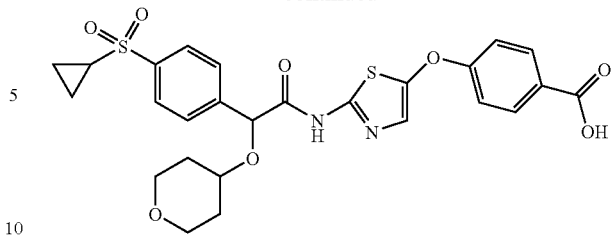

The compound of example B29 was obtained by similar method described in example B28 using 4-{2-[2-(4-Cyclopropanesulfonyl-phenyl)-2-(2,4-difluoro-phenoxy)-acetylamino]-thiazol-5-yloxy}-benzoic acid methyl ester (0.17 g, 0.29 mmol), LiOH (0.062 g, 1.48 mmol) in THF: MeOH: Water (1:1:1, 9 mL) to provide the title compound (0.117 g, 72%).

$^1$H NMR (DMSO-d$_6$, 400 MHz): δ-1.03-1.06 (m, 2H), 1.10-1.34 (m, 2H), 1.46-1.60 (m, 2H), 1.85-1.94 (m, 2H), 2.83-2.89 (m, 1H), 3.29-3.39 (m, 2H), 3.63-3.68 (m, 1H), 3.77-3.85 (m, 2H), 5.48 (s, 1H), 7.18 (d, J=9.2 Hz, 2H), 7.38 (s, 1H), 7.78 (d, J=8.0 Hz, 2H), 7.93-7.95 (m, 4H). MS (EI) m/z: 558.8 (M+1).

Example B31

4-(2-{2-(4-Cyclopropanesulfonyl-phenyl)-2-[(R)-(tetrahydro-furan-3-yl)oxy]-acetylamino}-thiazol-5-yloxy)-benzoic acid

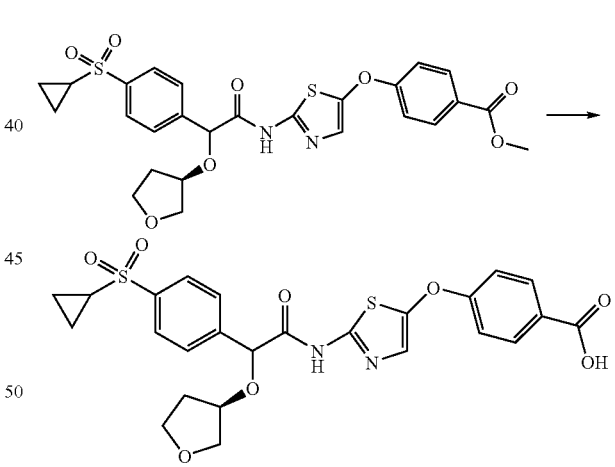

The compound of example B30 was obtained by similar method described in example B28 using 4-(2-{2-(4-Cyclopropanesulfonyl-phenyl)-2-[(R)-(tetrahydro-furan-3-yl)oxy]-acetylamino}-thiazol-5-yloxy)-benzoic acid methyl ester (0.180 g, 0.32 mmol), LiOH (0.067 g, 1.61 mmol) in THF: MeOH: Water (1:1:1, 9 mL) to provide the title compound (0.160 mg, 92%).

$^1$H NMR (DMSO-d$_6$, 400 MHz): 3-1.01-1.05 (m, 2H), 1.09-1.31 (m, 2H), 1.94-1.99 (m, 2H), 2.80-2.68 (m, 1H), 3.60-3.85 (m, 4H), 4.20-4.30 (m, 1H), 5.36 (s, 1H), 7.16 (d, J=7.2 Hz, 2H), 7.38 (s, 1H), 7.73-7.76 (m, 2H), 7.92 (d, J=8.4 Hz, 4H). MS (EI) m/z: 544.9 (M+1).

Examples B32 to B103 were Prepared in Analogues Manner of Examples B28-B30 from the Appropriate Intermediate that are Available Commercially or Synthesized as above.

| Example No. | MS (EI)m/z: (M + 1). | IUPAC Name |
|---|---|---|
| B32 | 500.8 | {5-Chloro-2-[2-(4-cyclopropanesulfonyl-phenyl)-2-(tetrahydro-furan-3-yloxy)-acetylamino]-thiazol-4-yl}-acetic acid |
| B33 | 584 (M − 1) | (5-Chloro-2-{2-(2,4-difluoro-phenoxy)-2-[4-(piperidine-1-sulfonyl)-phenyl]-acetylamino}-thiazol-4-yl)-acetic acid |
| B34 | 632.3 | 4-(2-{2-(2,4-Difluoro-phenoxy)-2-[4-(morpholine-4-sulfonyl)-phenyl]-acetylamino}-thiazol-5-yloxy)-benzoic acid |
| B35 | 588.3 | (5-Chloro-2-{2-(2,4-difluoro-phenoxy)-2-[4-(morpholine-4-sulfonyl)-phenyl]-acetylamino}-thiazol-4-yl)-acetic acid |
| B36 | 632.3 | 3-(2-{2-(2,4-Difluoro-phenoxy)-2-[4-(morpholine-4-sulfonyl)-phenyl]-acetylamino}-thiazol-5-yloxy)-benzoic acid |
| B37 | 607.4 | 1-(2-{2-(2,4-Difluoro-phenoxy)-2-[4-(pyrrolidine-1-sulfonyl)-phenyl]-acetylamino}-thiazol-5-yl)-piperidine-4-carboxylic acid |
| B38 | 614.1 (M − 1) | 4-(2-{2-(2,4-Difluoro-phenoxy)-2-[4-(pyrrolidine-1-sulfonyl)-phenyl]-acetylamino}-thiazol-5-yloxy)-benzoic acid |
| B39 | 614.2 (M − 1) | 3-(2-{2-(2,4-Difluoro-phenoxy)-2-[4-(pyrrolidine-1-sulfonyl)-phenyl]-acetylamino}-thiazol-5-yloxy)-benzoic acid |
| B40 | 572 | (5-Chloro-2-{2-(2,4-difluoro-phenoxy)-2-[3-(pyrrolidine-1-sulfonyl)-phenyl]-acetylamino}-thiazol-4-yl)-acetic acid |
| B41 | 557.90 | {2-[2-[3-(Azetidine-1-sulfonyl)-phenyl]-2-(2,4-difluoro-phenoxy)-acetylamino]-5-chloro-thiazol-4-yl}-aceticacid |
| B42 | 557.90 | {2-[2-[4-(Azetidine-1-sulfonyl)-phenyl]-2-(2,4-difluoro-phenoxy)-acetylamino]-5-chloro-thiazol-4-yl}-acetic acid |
| B43 | 582.0 | (5-Chloro-2-{2-(4-chloro-phenoxy)-2-[4-(piperidine-1-sulfonyl)-phenyl]-acetylamino}-thiazol-4-yl)-acetic acid |
| B44 | 604.1 | (5-Chloro-2-{2-(4-chloro-2-fluoro-phenoxy)-2-[4-(piperidine-1-sulfonyl)-phenyl]-acetylamino}-thiazol-4-yl)-acetic acid |
| B45 | 585.9 | (5-Chloro-2-{2-(4-chloro-phenoxy)-2-[4-(morpholine-4-sulfonyl)-phenyl]-acetylamino}-thiazol-4-yl)-acetic acid |
| B46 | 628.2 | 3-(2-{2-(4-Chloro-phenoxy)-2-[4-(piperidine-1-sulfonyl)-phenyl]-acetylamino}-thiazol-5-yloxy)-benzoic acid |
| B47 | 628.0 | 4-(2-{2-(4-Chloro-phenoxy)-2-[4-(piperidine-1-sulfonyl)-phenyl]-acetylamino}-thiazol-5-yloxy)-benzoic acid |
| B48 | 621.4 | 1-(2-{2-(2,4-Difluoro-phenoxy)-2-[4-(piperidine-1-sulfonyl)-phenyl]-acetylamino}-thiazol-5-yl)-iperidine-4-carboxylic acid |
| B49 | 603.5 | (5-Chloro-2-{2-(4-chloro-2-fluoro-phenoxy)-2-[4-(morpholine-4-sulfonyl)-phenyl]-acetylamino}-thiazol-4-yl)-acetic acid |
| B50 | 630.2 | 4-(2-{2-(2,4-Difluoro-phenoxy)-2-[4-(piperidine-1-sulfonyl)-phenyl]-acetylamino}-thiazol-5-yloxy)-benzoic acid |
| B51 | 630.2 | 3-(2-{2-(2,4-Difluoro-phenoxy)-2-[4-(piperidine-1-sulfonyl)-phenyl]-acetylamino}-thiazol-5-yloxy)-benzoic acid |
| B52 | 570.1 | (2-{2-(4-Chloro-2-fluoro-phenoxy)-2-[4-(morpholine-4-sulfonyl)-phenyl]-acetylamino}-thiazol-4-yl)-acetic acid |
| B53 | 631.30 | 4-(2-{2-(2,4-Difluoro-phenoxy)-2-[4-(tetrahydro-pyran-4-sulfonyl)-phenyl]-acetylamino}-thiazol-5-yloxy)-benzoic acid |
| B54 | 578.30 | 1-{2-[2-(4-Cyclopropanesulfonyl-phenyl)-2-(2,4-difluoro-phenoxy)-acetylamino]-thiazol-5-yl}-piperidine-4-carboxylic acid |
| B55 | 587.3 | 3-{2-[2-(4-Cyclopropanesulfonyl-phenyl)-2-(2,4-difluoro-phenoxy)-acetylamino]-thiazol-5-yloxy}-benzoic acid |
| B56 | 509.20 | {2-[2-(4-Cyclopropanesulfonyl-phenyl)-2-(2,4-difluoro-phenoxy)-acetylamino]-thiazol-5-yl}-acetic acid |
| B57 | 489.20 | 6-[2-(4-Cyclopropanesulfonyl-phenyl)-2-(2,4-difluoro-phenoxy)-acetylamino]-nicotinic acid |
| B58 | 584.9 | 4-{2-[2-(4-Chloro-phenoxy)-2-(4-cyclopropanesulfonyl-phenyl)-acetylamino]-thiazol-5-yloxy}-benzoic acid |
| B59 | 568.6 | 4-{2-[2-(4-Cyclopropanesulfonyl-phenyl)-2-(4-fluoro-phenoxy)-acetylamino]-thiazol-5-yloxy}-benzoic acid |
| B60 | 619.1 | 4-{2-[2-(4-Cyclopropanesulfonyl-phenyl)-2-(3,4-dichloro-phenoxy)-acetylamino]-thiazol-5-yloxy}-benzoic acid |
| B61 | 587.2 | 4-{2-[2-(4-Cyclopropanesulfonyl-phenyl)-2-(3,4-difluoro-phenoxy)-acetylamino]-thiazol-5-yloxy}-benzoic acid |
| B62 | 569.2 | 4-{2-[2-(4-Cyclopropanesulfonyl-phenyl)-2-(3-fluoro-phenoxy)-acetylamino]-thiazol-5-yloxy}-benzoic acid |
| B63 | 617.2 | 4-{2-[2-(3-Chloro-4-fluoro-phenoxy)-2-(4cyclopropanesulfonyl-phenyl)-acetylamino]-thiazol-5-yloxy}-benzoic acid |
| B64 | 492.1 | {3-[2-(4-Cyclopropanesulfonyl-phenyl)-2-(2,4-difluoro-phenoxy)-acetylamino]-pyrazol-1-yl}-acetic acid |
| B65 | 581.20 | 4-{2-[2-(4-Cyclopropanesulfonyl-phenyl)-2-(4-methoxy-phenoxy)-acetylamino]-thiazol-5-yloxy}-benzoic acid |

-continued

| Example No. | MS (EI)m/z: (M + 1). | IUPAC Name |
|---|---|---|
| B66 | 581.20 | 4-{2-[2-(4-Cyclopropanesulfonyl-phenyl)-2-(3-methoxy-phenoxy)-acetylamino]-thiazol-5-yloxy}-benzoic acid |
| B67 | 619.20 | 4-{2-[2-(4-Cyclopropanesulfonyl-phenyl)-2-(4-trifluoromethyl-phenoxy)-acetylamino]-thiazol-5-yloxy}-benzoic acid |
| B68 | 619.20 | 4-{2-[2-(4-Cyclopropanesulfonyl-phenyl)-2-(3-trifluoromethyl-phenoxy)-acetylamino]-thiazol-5-yloxy}-benzoic acid |
| B69 | 635.20 | 4-{2-[2-(4-Cyclopropanesulfonyl-phenyl)-2-(4-trifluoromethoxy-phenoxy)-acetylamino]-thiazol-5-yloxy}-benzoic acid |
| B70 | 588.20 | 6-{2-[2-(4-Cyclopropanesulfonyl-phenyl)-2-(2,4-difluoro-phenoxy)-acetylamino]-thiazol-5-yloxy}-nicotinicacid |
| B71 | 565.2 | 4-{2-[2-(4-Cyclopropanesulfonyl-phenyl)-2-(4-methyl-phenoxy)-acetylamino]-thiazol-5-yloxy}-benzoic acid |
| B72 | 551.1 | 4-{2-[2-(4-Cyclopropanesulfonyl-phenyl)-2-phenoxy-acetylamino]-thiazol-5-yloxy}-benzoic acid |
| B73 | 545.1 | 4-{2-[2-(4-Cyclopropanesulfonyl-phenyl)-2-(tetrahydro-furan-3-yloxy)-acetylamino]-thiazol-5-yloxy}-benzoic acid |
| B74 | 521.1 | {5-Chloro-2-[2-(4-cyclopropanesulfonyl-phenyl)-2-p-tolyloxy-acetylamino]-thiazol-4-yl}-acetic acid |
| B75 | 571.00 | 4-{2-[2-(4-Cyclopropanesulfonyl-phenyl)-2-(2,4-difluoro-phenoxy)-acetylamino]-thiazol-4-yl}-benzoic acid |
| B76 | 601.1 | (4-{2-[2-(4-Cyclopropanesulfonyl-phenyl)-2-(2,4-difluoro-phenoxy)-acetylamino]-thiazol-5-yloxy}-phenyl)-acetic acid |
| B77 | 519.1 | {2-[2-(4-Cyclopropanesulfonyl-phenyl)-2-(2,4-difluoro-phenoxy)-acetylamino]-thiazol-5-yl}-propynoic acid |
| B78 | 600.8 | 4-{2-[2-(4-Cyclopropanesulfonyl-phenyl)-2-(2,4-difluoro-phenoxy)-acetylamino]-4-methyl-thiazol-5-yloxy}-benzoic acid |
| B79 | 604.8 | 4-{2-[2-(4-Cyclopropanesulfonyl-phenyl)-2-(2,4-difluoro-phenoxy)-acetylamino]-thiazol-5-yloxy}-3-fluoro-benzoic acid |
| B80 | 604.8 | 4-{2-[2-(4-Cyclopropanesulfonyl-phenyl)-2-(2,4-difluoro-phenoxy)-acetylamino]-thiazol-5-yloxy}-2-fluoro-benzoic acid |
| B81 | 570.8 | 4-{2-[2-(4-Cyclopropanesulfonyl-phenyl)-2-(2,4-difluoro-phenoxy)-acetylamino]-thiazol-5-yl}-benzoic acid |
| B82 | 584.80 | 4-{2-[2-(4-Cyclopropanesulfonyl-phenyl)-2-(2,4-difluoro-phenoxy)-acetylamino]-thiazol-5-ylmethyl}-benzoic acid |
| B83 | 567.9 | 4-{3-[2-(4-Cyclopropanesulfonyl-phenyl)-2-(2,4-difluoro-phenoxy)-acetylamino]-pyrazol-1-ylmethyl}-benzoic acid |
| B84 | 500.9 | (5-Chloro-2-{2-(4-cyclopropanesulfonyl-phenyl)-2-[(R)-(tetrahydro-furan-3-yl)oxy]-acetylamino}-thiazol-4-yl)-acetic acid |
| B85 | 544.9 | 4-(2-{2-(4-Cyclopropanesulfonyl-phenyl)-2-[(S)-(tetrahydro-furan-3-yl)oxy]-acetylamino}-thiazol-5-yloxy)-benzoic acid |
| B86 | 500.9 | (5-Chloro-2-{2-(4-cyclopropanesulfonyl-phenyl)-2-[(S)-(tetrahydro-furan-3-yl)oxy]-acetylamino}-thiazol-4-yl)-acetic acid |
| B87 | 592.0 | 1-{2-[2-(4-Cyclopropanesulfonyl-phenyl)-2-(2,4-difluoro-phenoxy)-acetylamino]-thiazol-5-ylmethyl}-piperidine-4-carboxylic acid |
| B88 | 578.0 | 1-{2-[2-(4-Cyclopropanesulfonyl-phenyl)-2-(2,4-difluoro-phenoxy)-acetylamino]-thiazol-5-ylmethyl}-pyrrolidine-2-carboxylic acid |
| B89 | 575.8 | {2-[2-(4-Cyclopropanesulfonyl-phenyl)-2-(2,4-difluoro-phenoxy)-acetylamino]-thiazolo[5,4-b]pyridin-5-yloxy}-acetic acid |
| B90 | 540.3 | 4-{3-[2-(4-Cyclopropanesulfonyl-phenyl)-2-(tetrahydro-pyran-4-yloxy)-acetylamino]-pyrazol-1-ylmethyl}-benzoic acid |
| B91 | 514.90 | {5-Chloro-2-[2-(4-cyclopropanesulfonyl-phenyl)-2-(tetrahydro-pyran-4-yloxy)-acetylamino]-thiazol-4-yl}-acetic acid |
| B92 | 558.9 | 3-{2-[2-(4-Cyclopropanesulfonyl-phenyl)-2-(tetrahydro-pyran-4-yloxy)-acetylamino]-thiazol-5-yloxy}-benzoic acid |
| B93 | 576.9 | 4-{2-[2-(4-Cyclopropanesulfonyl-phenyl)-2-(tetrahydro-pyran-4-yloxy)-acetylamino]-thiazol-5-yloxy}-2-fluoro-benzoic acid |
| B94 | 576.9 | 4-{2-[2-(4-Cyclopropanesulfonyl-phenyl)-2-(tetrahydro-pyran-4-yloxy)-acetylamino]-thiazol-5-yloxy}-3-fluoro-benzoic acid |
| B95 | 548.0 | {2-[2-(4-Cyclopropanesulfonyl-phenyl)-2-(tetrahydro-pyran-4-yloxy)-acetylamino]-thiazolo[5,4-b]pyridin-5-yloxy}-acetic acid |
| B96 | 638.00 | 4-{2-[2-(4-Cyclopropanesulfonyl-phenyl)-2-(2,4-difluoro-phenoxy)-acetylamino]-thiazolo[5,4-b]pyridin-5-yloxy}-benzoic acid |
| B97 | 610.20 | 4-{2-[2-(4-Cyclopropanesulfonyl-phenyl)-2-(tetrahydro-pyran-4-yloxy)-acetylamino]-thiazolo[5,4-b]pyridin-5-yloxy}-benzoic acid |
| B98 | 615.9 | 4-[(4-Carboxymethyl-5-chloro-thiazol-2-ylcarbamoyl)-(4-cyclopropanesulfonyl-phenyl)-methoxy]-piperidine-1-carboxylic acid tert-butyl ester |

-continued

| Example No. | MS (EI)m/z: (M + 1). | IUPAC Name |
|---|---|---|
| B99 | 515 | {5-Chloro-2-[2-(4-cyclopropanesulfonyl-phenyl)-2-(piperidin-4-yloxy)-acetylamino]-thiazol-4-yl}-acetic acid |
| B100 | 573.2 | (4-{2-[2-(4-Cyclopropanesulfonyl-phenyl)-2-(tetrahydro-pyran-4-yloxy)-acetylamino]-thiazol-5-yloxy}-phenyl)-acetic acid |
| B101 | 517.2 | 2-[2-(4-Cyclopropanesulfonyl-phenyl)-2-(tetrahydro-pyran-4-yloxy)-acetylamino]-benzothiazole-6-carboxylic acid |
| B102 | 503.2 | 2-{2-(4-Cyclopropanesulfonyl-phenyl)-2-[(R)-(tetrahydro-furan-3-yl)oxy]-acetylamino}-benzothiazole-6-carboxylic acid |
| B103 | 587.0 | (5-Chloro-2-{2-(2,4-difluoro-phenoxy)-2-[4-(tetrahydro-pyran-4-sulfonyl)-phenyl]-acetylamino}-thiazol-4-yl)-acetic acid |

Example C1

(−)-{5-Chloro-2-[2-(4-cyclopropanesulfonylphenyl)-2-(2,4-difluorophenoxy)acetylamino]thiazol-4-yl}-acetic acid, ethyl ester

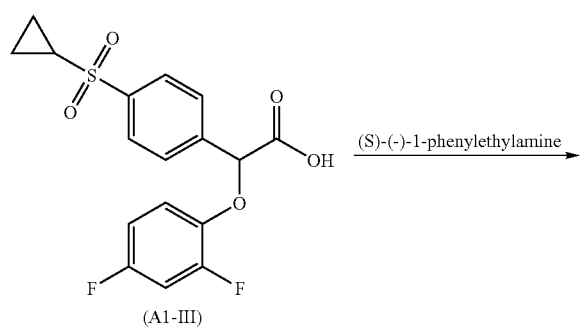

(A1-III)

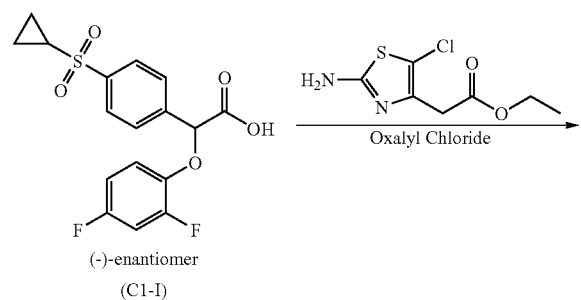

(−)-enantiomer
(C1-I)

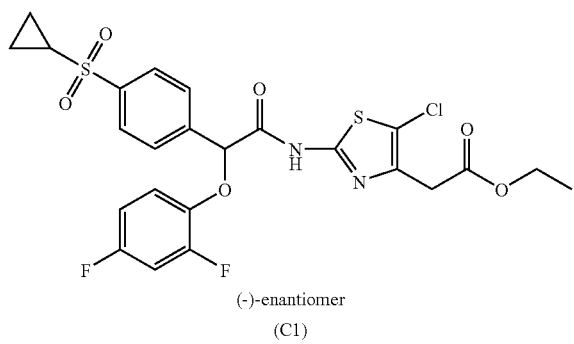

(−)-enantiomer
(C1)

Step I: Preparation of (−)-(4-Cyclopropanesulfonylphenyl)-(2,4-difluorophenoxy)acetic acid (C1-I):

To a solution of (4-cyclopropanesulfonylphenyl)-(2,4-difluorophenoxy)acetic acid (obtained in example A1-step III) in ethyl acetate was added (S)-(−)-1-phenylethylamine drop wise at −15° C., after completion of addition the reaction was stirred for 4-6 hours. Solid was filtered and washed with ethyl acetate. The solid was then taken in 1N HCl and extracted with ethyl acetate, ethyl acetate layer was washed with brine, dried over anhydrous sodium sulfate. Solvent was removed under reduced pressure to obtain (−)-(4-cyclopropanesulfonylphenyl)-(2,4-difluorophenoxy)acetic acid. Enantiomeric enrichment was done by repeating the diasteriomeric crystallization.

$[\alpha]^{23}_{589}$=−107.1° (c=2% Chloroform)

Enantiomeric purity >99.% (chiral HPLC)

Step II: (−)-{5-Chloro-2-[2-(4-cyclopropanesulfonylphenyl)-2-(2,4-difluorophenoxy)acetylamino]thiazol-4-yl}-acetic acid ethyl ester To a solution of (−)-4-cyclopropanesulfonylphenyl)-(2,4-difluorophenoxy)acetic acid (C1-I) in DCM, was added DMF and cooled to 0° C., followed by the addition of oxalyl chloride under stirring. Stirring was continued for 1 hour at the same temperature. The resulting mixture was further cooled to −35° C. and to that, a solution of excess (2-amino-5-chlorothiazol-4-yl)acetic acid ethyl ester in DCM was added drop wise. After completion of reaction, the reaction mixture was poured into 1N aqueous HCl under stirring, organic layer was washed with 1N HCl, followed by 5% brine, dried over anhydrous sodium sulfate, solvent was removed under reduced pressure to get the crude compound which was purified by preparative TLC to get the title compound.

$[\alpha]^{23}_{589}$=−ve(c=2% Chloroform)

$^1$H NMR(400 MHz, CDCl$_3$): δ 1.06-1.08 (m, 2H), 1.30 (t, J=7.2 Hz, 3H), 1.33-1.38 (m, 2H), 2.42-2.50 (m, 1H), 3.73 (d, J=2 Hz, 2H), 4.22 (q, J=7.2 Hz, 2H), 5.75 (s, 1H), 6.76-6.77 (m, 1H), 6.83-6.86 (m, 1H), 6.90-6.98 (m, 1H), 7.73 (d, J=8.4 Hz, 2H), 7.96 (d, J=8.4 Hz, 2H), 9.96 (bs, 1H).

MS (EI) m/z: 571.1 and 573.1 (M+1; for $^{35}$Cl and $^{37}$Cl respectively).

Examples C2 and C3 were Prepared in Analogues Manner of Example (C1) from the Appropriate Chiral Intermediate

| Example No. | MS (EI)m/z: (M + 1). | IUPAC Name |
|---|---|---|
| C2 | 599.1 | (−)-{5-Chloro-2-[2-(4-cyclopentanesulfonyl-phenyl)-2-(2,4-difluorophenoxy)acetyl-amino]thiazol-4-yl}acetic acid ethyl ester |
| C3 | 537.1 | (−)-{2-[2-(4-Cyclopropanesulfonylphenyl)-2-(2,4-difluorophenoxy)acetylamino]thiazol-4-yl}acetic acid ethyl ester |

Example D1

(+)-{5-Chloro-2-[2-(4-cyclopropanesulfonylphenyl)-2-(2,4-difluorophenoxy)acetylamino]thiazol-4-yl}acetic acid, ethyl ester

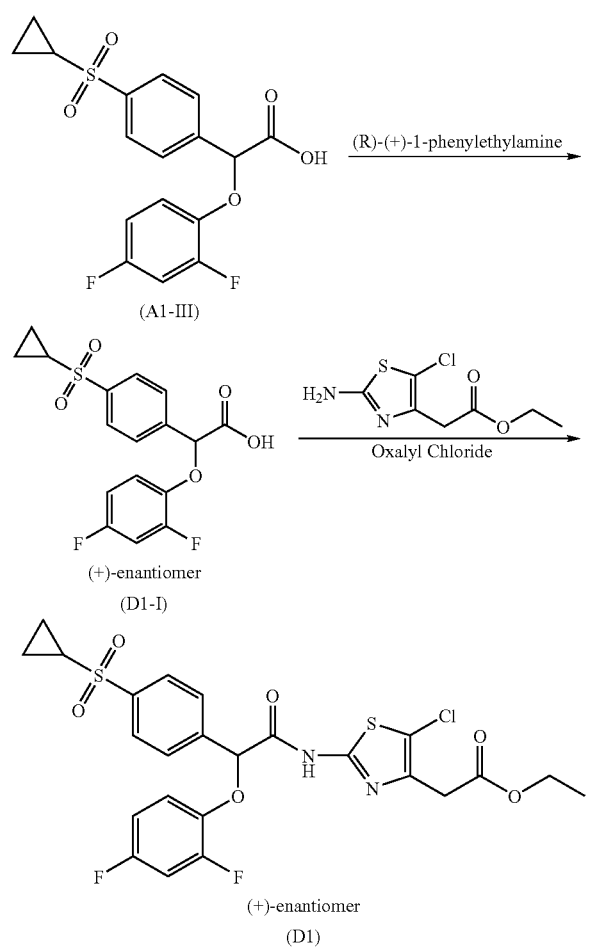

Preparation of (+)-(4-Cyclopropanesulfonylphenyl)-(2,4-difluorophenoxy)acetic acid (D1-I)

To a solution of (4-cyclopropanesulfonylphenyl)-(2,4-difluorophenoxy)acetic acid (obtained in example A1-step III) in ethyl acetate was added (R) (+)-1-phenylethylamine drop wise at −15° C., after completion of addition the reaction was stirred for 4-6 hours. Solid was filtered and washed with ethyl acetate. The solid was then taken in 1N HCl and extracted with ethyl acetate, ethyl acetate layer was washed with brine, dried over anhydrous sodium sulfate. Solvent was removed under reduced pressure to obtain (+)-(4-Cyclopropanesulfonylphenyl)-(2,4-difluorophenoxy)acetic acid. Enantiomeric enrichment was done by repeating the diasteriomeric crystallization.

$[\alpha]^{23}_{589}$=+93.07° (c=2% Chloroform)

Enantiomeric purity >99.% (by chiral HPLC)

(+)-(4-Cyclopropanesulfonylphenyl)-(2,4-difluorophenoxy)acetic acid ethyl ester (D1)

The example D1 was prepared using (+)-4-cyclopropanesulfonylphenyl)-(2,4-difluorophenoxy)acetic acid (D1-I), and following the same reaction condition for amide coupling as described in example C1, $[\alpha]^{23}_{589}$=+ve(c=2% Chloroform)

Examples D2 and D3 were Prepared in Analogues Manner of Example (D1) from the Appropriate Chiral Intermediate

| Example No. | MS (EI)m/z: (M + 1). | IUPAC Name |
|---|---|---|
| D2 | 599.1 | (+)-{5-Chloro-2-[2-(4-cyclopentanesulfonyl-phenyl)-2-(2,4-difluorophenoxy)-acetyl-amino]thiazol-4-yl}acetic acid ethyl ester |
| D3 | 537.1 | (+)-{2-[2-(4-Cyclopropanesulfonylphenyl)-2-(2,4-difluorophenoxy)-acetylamino]thiazol-4-yl}acetic acid ethyl ester |

Hydrolysis of Example (C's) and (D's) using method of example (B1) provided the following examples

| Example No. | MS (EI)m/z: (M + 1). | IUPAC Name |
|---|---|---|
| E1 | 543.0 | (−)-{5-Chloro-2-[2-(4-cyclopropanesulfonyl-phenyl)-2-(2,4-difluorophenoxy)acetyl-amino]thiazol-4-yl}acetic acid |
| E2 | 571.1 | (−)-{5-Chloro-2-[2-(4-cyclopentanesulfonyl-phenyl)-2-(2,4-difluorophenoxy)acetyl-amino]thiazol-4-yl}-acetic acid |
| E3 | 509.1 | (−){2-[2-(4-Cyclopropanesulfonylphenyl)-2-(2,4-difluorophenoxy)acetylamino]-thiazol-4-yl}acetic acid |
| F1 | 543.0 | (+)-{5-Chloro-2-[2-(4-cyclopropanesulfonyl-phenyl)-2-(2,4-difluorophenoxy)acetyl-amino]thiazol-4-yl}-acetic acid |
| F2 | 571.1 | (+)-{5-Chloro-2-[2-(4-cyclopentanesulfonyl-phenyl)-2-(2,4-difluorophenoxy)acety-lamino]thiazol-4-yl}acetic acid |
| F3 | 509.1 | (+)-{2-[2-(4-Cyclopropanesulfonylphenyl)-2-(2,4-difluorophenoxy)acetylamino]thiazol-4-yl}acetic acid |

Example G1
N-{5-[3-(Azetidine-1-carbonyl)-phenoxy]-thiazol-2-yl}-2-(4-cyclopropanesulfonyl-phenyl)-2-(2,4-difluoro-phenoxy)-acetamide

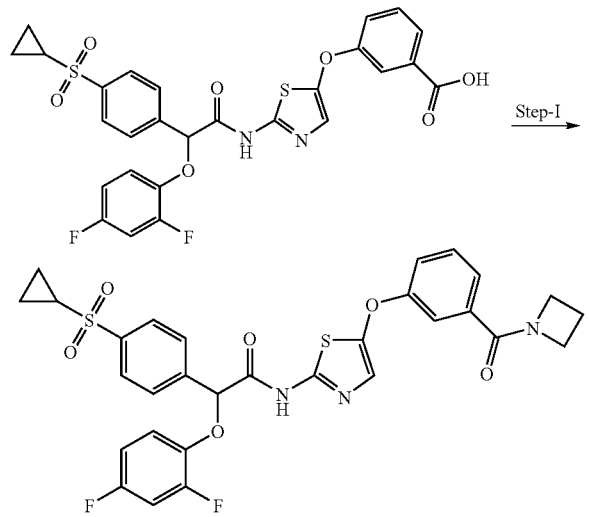

To a solution of 3-{2-[2-(4-cyclopropanesulfonyl-phenyl)-2-(2,4-difluoro-phenoxy)-acetylamino]-yhiazol-5-yloxy}-benzoic acid (0.05 gm, 0.088 mmol) in DMF (2 ml) was added azetidine hydrochloride (0.01 gm, 0.11 mmol), HoAt (0.5M in DMF) (0.22 ml, 0.106 mmol), EDCI (0.02 gm, 0.104 mmol) and diisopropylethylamine (0.037 ml, 0.22 mmol) and mixture was stirred for 18 hours at 25° C. under argon atmosphere.

Reaction mixture was diluted with water (25 ml) and extracted with ethylacetate (3×25 ml), combined organic layer was washed with brine solution, dried over anhydrous sodium sulfate, filtered and concentrated under reduced pressure. The residue was triturated with diisopropylether to the title compound (0.026 gm).

$^1$H NMR (400 MHz, DMSOd$_6$): δ 1.04-1.13 (m, 4H), 2.17-2.25 (m, 2H), 2.84-2.91 (m, 1H), 3.98 (t, J=7.58 Hz, 2H), 4.22 (t, J=7.58 Hz, 2H), 6.18 (s, 1H), 7.02-7.06 (m, 1H), 7.10-7.16 (m, 1H), 7.25 (s, 1H), 7.26 (s, 1H), 7.34-7.46 (m, 4H), 7.87 (d, J=8.03 Hz, 2H), 7.98 (d, J=8.3 Hz, 2H), 13.0 (brs, 1H). MS (EI) m/z: 626.3 (M+1).

Examples G2 to G9 were Prepared in Analogues Manner of Example G1

Example H1A/B-H13A/B Chirally Pure Compounds

Analytical Methods Used for Chiral Separation:

Method-1:-Column-OJ-RH (150×4.6)mm, 5 μm; Flow:1.0 ml min$^{-1}$; M.Phase:(98:02) Methanol: 0.05% Formic acid in water; Column Temp.: 40° C., Detection wavelength: 220 nm.

Method-2:-Column-OJ-RH (150×4.6)mm, 5 μm; Flow:1.0 ml min$^{-1}$; M.Phase: 100% Methanol, Column Temp.: ambient, Detection wavelength : 220 nm.

Method-3:-Column-OJ-RH (150×4.6)mm, 5 μm; Flow:1.0 ml min$^{-1}$; M.Phase:(95:5) Methanol: 0.05% Formic acid in water; Column Temp.: 40° C., Detection wavelength: 220/295 nm.

Method-4:-Column-OJ-RH (150×4.6)mm, 5 μm; Flow:1.0 ml min$^{-1}$; M.Phase:(98:2) Methanol (0.05% Formic acid): 0.05% Formic acid in water; Column Temp.: 40° C., Detection wavelength: 220 nm.

Method-5:-Column-OJ-RH (150×4.6)mm, 5 μm; Flow:0.7 ml min$^{-1}$; M.Phase:(90:10) Methanol: 0.05% Formic acid in water; Column Temp.: 40° C., Detection wavelength: 220 nm.

Method-6:-Column-OJ-RH (150×4.6)mm, 5 μm; Flow:1.4 ml min$^{-1}$; M.Phase:(95:5) Methanol: 0.05% Formic acid in water; Column Temp.: 40° C., Detection wavelength: 274 nm.

Method-7:-Column-OJ-RH (150×4.6)mm, 5 μm; Flow:1.0 ml min$^{-1}$; M.Phase: 100% Methanol, Column Temp.: 40° C. Detection wavelength : 220 nm.

Method-8:-Column-OJ-RH (150×4.6)mm, 5 μm; Flow:1.0 ml min$^{-1}$; M.Phase:(90:10) Methanol (0.05% Formic acid): 0.05% Formic acid in water; Column Temp.: 40° C., Detection wavelength: 220 nm.

Method-9:-Column-OJ-RH (150×4.6)nm, 5 μm; Flow:1.5 ml min$^{-1}$; M.Phase: Methanol, Column Temp.: 40° C. Detection wavelength: 220 nm.

Method-10:-Column-OJ-RH (150×4.6)mm, 5 μm; Flow: 0.5 ml min$^{-1}$; M.Phase:(30:70) Water: Acetonitrile, Column Temp.: ambient, Detection wavelength : 220 nm.

| Example No. | MS (EI)m/z: (M + 1). | IUPAC Name |
|---|---|---|
| G2 | 626.3 | N-{5-[4-(Azetidine-1-carbonyl)-phenoxy]-thiazol-2-yl}-2-(4-cyclopropanesulfonyl-phenyl)-2-(2,4-difluoro-phenoxy)-acetamide |
| G3 | 586.2 | 3-{2-[2-(4-Cyclopropanesulfonyl-phenyl)-2-(2,4-difluoro-phenoxy)-acetylamino]-thiazol-5-yloxy}-benzamide |
| G4 | 586.2 | 4-{2-[2-(4-Cyclopropanesulfonyl-phenyl)-2-(2,4-difluoro-phenoxy)-acetylamino]-thiazol-5-yloxy}-benzamide |
| G5 | 543.9 | 4-{2-[2-(4-Cyclopropanesulfonyl-phenyl)-2-(tetrahydro-furan-3-yloxy)-acetylamino]-thiazol-5-yloxy}-benzamide |
| G6 | 597.9 | N-{5-[4-(Azetidine-1-carbonyl)-phenoxy]-thiazol-2-yl}-2-4-cyclopropanesulfonyl-phenyl)-2-(tetrahydro-pyran-4-yloxy)-acetamide |
| G7 | 581.9 | N-[4-(2-Azetidin-1-yl-2-oxo-ethyl)-5-chloro-thiazol-2-yl]-2-(4-cyclopropanesulfonyl-phenyl)-2-(2,4-difluoro-phenoxy)-acetamide |
| G8 | 554.9 | N-[4-(2-Azetidin-1-yl-2-oxo-ethyl)-5-chloro-thiazol-2-yl]-2-(4-cyclopropanesulfonyl-phenyl)-2-(tetrahydro-pyran-4-yloxy)-acetamide |

| Example No. | MS (EI)m/z: (M + 1). | IUPAC Name | Racemic Example Used/Method Used |
|---|---|---|---|
| H1A | 545.0 | (−)2-(2,4-Difluoro-phenoxy)-2-[4-(piperidine-1-sulfonyl)-phenyl]-N-thiazolo[5,4-b]pyridin-2-yl-acetamide | A-78 Method-3 |
| H1B | 545.0 | (+)2-(2,4-Difluoro-phenoxy)-2-[4-(piperidine-1-sulfonyl)-phenyl]-N-thiazolo[5,4-b]pyridin-2-yl-acetamide | |
| H2A | 587.8 | (−) (5-Chloro-2-{2-(2,4-difluoro-phenoxy)-2-[4-(morpholine-4-sulfonyl)-phenyl]-acetylamino}-thiazol-4-yl)-acetic acid | B-35 Method-4 |
| H2B | 587.8 | (+) (5-Chloro-2-{2-(2,4-difluoro-phenoxy)-2-[4-(morpholine-4-sulfonyl)-pheny]-acetylamino}-thiazol-4-yl)-acetic acid | |
| H3A | 585.8 | (−) (5-Chloro-2-{2-(2,4-difluoro-phenoxy)-2-[4-(piperidine-1-sulfonyl)-phenyl]-acetylamino}-thiazol-4-yl)-acetic acid | B-33 Method-5 |
| H3B | 585.8 | (+) (5-Chloro-2-{2-(2,4-difluoro-phenoxy)-2-[4-(piperidine-1-sulfonyl)-phenyl]-acetylamino}-thiazol-4-yl)-acetic acid | |
| H4A | 587 | (+)4-{2-[2-(4-Cyclopropanesulfonyl-phenyl)-2-(2,4-difluoro-phenoxy)-acetylamino]-thiazol-5-yloxy}-benzoic acid | B-29 Method-6 |
| H4B | 587 | (−)4-{2-[2-(4-Cyclopropanesulfonyl-phenyl)-2-(2,4-difluoro-phenoxy)-acetylamino]-thiazol-5-yloxy}-benzoic acid | |
| H5A | 485.1 | (−)N-(5-Chloro-thiazol-2-yl)-2-(4-cyclopropanesulfonyl-phenyl)-2-(2,4-difluoro-phenoxy)-acetamide | A-2 Method-10 |
| H5B | 485.1 | (+)N-(5-Chloro-thiazol-2-yl)-2-(4-cyclopropanesulfonyl-phenyl)-2-(2,4-difluoro-phenoxy)-acetamide | |
| H6A | 626.0 | (+)N-{5-[4-(Azetidine-1-carbonyl)-phenoxy]-thiazol-2-yl}-2-(4-cyclopropanesulfonyl-phenyl)-2-(2,4-difluoro-phenoxy)-acetamide | G-2 Method-3 |
| H6B | 626.0 | (−)N-{5-[4-(Azetidine-1-carbonyl)-phenoxy]-thiazol-2-yl}-2-(4-cyclopropanesulfonyl-phenyl)-2-(2,4-difluoro-phenoxy)-acetamide | |
| H7A | 559.3 | (+) 4-{2-[2-(4-Cyclopropanesulfonyl-phenyl)-2-(tetrahydro-pyran-4-yloxy)-acetylamino]-thiazol-5-yloxy}-benzoic acid | B-30 Method-7 |
| H7B | 559.3 | (−) 4-{2-[2-(4-Cyclopropanesulfonyl-phenyl)-2-(tetrahydro-pyran-4-yloxy)-acetylamino]-thiazol-5-yloxy}-benzoic acid | |
| H8A | 544.9 | 4-(2-{2-(4-Cyclopropanesulfonyl-phenyl)-2-[(S)-(tetrahydro-furan-3-yl)oxy]-acetylamino}-thiazol-5-yloxy)-benzoic acid | B-85 Method-1 |
| H8B | 544.9 | 4-(2-{2-(4-Cyclopropanesulfonyl-phenyl)-2-[(S)-(tetrahydro-furan-3-yl)oxy]-acetylamino}-thiazol-5-yloxy)-benzoic acid | |
| H9A | 545.0 | 4-(2-{2-(4-Cyclopropanesulfonyl-phenyl)-2-[(R)-(tetrahydro-furan-3-yl)oxy]-acetylamino}-thiazol-5-yloxy)-benzoic acid | B-31 Method-1 |
| H9B | 545.0 | 4-(2-{2-(4-Cyclopropanesulfonyl-phenyl)-2-[(R)-(tetrahydro-furan-3-yl)oxy]-acetylamino}-thiazol-5-yloxy)-benzoic acid | |
| H10A | 474.00 | (−)2-(4-Cyclopropanesulfonyl-phenyl)-2-(tetrahydro-pyran-4-yloxy)-N-thiazolo[5,4-b]pyridin-2-yl-acetamide | A-79 Method-2 |
| H10B | 474.00 | (+)2-(4-Cyclopropanesulfonyl-phenyl)-2-(tetrahydro-pyran-4-yloxy)-N-thiazolo[5,4-b]pyridin-2-yl-acetamide | |

-continued

| Example No. | MS (EI)m/z: (M + 1). | IUPAC Name | Racemic Example Used/Method Used |
|---|---|---|---|
| H11A | 603.5 | (−)(5-Chloro-2-{2-(4-chloro-2-fluoro-phenoxy)-2-[4-(morpholine-4-sulfonyl)-phenyl]-acetylamino}-thiazol-4-yl)-acetic acid | B-49 Method-8 |
| H11B | 603.5 | (+)(5-Chloro-2-{2-(4-chloro-2-fluoro-phenoxy)-2-[4-(morpholine-4-sulfonyl)-phenyl]-acetylamino}-thiazol-4-yl)-acetic acid | |
| H12A | 504.20 | (+)2-(4-Cyclopropanesulfonyl-phenyl)-N-(5-methoxy-thiazolo[5,4-b]pyridin-2-yl)-2-(tetrahydro-pyran-4-yloxy)-Acetamide | A-80 Method-9 |
| H12B | 504.20 | (−)2-(4-Cyclopropanesulfonyl-phenyl)-N-(5-methoxy-thiazolo[5,4-b]pyridin-2-yl)-2-(tetrahydro-pyran-4-yloxy)-Acetamide | |
| H13A | 518.20 | (+)2-(4-Cyclopropanesulfonyl-phenyl)-N-(5-ethoxy-thiazolo[5,4-b]pyridin-2-yl)-2-(tetrahydro-pyran-4-yloxy)-a Cetamide | A-81 Method-2 |
| H13B | 518.20 | (−)2-(4-Cyclopropanesulfonyl-phenyl)-N-(5-ethoxy-thiazolo[5,4-b]pyridin-2-yl)-2-(tetrahydro-pyran-4-yloxy)-a Cetamide | |

Example I1: 2-(4-Cyclopropanesulfonyl-phenyl)-2-(tetrahydro-pyran-4-yloxy)-N-{5-[4-(2H-tetrazol-5-yl)-phenoxy]-thiazol-2-yl}-acetamide

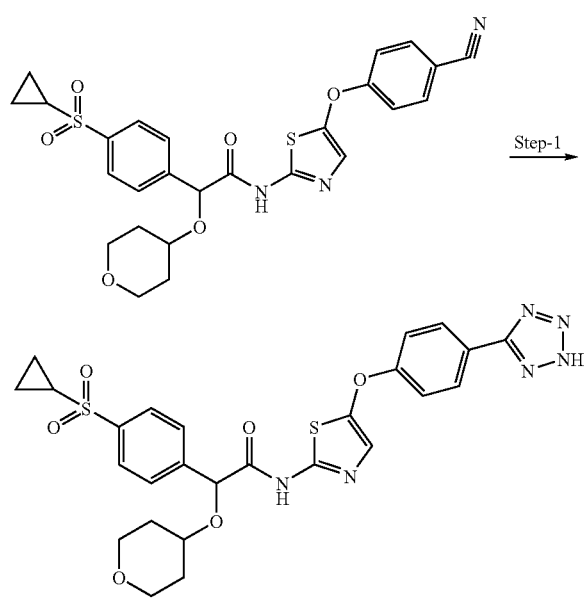

The mixture of N-[5-(4-Cyano-phenoxy)-thiazol-2-yl]-2-(4-cyclopropanesulfonyl-henyl)-2-(tetrahydro-pyran-4-yloxy)-acetamide (0.25 g, 0.46 mmol), Sodium azide (0.24 g, 3.71 mmol) and Ammonium chloride (0198 g, 3.71 mmol) in DMF (10 ml) was refluxed for 4-5 hr. After completion, reaction mixture was diluted with water and extracted with ethyl acetate, washed with water and brine, dried ($Na_2SO_4$) and concentrated in vacuo. Purified by PREP TLC to afford title compound.(0.120 g, 44%).

$^1$H NMR (400 MHz, $CDCl_3$): δ 1.03-1.08 (m, 2H), 1.34-1.49 (m, 2H), 1.73-1.81 (m, 2H), 1.87-2.05 (m, 2H), 2.43-2.48 (m, 1H), 3.37-3.44 (m, 2H), 3.67-3.74 (m, 1H), 3.93-4.03 (m, 2H), 5.24 (s, 1H), 7.16 (d, J=8.8 Hz, 2H), 7.18 (s, 1H), 7.69 (d, J=8.4 Hz, 2H), 7.91 (d, J=8.8 Hz, 2H), 8.02 (d, J=8.8 Hz, 2H).

MS (EI) m/z: 583.30 (M+1).

The below list of examples, but not to be limited to these, can also be synthesized following the general synthesis described above:

(+) (5-Chloro-2-{2-(2,4-difluorophenoxy)-2-[4(tetrahydro-pyran-4-sulfonyl)phenyl]acetylamino}thiazol-4-yl)acetic acid (−) (5-Chloro-2-{2-(2,4-difluorophenoxy)-2-[4-(tetrahydro-pyran-4-sulfonyl)phenyl]acetylamino}thiazol-4-yl)acetic acid (5-Chloro-2-{2-(4-chlorophenoxy)-2-[4-(tetrahydropyran-4-sulfonyl)phenyl]acetylamino}thiazol-4-yl)acetic acid (+) (5-Chloro-2-{2-(4-chlorophenoxy)-2-[4-(tetrahydropyran-4-sulfonyl)phenyl]acetylamino}thiazol-4-yl)acetic acid (−) (5-Chloro-2-{2-(4-chlorophenoxy)-2-[4-(tetrahydropyran-4-sulfonyl)phenyl]acetylamino}thiazol-4-yl)acetic acid 2-(4-Chlorophenoxy)-N-(5-fluorothiazol-2-yl)-2-[4-(tetrahydropyran-4-sulfonyl)phenyl]acetamide (+) 2-(4-Chlorophenoxy)-N-(5-fluorothiazol-2-yl)-2-[4-(tetrahydropyran-4-sulfonyl)phenyl]acetamide (−) 2-(4-Chlorophenoxy)-N-(5-fluorothiazol-2-yl)-2-[4-(tetrahydropyran-4-sulfonyl)phenyl]acetamide 2-(2,4-Difluorophenoxy)-N-(5-fluorothiazol-2-yl)-2-[4-(tetrahydropyran-4-sulfonyl)phenyl]acetamide (+) 2-(2,4-Difluorophenoxy)-N-(5-fluorothiazol-2-yl)-2-[4-(tetrahydropyran-4-sulfonyl)phenyl]acetamide (−) 2-(2,4-Difluorophenoxy)-N-(5-fluorothiazol-2-yl)-2-[4-(tetrahydropyran-4-sulfonyl)phenyl]acetamide (5-Chloro-2-{2-(2,4-difluorophenoxy)-2-[4(3-oxocyclopentanesulfonyl)phenyl]acetylamino}thiazol-4-yl)acetic acid (+) (5-Chloro-2-{2-(2,4-difluorophenoxy)-2-[4(3-oxocyclopentanesulfonyl)phenyl]acetylamino}thiazol-4-yl)acetic acid (−) (5-Chloro-2-{2-(2,4-difluorophenoxy)-2-[4(3-oxocyclopentanesulfonyl)phenyl]acetylamino}thiazol-4-yl)acetic acid 2-(2,4-Difluorophenoxy)-N-(5-fluorothiazol-2-yl)-2-[4(3-oxocyclopentanesulfonyl)phenyl]acetamide (+) 2-(2,4-Difluorophenoxy)-N-(5-fluorothiazol-2-yl)-2-[4(3-oxocyclopentanesulfonyl)phenyl]acetamide (−) 2-(2,4-Difluorophenoxy)-N-(5-fluorothiazol-2-yl)-2-[4(3-oxocyclopentanesulfonyl)phenyl]acetamide 2-(4-Chlorophenoxy)-N-(5-fluorothiazol-2-yl)-2-[4(3-oxocyclopentanesulfonyl)phenyl]acetamide (+) 2-(4-Chlorophenoxy)-N-(5-fluorothiazol-2-yl)-2-[4-(3-oxocyclopentanesulfonyl)phenyl]acetamide (−) 2-(4-Chlorophenoxy)-N-(5-fluorothiazol-2-yl)-2-[4(3-oxocyclopentanesulfonyl)phenyl]acetamide (5-Chloro-2-{2-(4-chlorophenoxy)-2-[4-(3-oxocyclopentanesulfonyl)phenyl]acetylamino}thiazol-4-yl)acetic acid (+) (5-Chloro-2-{2-(4-chlorophenoxy)-2-[4(3-oxocyclopentanesulfonyl)phenyl]acetylamino}thiazol-4-yl)acetic acid (−) (5-Chloro-2-{2-(4-chlorophenoxy)-2-[4(3-oxocyclopentanesulfonyl)phenyl]acetylamino}thiazol-4-yl)acetic acid 5-Chloro-2-{2-(2,4-difluorophenoxy)-2-[4(2-oxopiperidine-4-sulfonyl)phenyl]acetylamino}thiazol-4-yl)acetic acid (+) 5-Chloro-2-{2-(2,4-difluorophenoxy)-2-[4(2-oxopiperidine-4-sulfonyl)phenyl]acetylamino}thiazol-4-yl)acetic acid (−) 5-Chloro-2-{2-(2,4-difluorophenoxy)-2-[4(2-oxopiperidine-4-sulfonyl)phenyl]acetylamino}thiazol-4-yl)acetic acid (5-Chloro-2-{2-(4-chlorophenoxy)-2-[4(2-oxopiperidine-4-sulfonyl)phenyl]acetylamino}thiazol-4-yl)acetic acid (+) (5-Chloro-2-{2-(4-chlorophenoxy)-2-[4(2-oxopiperidine-4-sulfonyl)phenyl]acetylamino}thiazol-4-yl)acetic acid (−) (5-Chloro-2-{2-(4-chlorophenoxy)-2-[4(2-oxopiperidine-4-sulfonyl)phenyl]acetylamino}thiazol-4-yl)acetic acid 2-(2,4-Difluorophenoxy)-N-(5-fluorothiazol-2-yl)-2-[4-(2-oxopiperidine-4-sulfonyl)phenyl]acetamide (+) 2-(2,4-Difluorophenoxy)-N-(5-fluorothiazol-2-yl)-2-[4(2-oxopiperidine-4-sulfonyl)phenyl]acetamide (−) 2-(2,4-Difluorophenoxy)-N-(5-fluorothiazol-2-yl)-2-[4(2-oxopiperidine-4-sulfonyl)phenyl]acetamide 2-(4-Chlorophenoxy)-N-(5-fluorothiazol-2-yl)-2-[4(2-oxopiperidine-4-sulfonyl)phenyl]acetamide (+) 2-(4-Chlorophenoxy)-N-(5-fluorothiazol-2-yl)-2-[4(2-oxopiperidine-4-sulfonyl)phenyl]acetamide (−) 2-(4-Chlorophenoxy)-N-(5-fluorothiazol-2-yl)-2-[4(2-oxopiperidine-4-sulfonyl)phenyl]acetamide {5-Chloro-2-[2-[4-(cyclohex-1-enesulfonyl)phenyl]-2-(2,4-difluorophenoxy)acetylamino]thiazol-4-yl}acetic acid (+) {5-Chloro-2-[2-[4-(cyclohex-1-enesulfonyl)phenyl]-2-(2,4-difluorophenoxy)acetylamino]thiazol-4-yl}acetic acid (−) {5-Chloro-2-[2-[4-(cyclohex-1-enesulfonyl)phenyl]-2-(2,4-difluorophenoxy)acetylamino]thiazol-4-yl}acetic acid (5-Chloro-2-{2-(4-chlorophenoxy)-2-[4(cyclohex-1-enesulfonyl)phenyl]acetylamino}thiazol-4-yl)-acetic acid (+) (5-Chloro-2-{2-(4-chlorophenoxy)-2-[4(cyclohex-1-enesulfonyl)phenyl]acetylamino}thiazol-4-yl)-acetic acid (−) (5-Chloro-2-{2-(4-chlorophenoxy)-2-[4(cyclohex-1-enesulfonyl)phenyl]acetylamino}thiazol-4-yl)-acetic acid 2-[4-(Cyclohex-1-enesulfonyl)phenyl]-2-(2,4-difluorophenoxy)-N-(5-fluorothiazol-2-yl)acetamide (+) 2-[4-(Cyclohex-1-enesulfonyl)phenyl]-2-(2,4-difluorophenoxy)-N-(5-fluorothiazol-2-yl)acetamide (−) 2-[4-(Cyclohex-1-enesulfonyl)phenyl]-2-(2,4-difluorophenoxy)-N-(5-fluorothiazol-2-yl)acetamide 2-(4-Chlorophenoxy)-2-[4(cyclohex-1-enesulfonyl)phenyl]-N-(5-fluorothiazol-2-yl(acetamide (+) 2-(4-Chlorophenoxy)-2-[4(cyclohex-1-enesulfonyl)phenyl]-N-(5-fluorothiazol-2-yl(acetamide (−) 2-(4-Chlorophenoxy)-2-[4(cyclohex-1-enesulfonyl)phenyl]-N-(5-fluorothiazol-2-yl)acetamide (5-Chloro-2-{2-(2,4-difluorophenoxy)-2-[4-(tetrahydrofuran-3-sulfonyl)phenyl]acetylamino}thiazol-4-yl)-acetic acid (+) (5-Chloro-2-{2-(2,4-difluorophenoxy)-2-[4-(tetrahydrofuran-3-sulfonyl)phenyl]acetylamino}thiazol-4-yl)-acetic acid (−) (5-Chloro-2-{2-(2,4-difluorophenoxy)-2-[4-(tetrahydrofuran-3-sulfonyl)phenyl]acetylamino}thiazol-4-yl)-acetic acid (5-Chloro-2-{2-(4-chlorophenoxy)-2-[4-(tetrahydrofuran-3-sulfonyl)phenyl]acetylamino}thiazol-4-yl)acetic acid (+) (5-Chloro-2-{2-(4-chlorophenoxy)-2-[4-(tetrahydrofuran-3-sulfonyl)phenyl]acetylamino}thiazol-4-yl)acetic acid (−) (5-Chloro-2-{2-(4-chlorophenoxy)-2-[4-(tetrahydrofuran-3-sulfonyl)phenyl]acetylamino}thiazol-4-yl)acetic acid 2-(2,4-Difluorophenoxy)-N-(5-fluorothiazol-2-yl)-2-[4-(tetrahydrofuran-3-sulfonyl)phenyl]acetamide (+) 2-(2,4-Difluorophenoxy)-N-(5-fluorothiazol-2-yl)-2-[4-(tetrahydrofuran-3-sulfonyl)phenyl]acetamide (−) 2-(2,4-Difluorophenoxy)-N-(5-fluorothiazol-2-yl)-2-[4-(tetrahydrofuran-3-sulfonyl)phenyl]acetamide 2-(4-Chlorophenoxy)-N-(5-fluorothiazol-2-yl)-2-[4-(tetrahydrofuran-3-sulfonyl)phenyl]acetamide (+) 2-(4-Chlorophenoxy)-N-(5-fluorothiazol-2-yl)-2-[4-(tetrahydrofuran-3-sulfonyl)phenyl]acetamide (−) 2-(4-Chlorophenoxy)-N-(5-fluorothiazol-2-yl)-2-[4-(tetrahydrofuran-3-sulfonyl)phenyl]acetamide {2-[2-(4-Cyclopropanesulfonylphenyl)-2-(2,4-difluorophenoxy)acetylamino]-5-fluorothiazol-4-yl}acetic acid (+) {2-[2-(4-Cyclopropanesulfonylphenyl)-2-(2,4-difluorophenoxy)acetylamino]-5-fluorothiazol-4-yl}acetic acid (−) {2-[2-(4-Cyclopropanesulfonylphenyl)-2-(2,4-difluorophenoxy)acetylamino]-5-fluorothiazol-4-yl}acetic acid {2-[2-(4-Chlorophenoxy)-2-(4-cyclopropanesulfonylphenyl(acetylamino]-5-fluorothiazol-4-yl}acetic acid (+) {2-[2-(4-Chlorophenoxy)-2-(4-cyclopropanesulfonylphenyl)acetylamino]-5-fluorothiazol-4-yl}acetic acid (−) {2-[2-(4-Chlorophenoxy)-2-(4-cyclopropanesulfonylphenyl(acetylamino]-5-fluorothiazol-4-yl}acetic acid {2-[2-(4-Cyclopentanesulfonylphenyl)-2-(2,4-difluorophenoxy)acetylamino]-5-fluorothiazol-4-yl}acetic acid (+) {2-[2-(4-Cyclopentanesulfonylphenyl)-2-(2,4-difluorophenoxy)acetylamino]-5-fluorothiazol-4-yl}acetic acid (−) {2-[2-(4-Cyclopentanesulfonylphenyl)-2-(2,4-difluorophenoxy)acetylamino]-5-fluorothiazol-4-yl}acetic acid 6-{2-(2,4-Difluoro-phenoxy)-2-[4-(piperidine-1-sulfonyl)-phenyl]-acetylamino}-nicotinic acid 1-(2-{2-(2,4-Difluoro-phenoxy)-2-[4(morpholine-4-sulfonyl)-phenyl]-acetylamino}-thiazol-5-yl)-piperidine-4-carboxylic acid 6-{2-(2,4-Difluoro-phenoxy)-2-[4(morpholine-4-sulfonyl)-phenyl]-acetylamino}-nicotinic acid 2-(2,4-Difluoro-phenoxy)-N-(1-methyl-1H-pyrazol-3-yl)-2-[4-(pyrrolidine-1-sulfonyl)-phenyl]-acetamide 6-{2-(2,4-Difluoro-phenoxy)-2-[4-(pyrrolidine-1-sulfonyl)-phenyl]-acetylamino}-nicotinic acid (5-Chloro-2-{2-(2,4-difluoro-phenoxy)-2-[4-(pyrazole-1-sulfonyl)-phenyl]-acetylamino}-thiazol-4-yl)-acetic acid 2-(2,4-Difluoro-phenoxy)-N-(5-morpholin-4-yl-thiazol-2-yl)-2-[4-(tetrahydro-pyran-4-sulfonyl)-phenyl]-acetamide 1-(2-{2-(2,4-Difluoro-phenoxy)-2-[4-(tetrahydro-pyran-4-sulfonyl)-phenyl]-acetylamino}-thiazol-5-yl)-piperidine-4-carboxylic acid 2-(2,4-Difluoro-phenoxy)-2-[4-(tetrahydro-pyran-4-sulfonyl)-phenyl]-N-thiazolo[5,4-b]pyridin-2-yl-acetamide 6-{2-(2,4-Difluoro-phenoxy)-2-[4-(tetrahydro-pyran-4-sulfonyl)-phenyl]-acetylamino}-nicotinic acid 2-(2,4-Difluoro-phenoxy)-N-(1-methyl-1H-pyrazol-3-yl)-2-[4-(tetrahydro-pyran-4-sulfonyl)-phenyl]-acetamide N-{5-[4-(Azetidine-1-carbonyl)-phenoxy]-thiazol-2-yl}-2-(2,4-difluoro-phenoxy)-2-[4-(tetrahydro-pyran-4-sulfonyl)-phenyl]-acetamide N-{5-[3-(Azetidine-1-carbonyl)-phenoxy]-thiazol-2-yl}-2-(2,4-difluoro-phenoxy)-2-[4-(tetrahydro-pyran-4-sulfonyl)-phenyl]-acetamide (5-Chloro-2-{2-(2,4-difluoro-phenoxy)-2-[4-(tetrahydro-furan-3-sulfonyl)-phenyl]-acetylamino}-thiazol-4-yl)-acetic acid 4-(2-{2-(2,4-Difluoro-phenoxy)-2-[4-(tetrahydro-furan-3-sulfonyl)-phenyl]-acetylamino}-thiazol-5-yloxy)-benzoic acid 2-(2,4-Difluoro-phenoxy)-N-(5-morpholin-4-yl-thiazol-2-yl)-2-[4-(tetrahydro-furan-3-sulfonyl)-phenyl]-acetamide 1-(2-{2-(2,4-Difluoro-phenoxy)-2-[4-(tetrahydro-furan-3-sulfonyl)-phenyl]-acetylamino}-thiazol-5-yl)-piperidine-4-carboxylic acid 2-(2,4-Difluoro-phenoxy)-2-[4-(tetrahydro-furan-3-sulfonyl)-phenyl]-N-thiazolo[5,4-b]pyridin-2-yl-acetamide 6-{2-(2,4-Difluoro-phenoxy)-2-[4-(tetrahydro-furan-3-sulfonyl)-phenyl]-acetylamino}-nicotinic acid 2-(2,4-Difluoro-phenoxy)-N-(1-methyl-1H-pyrazol-3-yl)-2-[4-(tetrahydro-furan-3-sulfonyl)-phenyl]-acetamide N-{5-[4-(Azetidine-1-carbonyl)-phenoxy]-thiazol-2-yl}-2-(2,4-difluoro-phenoxy)-2-[4-(tetrahydro-furan-3-sulfonyl)-phenyl]-acetamide N-{5-[3-(Azetidine-1-carbonyl)-phenoxy]-thiazol-2-yl}-2-(2,4-difluoro-phenoxy)-2-[4-(tetrahydro-furan-3-sulfonyl)-phenyl]-acetamide (5-Chloro-2-{2-(2,4-difluoro-phenoxy)-2-[4-(piperidine-4-sulfonyl)-phenyl]-acetylamino}-thiazol-4-yl)-acetic acid 4-(2-{2-(2,4-Difluoro-phenoxy)-2-[4-(piperidine-4-sulfonyl)-phenyl]-acetylamino}-thiazol-5-yloxy)-benzoic acid 2-(2,4-Difluoro-phenoxy)-N-(5-morpholin-4-yl-thiazol-2-yl)-2-[4-(piperidine-4-sulfonyl)-phenyl]-acetamide 1-(2-{2-(2,4-Difluoro-phenoxy)-2-[4-(piperidine-4-sulfonyl)-phenyl]-acetylamino}-thiazol-5-yl)-piperidine-4-carboxylic acid 2-(2,4-Difluoro-phenoxy)-2-[4-(piperidine-4-sulfonyl)-phenyl]-N-thiazolo[5,4-b]pyridin-2-yl-acetamide 6-{2-(2,4-Difluoro-phenoxy)-2-[4-(piperidine-4-sulfonyl)-phenyl]-acetylamino}-nicotinic acid 2-(2,4-Difluoro-phenoxy)-N-(1-methyl-1H-pyrazol-3-yl)-2-[4-(piperidine-4-sulfonyl)-phenyl]-acetamide N-{5-[4-(Azetidine-1-carbonyl)-phenoxy]-thiazol-2-yl}-2-(2,4-difluoro-phenoxy)-2-[4-(piperidine-4-sulfonyl)-phenyl]-acetamide N-{5-[3-(Azetidine-1-carbonyl)-phenoxy]-thiazol-2-yl}-2-(2,4-difluoro-phenoxy)-2-[4-(piperidine-4-sulfonyl)-phenyl]-acetamide (5-Chloro-2-{2-(2,4-difluoro-phenoxy)-2-[4-(3-oxo-cyclopentanesulfonyl)-phenyl]-acetylamino}-thiazol-4-yl)-acetic acid 2-(4-Cyclopropanesulfonyl-phenyl)-2-(2,4-difluoro-phenoxy)-N-{5-[4-(pyrrolidine-1-carbonyl)-phenoxy]-thiazol-2-yl}-acetamide 2-(4-Cyclopropanesulfonyl-phenyl)-2-(2,4-difluoro-phenoxy)-N-{5-[4-(piperidine-1-carbonyl)-phenoxy]-thiazol-2-yl}-acetamide 4-{2-[2-(4-Cyclopropanesulfonyl-phenyl)-2-(pyrrolidin-3-yloxy)-acetylamincd]-thiazol-5-yloxyl}-benzoic acid 4-{2-[2-(4-Cyclopropanesulfonyl-phenyl)-2-(1-methyl-pyrrolidin-3-yloxy)-acetylamino]-thiazol-5-yloxy}-benzoic acid 4-{2-[2-(4-Cyclopropanesulfonyl-phenyl)-2-(piperidin-4-yloxy)-acetylamino]-thiazol-5-yloxyl}-benzoic acid 4-{2-[2-(4-Cyclopropanesulfonyl-phenyl)-2-(1-methyl-piperidin-4-yloxy)-acetylamino]-thiazol-5-yloxy}-benzoic acid {5-Chloro-2-[2-(4-cyclopropanesulfonyl-phenyl)-2-(1-methyl-piperidin-4-yloxy)-acetylamino]-thiazol-4-yl}-acetic acid {5-Chloro-2-[2-(4-cyclopropanesulfonyl-phenyl)-2-(pyrrolidin-3-yloxy)-acetylamino]-thiazol-4-yl}-acetic acid {5-Chloro-2-[2-(4-cyclopropanesulfonyl-phenyl)-2-(1-methyl-pyrrolidin-3-yloxy)-acetylamino]-thiazol-4-yl}-acetic acid 2-(4-Cyclopropanesulfonyl-phenyl)-2-(1-methyl-pyrrolidin-3-yloxy)-N-thiazolo[5,4-b]pyridin-2-yl-acetamide 2-(4-Cyclopropanesulfonyl-phenyl)-2-(pyrrolidin-3-yloxy)-N-thiazolo[5,4-b]pyridin-2-yl-acetamide 2-(4-Cyclopropanesulfonyl-phenyl)-2-(1-methyl-piperidin-4-yloxy)-N-thiazolo[5,4-b]pyridin-2-yl-acetamide 2-(4-Cyclopropanesulfonyl-phenyl)-2-(piperidin-4-yloxy)-N-thiazolo[5,4-b]pyridin-2-yl-acetamide {2[2-[5-(Azetidine-1-carbonyl)-pyrazin-2-yloxy]-2-(4-cyclopropanesulfonyl-phenyl)-acetylamino]-5-chloro-thiazol-4-yl}-acetic acid Glucokinase Activity Assay:

The glucokinase (GK) assay is a coupled enzymatic assay. GK catalyzes the first step of glycolysis, the conversion of glucose to glucose-6-phosphate (G6P) in the presence of ATP. G6P in turn is converted by glucose-6-phosphate dehydrogenase (G6PD) to 6-phosphogluconate, a process that requires NAD, resulting in NADH formation. Since the GK-catalyzed step is the rate-limiting step of this coupled enzymatic process, the rate of accumulation of 6-phosphogluconate and NADH is directly proportional to the rate of glucose phosphorylation by GK. The rate of the GK-catalyzed reaction can therefore be measured by monitoring the increase in NADH absorbance at 340 nm.

The assay is carried out according to the protocol outlined in Hariharan et al (1997), Diabetes 46: 11-16. Briefly, the test compounds are incubated in a reaction mix containing 25 mM HEPES (pH 7.2), 10 mM MgCl$_2$, 100 mM KCl, 5 mM ATP, 2 mM DTT, 0.5 mM NAD, 1 U/ml *Leuconostoc mesenteroides* G6PD, 0.3 U/ml of purified human recombinant GK, and different concentrations of glucose. Enzymatic activity is calculated from the initial reaction velocity, measured from the change in NADH absorbance as a function of time.

Compounds described in formula (I), in concentration ranges from 1.0 nM to 500 are tested in the purified human recombinant glucokinase assay described above.

A compound is considered to be a glucokinase activator if it, in its testable range of concentrations, yields a higher rate of glucose phosphorylation than in its absence at a particular glucose concentration, for example at 5 mM glucose.

Characterization of glucokinase activators from the in vitro glucokinase assay:

Compounds of general formula (I) are tested in the in vitro GK enzymatic assay to monitor dose-dependent effect on glucokinase activation (in kinetic mode), as described above, at various glucose concentrations. The $S_{0.5}$ of glucokinase for glucose at different concentration of each compound of interest is calculated from the following modified version of the Michaelis-Menten equation, $V=V_{max}[S]^n/(S_{0.5}{}^n+[S]^n)$, where [S] is the glucose concentration and n is the Hill coefficient (taken as 1.7 to account for the sigmoidal kinetics of glucokinase with respect to glucose). The $S_{0.5}$ is plotted against the log of the compound concentration. The change in the $S_{0.5}$ of glucokinase ($\Delta S_{0.5}$) for glucose is calculated by subtracting the $S_{0.5}$ at each concentration of the compound from the $S_{0.5}$ in the vehicle control. The $\Delta S_{0.5}$ is then normalized to a percent scale, where the $S_{0.5}$ in the vehicle control is set to 0% and 0 mM glucose is set to 100%. The % $\Delta S_{0.5}$ is then plotted against the log of the compound concentration. The $EC_{50}$ and $E_{max}$ of % change in $S_{0.5}$ is obtained from the sigmoidal fit of the data. Detailed protocol has been described in our copending application no. WO 2008/104994 which is incorporated herein by reference. Characterization data of some representative glucokinase activators of the present disclosure, which are illustrative but not limiting, are given in table 1 below.

TABLE I $EC_{50}$ and $E_{max}$ (with respect to % $\Delta S_{0.5}$) of GK activators

| Example-No. | $EC_{50}$ (µM) | % $E_{max}$ |
|---|---|---|
| A2 | 0.13 | 95 |
| A3 | 0.2 | 95 |
| A10 | 0.11 | 95 |
| A11 | 0.11 | 95 |
| A12 | 0.17 | 90 |
| A16 | 7.1 | 90 |
| A27 | 1.27 | 90 |
| A28 | 0.64 | 90 |
| A29 | 0.59 | 90 |
| A36 | 0.11 | 95 |
| A37 | 2.0 | 90 |
| A38 | 0.39 | 95 |
| A41 | 0.46 | 90 |
| A42 | 0.12 | 95 |
| A43 | 0.15 | 95 |
| A45 | 1.3 | 90 |
| A46 | 1.37 | 90 |
| A47 | 1.2 | 90 |
| B6 | 0.83 | 90 |
| B12 | >10 | |
| B14 | 1.6 | 90 |
| B15 | 0.67 | 95 |
| B16 | 1.0 | 90 |
| B19 | 3.3 | 95 |
| B20 | 6.8 | 90 |
| B22 | >10 | |
| B26 | >10 | |
| E1 | 1.55 | 95 |
| E2 | 0.37 | 95 |
| E3 | 2.37 | 90 |
| F1 | 1.27 | 90 |
| F2 | 0.67 | 95 |
| F3 | 2.47 | 90 |
| H4A | 0.034 | 95 |
| H7A | 0.069 | 92 |
| H9A | 0.022 | 88 |
| B92 | 0.17 | 91 |
| B94 | 0.045 | 91 |
| B100 | 0.22 | 91 |
| G3 | 0.2 | 90 |
| H6A | 0.11 | 93 |
| G6 | 0.11 | 90 |
| A117 | 0.15 | 92 |
| I1 | 0.099 | 88 |
| A75 | 0.076 | 93 |
| H10A | 0.15 | 94 |
| H12A | 0.068 | 95 |
| A81 | 0.054 | 92 |
| A82 | 0.24 | 94 |
| A114 | 0.15 | 92 |
| B101 | 0.1 | 75 |
| H3A | 0.43 | 90 |
| H1A | 0.084 | 85 |
| B50 | 0.28 | 90 |

Measurement of Glycogen Synthesis in Primary Rat Hepatocytes:

Primary hepatocytes are collected from male Wistar rats, and tested for viability by trypan blue exclusion. Primary hepatocytes cultures with viability greater than 95% are selected for the glycogen synthesis assay. The cells are seeded in a 48-well plate at a density of 200,000 cells/well in 250 µl Minimal Essential Medium (MEM) containing 10% foetal calf serum (FCS) and 1.7 µM insulin, and incubated for 4 hours at 37° C. to allow attachment. The medium is replaced with fresh MEM containing 10% FCS, 1.7 µM insulin and 10 nM dexamethasone, and the cells are incubated for 16 hours at 37° C. The medium is then replaced with fresh MEM (serum-free) containing 2 µCi/ml of D-[$U^{14}C$]-Glucose along with 10 µM of the compound in a final DMSO concentration of 0.1%. The final glucose concentration is brought to 10 mM by the addition of D-Glucose (MEM already contains 5 mM glucose). The cells are incubated for 3 hours at 37° C. The cells are washed twice with 150 mM NaCl, lysed with 0.1 N NaOH, and the lysate precipitated with 8% w/v trichloroacetic acid (TCA) and 1 mg/well unlabeled glycogen as carrier. Cell debris is pelleted by centrifugation, the supernatant is removed, and the glycogen is precipitated with 63% ethanol. After another round of centrifugation, the supernatant is removed, and the pellet containing the precipitated glycogen is dried overnight. De novo synthesized glycogen is estimated in a scintillation counter (MicroBeta Trilux, Perkin Elmer), and expressed as fold increase over DMSO control.

The protocol for the glycogen assay is based on the method described in "Biochem J. 1990 Feb. 15; 266(1): 91-102" with a few minor modifications. The protocol for isolation of primary rat hepatocytes is based on the method described in "Methods in Enzymology, Vol. III. pp 34-50. Ed. by S. P. Colowick and N. O. Kaplan. New York, Academic Press, 1957" with a few minor modifications.

Compounds described in formula (I), in concentration ranges from 1.0 nM to 500 µM, are tested in glycogen synthesis assay described above.

A compound is considered to be a glucokinase activator in a cellular environment if it demonstrates significant increase of glycogen synthesis over DMSO control as described in the above mentioned glycogen synthesis assay.

The glycogen synthesis data of some representative compounds of the present invention, which are illustrative but not limiting, is given in the table 2 below.

TABLE 2

Glycogen synthesis data

| Example | Fold increase in glycogen synthesis at 10 μM compound |
|---------|--------------------------------------------------------|
| A3      | 2.9   |
| A10     | 4.3   |
| A15     | 3.7   |
| B6      | 8.6   |
| B16     | 5.5   |
| B19     | 3.3   |
| B20     | 6.8   |
| E1      | 8.1   |
| E2      | 8.8   |
| E3      | 9.5   |
| F1      | 4.5   |
| F2      | 7.2   |
| F3      | 7.0   |
| H4A     | 15.5  |
| H7A     | 7.7   |
| H9A     | 11    |
| B92     | 7.8   |
| B94     | 8.7   |
| G3      | 13.5  |
| G6      | 6.2   |
| A75     | 7.1   |
| H10A    | 4.1   |
| H12A    | 5     |

Although the subject matter has been described in considerable details with reference to certain preferred embodiments thereof, other embodiment are possible. As such, the spirit and scope of the appended claims should not be limited to the description of the preferred embodiments contained therein.

We claim:

1. A compound of formula (I)

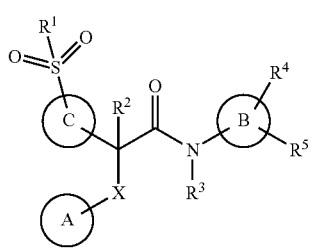

(I)

or its stereoisomers, tautomers, prodrugs, pharmaceutically acceptable salts, and solvates, wherein, ring A and ring C are mono or bicyclic ring independently selected from aryl, heteroaryl or heterocyclyl;

wherein aryl and heteroaryl are optionally substituted with 1 to 4 substituents independently selected from halogen, monohaloalkyl, dihaloalkyl or perhaloalkyl, monohaloalkoxy, dihaloalkoxy or perhaloalkoxy, cyano, nitro, alkyl, alkenyl, alkynyl, methylenedioxy, amidino —$NR^6R^7$, —$OR^6$, —$S(O)_pR^6$, —$S(O)_p NR^6R^7$, —$NR^6S(O)_pR^7$, —$NR^6C(O)R^7$, —$OS(O)_pR^7$, —$NR^6C(O)OR^7$, —$NR^6C(O)NR^6R^7$, —$(CR^8R^9)_nC(O)OR^6$, —$(CR^8R^9)_nC(O)NR^6R^7$, —$(CR^8R^9)_nC(O)R^6$, cycloalkyl, cycloalkylalkyl, heterocyclyl, heterocycloalkyl, aryl, arylalkyl, heteroaryl, heteroarylalkyl, cycloalkenyl, aryloxy, or heteroaryloxy groups;

heterocyclyl is optionally substituted with 1 to 4 substituents independently selected from halogen, monohaloalkyl, dihaloalkyl or perhaloalkyl, monohaloalkoxy, dihaloalkoxy or perhaloalkoxy, oxo, cyano, nitro, alkyl, alkenyl, alkynyl, methylenedioxy, amidino —$NR^6R^7$, —$OR^6$, —$S(O)_pR^6$, —$S(O)_p NR^6R^7$, —$NR^6S(O)_pR^7$, —$NR^6C(O)R^7$, —$OS(O)_pR^7$, —$NR^6C(O)OR^7$, —$NR^6C(O)NR^6R^7$, —$(CR^8R^9)_nC(O)OR^6$, —$(CR^8R^9)_nC(O)NR^6R^7$, —$(CR^8R^9)_nC(O)R^6$, cycloalkyl, cycloalkylalkyl, heterocyclyl, heterocycloalkyl, aryl, arylalkyl, heteroaryl, heteroarylalkyl, aryloxy, or heteroaryloxy groups;

p=0-2; n=0-4;

$R^6$ and $R^7$ are independently selected from the group consisting of hydrogen, alkyl, alkenyl, alkynyl, aryl, arylalkyl, heteroaryl, heteroarylalkyl, cycloalkyl, cycloalkylalkyl, heterocyclyl and heterocyclylalkyl, further substituted; or $R^6$ and $R^7$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, alkenyl, alkynyl, nito, cyano, —$OR^6$, —$SR^6$, —$NR^6R^7$, oxo, alkylsulfonyl, —$COOR^6$, —$C(O)NR^6R^7$, cycloalkyl, cycloalkylalkyl, aryl, arylalkyl, heterocyclyl, heterocyclylalkyl, heteroaryl, or heteroarylalkyl;

wherein $R^6$ and $R^7$ are as described above;

$R^8$ and $R^9$ are independently selected from the group consisting of hydrogen, fluorine, $OR^6$, alkyl, and perfluoroalkyl; or $R^8$ and $R^9$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, alkenyl, alkynyl, nito, cyano, oxo, —$OR^6$, —$SR^6$, —$NR^6R^7$, alkylsulfonyl, —$COOR^6$, —$C(O)NR^6R^7$, cycloalkyl, cycloalkylalkyl, aryl, arylalkyl, heterocyclyl, heterocyclylalkyl, heteroaryl, or heteroarylalkyl;

wherein $R^6$ and $R^7$ are as described above;

X represents O, $NR^6$, or $S(O)_p$ wherein $R^6$ is as described above;

p=0-2;

$R^1$ is selected from cycloalkyl or heterocyclyl, each optionally substituted with halogen, monohaloalkyl, dihaloalkyl, perhaloalkyl, monohaloalkoxy, dihaloalkoxy, perhaloalkoxy, oxo, cyano, nitro, alkyl, alkenyl, alkynyl, methylenedioxy, amidino —$NR^6R^7$, —$OR^6$, —$S(O)_p R^6$, —$S(O)_p NR^6R^7$, —$NR^6S(O)_pR^7$, —$NR^6C(O)R^7$, —$OS(O)_pR^7$, —$NR^6C(O)OR^7$, —$NR^6C(O)NR^6R^7$, —$(CR^8R^9)_nC(O)OR^6$, —$(CR^8R^9)_nC(O)NR^6R^7$, —$(CR^8R^9)_nC(O)R^6$, cycloalkyl, cycloalkylalkyl, heterocyclyl, heterocycloalkyl, aryl, arylalkyl, heteroaryl, heteroarylalkyl, aryloxy or heteroaryloxy;

$R^2$ is hydrogen;

$R^3$ is selected from the group consisting of hydrogen, alkyl and perfluoroalkyl;

ring-B is an optionally substituted 4-12 membered mono or bicyclic ring containing 1-4 hetero atoms selected from N, O, S with at least one nitrogen in the ring;

$R^4$ and $R^5$ are independently selected from the group consisting of hydrogen, halogen, alkyl, alkenyl, alkynyl, cycloalkyl, cycloalkylalkyl, heterocyclyl, heterocycloalkyl, aryl, arylalkyl, heteroaryl, heteroarylalkyl, mono, di or tri substituted haloalkyl, nitrile, nitro, oxo, —NR⁶R⁷, —OR⁶, —S(O)ₚR⁶, —S(O)ₚNR⁶R⁷, —NR⁶S(O)ₚR⁷, —NR⁶C(O)R⁷, —OS(O)ₚR⁷, —NR⁶C(O)OR⁷, —(CR⁸R⁹)ₙC(O)OR⁶, —(CR⁸R⁹)ₙ(CO)NR⁶R⁷, —(CR⁸R⁹)ₙS(O)ₚNR⁶R⁷, —(CR⁸R⁹)ₙN(R⁶)C(O)R⁶, —(CR⁸R⁹)ₙOR⁶, —C(CR⁸R⁹)ₙNR⁶R⁷, —C(R⁸R⁹)ₙCO(R⁶) and —S(O)ₚC(R⁸R⁹)ₙC(O)OR⁶;
wherein each of R⁴ and R⁵ is optionally substituted with one or more substituents selected from halo, straight chain or branched chain alkyl, alkenyl, alkynyl, cycloalkyl, aryl, heteroaryl, heterocycle, alkylsulfonyl, oxo, nitro, cyano, —COOR⁶, —C(O)NR⁶R⁷, —OR⁶, —SR⁶ or —NR⁶R⁷;

wherein n=0-4;

R⁶, R⁷, R⁸ and R⁹ are as described above;

in addition to R⁴ and R⁵, ring-B is further optionally substituted with one or more substituents selected from halo, straight chain or branched chain alkyl, alkenyl, alkynyl, cycloalkyl, aryl, heteroaryl, heterocyclyl, alkylsulfonyl, oxo, nitro, cyano, —COOR⁶, —C(O)NR⁶R⁷, —OR⁶, —SR⁶ or —NR⁶R⁷, wherein R⁶ and R⁷ are as described above.

2. The compound as claimed in claim 1, or its stereoisomers, tautomers, prodrugs, pharmaceutically acceptable salts, and solvates thereof wherein ring-A is selected from 3. The compound as claimed in claim 1, or its stereoisomers, tautomers, prodrugs, pharmaceutically acceptable salts, and solvates wherein ring-B is selected from

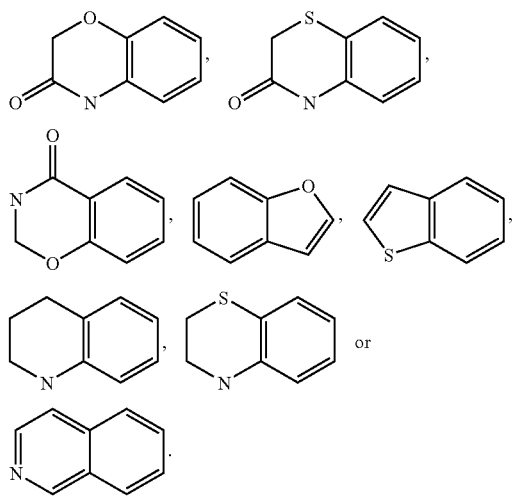

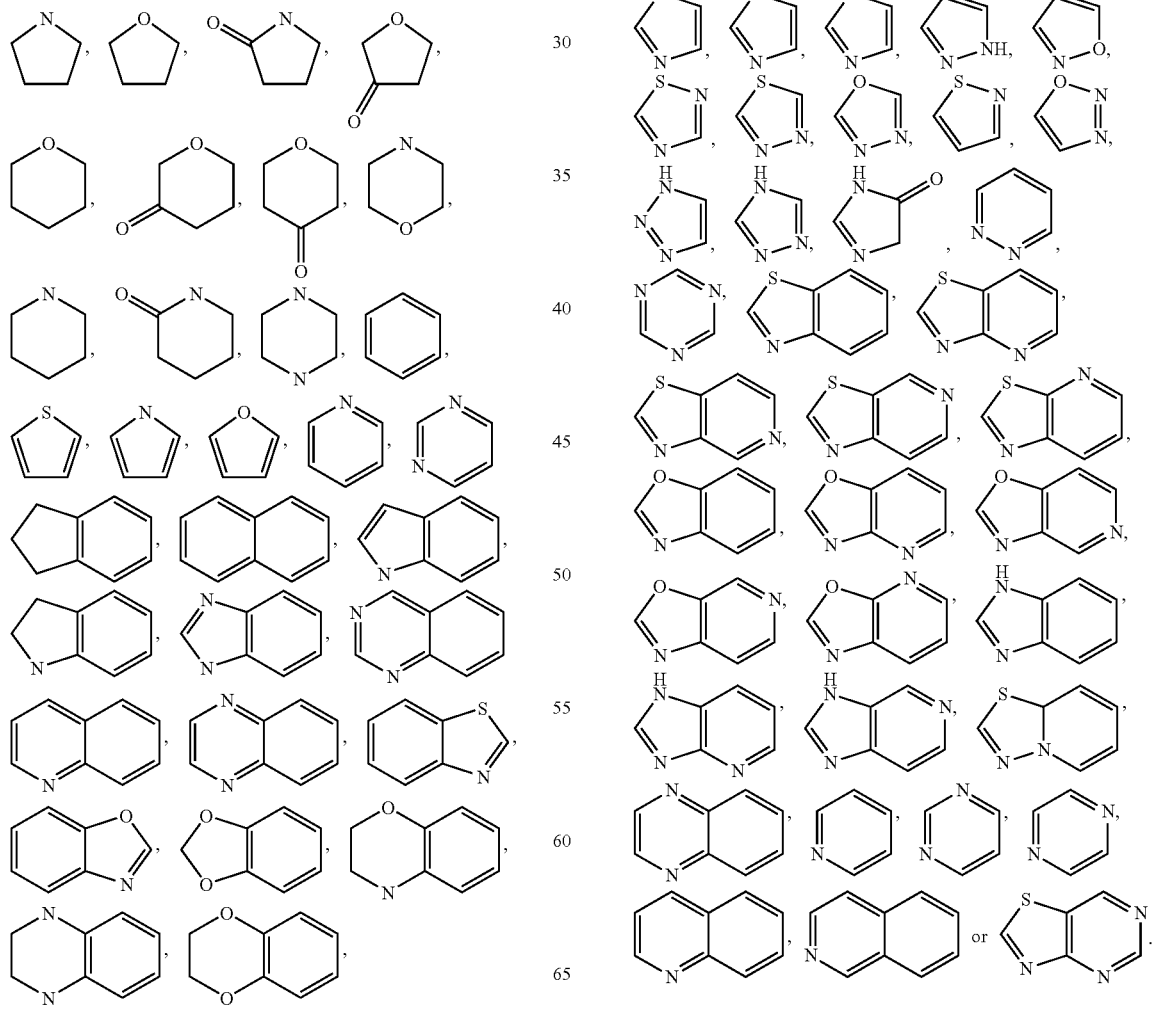

4. The compound as claimed in claim 1, or its stereoisomers, tautomers, prodrugs, pharmaceutically acceptable salts, and solvates thereof, wherein ring-C is selected from

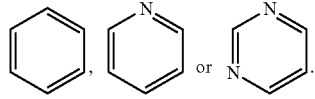

5. The compound as claimed in claim 1, or its stereoisomers, tautomers, prodrugs, pharmaceutically acceptable salts, and solvates thereof, wherein $R^1$ is selected from

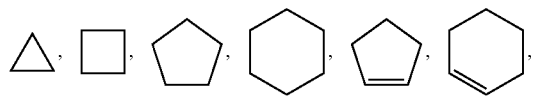

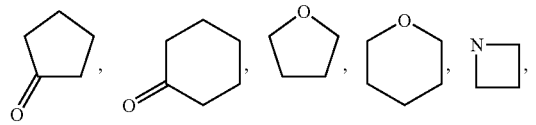

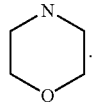

6. The compound as claimed in claim 1, or its stereoisomers, tautomers, prodrugs, pharmaceutically acceptable salts, and solvates thereof wherein ring-A is selected from

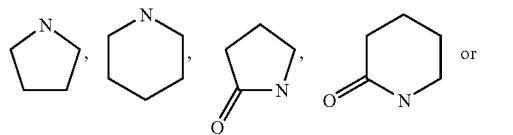

ring-B is selected from

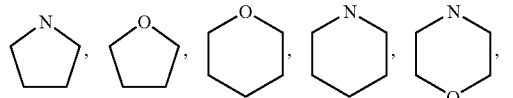

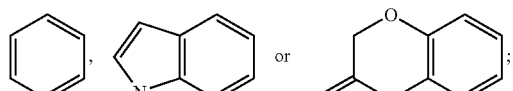

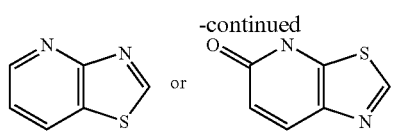

ring-C is

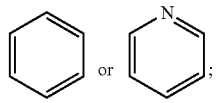

ring A is optionally substituted with 1 to 4 substituents independently selected from alkyl, alkenyl, alkynyl, halogen, monohaloalkyl, dihaloalkyl or perhaloalkyl, monohaloalkoxy, dihaloalkoxy or perhaloalkoxy, nitrile, nitro, —NR⁶R⁷, —OR⁶, —S(O)$_p$R⁶, —S(O)$_p$NR⁶R⁷, —NR⁶S(O)$_p$R⁷, —NR⁶C(O)R⁷, —OS(O)$_p$R⁷, —NR⁶C(O)OR⁷, —(CR⁸R⁹)$_n$C(O)OR⁶, —(CR⁸R⁹)$_n$C(O)NR⁶R⁷, —(CR⁸R⁹)$_n$C(O)R⁶, cycloalkyl, or cycloalkylalkyl;

ring C is optionally substituted with up 1 to 4 substituents independently selected from alkyl, alkenyl, alkynyl, halogen, mono, di or perhaloalkyl, nitrile, nitro, —NR⁶R⁷, —OR⁶, —NR⁶S(O)$_p$R⁷, —NR⁶C(O)R⁷, —NR⁶c(o)OR⁷, —(CR⁸R⁹)$_n$C(O)OR⁶, —(CR⁸R⁹)—C(O)NR⁶R⁷, —(CR⁸R⁹)—C(O)R⁶, or cycloalkyl, cycloalkylalkyl;

wherein p=0-2; n=0-4;

X is O;

$R^1$ is selected from $C_3$-$C_6$ cycloalkyl or heterocyclyl;

$R^2$ and $R^3$ are hydrogen;

$R^4$ and $R^5$ are independently selected from the group consisting of hydrogen, halogen, alkyl, alkenyl, alkynyl, cycloalkyl, cycloalkylalkyl, aryl, arylalkyl, heterocyclyl, heterocyclylalkyl, heteroaryl, heteroarylalkyl, —OR⁶, —S(O)$_p$R⁶, —NR⁶C(O)R⁷, —(CR⁸R⁹)$_n$C(O)OR⁶, —(CR⁸R⁹)$_n$OR⁶, and —C(R⁸R⁹)$_n$CO(R⁶), wherein n=0-4; wherein each of $R^4$ and $R^5$ is optionally substituted with one or more substituents selected from halo, straight chain or branched chain alkyl, alkenyl, alkynyl, cycloalkyl, aryl, heteroaryl, heterocycle, alkylsulfonyl, oxo, nitro, cyano, —COOR⁶, —C(O)NR⁶R⁷, —OR⁶, —SR⁶ or —NR⁶R⁷;

$R^6$ and $R^7$ are independently selected from the group consisting of hydrogen, alkyl, alkenyl, alkynyl, cycloalkyl, aryl, heterocyclyl and heteroaryl; or $R^6$ and $R^7$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, cyano, —OR⁶, —SR⁶, —NR⁶R⁷, —COOR⁶, —C(O)NR⁶R⁷, cycloalkyl, cycloalkylalkyl, aryl, arylalkyl, heterocyclyl, heterocyclylalkyl, heteroaryl, or heteroarylalkyl;

$R^8$ and $R^9$ are independently selected from the group consisting of hydrogen, fluorine, OR⁶, alkyl and perfluoroalkyl.

7. A compound as claimed in claim 1 which is 2-(4-Cyclopropanesulfonylphenyl)-2-(2,4-difluoro-phenoxy)-N-thiazol-2-yl-acetamide and its (+) and (−) enantiomers;

N-(5-Chlorothiazol-2-yl)-2-(4-cyclopropanesulfonylphenyl)-2-(2,4-difluorophenoxy)acetamide and its (+) and (−) enantiomers;

2-(4-Cyclopropanesulfonylphenyl)-2-(2,4-difluorophenoxy)-N-(5-fluorothiazol-2-yl)acetamide and its (+) and (−) enantiomers;

2-(4-Cyclopropanesulfonylphenyl)-2-(4-fluorophenoxy)-N-thiazol-2-yl-acetamide and its (+) and (−) enantiomers;

2-(4-Chlorophenoxy)-2-(4-cyclopropanesulfonylphenyl)-N-thiazol-2-yl-acetamide and its (+) and (−) enantiomers;

2-(3-Chloro-4-fluorophenoxy)-2-(4-cyclopropanesulfonylphenyl)-N-thiazol-2-yl-acetamide and its (+) and (−) enantiomers;

N-(5-Chlorothiazol-2-yl)-2-(4-cyclopropanesulfonylphenyl)-2-(4-fluoro-phenoxy)acetamide and its (+) and (−) enantiomers;

2-(4-Chlorophenoxy)-N-(5-chlorothiazol-2-yl)-2-(4-cyclopropanesulfonylphenyl(acetamide and its (+) and (−) enantiomers;

2-(3-Chloro-4-fluorophenoxy)-N-(5-chlorothiazol-2-yl)-2-(4-cyclopropanesulfonylphenyl)acetamide and its (+) and (−) enantiomers;

2-(4-Cyclopentanesulfonylphenyl)-2-(2,4-difluorophenoxy)-N-thiazol-2-yl-acetamide and its (+) and (−) enantiomers;

2-(4-Cyclopentanesulfonylphenyl)-2-(2,4-difluorophenoxy)-N-(5-fluoro-thiazol-2-yl)acetamide and its (+) and (−) enantiomers;

2-(4-Chlorophenoxy)-2-(4-cyclopentanesulfonylphenyl)-N-thiazol-2-yl-acetamide and its (+) and (−) enantiomers;

2-(4-Chlorophenoxy)-2-(4-cyclopropanesulfonylphenyl)-N-(5-fluoro-thiazol-2-yl)acetamide and its (+) and (−) enantiomers;

2-(4-Cyclopropanesulfonylphenyl)-2-(2,4-difluorophenoxy)-N-(5-methyl-thiazol-2-yl)acetamide and its (+) and (−) enantiomers;

2-(4-Cyclopropanesulfonylphenyl)-2-(2,4-difluorophenoxy)-N-(4-methyl-thiazol-2-yl)acetamide and its (+) and (−) enantiomers;

2-(4-Cyclopropanesulfonylphenyl)-2-(2,4-difluorophenoxy)-N[1,3,4]thiadiazol-2-yl-acetamide and its (+) and (−) enantiomers;

2-(4-Cyclopropanesulfonylphenyl)-2-(3,4-difluorophenoxy)-N-thiazol-2-yl-acetamide and its (+) and (−) enantiomers;

2-(4-Cyclopropanesulfonylphenyl)-2-(4-fluorophenoxy)-N-(5-fluorothiazol-2-yl)acetamide and its (+) and (−) enantiomers;

2-(3-Chloro-4-cyclopropanesulfonylphenyl)-2-(2,4-difluorophenoxy)-N-thiazol-2-yl-acetamide and its (+) and (−) enantiomers;

2-(3-Chloro-4-cyclopropanesulfonylphenyl)-2-(2,4-difluorophenoxy)-N-(5-fluorothiazol-2-yl)acetamide and its (+) and (−) enantiomers;

2-(4-Cyclopentanesulfonylphenyl)-2-(2,4-difluorophenoxy)-N-pyrazin-2-yl-acetamide and its (+) and (−) enantiomers;

2-(4-Chlorophenoxy)-2-(4-cyclopentanesulfonylphenyl)-N-(5-fluoro-thiazol-2-yl)acetamide and its (+) and (−) enantiomers;

2-(4-Cyclohexanesulfonylphenyl)-2-(2,4-difluorophenoxy)-N-thiazol-2-yl-acetamide and its (+) and (−) enantiomers;

2-(3-Chloro-4-cyclopentanesulfonylphenyl)-N-(5-chlorothiazol-2-yl)-2-(2,4-difluoro-phenoxy)acetamide and its (+) and (−) enantiomers;

N-(5-Chlorothiazol-2-yl)-2-(4-cyclopentanesulfonylphenyl)-2-(2,4-difluorophenoxy)acetamide and its (+) and (−) enantiomers;

2-[2-(4-Cyclopentanesulfonylphenyl)-2-(2,4-difluorophenoxy)-acetylamino]-thiazole-4-carboxylic acid ethyl ester and its (+) and (−) enantiomers;

2-(4-Cyclopentanesulfonylphenyl)-2-(2,4-difluorophenoxy)-N [1,3,4]thiadiazol-2-yl-acetamide and its (+) and (−) enantiomers;

2-(4-Cyclopropanesulfonylphenyl)-N-(5-fluorothiazol-2-yl)-2-(1H-indol-5-yloxy)acetamide 2-(3-Acetylaminophenoxy)-2-(4-cyclopropanesulfonylphenyl)-N-(5-fluoro-thiazol-2-yl(acetamide and its (+) and (−) enantiomers;

N-(5-Chloropyridin-2-yl)-2-(4-cyclopropanesulfonylphenyl)-2-(2,4-difluoro-phenoxy)acetamide and its (+) and (−) enantiomers;

2-(4-Cyclopropanesulfonylphenyl)-2-(2,4-difluorophenoxy)-N-(1H-pyrazol-3-yl)acetamide and its (+) and (−) enantiomers;

2-(4-Cyclopropanesulfonylphenyl)-2-(2,4-difluorophenoxy)-N-pyridin-2-yl-acetamide and its (+) and (−) enantiomers;

6[2-(4-Cyclopropanesulfonylphenyl)-2-(2,4-difluorophenoxy)-acetylamino]nicotinic acid methyl ester and its (+) and (−) enantiomers;

{2-[2-(4-Cyclopropanesulfonylphenyl)-2-(2,4-difluorohenoxy)-acetylamino]-5-ethoxy-thiazol-4-yl}acetic acid ethyl ester and its (+) and (−) enantiomers;

2-(4-Cyclopropanesulfonylphenyl)-2-(3-oxo-3,4-dihydro-2H-benzo[1,4]oxazin-7-yloxy)-N-thiazol-2-yl-acetamide and its (+) and (−) enantiomers;

2-(3-Chloro-4-cyclopentanesulfonylphenyl)-2-(2,4-difluorophenoxy)-N-(5-fluoro-thiazol-2-yl)acetamide and its (+) and (−) enantiomers;

2-(3-Chloro-4-cyclopentanesulfonylphenyl)-2-(2,4-difluorophenoxy)-N-(1H-pyrazol-3-yl)acetamide and its (+) and (−) enantiomers;

2-(4-Cyclopentanesulfonylphenyl)-2-(2,4-difluorophenoxy)-N-(1-methyl-1H-pyrazol-3-yl)acetamide and its (+) and (−) enantiomers;

2-(4-Chloro-2-fluorophenoxy)-N-(5-chlorothiazol-2-yl)-2-(4-cyclopropanesulfonylphenyl)acetamide and its (+) and (−) enantiomers;

2-(4-Chloro-2-fluorophenoxy)-2-(4-cyclopropanesulfonylphenyl)-N-thiazol-2-yl-acetamide and its (+) and (−) enantiomers;

2-(4-Chloro-2-fluorophenoxy)-N-(5-chloropyridin-2-yl)-2-(4-cyclopropanesulfonylphenyl)-acetamideand its (+) and (−) enantiomers;

2-(4-Chloro-2-fluorophenoxy)-2-(4-cyclopropanesulfonylphenyl)-N-(5-fluorothiazol-2-yl)acetamide and its (+) and (−) enantiomers;

2-(4-Chloro-2-fluorophenoxy)-2-(4-cyclopropanesulfonylphenyl)-N-(5-methylthiazol-2-yl)acetamide and its (+) and (−) enantiomers;

2-(4-Chloro-2-fluorophenoxy)-2-(4-cyclopropanesulfonylphenyl)-N-[1,3,4]thiadiazol-2-yl-acetamide and its (+) and (−) enantiomers;

2-(4-Chloro-2-fluorophenoxy)-2-(4-cyclopropanesulfonylphenyl)-N-(1H-pyrazol-3-yl)acetamide and its (+) and (−) enantiomers;

2-(4-Chloro-2-fluorophenoxy)-2-(4-cyclopropanesulfonylphenyl)-N-(1-methyl-1H-pyrazol-3-yl(acetamideand its (+) and (−) enantiomers;

2-(4-Chloro-2-fluorophenoxy)-2-(4-cyclopropanesulfonylphenyl)-N-pyrazin-2-yl-acetamide and its (+) and (−) enantiomers;

{2-[2-(4-Cyclopropanesulfonylphenyl)-2-(4-fluoro-phenoxy)acetylamino]thiazol-4-yl}acetic acid ethyl ester and its (+) and (−) enantiomers;

{5-Chloro-2-[2-(4-cyclopropanesulfonylphenyl)-2-(2,4-difluorophenoxy)-acetylamino}-thiazol-4-yl]acetic acid ethyl ester and its (+) and (−) enantiomers;

{2-[2-(4-Chlorophenoxy)-2-(4-cyclopropanesulfonylphenyl)-acetylamino]-thiazol-4-yl}acetic acid ethyl ester and its (+) and (−) enantiomers;

{2-[2-(3-Chloro-4-fluorophenoxy)-2-(4-cyclopropanesulfonylphenyl)-acetylamino]thiazol-4-yl}acetic acid ethyl ester and its (+) and (−) enantiomers;

{5-Chloro-2-[2-(4-cyclopropanesulfonylphenyl)-2-(4-fluorophenoxy)acetylamino]-thiazol-4-yl}acetic acid ethyl ester and its (+) and (−) enantiomers;

{5-Chloro-2-[2-(4-chlorophenoxy)-2-(4-cyclopropanesulfonylphenyl)acetylamino] thiazol-4-yl}acetic acid ethyl ester and its (+) and (−) enantiomers;

{5-Chloro-2-[2-(3-chloro-4-fluorophenoxy)-2-(4-cyclopropanesulfonylphenyl)-acetylamino]thiazol-4-yl}acetic acid ethyl ester and its (+) and (−) enantiomers;

{5-Chloro-2-[2-(3-chloro-4-cyclopropanesulfonylphenyl)-2-(2,4-difluorophenoxy)-acetylamino]thiazol-4-yl}acetic acid ethyl ester and its (+) and (−) enantiomers;

{5-Chloro-2-[2-(4-cyclopentanesulfonyl-phenyl)-2-(2,4-difluoro-phenoxy)-acetylamino]-thiazol-4-yl}-acetic acid ethyl ester and its (+) and (−) enantiomers;

{2-[2-(3-Chloro-4-cyclopropanesulfonylphenyl)-2-(2,4-difluorophenoxy)acetylamino]-thiazol-4-yl}acetic acid ethyl ester and its (+) and (−) enantiomers;

{2-[2-(4-Cyclopropanesulfonylphenyl)-2-(2,4-difluorophenoxy)-acetylamino]thiazol-4-yl}acetic acid ethyl ester and its (+) and (−) enantiomers;

2-[2-(4-Cyclopropanesulfonylphenyl)-2-(2,4-difluorophenoxy)-acetylamino]-4-methylthiazole-5-carboxylic acid ethyl ester and its (+) and (−) enantiomers;

{5-Chloro-2-[2-(4-cyclopropanesulfonylphenyl)-2-(3,4-difluorophenoxy)-acetylamino]thiazol-4-yl}acetic acid ethyl ester and its (+) and (−) enantiomers;

{2-[2-(4-Cyclopentanesulfonylphenyl)-2-(2,4-difluorophenoxy)-acetylamino]thiazol-4-yl}acetic acid ethyl ester and its (+) and (−) enantiomers;

{5-Chloro-2-[2-(4-cyclohexanesulfonylphenyl)-2-(2,4-difluorophenoxy)acetylamino]-thiazol-4-yl}acetic acid ethyl ester and its (+) and (−) enantiomers;

{2-[2-(4-Cyclohexanesulfonyl-phenyl)-2-(2,-difluorophenoxy)acetylamino]thiazol-4-yl}acetic acid ethyl ester and its (+) and (−) enantiomers;

{2-[2-(3-Chloro-4-cyclopentanesulfonylphenyl)-2-(2,4-difluorophenoxy)-acetylamino]thiazol-4-yl}acetic acid ethyl ester and its (+) and (−) enantiomers;

{5-Chloro-2-[2-(3-chloro-4-cyclopentanesulfonylphenyl)-2-(2,4-difluorophenoxy) acetylamino]-thiazol-4-yl}acetic acid ethyl ester and its (+) and (−) enantiomers;

{5-Chloro-2-[2-(4-cyclopropanesulfonyl-phenyl)-2-(1H-indol-5-yloxy)-acetylamino]-thiazol-4-yl}-acetic acid ethyl ester and its (+) and (−) enantiomers;

{2-[2-(3-Acetylaminophenoxy)-2-(4-cyclopropanesulfonylphenyl)-acetylamino]-5-chlorothiazol-4-yl}acetic acid ethyl ester and its (+) and (−) enantiomers;

2-[2-(3-Chloro-4-cyclopentanesulfonylphenyl)-2-(2,4-difluorophenoxy)-acetylamino]thiazole-4-carboxylic acid ethyl ester and its (+) and (−) enantiomers;

{2-[2-(4-Chloro-2-fluorophenoxy)-2-(4-cyclopropanesulfonylphenyl)acetylamino]thiazol-4-yl}acetic acid ethyl ester and its (+) and (−) enantiomers;

{5-Chloro-2-[2-(4-chloro-2-fluorophenoxy)-2-(4-cyclopropanesulfonylphenyl)-acetylamino]thiazol-4-yl}acetic acid ethyl ester and its (+) and (−) enantiomers;

2-[2-(4-Chloro-2-fluorophenoxy)-2-(4-cyclopropanesulfonylphenyl)-acetylamino]thiazole-4-carboxylic acid ethyl ester and its (+) and (−) enantiomers;

{2-[2-(4-Cyclopropanesulfonylphenyl)-2-(2,4-difluorophenoxy)acetylamino]-thiazol-4-ylsulfanyl}acetic acid ethyl ester and its (+) and (−) enantiomers;

3-{2-[2-(4-Cyclopropanesulfonyl-phenyl)-2-(2,4-difluorophenoxy)acetylamino]-thiazol-4-yl}propionic acid ethyl ester and its (+) and (−) enantiomers;

4-{2-[2-(4-Cyclopropanesulfonyl-phenyl)-2-(2,4-difluoro-phenoxy)-acetylamino]-thiazol-5-yloxy}-benzoic acid methyl ester: and its (+) and (−) enantiomers;

2-(4-Cyclopropanesulfonyl-phenyl)-2-(2,4-difluoro-phenoxy)-N-(5-methoxy-thiazol-2-yl)-acetamide and its (+) and (−) enantiomers;

4-{2-[2-(4-Cyclopropanesulfonyl-phenyl)-2-(tetrahydro-pyran-4-yloxy)-acetylamino]thiazol-5-yloxy}-benzoic acid methyl ester and its (+) and (−) enantiomers;

4-(2-{2-(4-Cyclopropanesulfonyl-phenyl)-2-[(R)-(tetrahydro-furan-3-yl)oxy]-acetylamino}-thiazol-5-yloxy)-benzoic acid methyl ester and its (+) and (−) enantiomers;

2-(2,4-Difluoro-phenoxy)-2-[4-(piperidine-1-sulfonyl)-phenyl]-N-thiazolo[5,4-13]pyridin-2-yl-acetamide and its (+) and (−) enantiomers;

2-(4-Cyclopropanesulfonyl-phenyl)-2-(tetrahydro-pyran-4-yloxy)-N-thiazolo[5,4-b]pyridin-2-yl-acetamide and its (+) and (−) enantiomers;

2-(4-Cyclopropanesulfonyl-phenyl)-N-(5-methoxy-thiazolo[5,4-b]pyridin-2-yl)-2-(tetrahydro-pyran-4-yloxy)-acetamide and its (+) and (−) enantiomers;

2-(4-Cyclopropanesulfonyl-phenyl)-N-(5-ethoxy-thiazolo[5,4-b]pyridin-2-yl)-2-(tetrahydro-pyran-4-yloxy)-acetamide and its (+) and (−) enantiomers;

2-(4-Cyclopropanesulfonyl-phenyl)-N-(5-isopropoxy-thiazolo[5,4-b]pyridin-2-yl)-2-(tetrahydro-pyran-4-yloxy)-acetamide and its (+) and (−) enantiomers;

2-(2,4-Difluoro-phenoxy)-N-(5-fluoro-thiazol-2-yl)-2-[4-(piperidine-1-sulfonyl)-phenyl]-acetamide and its (+) and (−) enantiomers;

N-(5-Chloro-thiazol-2-yl)-2-(2,4-difluoro-phenoxy)-2-[4-(piperidine-1-sulfonyl)-phenyl]-acetamide and its (+) and (−) enantiomers;

2-(2,4-Difluoro-phenoxy)-N-(5-fluoro-thiazol-2-yl)-2-[3-(piperidine-1-sulfonyl)-phenyl]-acetamide and its (+) and (−) enantiomers;

N-(5-Chloro-thiazol-2-yl)-2-(2,4-difluoro-phenoxy)-2-[3-(piperidine-1-sulfonyl)-phenyl]-acetamide and its (+) and (−) enantiomers;

2-(2,4-Difluoro-phenoxy)-N-(5-fluoro-thiazol-2-yl)-2-[3-(pyrrolidine-1-sulfonyl)-phenyl]-acetamide and its (+) and (−) enantiomers;

2-(2,4-Difluoro-phenoxy)-N-(5-fluoro-thiazol-2-yl)-2-[4-(pyrrolidine-1-sulfonyl)-phenyl]-acetamide and its (+) and (−) enantiomers;

N-(5-Chloro-thiazol-2-yl)-2-(2,4-difluoro-phenoxy)-2-[3-(pyrrolidine-1-sulfonyl)-phenyl]-acetamide and its (+) and (−) enantiomers;

N-(5-Chloro-thiazol-2-yl)-2-(2,4-difluoro-phenoxy)-2-[4-(pyrrolidine-1-sulfonyl)-phenyl]-acetamide and its (+) and (−) enantiomers;
2-[3-(Azetidine-1-sulfonyl)-phenyl]-N-(5-chloro-thiazol-2-yl)-2-(2,4-difluoro-phenoxy)-acetamide and its (+) and (−) enantiomers;
2-[4-(Azetidine-1-sulfonyl)-phenyl]-N-(5-chloro-thiazol-2-yl)-2-(2,4-difluoro-phenoxy)-acetamide and its (+) and (−) enantiomers;
2-[4-(Azetidine-1-sulfonyl)-phenyl]-2-(2,4-difluoro-phenoxy)-N-(5-fluoro-thiazol-2-yl)-acetamide and its (+) and (−) enantiomers;
2-(2,4-Difluoro-phenoxy)-N-(5-fluoro-thiazol-2-yl)-2-[4-(morpholine-4-sulfonyl)-phenyl]-acetamide and its (+) and (−) enantiomers;
N-(5-Chloro-thiazol-2-yl)-2-(2,4-difluoro-phenoxy)-2-[4-(morpholine-4-sulfonyl)-phenyl]-acetamide and its (+) and (−) enantiomers;
2-(2,4-Difluoro-phenoxy)-2-[4-(piperidine-1-sulfonyl)-phenyl]-N-(1H-pyrazol-3-yl)-acetamide and its (+) and (−) enantiomers;
2-(4-Chloro-phenoxy)-2-[4(morpholine-4-sulfonyl)-phenyl]-N-(1H-pyrazol-3-yl)-acetamide and its (+) and (−) enantiomers;
2-(4-Chloro-phenoxy)-2-[4-(piperidine-1-sulfonyl)-phenyl]-N-(1H-pyrazol-3-yl)-acetamide and its (+) and (−) enantiomers;
2-(2,4-Difluoro-phenoxy)-N-(5-morpholin-4-yl-thiazol-2-yl)-2-[4-(piperidine-1-sulfonyl)-phenyl]-acetamide and its (+) and (−) enantiomers;
2-(2,4-Difluoro-phenoxy)-N-(1-methyl-1H-pyrazol-3-yl)-2-[4-(piperidine-1-sulfonyl)-phenyl]-acetamide and its (+) and (−) enantiomers;
2-(2,4-Difluoro-phenoxy)-N-(1-methyl-1H-pyrazol-3-yl)-2-[4(morpholine-4-sulfonyl)-phenyl]-acetamide and its (+) and (−) enantiomers;
2-(2,4-Difluoro-phenoxy)-2-[4(morpholine-4-sulfonyl)-phenyl]-N-pyrazin-2-yl-acetamide and its (+) and (−) enantiomers;
2-(2,4-Difluoro-phenoxy)-N-(5-morpholin-4-yl-thiazol-2-yl)-2-[4-(pyrrolidine-1-sulfonyl)-phenyl]-acetamide and its (+) and (−) enantiomers;
2-(2,4-Difluoro-phenoxy)-2-[4(morpholine-4-sulfonyl)-phenyl]-N-thiazolo[5,4-b]pyridin-2-yl-acetamide and its (+) and (−) enantiomers;
2-(2,4-Difluoro-phenoxy)-2-[4-(pyrrolidine-1-sulfonyl)-phenyl]-N-thiazolo[5,4-13]pyridin-2-yl-acetamide and its (+) and (−) enantiomers;
2-(4-Cyclopropanesulfonyl-phenyl)-2-(2,4-difluoro-phenoxy)-N-[5-(5-trifluoromethyl-pyridin-2-yloxy)-thiazol-2-yl]-acetamide and its (+) and (−) enantiomers;
2-(4-Cyclopropanesulfonyl-phenyl)-2-(2,4-difluoro-phenoxy)-N-[5-(5-trifluoromethyl-pyridin-2-yloxy)-thiazol-2-yl]-acetamide and its (+) and (−) enantiomers;
2-(4-Cyclopropanesulfonyl-phenyl)-2-(2,4-difluoro-phenoxy)-N-[5-(5-trifluoromethyl-pyridin-2-yloxy)-thiazol-2-yl]-acetamide and its (+) and (−) enantiomers;
2-(4-Cyclopropanesulfonyl-phenyl)-2-(2,4-difluoro-phenoxy)-N-(5-morpholin-4-yl-thiazol-2-yl)-acetamideand its (+) and (−) enantiomers;
2-(4-Cyclopropanesulfonyl-phenyl)-2-(2,4-difluoro-phenoxy)-N-thiazolo[5,4-b]pyridin-2-yl-acetamide and its (+) and (−) enantiomers;
2-(4-Cyclopropanesulfonyl-phenyl)-2-(2,4-difluoro-phenoxy)-N-pyrazin-2-yl-acetamide and its (+) and (−) enantiomers;
2-(4-Cyclopropanesulfonyl-phenyl)-2-(2,4-difluoro-phenoxy)-N-(5-pyrazol-1-yl-thiazol-2-yl)-acetamideand its (+) and (−) enantiomers;
2-(4-Cyclopropanesulfonyl-phenyl)-2-(2,4-difluoro-phenoxy)-N-(5-methoxy-thiazolo[5,4-b]pyridin-2-yl)-acetamide and its (+) and (−) enantiomers;
2-(4-Cyclopropanesulfonyl-phenyl)-N-(5-pyrazol-1-yl-thiazol-2-yl)-2-(tetrahydro-pyran-4-yloxy)-acetamide and its (+) and (−) enantiomers;
2-(4-Cyclopropanesulfonyl-phenyl)-N-(5-morpholin-4-yl-thiazol-2-yl)-2-(tetrahydro-pyran-4-yloxy)-acetamide and its (+) and (−) enantiomers;
2-(4-Cyclopropanesulfonyl-phenyl)-N-(5-fluoro-thiazol-2-yl)-2-(tetrahydro-pyran-4-yloxy)-acetamide and its (+) and (−) enantiomers;
2-(4-Cyclopropanesulfonyl-phenyl)-N-(1-methyl-1H-pyrazol-3-yl)-2-(tetrahydro-pyran-4-yloxy)-acetamide and its (+) and (−) enantiomers;
2-(4-Cyclopropanesulfonyl-phenyl)-N-pyrazin-2-yl-2-(tetrahydro-pyran-4-yloxy)-acetamide and its (+) and (−) enantiomers;
N-[5-(4-Cyano-phenoxy)-thiazol-2-yl]-2-(4-cyclopropanesulfonyl-phenyl)-2-(tetrahydro-pyran-4-yloxy)-acetamide and its (+) and (−) enantiomers;
2-(4-Cyclopropanesulfonyl-phenyl)-N-(5-methoxy-thiazol-2-yl)-2-(tetrahydro-pyran-4-yloxy)-acetamide and its (+) and (−) enantiomers;
(5-Chloro-2-{2-(2,4-difluoro-phenoxy)-2-[4-(piperidine-1-sulfonyl)-phenyl]-acetylamino}-thiazol-4-yl)-acetic acid ethyl ester and its (+) and (−) enantiomers;
4-{2-[2-(4-Cyclopropanesulfonyl-phenyl)-2-(2,4-difluoro-phenoxy)-acetylamino]-thiazol-4-yl}-benzoic acid methyl ester and its (+) and (−) enantiomers;
{3-[2-(4-Cyclopropanesulfonyl-phenyl)-2-(2,4-difluoro-phenoxy)-acetylamino]-pyrazol-1-yl}-acetic acid ethyl ester and its (+) and (−) enantiomers;
4-(2-{2-(2,4-Difluoro-phenoxy)-2-[4(morpholine-4-sulfonyl)-phenyl]-acetylamino}-thiazol-5-yloxy)-benzoic acid methyl ester and its (+) and (−) enantiomers;
(5-Chloro-2-{2-(2,4-difluoro-phenoxy)-2-[4-(morpholine-4-sulfonyl)-phenyl]-acetylamino}-thiazol-4-yl)-acetic acid ethyl ester and its (+) and (−) enantiomers;
3-(2-{2-(2,4-Difluoro-phenoxy)-2-[4(morpholine-4-sulfonyl)-phenyl]-acetylamino}-thiazol-5-yloxy)-benzoic acid methyl ester and its (+) and (−) enantiomers;
1-(2-{2-(2,4-Difluoro-phenoxy)-2-[4-(pyrrolidine-1-sulfonyl)-phenyl]-acetylamino}-thiazol-5-yl)-piperidine-4-carboxylic acid ethyl ester and its (+) and (−) enantiomers;
4-(2-{2-(2,4-Difluoro-phenoxy)-2-[4-(pyrrolidine-1-sulfonyl)-phenyl]-acetylamino}-thiazol-5-yloxy)-benzoic acid methyl ester and its (+) and (−) enantiomers;
3-(2-{2-(2,4-Difluoro-phenoxy)-2-[4-(pyrrolidine-1-sulfonyl)-phenyl]-acetylamino}-thiazol-5-yloxy)-benzoic acid methyl ester and its (+) and (−) enantiomers;
(5-Chloro-2-{2-(2,4-difluoro-phenoxy)-2-[3-(pyrrolidine-1-sulfonyl)-phenyl]-acetylamino}-thiazol-4-yl)-acetic acid ethyl ester and its (+) and (−) enantiomers;
{2-[2-[3-(Azetidine-1-sulfonyl)-phenyl]-2-(2,4-difluoro-phenoxy)-acetylamino]-5-chloro-thiazol-4-yl}-aceticacid ethyl ester and its (+) and (−) enantiomers;
{2-[2-[4-(Azetidine-1-sulfonyl)-phenyl]-2-(2,4-difluoro-phenoxy)-acetylamino]-5-chloro-thiazol-4-yl}-acetic acid and its (+) and (−) enantiomers;
(5-Chloro-2-{2-(4-chloro-phenoxy)-2-[4-(piperidine-1-sulfonyl)-pheny]-acetylamino}-thiazol-4-yl)-acetic acid ethyl ester and its (+) and (−) enantiomers;

(5-Chloro-2-{2-(4-chloro-2-fluoro-phenoxy)-2-[4-(piperidine-1-sulfonyl)-phenyl]-acetylamino}-thiazol-4-yl)-acetic acid ethyl ester and its (+) and (−) enantiomers;
(5-Chloro-2-{2-(4-chloro-phenoxy)-2-[4(morpholine-4-sulfonyl)-phenyl]-acetylamino}-thiazol-4-yl)-acetic acid ethyl ester and its (+) and (−) enantiomers;
3-(2-{2-(4-Chloro-phenoxy)-2-[4-(piperidine-1-sulfonyl)-phenyl]-acetylamino}-thiazol-5-yloxy)-benzoic acid methyl ester and its (+) and (−) enantiomers;
4-(2-{2-(4-Chloro-phenoxy)-2-[4-(piperidine-1-sulfonyl)-phenyl]-acetylamino}-thiazol-5-yloxy)-benzoic acid methyl ester and its (+) and (−) enantiomers;
1-(2-{2-(2,4-Difluoro-phenoxy)-2-[4-(piperidine-1-sulfonyl)-phenyl]-acetylamino}-thiazol-5-yl)-iperidine-4-carboxylic acid ethyl ester and its (+) and (−) enantiomers;
(5-Chloro-2-{2-(4-chloro-2-fluoro-phenoxy)-2-[4(morpholine-4-sulfonyl)-phenyl]-acetylamino}-thiazol-4-yl)-acetic acid ethyl eter and its (+) and (−) enantiomers;
4-(2-{2-(2,4-Difluoro-phenoxy)-2-[4-(piperidine-1-sulfonyl)-phenyl]-acetylamino}-thiazol-5-yloxy)-benzoic acid methyl ester and its (+) and (−) enantiomers;
3-(2-{2-(2,4-Difluoro-phenoxy)-2-[4-(piperidine-1-sulfonyl)-phenyl]-acetylamino}-thiazol-5-yloxy)-benzoic acid methyl ester and its (+) and (−) enantiomers;
(2-{2-(4-Chloro-2-fluoro-phenoxy)-2-[4(morpholine-4-sulfonyl)-phenyl]-acetylamino}-thiazol-4-yl)-acetic acid ethyl ester and its (+) and (−) enantiomers;
4-(2-{2-(2,4-Difluoro-phenoxy)-2-[4-(tetrahydro-pyran-4-sulfonyl)-phenyl]-acetylamino}-thiazol-5-yloxy)-benzoic acid methyl ester and its (+) and (−) enantiomers;
1-{2-[2-(4-Cyclopropanesulfonyl-phenyl)-2-(2,4-difluoro-phenoxy)-acetylamino]-thiazol-5-yl}-piperidine-4-carboxylic acid ethyl ester and its (+) and (−) enantiomers;
3-{2-[2-(4-Cyclopropanesulfonyl-phenyl)-2-(2,4-difluoro-phenoxy)-acetylamino]-thiazol-5-yloxy}-benzoic acid methyl ester and its (+) and (−) enantiomers;
{2-[2-(4-Cyclopropanesulfonyl-phenyl)-2-(2,4-difluoro-phenoxy)-acetylamino]-thiazol-5-yl}-acetic acid methyl ester and its (+) and (−) enantiomers;
6-[2-(4-Cyclopropanesulfonyl-phenyl)-2-(2,4-difluoro-phenoxy)-acetylamino]-nicotinic acid methyl ester and its (+) and (−) enantiomers;
4-{2-[2-(4-Chloro-phenoxy)-2-(4-cyclopropanesulfonyl-phenyl)-acetylamino]-thiazol-5-yloxy}-benzoic acid methyl ester and its (+) and (−) enantiomers;
4-{2-[2-(4-Cyclopropanesulfonyl-phenyl)-2-(4-fluoro-phenoxy)-acetylamino]-thiazol-5-yloxy}-benzoic acid methyl ester and its (+) and (−) enantiomers;
{5-Chloro-2-[2-(4-cyclopropanesulfonyl-phenyl)-2-tetrahydro-furan-3-yloxy)-acetylamino]-thiazol-4-yl}-acetic acid ethyl ester and its (+) and (−) enantiomers;
4-{2-[2-(4-Cyclopropanesulfonyl-phenyl)-2-(3,4-dichloro-phenoxy)-acetylamino]-thiazol-5-yloxy}-benzoic acid methyl ester and its (+) and (−) enantiomers;
4-{2-[2-(4-Cyclopropanesulfonyl-phenyl)-2-(3,4-difluoro-phenoxy)-acetylamino]-thiazol-5-yloxy}-benzoic acid methyl ester and its (+) and (−) enantiomers;
4-{2-[2-(4-Cyclopropanesulfonyl-phenyl)-2-(3-fluoro-phenoxy)-acetylamino]-thiazol-5-yloxy}-benzoic acid methyl ester and its (+) and (−) enantiomers;
4-{2-[2-(3-Chloro-4-fluoro-phenoxy)-2-(4-cyclopropanesulfonyl-phenyl)-acetylamino]-thiazol-5-yloxy}-benzoic acid methyl ester and its (+) and (−) enantiomers;
4-{2-[2-(4-Cyclopropanesulfonyl-phenyl)-2-(4-methoxy-phenoxy)-acetylamino]-thiazol-5-yloxy}-benzoic acid methyl ester and its (+) and (−) enantiomers;
4-{2-[2-(4-Cyclopropanesulfonyl-phenyl)-2-(3-methoxy-phenoxy)-acetylamino]-thiazol-5-yloxy}-benzoic acid ethyl ester and its (+) and (−) enantiomers;
4-{2-[2-(4-Cyclopropanesulfonyl-phenyl)-2-(4-trifluoromethyl-phenoxy)-acetylamino]-thiazol-5-yloxy}-benzoic acid methyl ester and its (+) and (−) enantiomers;
4-{2-[2-(4-Cyclopropanesulfonyl-phenyl)-2-(3-trifluoromethyl-phenoxy)-acetylamino]-thiazol-5-yloxy}-benzoic acid methyl ester and its (+) and (−) enantiomers;
4-{2-[2-(4-Cyclopropanesulfonyl-phenyl)-2-(4-trifluoromethoxy-phenoxy)-acetylamino]-thiazol-5-yloxy}-benzoic acid methyl ester and its (+) and (−) enantiomers;
6-{2-[2-(4-Cyclopropanesulfonyl-phenyl)-2-(2,4-difluoro-phenoxy)-acetylamino]-thiazol-5-yloxy}-nicotinic acid methyl ester and its (+) and (−) enantiomers;
4-{2-[2-(4-Cyclopropanesulfonyl-phenyl)-2-(4-methyl-phenoxy)-acetylamino]-thiazol-5-yloxy}-benzoic acid methyl ester and its (+) and (−) enantiomers;
4-{2-[2-(4-Cyclopropanesulfonyl-phenyl)-2-phenoxy-acetylamino]-thiazol-5-yloxy}-benzoic acid methyl ester and its (+) and (−) enantiomers;
4-{2-[2-(4-Cyclopropanesulfonyl-phenyl)-2-(tetrahydro-furan-3-yloxy)-acetylamino]-thiazol-5-yloxy}-benzoic acid methyl ester and its (+) and (−) enantiomers;
{5-Chloro-2-[2-(4-cyclopropanesulfonyl-phenyl)-2-p-tolyloxy-acetylamino]-thiazol-4-yl}-acetic acid ethyl ester and its (+) and (−) enantiomers;
(4-{2-[2-(4-Cyclopropanesulfonyl-phenyl)-2-(2,4-difluoro-phenoxy)-acetylamino]-thiazol-5-yloxy}-phenyl)-acetic acid methyl ester and its (+) and (−) enantiomers;
{2-[2-(4-Cyclopropanesulfonyl-phenyl)-2-(2,4-difluoro-phenoxy)-acetylamino]-thiazol-5-yl}-propynoic acid ethyl ester and its (+) and (−) enantiomers;
4-{2-[2-(4-Cyclopropanesulfonyl-phenyl)-2-(2,4-difluoro-phenoxy)-acetylamino]-4-methyl-thiazol-5-yloxy}-benzoic acid methyl ester and its (+) and (−) enantiomers;
4-{2-[2-(4-Cyclopropanesulfonyl-phenyl)-2-(2,4-difluoro-phenoxy)-acetylamino]-thiazol-5-yloxy}-3-fluoro-benzoic acid methyl ester and its (+) and (−) enantiomers;
4-{2-[2-(4-Cyclopropanesulfonyl-phenyl)-2-(2,4-difluoro-phenoxy)-acetylamino]-thiazol-5-yloxy}-2-fluoro-benzoic acid methyl ester and its (+) and (−) enantiomers;
4-{2-[2-(4-Cyclopropanesulfonyl-phenyl)-2-(2,4-difluoro-phenoxy)-acetylamino]-thiazol-5-yl}-benzoic acid methyl ester and its (+) and (−) enantiomers;
4-{2-[2-(4-Cyclopropanesulfonyl-phenyl)-2-(2,4-difluoro-phenoxy)-acetylamino]-thiazol-5-ylmethyl}-benzoic acid ethyl ester and its (+) and (−) enantiomers;
4-{3-[2-(4-Cyclopropanesulfonyl-phenyl)-2-(2,4-difluoro-phenoxy)-acetylamino]-pyrazol-1-ylmethyl}-benzoic acid methyl ester and its (+) and (−) enantiomers;

(5-Chloro-2-{2-(4-cyclopropanesulfonyl-phenyl)-2-[(R)-(tetrahydro-furan-3-yl)oxy]-acetylamino}-thiazol-4-yl)-acetic acid ethyl ester and its (+) and (−) enantiomers;

4-(2-{2-(4-Cyclopropanesulfonyl-phenyl)-2-[(S)-(tetrahydro-furan-3-yl)oxy]-acetylamino}-thiazol-5-yloxy)-benzoic acid methyl ester and its (+) and (−) enantiomers;

(5-Chloro-2-{2-(4-cyclopropanesulfonyl-phenyl)-2-[(S)-(tetrahydro-furan-3-yl)oxy]-acetylamino}-thiazol-4-yl)-acetic acid ethyl ester and its (+) and (−) enantiomers;

1-{2-[2-(4-Cyclopropanesulfonyl-phenyl)-2-(2,4-difluoro-phenoxy)-acetylamino]-thiazol-5-ylmethyl}-piperidine-4-carboxylicacid ethyl ester and its (+) and (−) enantiomers;

1-{2-[2-(4-Cyclopropanesulfonyl-phenyl)-2-(2,4-difluoro-phenoxy)-acetylamino]-thiazol-5-ylmethyl}-pyrrolidine-2-carboxylic acid ethyl ester and its (+) and (−) enantiomers;

{2-[2-(4-Cyclopropanesulfonyl-phenyl)-2-(2,4-difluorophenoxy)-acetylamino]-thiazolo[5,4-b]pyridin-5-yloxy}-acetic acid ethyl ester and its (+) and (−) enantiomers;

4-{3-[2-(4-Cyclopropanesulfonyl-phenyl)-2-(tetrahydro-pyran-4-yloxy)-acetylamino]-pyrazol-1-ylmethyl}-benzoic acid methyl ester and its (+) and (−) enantiomers;

{5-Chloro-2-[2-(4-cyclopropanesulfonyl-phenyl)-2-(tetrahydro-pyran-4-yloxy)-acetylamino]-thiazol-4-yl}-acetic acid ethyl ester and its (+) and (−) enantiomers;

3-{2-[2-(4-Cyclopropanesulfonyl-phenyl)-2-(tetrahydro-pyran-4-yloxy)-acetylamino]-thiazol-5-yloxy}-benzoic acid methyl ester and its (+) and (−) enantiomers;

4-{2-[2-(4-Cyclopropanesulfonyl-phenyl)-2-(tetrahydro-pyran-4-yloxy)-acetylamino]-thiazol-5-yloxy}-2-fluoro-benzoic acid methyl ester and its (+) and (−) enantiomers;

4-{2-[2-(4-Cyclopropanesulfonyl-phenyl)-2-(tetrahydro-pyran-4-yloxy)-acetylamino]-thiazol-5-yloxy}-3-fluoro-benzoic acid methyl ester and its (+) and (−) enantiomers;

{2-[2-(4-Cyclopropanesulfonyl-phenyl)-2-(tetrahydro-pyran-4-yloxy)-acetylamino]-thiazolo[5,4-b]pyridin-5-yloxy}-acetic acid ethyl ester and its (+) and (−) enantiomers;

2-(4-Cyclopropanesulfonyl-phenyl)-N-(6-methoxy-benzothiazol-2-yl)-2-(tetrahydro-pyran-4-yloxy)-acetamide and its (+) and (−) enantiomers;

2-(4-Cyclopropanesulfonyl-phenyl)-N-(5-methoxy-thiazolo[5,4-b]pyridin-2-yl)-2-[(R)-(tetrahydro-furan-3-yl)oxy]-acetamide and its (+) and (−) enantiomers;

4-[(4-Cyclopropanesulfonyl-phenyl)-(5-fluoro-thiazol-2-ylcarbamoyl)-methoxy]-piperidine-1-carboxylic acid tert-butyl ester and its (+) and (−) enantiomers;

2-(4-Cyclopropanesulfonyl-phenyl)-N-(5-fluoro-thiazol-2-yl)-2-(piperidin-4-yloxy)-acetamide and its (+) and (−) enantiomers;

2-(4-Cyclopropanesulfonyl-phenyl)-N-(5-oxo-4,5-dihydro-thiazolo[5,4-b]pyridin-2-yl)-2-(tetrahydro-pyran-4-yloxy)-acetamide and its (+) and (−) enantiomers;

2-(4-Cyclopropanesulfonyl-phenyl)-N-(5-isopropoxy-thiazolo[5,4-b]pyridin-2-yl)-2-[(R)-(tetrahydro-furan-3-yl)oxy]-acetamide and its (+) and (−) enantiomers;

N-(5-Fluoro-thiazol-2-yl)-2-[4-(piperidine-1-sulfonyl)-phenyl]-2-(tetrahydro-pyran-4-yloxy)-acetamide and its (+) and (−) enantiomers;

2-[4-(Piperidine-1-sulfonyl)-phenyl]-2-(tetrahydro-pyran-4-yloxy)-N-thiazolo[5,4-b]pyridin-2-yl-acetamide and its (+) and (−) enantiomers;

N-(5-Methoxy-thiazolo[5,4-b]pyridin-2-yl)-2-[4-(piperidine-1-sulfonyl)-phenyl]-2-(tetrahydro-pyran-4-yloxy)-acetamide and its (+) and (−) enantiomers;

(5-Chloro-2-{2-(2,4-difluoro-phenoxy)-2-[4-(tetrahydro-pyran-4-sulfonyl)-phenyl]-acetylamino}-thiazol-4-yl)-acetic acid ethyl ester and its (+) and (−) enantiomers;

{2-[2-(4-Cyclopropanesulfonylphenyl)-2-(4-fluorophenoxy)acetylamino]thiazol-4-yl}acetic acid and its (+) and (−) enantiomers;

{5-Chloro-2-[2-(4-cyclopropanesulfonylphenyl)-2-(2,4-difluorophenoxy)acetylamino]thiazol-4-yl}acetic acid and its (+) and (−) enantiomers;

{2-[2-(4-Chloro-phenoxy)-2-(4-cyclopropanesulfonylphenyl(acetylamino]thiazol-4-yl}acetic acid and its (+) and (−) enantiomers;

{2-[2-(3-Chloro-4-fluorophenoxy)-2-(4-cyclopropanesulfonylphenyl(acetylamino]thiazol-4-yl}acetic acid and its (+) and (−) enantiomers;

{5-Chloro-2-[2-(4-cyclopropanesulfonylphenyl)-2-(4-fluorophenoxy)-acetylamino]-thiazol-4-yl}acetic acid and its (+) and (−) enantiomers;

{5-Chloro-2-[2-(4-chlorophenoxy)-2-(4-cyclopropanesulfonylphenyl)-acetylaminoPhiazol]-thiazol4-yl}acetic acid and its (+) and (−) enantiomers;

{5-Chloro-2-[2-(3-chloro-4-fluorophenoxy)-2-(4-cyclopropanesulfonylphenyl(acetylamino]thiazol-4-yl}acetic acid and its (+) and (−) enantiomers;

{5-Chloro-2-[2-(3-chloro-4-cyclopropanesulfonylphenyl)-2-(2,4-difluorophenoxy)acetylamino]thiazol-4-yl}acetic acid and its (+) and (−) enantiomers;

{5-Chloro-2-[2-(4-cyclopentanesulfonylphenyl)-2-(2,4-difluorophenoxy)acetylamino]-thiazol-4-yl}acetic acid and its (+) and (−) enantiomers;

{2-[2-(3-Chloro-4-cyclopropanesulfonylphenyl)-2-(2,4-difluorophenoxy)acetylamino]thiazol-4-yl}acetic acid and its (+) and (−) enantiomers;

{2-[2-(4-Cyclopropanesulfonylphenyl)-2-(2,4-difluorophenoxy)acetylamino]-thiazol-4-yl}acetic acid and its (+) and (−) enantiomers;

2-[2-(4-Cyclopropanesulfonylphenyl)-2-(2,4-difluorophenoxy)acetylamino]-4-methylthiazole-5-carboxylic acid and its (+) and (−) enantiomers;

{5-Chloro-2-[2-(4-cyclopropanesulfonylphenyl)-2-(3,4-difluorophenoxy)acetylamino]thiazol-4-yl}acetic acid and its (+) and (−) enantiomers;

{2-[2-(4-Cyclopentanesulfonylphenyl)-2-(2,4-difluorophenoxy)-acetylamino]-thiazol-4-yl}acetic acid and its (+) and (−) enantiomers;

{5-Chloro-2-[2-(4-cyclohexanesulfonylphenyl)-2-(2,4-difluorophenoxy)acetylamino]-thiazol-4-yl}acetic acid and its (+) and (−) enantiomers;

{2-[2-(4-Cyclohexanesulfonylphenyl)-2-(2,4-difluorophenoxy)acetylamino]-thiazol-4-yl}acetic acid and its (+) and (−) enantiomers;

{2-[2-(3-Chloro-4-cyclopentanesulfonylphenyl)-2-(2,4-difluorophenoxy)acetylamino]thiazol-4-yl}aceticacid and its (+) and (−) enantiomers;

{5-Chloro-2-[2-(3-chloro-4-cyclopentanesulfonylphenyl)-2-(2,4-difluorophenoxy)acetylamino]-thiazol-4-yl}acetic acid and its (+) and (−) enantiomers;

{5-Chloro-2-[2-(4-cyclopropanesulfonylphenyl)-2-(1H-indol-5-yloxy)acetylamino]thiazol-4-yl}acetic acid and its (+) and (−) enantiomers;

{2-[2-(3-Acetylaminophenoxy)-2-(4-cyclopropanesulfo-nylphenyl(acetylamino]-5-chloro-thiazol-4-yl}acetic acid and its (+) and (−) enantiomers;

2-[2-(4-Cyclopentanesulfonylphenyl)-2-(2,4-difluo-rophenoxy)-acetylamino]thiazole-4-carboxylic acid and its (+) and (−) enantiomers;

{2-[2-(4-Cyclopropanesulfonylphenyl)-2-(2,4-difluo-rophenoxy)acetylamino]-5-ethoxy-thiazol-4-yl}acetic acid and its (+) and (−) enantiomers;

2-[2-(3-Chloro-4-cyclopentanesulfonylphenyl)-2-(2,4-di-fluorophenoxy)acetylamino]thiazole-4-carboxylic acid and its (+) and (−) enantiomers;

{2-[2-(4-Chloro-2-fluorophenoxy)-2-(4-cyclopropane-sulfonylphenyl(acetylamino]thiazol-4-yl}acetic acid and its (+) and (−) enantiomers;

{5-Chloro-2-[2-(4-chloro-2-fluorophenoxy)-2-(4-cyclo-propanesulfonylphenyl)acetylamino]thiazol-4-yl}acetic acid and its (+) and (−) enantiomers;

2-[2-(4-Chloro-2-fluorophenoxy)-2-(4-cyclopropane-sulfonylphenyl(acetylamino]thiazole-4-carboxylic acid and its (+) and (−) enantiomers;

{2-[2-(4-Cyclopropanesulfonyl-phenyl)-2-(2,4-difluoro-phenoxy)-acetylamino]-thiazol-4-ylsulfanyl}-acetic acid and its (+) and (−) enantiomers;

3-{2-[2-(4-Cyclopropanesulfonyl-phenyl)-2-(2,4-dif-luoro-phenoxy)-acetylamino]-thiazol-4-yl}-propionic acid and its (+) and (−) enantiomers;

4-{2-[2-(4-Cyclopropanesulfonyl-phenyl)-2-(2,4-dif-luoro-phenoxy)-acetylamino]-thiazol-5-yloxy}-ben-zoic acid and its (+) and (−) enantiomers;

4-{2-[2-(4-Cyclopropanesulfonyl-phenyl)-2-(tetrahydro-pyran-4-yloxy)-acetylamino]-thiazol-5-yloxy}-ben-zoic acid and its (+) and (−) enantiomers;

4-(2-{2-(4-Cyclopropanesulfonyl-phenyl)-2-[(R)-(tet-rahydro-furan-3-ypoxy]-acetylamino}-thiazol-5-yloxy)-benzoic acid and its (+) and (−) enantiomers;

{5-Chloro-2-[2-(4-cyclopropanesulfonyl-phenyl)-2-(tet-rahydro-furan-3-yloxy)-acetylamino]-thiazol-4-yl}-acetic acid and its (+) and (−) enantiomers;

(5-Chloro-2-{2-(2,4-difluoro-phenoxy)-2-[4-(piperidine-1-sulfonyl)-phenyl]-acetylamino}-thiazol-4-yl)-acetic acid and its (+) and (−) enantiomers;

4-(2-{2-(2,4-Difluoro-phenoxy)-2-[4(morpholine-4-sul-fonyl)-phenyl]-acetylamino}-thiazol-5-yloxy)-benzoic acid and its (+) and (−) enantiomers;

(5-Chloro-2-{2-(2,4-difluoro-phenoxy)-2-[4-(morpho-line-4-sulfonyl)-phenyl]-acetylamino}-thiazol-4-yl)-acetic acid and its (+) and (−) enantiomers;

3-(2-{2-(2,4-Difluoro-phenoxy)-2-[4(morpholine-4-sul-fonyl)-phenyl]-acetylamino}-thiazol-5-yloxy)-benzoic acid and its (+) and (−) enantiomers;

1-(2-{2-(2,4-Difluoro-phenoxy)-2-[4-(pyrrolidine-1-sul-fonyl)-phenyl]-acetylamino}-thiazol-5-yl)-piperidine-4-carboxylic acid and its (+) and (−) enantiomers;

4-(2-{2-(2,4-Difluoro-phenoxy)-2-[4-(pyrrolidine-1-sul-fonyl)-phenyl]-acetylamino}-thiazol-5-yloxy)-benzoic acid and its (+) and (−) enantiomers;

3-(2-{2-(2,4-Difluoro-phenoxy)-2-[4-(pyrrolidine-1-sul-fonyl)-phenyl]-acetylamino}-thiazol-5-yloxy)-benzoic acid and its (+) and (−) enantiomers;

(5-Chloro-2-{2-(2,4-difluoro-phenoxy)-2-[3-(pyrroli-dine-1-sulfonyl)-phenyl]-acetylamino}-thiazol-4-yl)-acetic acid and its (+) and (−) enantiomers;

{2-[2-3-(Azetidine-1-sulfonyl)-phenyl]-2-(2,4-difluoro-phenoxy)-acetylamino]-5-chloro-thiazol-4-yl}-acetic acid and its (+) and (−) enantiomers;

{2-[2-[4-(Azetidine-1-sulfonyl)-phenyl]-2-(2,4-difluoro-phenoxy)-acetylamino]-5-chloro-thiazol-4-yl}-acetic acid and its (+) and (−) enantiomers;

(5-Chloro-2-{2-(4-chloro-phenoxy)-2-[4-(piperidine-1-sulfonyl)-phenyl]-acetylamino}-thiazol-4-yl)-acetic acid and its (+) and (−) enantiomers;

(5-Chloro-2-{2-(4-chloro-2-fluoro-phenoxy)-2-[4-(pip-eridine-1-sulfonyl)-phenyl]-acetylamino}-thiazol-4-yl)-acetic acid and its (+) and (−) enantiomers;

(5-Chloro-2-{2-(4-chloro-phenoxy)-2-[4(morpholine-4-sulfonyl)-phenyl]-acetylamino}-thiazol-4-yl)-acetic acid and its (+) and (−) enantiomers;

3-(2-{2-(4-Chloro-phenoxy)-2-[4-(piperidine-1-sulfo-nyl)-phenyl]-acetylamino}-thiazol-5-yloxy)-benzoic acid and its (+) and (−) enantiomers;

4-(2-{2-(4-Chloro-phenoxy)-2-[4-(piperidine-1-sulfo-nyl)-phenyl]-acetylamino}-thiazol-5-yloxy)-benzoic acid and its (+) and (−) enantiomers;

1-(2-{2-(2,4-Difluoro-phenoxy)-2-[4-(piperidine-1-sulfo-nyl)-phenyl]-acetylamino}-thiazol-5-yl)-iperidine-4-carboxylic acid and its (+) and (−) enantiomers;

(5-Chloro-2-{2-(4-chloro-2-fluoro-phenoxy)-2-[4(mor-pholine-4-sulfonyl)-phenyl]-acetylamino}-thiazol-4-yl)-acetic acid and its (+) and (−) enantiomers;

4-(2-{2-(2,4-Difluoro-phenoxy)-2-[4-(piperidine-1-sul-fonyp-phenyl]-acetylamino}-thiazol-5-yloxy)-benzoic acid and its (+) and (−) enantiomers;

3-(2-{2-(2,4-Difluoro-phenoxy)-2-[4-(piperidine-1-sulfo-nyl)-phenyl]-acetylamino}-thiazol-5-yloxy)-benzoic acid and its (+) and (−) enantiomers;

(2-{2-(4-Chloro-2-fluoro-phenoxy)-2-[4(morpholine-4-sulfonyl)-phenyl]-acetylamino}-thiazol-4-yl)-acetic acid and its (+) and (−) enantiomers;

4-(2-{2-(2,4-Difluoro-phenoxy)-2-[4-(tetrahydro-pyran-4-sulfonyl)-phenyl]-acetylamino}-thiazol-5-yloxy)-benzoic acid and its (+) and (−) enantiomers;

1-{2-[2-(4-Cyclopropanesulfonyl-phenyl)-2-(2,4-dif-luoro-phenoxy)-acetylamino]-thiazol-5-yl}-piperidine-4-carboxylic acid and its (+) and (−) enantiomers;

3-{2-[2-(4-Cyclopropanesulfonyl-phenyl)-2-(2,4-dif-luoro-phenoxy)-acetylamino]-thiazol-5-yloxy}-ben-zoic acid and its (+) and (−) enantiomers;

{2-[2-(4-Cyclopropanesulfonyl-phenyl)-2-(2,4-difluoro-phenoxy)-acetylamino]-thiazol-5-yl}-acetic acid and its (+) and (−) enantiomers;

6-[2-(4-Cyclopropanesulfonyl-phenyl)-2-(2,4-difluoro-phenoxy)-acetylamino]-nicotinic acid and its (+) and (−) enantiomers;

4-{2-[2-(4-Chloro-phenoxy)-2-(4-cyclopropanesulfonyl-phenyl)-acetylamino]-thiazol-5-yloxy}-benzoic acid and its (+) and (−) enantiomers;

4-{2-[2-(4-Cyclopropanesulfonyl-phenyl)-2-(4-fluoro-phenoxy)-acetylamino]-thiazol-5-yloxy}-benzoic acid and its (+) and (−) enantiomers;

4-{2-[2-(4-Cyclopropanesulfonyl-phenyl)-2-(3,4-dichloro-phenoxy)-acetylamino]-thiazol-5-yloxy}-benzoic acid and its (+) and (−) enantiomers;

4-{2-[2-(4-Cyclopropanesulfonyl-phenyl)-2-(3,4-dif-luoro-phenoxy)-acetylamino]-thiazol-5-yloxy}-ben-zoic acid and its (+) and (−) enantiomers;

4-{2-[2-(4-Cyclopropanesulfonyl-phenyl)-2-(3-fluoro-phenoxy)-acetylamino]-thiazol-5-yloxy}-benzoic acid and its (+) and (−) enantiomers;

4-{2-[2-(3-Chloro-4-fluoro-phenoxy)-2-(4cyclopropane-sulfonyl-phenyl)-acetylamino]-thiazol-5-yloxy}-ben-zoic acid and its (+) and (−) enantiomers;

{3-[2-(4-Cyclopropanesulfonyl-phenyl)-2-(2,4-difluoro-phenoxy)-acetylamino]-pyrazol-1-yl}-acetic acid and its (+) and (−) enantiomers;

4-{2-[2-(4-Cyclopropanesulfonyl-phenyl)-2-(4-methoxy-phenoxy)-acetylamino]-thiazol-5-yloxy}-benzoic acid and its (+) and (−) enantiomers;

4-{2-[2-(4-Cyclopropanesulfonyl-phenyl)-2-(3-methoxy-phenoxy)-acetylamino]-thiazol-5-yloxy}-benzoic acid and its (+) and (−) enantiomers;

4-{2-[2-(4-Cyclopropanesulfonyl-phenyl)-2-(4-trifluoromethyl-phenoxy)-acetylamino]-thiazol-5-yloxy}-benzoic acid and its (+) and (−) enantiomers;

4-{2-[2-(4-Cyclopropanesulfonyl-phenyl)-2-(3-trifluoromethyl-phenoxy)-acetylamino]-thiazol-5-yloxy}-benzoic acid and its (+) and (−) enantiomers;

4-{2-[2-(4-Cyclopropanesulfonyl-phenyl)-2-(4-tiifluoromethoxy-phenoxy)-acetylamino]-thiazol-5-yloxy}-benzoic acid and its (+) and (−) enantiomers;

6-{2-[2-(4-Cyclopropanesulfonyl-phenyl)-2-(2,4-difluoro-phenoxy)-acetylamino]-thiazol-5-yloxy}-nicotinicacid and its (+) and (−) enantiomers;

4-{2-[2-(4-Cyclopropanesulfonyl-phenyl)-2-(4-methyl-phenoxy)-acetylamino]-thiazol-5-yloxy}-benzoic acid and its (+) and (−) enantiomers;

4-{2-[2-(4-Cyclopropanesulfonyl-phenyl)-2-phenoxy-acetylamino]-thiazol-5-yloxy}-benzoic acid and its (+) and (−) enantiomers;

4-{2-[2-(4-Cyclopropanesulfonyl-phenyl)-2-(tetrahydro-furan-3-yloxy)-acetylamino]thiazol-5-yloxy}-benzoic acid and its (+) and (−) enantiomers;

{5-Chloro-2-[2-(4-cycloprop anesulfonyl-phenyl)-2-p-tolyloxy-acetylamino]-thiazol-4-yl}-acetic cid and its (+) and (−) enantiomers;

4-{2-[2-(4-Cyclopropanesulfonyl-phenyl)-2-(2,4-difluoro-phenoxy)-acetylamino]thiazol-4-yl}-benzoic acid and its (+) and (−) enantiomers;

(4-{2-[2-(4-Cyclopropanesulfonyl-phenyl)-2-(2,4-difluoro-phenoxy)-acetylamino]-thiazol-5-yloxy}-phenyl)-acetic acid and its (+) and (−) enantiomers;

{2-[2-(4-Cyclopropanesulfonyl-phenyl)-2-(2,4-difluoro-phenoxy)-acetylamino]-thiazol-5-yl}-propynoic acid and its (+) and (−) enantiomers;

4-{2-[2-(4-Cyclopropanesulfonyl-phenyl)-2-(2,4-difluoro-phenoxy)-acetylamino]-4-methyl-thiazol-5-yloxy}-benzoic acid and its (+) and (−) enantiomers;

4-{2-[2-(4-Cyclopropanesulfonyl-phenyl)-2-(2,4-difluoro-phenoxy)-acetylamino]-thiazol-5-yloxy}-3-fluoro-benzoic acid and its (+) and (−) enantiomers;

4-{2-[2-(4-Cyclopropanesulfonyl-phenyl)-2-(2,4-difluoro-phenoxy)-acetylamino]-thiazol-5-yloxy}-2-fluoro-benzoic acid and its (+) and (−) enantiomers;

4-{2-[2-(4-Cyclopropanesulfonyl-phenyl)-2-(2,4-difluoro-phenoxy)-acetylamino]-thiazol-5-yl}-benzoic acid and its (+) and (−) enantiomers;

4-{2-[2-(4-Cyclopropanesulfonyl-phenyl)-2-(2,4-difluoro-phenoxy)-acetylamino]-thiazol-5-ylmethyl}-benzoic acid and its (+) and (−) enantiomers;

4-{3-[2-(4-Cyclopropanesulfonyl-phenyl)-2-(2,4-difluoro-phenoxy)-acetylamino]-pyrazol-1-ylmethyl}-benzoic acid and its (+) and (−) enantiomers;

(5-Chloro-2-{2-(4-cyclopropanesulfonyl-phenyl)-2-[(R)-(tetrahydro-furan-3-yl)oxy]-acetylamino}-thiazol-4-yl)-acetic acid and its (+) and (−) enantiomers;

4-(2-{2-(4-Cyclopropanesulfonyl-phenyl)-2-[(S)-(tetrahydro-furan-3-yl)oxy]-acetylamino}-thiazol-5-yloxy)-benzoic acid and its (+) and (−) enantiomers;

(5-Chloro-2-{2-(4-cyclopropanesulfonyl-phenyl)-2-[(S)-(tetrahydro-furan-3-yl)oxy]-acetylamino}-thiazol-4-yl)-acetic acid and its (+) and (−) enantiomers;

1-{2-[2-(4-Cyclopropanesulfonyl-phenyl)-2-(2,4-difluoro-phenoxy)-acetylamino]-thiazol-5-ylmethyl}-piperidine-4-carboxylic acid and its (+) and (−) enantiomers;

1-{2-[2-(4-Cyclopropanesulfonyl-phenyl)-2-(2,4-difluoro-phenoxy)-acetylamino]-thiazol-5-ylmethyl}-pyrrolidine-2-carboxylic acid and its (+) and (−) enantiomers;

{2-[2-(4-Cyclopropanesulfonyl-phenyl)-2-(2,4-difluoro-phenoxy)-acetylamino]-thiazolo[5,4-b]pyridin-5-yloxy}-acetic acid and its (+) and (−) enantiomers;

4-{3-[2-(4-Cyclopropanesulfonyl-phenyl)-2-(tetrahydro-pyran-4-yloxy)-acetylamino]-pyrazol-1-ylmethyl}-benzoic acid and its (+) and (−) enantiomers;

{5-Chloro-2-[2-(4-cyclopropanesulfonyl-phenyl)-2-(tetrahydro-pyran-4-yloxy)-acetylamino]-thiazol-4-yl}-acetic acid and its (+) and (−) enantiomers;

3-{2-[2-(4-Cyclopropanesulfonyl-phenyl)-2-(tetrahydro-pyran-4-yloxy)-acetylamino]-thiazol-5-yloxy}-benzoic acid and its (+) and (−) enantiomers;

4-{2-[2-(4-Cyclopropanesulfonyl-phenyl)-2-(tetrahydro-pyran-4-yloxy)-acetylamino]-thiazol-5-yloxy}-2-fluoro-benzoic acid and its (+) and (−) enantiomers;

4-{2-[2-(4-Cyclopropanesulfonyl-phenyl)-2-(tetrahydro-pyran-4-yloxy)-acetylamino]-thiazol-5-yloxy}-3-fluoro-benzoic acid and its (+) and (−) enantiomers;

{2-[2-(4-Cyclopropanesulfonyl-phenyl)-2-(tetrahydro-pyran-4-yloxy)-acetylamino]-thiazolo[5,4-b]pyridin-5-yloxy}-acetic acid and its (+) and (−) enantiomers;

4-{2-[2-(4-Cyclopropanesulfonyl-phenyl)-2-(2,4-difluoro-phenoxy)-acetylamino]-thiazolo[5,4-b]pyridin-5-yloxy}-benzoic acid and its (+) and (−) enantiomers;

4-{2-[2-(4-Cyclopropanesulfonyl-phenyl)-2-(tetrahydro-pyran-4-yloxy)-acetylamino]-thiazolo[5,4-b]pyridin-5-yloxy}-benzoic acid and its (+) and (−) enantiomers;

4-[(4-Carboxymethyl-5-chloro-thiazol-2-ylcarbamoyl)-(4-cyclopropanesulfonyl-phenyl)-methoxy]-piperidine-1-carboxylic acid tert-butyl ester and its (+) and (−) enantiomers;

{5-Chloro-2-[2-(4-cyclopropanesulfonyl-phenyl)-2-(piperidin-4-yloxy)-acetylamino]-thiazol-4-yl}-acetic acid and its (+) and (−) enantiomers;

(4-{2-[2-(4-Cyclopropanesulfonyl-phenyl)-2-(tetrahydro-pyran-4-yloxy)-acetylamino]-thiazol-5-yloxy}-phenyl)-acetic acid and its (+) and (−) enantiomers;

2-[2-(4-Cyclopropanesulfonyl-phenyl)-2-(tetrahydro-pyran-4-yloxy)-acetylamino]-benzothiazole-6-carboxylic acid and its (+) and (−) enantiomers;

2-{2-(4-Cyclopropanesulfonyl-phenyl)-2-[(R)-(tetrahydro-furan-3-yl)oxy]-acetylamino}-benzothiazole-6-carboxylic acid and its (+) and (−) enantiomers;

(5-Chloro-2-{2-(2,4-difluoro-phenoxy)-2-[4-(tetrahydro-pyran-4-sulfonyl)-phenyl]-acetylamino}-thiazol-4-yl)-acetic acid and its (+) and (−) enantiomers;

N-{5-[3-(Azetidine-1-carbonyl)-phenoxy]-thiazol-2-yl}-2-(4-cyclopropanesulfonyl-phenyl)-2-(2,4-difluoro-phenoxy)-acetamide: and its (+) and (−) enantiomers;

N-{5-[4-(Azetidine-1-carbonyl)-phenoxy]-thiazol-2-yl}-2-(4-cyclopropanesulfonyl-phenyl)-2-(2,4-difluoro-phenoxy)-acetamide and its (+) and (−) enantiomers;

N-{5-[3-(Azetidine-1-carbonyl)-phenoxyl]-thiazol-2-yl}-2-(4-cyclopropanesulfonyl-phenyl)-2-(2,4-difluoro-phenoxy)-acetamide and its (+) and (−) enantiomers;

3-{2-[2-(4-Cyclopropanesulfonyl-phenyl)-2-(2,4-difluoro-phenoxy)-acetylamino]-thiazol-5-yloxy}-benzamide and its (+) and (−) enantiomers;
4-{2-[2-(4-Cyclopropanesulfonyl-phenyl)-2-(2,4-difluoro-phenoxy)-acetylamino]-thiazol-5-yloxy}-benzamide and its (+) and (−) enantiomers;
4-{2-[2-(4-Cyclopropanesulfonyl-phenyl)-2-(tetrahydrofuran-3-yloxy)-acetylamino]-thiazol-5-yloxy}-benzamide and its (+) and (−) enantiomers;
N-{5-[4-(Azetidine-1-carbonyl)-phenoxy]-thiazol-2-yl}-2-4-cyclopropanesulfonyl-phenyl)-2-(tetrahydro-pyran-4-yloxy)-acetamide and its (+) and (−) enantiomers;
N-[4-(2-Azetidin-1-yl-2-oxo-ethyl)-5-chloro-thiazol-2-yl]-2-(4-cyclopropanesulfonyl-phenyl)-2-(2,4-difluoro-phenoxy)-acetamide and its (+) and (−) enantiomers;
N-[4-(2-Azetidin-1-yl-2-oxo-ethyl)-5-chloro-thiazol-2-yl]-2-(4-cyclopropanesulfonyl-phenyl)-2-(tetrahydropyran-4-yloxy)-acetamide and its (+) and (−) enantiomers;
2-(4-Cyclopropanesulfonyl-phenyl)-2-(tetrahydro-pyran-4-yloxy)-N-{5-[4-(2H-tetrazol-5-yl)-phenoxy]-thiazol-2-yl}-acetamide and its (+) and (−) enantiomers;
(5-Chloro-2-{2-(2,4-difluorophenoxy)-2-[4-(tetrahydropyran-4-sulfonyl)phenyl]acetylamino}thiazol-4-yl)acetic acid and its (+) and (−) enantiomers;
(5-Chloro-2-{2-(4-chlorophenoxy)-2-[4-(tetrahydropyran-4-sulfonyl)phenyl]acetylamino}thiazol-4-yl)acetic acid and its (+) and (−) enantiomers;
2-(4-Chlorophenoxy)-N-(5-fluorothiazol-2-yl)-2-[4-(tetrahydropyran-4-sulfonyl)phenyl]acetamide and its (+) and (−) enantiomers;
2-(2,4-Difluorophenoxy)-N-(5-fluorothiazol-2-yl)-2-[4-(tetrahydropyran-4-sulfonyl)phenyl]acetamide and its (+) and (−) enantiomers;
(5-Chloro-2-{2-(2,4-difluorophenoxy)-2-[4(3-oxocyclopentanesulfonyl)phenyl]acetylamino}thiazol-4-yl)acetic acid and its (+) and (−) enantiomers;
2-(2,4-Difluorophenoxy)-N-(5-fluorothiazol-2-yl)-2-[4 (3-oxocyclopentanesulfonyl)phenyl]acetamide and its (+) and (−) enantiomers;
2-(4-Chlorophenoxy)-N-(5-fluorothiazol-2-yl)-2-[4(3-oxocyclopentanesulfonyl)phenyl]acetamide and its (+) and (−) enantiomers;
(5-Chloro-2-{2-(4-chlorophenoxy)-2-[4-(3-oxocyclopentanesulfonyl)phenyl]acetylamino}thiazol-4-yl)acetic acid and its (+) and (−) enantiomers;
5-Chloro-2-{2-(2,4-difluorophenoxy)-2-[4(2-oxopiperidine-4-sulfonyl)phenyl]acetylamino}thiazol-4-yl)acetic acid and its (+) and (−) enantiomers;
(5-Chloro-2-{2-(4-chlorophenoxy)-2-[4-(2-oxopiperidine-4-sulfonyl)phenyl]acetylamino}thiazol-4-yl)acetic acid and its (+) and (−) enantiomers;
2-(2,4-Difluorophenoxy)-N-(5-fluorothiazol-2-yl)-2-[4 (2-oxopiperidine-4-sulfonyl)phenyl]acetamide and its (+) and (−) enantiomers;
2-(4-Chlorophenoxy)-N-(5-fluorothiazol-2-yl)-2-[4-(2-oxopiperidine-4-sulfonyl)phenyl]acetamide and its (+) and (−) enantiomers;
{5-Chloro-2-[2-[4-(cyclohex-1-enesulfonyl)phenyl]-2-(2,4-difluorophenoxy)acetylamino]thiazol-4-yl}acetic acid and its (+) and (−) enantiomers;
(5-Chloro-2-{2-(4-chlorophenoxy)-2-[4(cyclohex-1-enesulfonyl)phenyl]acetylamino}thiazol-4-yl)-acetic acid and its (+) and (−) enantiomers;
2-[4-(Cyclohex-1-enesulfonyl)phenyl]-2-(2,4-difluorophenoxy)-N-(5-fluorothiazol-2-yl(acetamide and its (+) and (−) enantiomers;
2-(4-Chlorophenoxy)-2-[4(cyclohex-1-enesulfonyl)phenyl]-N-(5-fluorothiazol-2-yl)acetamide and its (+) and (−) enantiomers;
(5-Chloro-2-{2-(2,4-difluorophenoxy)-2-[4-(tetrahydrofuran-3-sulfonyl)phenyl]acetylamino}thiazol-4-yl)-acetic acid and its (+) and (−) enantiomers;
(5-Chloro-2-{2-(4-chlorophenoxy)-2-[4-(tetrahydrofuran-3-sulfonyl)phenyl]acetylamino}thiazol-4-yl)acetic acid and its (+) and (−) enantiomers;
2-(2,4-Difluorophenoxy)-N-(5-fluorothiazol-2-yl)-2-[4-(tetrahydrofuran-3-sulfonyl)phenyl]acetamide and its (+) and (−) enantiomers;
2-(4-Chlorophenoxy)-N-(5-fluorothiazol-2-yl)-2-[4-(tetrahydrofuran-3-sulfonyl)phenyl]acetamide and its (+) and (−) enantiomers;
{2-[2-(4-Cyclopropanesulfonylphenyl)-2-(2,4-difluorophenoxy)acetylamino]-5-fluorothiazol-4-yl}acetic acid and its (+) and (−) enantiomers;
{2-[2-(4-Chlorophenoxy)-2-(4-cyclopropanesulfonylphenyl)acetylamino]-5-fluorothiazol-4-yl}acetic acid and its (+) and (−) enantiomers;
{2-[2-(4-Cyclopentanesulfonylphenyl)-2-(2,4-difluorophenoxy)acetylamino]-5-fluorothiazol-4-yl}acetic acid and its (+) and (−) enantiomers;
6-{2-(2,4-Difluoro-phenoxy)-2-[4-(piperidine-1-sulfonyl)-phenyl]acetylamino}-nicotinic acid and its (+) and (−) enantiomers;
1-(2-{2-(2,4-Difluoro-phenoxy)-2-[4(morpholine-4-sulfonyl)-phenyl]-acetylamino}-thiazol-5-yl)-piperidine-4-carboxylic acid and its (+) and (−) enantiomers;
6-{2-(2,4-Difluoro-phenoxy)-2-[4(morpholine-4-sulfonyl)-phenyl]-acetylamino}-nicotinic acid and its (+) and (−) enantiomers;
2-(2,4-Difluoro-phenoxy)-N-(1-methyl-1H-pyrazol-3-yl)-2-[4-(pyrrolidine-1-sulfonyl)-phenyl]-acetamide and its (+) and (−) enantiomers;
6-{2-(2,4-Difluoro-phenoxy)-2-[4-(pyrrolidine-1-sulfonyl)-phenyl]-acetylamino}-nicotinic acid and its (+) and (−) enantiomers;
(5-Chloro-2-{2-(2,4-difluoro-phenoxy)-2-[4-(pyrazole-1-sulfonyl)-phenyl]-acetylamino}-thiazol-4-yl)-acetic acid and its (+) and (−) enantiomers;
2-(2,4-Difluoro-phenoxy)-N-(5-morpholin-4-yl-thiazol-2-yl)-2-[4-(tetrahydro-pyran-4-sulfonyl)-phenyl]-acetamide and its (+) and (−) enantiomers;
1-(2-{2-(2,4-Difluoro-phenoxy)-2-[4-(tetrahydro-pyran-4-sulfonyl)-phenyl]-acetylamino}-thiazol-5-yl)-piperidine-4-carboxylic acid and its (+) and (−) enantiomers;
2-(2,4-Difluoro-phenoxy)-2-[4-(tetrahydro-pyran-4-sulfonyl)-phenyl]-N-thiazolo[5,4-b]pyridin-2-yl-acetamide and its (+) and (−) enantiomers;
6-{2-(2,4-Difluoro-phenoxy)-2-[4-(tetrahydro-pyran-4-sulfonyl)-phenyl]-acetylamino}-nicotinic acid and its (+) and (−) enantiomers;
2-(2,4-Difluoro-phenoxy)-N-(1-methyl-1H-pyrazol-3-yl)-2-[4-(tetrahydro-pyran-4-sulfonyl)-phenyl]-acetamide and its (+) and (−) enantiomers;
N-{5-[4-(Azetidine-1-carbonyl)-phenoxy]-thiazol-2-yl}-2-(2,4-difluoro-phenoxy)-2-[4-(tetrahydro-pyran-4-sulfonyl)-phenyl]-acetamide and its (+) and (−) enantiomers;

N-{5-[3-(Azetidine-1-carbonyl)-phenoxy]-thiazol-2-yl}-2-(2,4-difluoro-phenoxy)-2-[4-(tetrahydro-pyran-4-sulfonyl)-phenyl]-acetamide and its (+) and (−) enantiomers;

(5-Chloro-2-{2-(2,4-difluoro-phenoxy)-2-[4-(tetrahydro-furan-3-sulfonyl)-phenyl]-acetylamino}-thiazol-4-yl)-acetic acid and its (+) and (−) enantiomers;

4-(2-{2-(2,4-Difluoro-phenoxy)-2-[4-(tetrahydro-furan-3-sulfonyl)-phenyl]-acetylamino}-thiazol-5-yloxy)-benzoic acid and its (+) and (−) enantiomers;

2-(2,4-Difluoro-phenoxy)-N-(5-morpholin-4-yl-thiazol-2-yl)-2-[4-(tetrahydro-furan-3-sulfonyl)-phenyl]-acetamide and its (+) and (−) enantiomers;

1-(2-{2-(2,4-Difluoro-phenoxy)-2-[4-(tetrahydro-furan-3-sulfonyl)-phenyl]-acetylamino}-thiazol-5-yl)-piperidine-4-carboxylic acid and its (+) and (−) enantiomers;

2-(2,4-Difluoro-phenoxy)-2-[4-(tetrahydro-furan-3-sulfonyl)-phenyl]-N-thiazolo[5,4-b]pyridin-2-yl-acetamide and its (+) and (−) enantiomers;

6-{2-(2,4-Difluoro-phenoxy)-2-[4-(tetrahydro-furan-3-sulfonyl)-phenyl]acetylamino}-nicotinic acid and its (+) and (−) enantiomers;

2-(2,4-Difluoro-phenoxy)-N-(1-methyl-1H-pyrazol-3-yl)-2-[4-(tetrahydro-furan-3-sulfonyl)-phenyl]-acetamide and its (+) and (−) enantiomers;

N-{5-[4-(Azetidine-1-carbonyl)-phenoxy]-thiazol-2-yl}-2-(2,4-difluoro-phenoxy)-2-[4-(tetrahydro-furan-3-sulfonyp-phenyl]-acetamide and its (+) and (−) enantiomers;

N-{5-[3-(Azetidine-1-carbonyl)-phenoxy]-thiazol-2-yl}-2-(2,4-difluoro-phenoxy)-2-[4-(tetrahydro-furan-3-sulfonyl)-phenyl]-acetamide and its (+) and (−) enantiomers;

(5-Chloro-2-{2-(2,4-difluoro-phenoxy)-2-[4-(piperidine-4-sulfonyl)-phenyl]-acetylamino}-thiazol-4-yl)-acetic acid and its (+) and (−) enantiomers;

4-(2-{2-(2,4-Difluoro-phenoxy)-2-[4-(piperidine-4-sulfonyl)-phenyl]-acetylamino}-thiazol-5-yloxy)-benzoic acid and its (+) and (−) enantiomers;

2-(2,4-Difluoro-phenoxy)-N-(5-morpholin-4-yl-thiazol-2-yl)-2-[4-(piperidine-4-sulfonyl)-phenyl]-acetamide and its (+) and (−) enantiomers;

1-(2-{2-(2,4-Difluoro-phenoxy)-2-[4-(piperidine-4-sulfonyl)-phenyl]-acetylamino}-thiazol-5-yl)-piperidine-4-carboxylic acid and its (+) and (−) enantiomers;

2-(2,4-Difluoro-phenoxy)-2-[4-(piperidine-4-sulfonyl)-phenyl]-N-thiazolo[5,4-b]pyridin-2-yl-acetamide and its (+) and (−) enantiomers;

6-{2-(2,4-Difluoro-phenoxy)-2-[4-(piperidine-4-sulfonyl)-phenyl]- acetylamino}-nicotinic acid and its (+) and (−) enantiomers;

2-(2,4-Difluoro-phenoxy)-N-(1-methyl-1H-pyrazol-3-yl)-2-[4-(piperidine-4-sulfonyl)-phenyl]-acetamide and its (+) and (−) enantiomers;

N-{5-[4-(Azetidine-1-carbonyl)-phenoxy]-thiazol-2-yl}-2-(2,4-difluoro-phenoxy)-2-[4-(piperidine-4-sulfonyl)-phenyl]-acetamide and its (+) and (−) enantiomers;

N-5-[3-(Azetidine-1-carbonyp-phenoxy]-thiazol-2-yl)-2-(2,4-difluoro-phenoxy)-2-[4(piperidine-4-sulfonyl)-phenyl]-acetamide and its (+) and (−) enantiomers;

(5-Chloro-2-{2-(2,4-difluoro-phenoxy)-2-[4(3-oxo-cyclopentanesulfonyl)-phenyl]-acetylamino}-thiazol-4-yl)-acetic acid and its (+) and (−) enantiomers;

2-(4-Cyclopropanesulfonyl-phenyl)-2-(2,4-difluoro-phenoxy)-N-{5-[4-(pyrrolidine-1-carbonyl)-phenoxy]-thiazol-2-yl}-acetamide and its (+) and (−) enantiomers;

2-(4-Cyclopropanesulfonyl-phenyl)-2-(2,4-difluoro-phenoxy)-N-{5-[4-(piperidine-1-carbonyl)-phenoxy]-thiazol-2-yl}-acetamide and its (+) and (−) enantiomers;

4-{2-[2-(4-Cyclopropanesulfonyl-phenyl)-2-(pyrrolidin-3-yloxy)-acetylamino]-thiazol-5-yloxy}-benzoic acid and its (+) and (−) enantiomers;

4-{2-[2-(4-Cyclopropanesulfonyl-phenyl)-2-(1-methyl-pyrrolidin-3-yloxy)-acetylamino]-thiazol-5-yloxy}-benzoic acid and its (+) and (−) enantiomers;

4-{2-[2-(4-Cyclopropanesulfonyl-phenyl)-2-(piperidin-4-yloxy)-acetylamino]-thiazol-5-yloxy}-benzoic acid and its (+) and (−) enantiomers;

4-{2-[2-(4-Cyclopropanesulfonyl-phenyl)-2-(1-methyl-pip eridin-4-yloxy)-acetylamino]-thiazol-5-yloxy}-benzoic acid and its (+) and (−) enantiomers;

{5-Chloro-2-[2-(4-cyclopropanesulfonyl-phenyl)-2-(1-methyl-piperidin-4-yloxy)-acetylamino]-thiazol-4-yl}-acetic acid and its (+) and (−) enantiomers;

{5-Chloro-2-[2-(4-cyclopropanesulfonyl-phenyl)-2-(pyrrolidin-3-yloxy)-acetylamino]-thiazol-4-yl}-acetic acid and its (+) and (−) enantiomers;

{5-Chloro-2-[2-(4-cyclopropanesulfonyl-phenyl)-2-(1-methyl-pyrrolidin-3-yloxy)-acetylamino]-thiazol-4-yl}-acetic acid and its (+) and (−) enantiomers;

2-(4-Cyclopropanesulfonyl-phenyl)-2-(1-methyl-pyrrolidin-3-yloxy)-N-thiazolo[5,4-b]pyridin-2-yl-acetamide and its (+) and (−) enantiomers;

2-(4-Cyclopropanesulfonyl-phenyl)-2-(pyrrolidin-3-yloxy)-N-thiazolo[5,4-b]pyridin-2-yl-acetamide and its (+) and (−) enantiomers;

2-(4-Cyclopropanesulfonyl-phenyl)-2-(1-methyl-piperidin-4-yloxy)-N-thiazolo[5,4-b]pyridin-2-yl-acetamide and its (+) and (−) enantiomers;

2-(4-Cyclopropanesulfonyl-phenyl)-2-(piperidin-4-yloxy)-N-thiazolo[5,4-b]pyridin-2-yl-acetamide and its (+) and (−) enantiomers; or {2-[2-[5-(Azetidine-1-carbonyl)-pyrazin-2-yloxy]-2-(4-cyclopropanesulfonyl-phenyl)-acetylamino]-5-chloro-thiazol-4-yl}-acetic acid and its (+) and (−) enantiomers.

8. A method of activating Glucokinase in a subject, the method comprising administering to the subject a compound of formula (I), as claimed in claim 1, or its stereoisomers, tautomers, prodrugs, pharmaceutically acceptable salts, and solvates thereof.

9. A method of deinhibiting Glucokinase in a subject, the method comprising administering to the subject a compound of formula (I), as claimed in claim 1, or its stereoisomers, tautomers, prodrugs, pharmaceutically acceptable salts, and solvates thereof.

10. A method of treating hyperglycemia, diabetes or type II diabetes in a subject, the method comprising administering to the subject a compound of formula (I), as claimed in claim 1, or its stereoisomers, tautomers, prodrugs, pharmaceutically acceptable salts, and solvates thereof.

11. A method of treating a subject demonstrating pre-diabetic hyperglycemia or impaired glucose tolerance, the method comprising administering to the subject a compound of formula (I), as claimed in claim 1, or its stereoisomers, tautomers, prodrugs, pharmaceutically acceptable salts, and solvates thereof.

12. A method of treating diabetes and obesity in a subject, the method comprising administering to the subject a compound of formula (I), as claimed in claim 1, or its stereoisomers, tautomers, prodrugs, pharmaceutically acceptable salts, and solvates thereof.

13. A method of treating obesity in a subject, the method comprising administering to the subject a compound of formula (I), as claimed in claim 1, or its stereoisomers, tautomers, prodrugs, pharmaceutically acceptable salts, and solvates thereof.

14. A method of treating dyslipidemia in a subject, the method comprising administering to the subject a compound of formula (I), as claimed in claim 1, or its stereoisomers, tautomers, prodrugs, pharmaceutically acceptable salts, and solvates thereof.

15. A method of treating hyperglycemia, IGT, Syndrome X, type 2 diabetes, type 1 diabetes, dyslipidemia or hyperlipidemia, hypertension, or obesity, or of lowering of food intake, or of regulating appetite, or of regulating feeding behavior in a subject, the method comprising administering to the subject a compound of formula (I), as claimed in claim 1, or its stereoisomers, tautomers, prodrugs, pharmaceutically acceptable salts, and solvates thereof.

16. A method of enhancing the secretion of enteroincretins, GLP-1 or GIP in a subject, the method comprising administering to the subject a compound of formula (I), as claimed in claim 1, or its stereoisomers, tautomers, prodrugs, pharmaceutically acceptable salts, and solvates thereof.

17. A pharmaceutical composition comprising, as an active ingredient, at least one compound of formula (I), as claimed in claim 1, or its stereoisomers, tautomers, prodrugs, pharmaceutically acceptable salts, and solvates thereof, together with one or more pharmaceutically acceptable carriers or excipients.

18. A pharmaceutical composition comprising, as an active ingredient, at least one compound of formula (I), as claimed in claim 1, or its stereoisomers, tautomers, prodrugs, pharmaceutically acceptable salts, and solvates thereof, in combination with one or more pharmaceutically acceptable therapeutically active agents.

19. The pharmaceutical composition as claimed in claim 17 wherein, the pharmaceutically acceptable therapeutically active agent is selected from anti-diabetic agents, anti-hyperglycemic agents, anti-obesity agents, anti-hypertensive agents or anti-dyslipidemic agents.

20. The pharmaceutical composition as claimed in claim 17 wherein the pharmaceutically acceptable therapeutically active agents is selected from: insulin secretagogues, sulfonylureas, insulinotropic sulfonyl urea receptor ligands, meglitinides, biguanides, glucagon antagonists, peptide glucagon antagonists, non-peptide glucagon antagonists, glucosidase inhibitors, glucose sensitive insulinotropic agents, GLP-1 mimetics, insulin sensitizers, dipeptidyl peptidase-IV inhibitors, fibrates, niacin, statins, cholesterol absorption inhibitors, bile acid sequestrants, diuretics, angiotensin converting enzyme (ACE) inhibitors, angiotensin-II receptor type-I blockers (ARB), rennin inhibitors, β-adrenergic receptor blockers, calcium channel blockers, aldosterone receptor antagonists, or aldosterone synthase inhibitors.

21. The pharmaceutical composition as claimed in claim 17 wherein the pharmaceutically acceptable therapeutically active agents is selected from: amaryl, glyburide, glimepiride, glipyride, glipizide, nateglinide, rapaglinide, metformin, phenformin, buformin, acarbose, miglitol, GLP-1, exendin-4, troglitazone, rosiglitazone, pioglitazone, sitagliptin, vildagliptin, sibutramine, orlistat, rimonabant, gemfibrozil, fenofibrate, niacin, rosuvatatin, atorvastatin, simvastatin, ezetimibe, cholestyramine, hydrochlorothiazides, mannitol, indapamide, furosemide, captopril, enalapril, losartan, irbesartan, aliskerin, atenolol, metoprolol, amlodipine, nifedipine, spironolactone, or FAD286.

* * * * *